US011707456B2

(12) United States Patent
Zhang et al.

(10) Patent No.: US 11,707,456 B2
(45) Date of Patent: Jul. 25, 2023

(54) PROCESSES FOR PREPARING ARIMOCLOMOL CITRATE AND INTERMEDIATES THEREOF

(71) Applicant: KemPharm Denmark A/S, Copenhagen (DK)

(72) Inventors: Zhe Zhang, Simpsonville, SC (US); Mark Read, Greenville, SC (US); Elisabeth Vang Carstensen, Farum (DK); Marco Poppe, Linz (AT); Andreas Pelz, Freistadt (AT)

(73) Assignee: KemPharm Denmark A/S

( * ) Notice: Subject to any disclaimer, the term of this patent is extended or adjusted under 35 U.S.C. 154(b) by 0 days.

(21) Appl. No.: 17/691,989

(22) Filed: Mar. 10, 2022

(65) Prior Publication Data

US 2022/0273639 A1  Sep. 1, 2022

Related U.S. Application Data

(63) Continuation of application No. PCT/EP2021/082294, filed on Nov. 19, 2021.

(60) Provisional application No. 63/211,809, filed on Jun. 17, 2021, provisional application No. 63/115,749, filed on Nov. 19, 2020.

(30) Foreign Application Priority Data

Nov. 24, 2020 (EP) .................... 20209467

(51) Int. Cl.
*A61K 31/4545* (2006.01)
*A61K 9/20* (2006.01)
*A61K 9/50* (2006.01)

(52) U.S. Cl.
CPC ........ *A61K 31/4545* (2013.01); *A61K 9/2054* (2013.01); *A61K 9/5047* (2013.01)

(58) Field of Classification Search
CPC .. A61K 31/4545; A61K 31/00; C07D 401/12; C07D 213/89
See application file for complete search history.

(56) References Cited

U.S. PATENT DOCUMENTS

| | | | |
|---|---|---|---|
| 4,404,384 A | 9/1983 | Gebert et al. |
| 5,147,879 A | 9/1992 | Nagy et al. |
| 5,239,077 A | 8/1993 | Bertok et al. |
| 5,278,309 A | 1/1994 | Bertok et al. |
| 5,296,606 A | 3/1994 | Nagy et al. |
| 5,328,906 A | 7/1994 | Nagy et al. |
| 5,334,600 A | 8/1994 | Van Duzer et al. |
| 5,348,945 A | 9/1994 | Berberian et al. |
| 5,830,464 A | 11/1998 | Srivastava |
| 5,948,646 A | 9/1999 | Srivastava |
| 5,985,270 A | 11/1999 | Srivastava |
| 6,007,821 A | 12/1999 | Srivastava et al. |
| 6,139,841 A | 10/2000 | Srivastava |
| 6,187,312 B1 | 2/2001 | Srivastava |
| 6,375,953 B1 | 4/2002 | Srivastava et al. |
| 6,384,029 B1 | 5/2002 | Jednakovits et al. |
| 6,403,095 B1 | 6/2002 | Srivastava et al. |
| 6,475,490 B1 | 11/2002 | Srivastava et al. |
| 6,649,628 B1 | 11/2003 | Kurthy et al. |
| 6,653,326 B1 | 11/2003 | Vigh et al. |
| 6,855,802 B1 | 2/2005 | Triebel et al. |
| 7,070,785 B2 | 7/2006 | Lehner et al. |
| 7,125,843 B2 | 10/2006 | DeFrees et al. |
| 7,126,002 B2 | 10/2006 | Urogdi et al. |
| 7,148,239 B2 | 12/2006 | Vigh et al. |
| 7,326,574 B2 | 2/2008 | Boux et al. |
| 7,361,655 B2 | 4/2008 | Csakai et al. |
| 7,384,936 B2 | 6/2008 | Csakai et al. |
| 7,396,681 B1 | 7/2008 | Multhoff |
| 7,517,948 B2 | 4/2009 | Multhoff |
| 7,550,457 B2 | 6/2009 | Csakai et al. |
| 7,691,849 B2 | 4/2010 | Csakai et al. |
| 7,745,465 B2 | 6/2010 | Vigh et al. |
| 7,750,050 B2 | 7/2010 | Schuchman et al. |
| 8,540,985 B2 | 9/2013 | Kirkegaard et al. |
| 8,962,604 B2 | 2/2015 | Greensmith et al. |
| 9,289,472 B2 | 3/2016 | Jensen et al. |
| 9,662,375 B2 | 5/2017 | Jensen et al. |
| 9,884,058 B2 | 2/2018 | Jensen et al. |
| 10,532,085 B2 | 1/2020 | Jensen et al. |
| 10,543,204 B2 | 1/2020 | Jensen et al. |
| 11,045,460 B2 | 6/2021 | Jensen et al. |
| 11,253,505 B2 | 2/2022 | Hinsby et al. |
| 11,304,941 B2 | 4/2022 | Jensen et al. |

(Continued)

FOREIGN PATENT DOCUMENTS

| EP | 1020187 A1 | 7/2000 |
|---|---|---|
| EP | 0751957 B1 | 2/2004 |

(Continued)

OTHER PUBLICATIONS

Santos-Lozano et al (Annals of Translational Medicine, Dec. 2015, vol. 3, pp. 1-9) (Year: 2015).*
Atkinson et al. (Royal Society of Chemistry, 2017, vol. 15, pp. 9794-9799) (Year: 2017).*
Arav et al (Drug Development and Industrial Pharmacy, 2012, vol. 38, pp. 940-951) (Year: 2012).*
AdisInsight (2019) "Arimoclomol—Orphazyme" Springer [online]. Retrieved from: https://adisinsight.springer.com/drugs/800016664; retrieved on Jun. 14, 2019; 2 pages.
Ahmed, M. et al., Targeting Protein Homeostasis in Sporadic Inclusion Body Myositis, Sci. Tran Med; 8(331), 331ra41, Mar. 2016, 13 pages.

(Continued)

*Primary Examiner* — Mark V Stevens
(74) *Attorney, Agent, or Firm* — McAndrews, Held & Malloy, Ltd.

(57) ABSTRACT

The present disclosure relates to a process for preparing arimoclomol, arimoclomol citrate and key intermediates, such as ORZY-01, thereof. The disclosure further relates to a process for preparing high purity arimoclomol citrate and methods of using the same.

28 Claims, No Drawings

(56) References Cited

U.S. PATENT DOCUMENTS

| | | |
|---|---|---|
| 2001/0034042 A1 | 10/2001 | Srivastava |
| 2002/0006410 A1 | 1/2002 | Lukacs et al. |
| 2002/0035072 A1 | 3/2002 | Fan et al. |
| 2002/0037290 A1 | 3/2002 | Armen |
| 2002/0039583 A1 | 4/2002 | Subjeck et al. |
| 2002/0095135 A1 | 7/2002 | Meeker et al. |
| 2002/0119163 A1 | 8/2002 | Srikumaran |
| 2002/0127219 A1 | 9/2002 | Okkels et al. |
| 2002/0127718 A1 | 9/2002 | Kuppner et al. |
| 2002/0156250 A1 | 10/2002 | Wallen et al. |
| 2002/0172682 A1 | 11/2002 | Srivastava |
| 2002/0192230 A1 | 12/2002 | Srivastava |
| 2003/0012794 A1 | 1/2003 | Srivastava et al. |
| 2003/0035808 A1 | 2/2003 | Srivastava |
| 2003/0073094 A1 | 4/2003 | Young et al. |
| 2003/0129196 A1 | 7/2003 | Srivastava |
| 2003/0203846 A1 | 10/2003 | Srivastava et al. |
| 2003/0216315 A1 | 11/2003 | Nicchitta et al. |
| 2003/0236300 A1 | 12/2003 | Caplan et al. |
| 2004/0006232 A1* | 1/2004 | Urogdi ............... C07D 213/89 546/193 |
| 2004/0022796 A1 | 2/2004 | Srivastava |
| 2004/0047876 A1 | 3/2004 | Srivastava |
| 2005/0048608 A1 | 3/2005 | Chan et al. |
| 2005/0112640 A1 | 5/2005 | Davidson et al. |
| 2005/0153906 A1 | 7/2005 | Bedwell et al. |
| 2005/0202044 A1 | 9/2005 | Mizzen et al. |
| 2005/0267020 A1 | 12/2005 | Faure et al. |
| 2006/0009520 A1 | 1/2006 | Tall et al. |
| 2006/0089302 A1 | 4/2006 | Abulafia-Lapid et al. |
| 2006/0093612 A1 | 5/2006 | Srivastava |
| 2006/0264609 A1 | 11/2006 | Lehner et al. |
| 2006/0270833 A1 | 11/2006 | Henot et al. |
| 2007/0231337 A1 | 10/2007 | Multhoff |
| 2008/0009516 A1 | 1/2008 | Wustman |
| 2008/0014191 A1 | 1/2008 | Balch et al. |
| 2008/0019915 A1 | 1/2008 | Hadida-Ruah et al. |
| 2008/0026012 A1 | 1/2008 | Podack et al. |
| 2008/0039400 A1 | 2/2008 | Van Eden et al. |
| 2008/0039497 A1 | 2/2008 | Greensmith et al. |
| 2008/0132450 A1 | 6/2008 | Lee et al. |
| 2008/0161258 A1 | 7/2008 | Henning et al. |
| 2008/0305084 A1 | 12/2008 | Podsakoff et al. |
| 2009/0163500 A1 | 6/2009 | Lingwood et al. |
| 2009/0203065 A1 | 8/2009 | Gehman et al. |
| 2009/0203605 A1 | 8/2009 | Segatori et al. |
| 2009/0208524 A1 | 8/2009 | Srivastava et al. |
| 2009/0227572 A1 | 9/2009 | Barber et al. |
| 2009/0298857 A1 | 12/2009 | Chiiosis et al. |
| 2009/0318343 A1 | 12/2009 | Garigapati et al. |
| 2010/0004277 A1 | 1/2010 | Bulawa et al. |
| 2010/0087490 A1 | 4/2010 | Young |
| 2010/0130730 A1 | 5/2010 | Garigapati et al. |
| 2010/0168016 A1 | 7/2010 | Ackerman et al. |
| 2010/0196279 A1 | 8/2010 | Lockhart |
| 2010/0221225 A1 | 9/2010 | Byrne et al. |
| 2010/0266571 A1 | 10/2010 | Lockhart et al. |
| 2010/0317690 A1 | 12/2010 | Kawamura et al. |
| 2010/0329985 A1 | 12/2010 | Van Eden et al. |
| 2011/0027254 A1 | 2/2011 | Daniel et al. |
| 2011/0028403 A1 | 2/2011 | Le Poole et al. |
| 2011/0081428 A1 | 4/2011 | Lithgow et al. |
| 2011/0105560 A1 | 5/2011 | Wustman |
| 2011/0110938 A1 | 5/2011 | Chiu et al. |
| 2011/0123512 A1 | 5/2011 | Prahlad et al. |
| 2014/0080769 A1 | 3/2014 | Platt et al. |
| 2015/0004151 A1 | 1/2015 | Jensen et al. |
| 2015/0126551 A1 | 5/2015 | Greensmith et al. |
| 2015/0284472 A1 | 10/2015 | Sardi et al. |
| 2015/0284475 A1 | 10/2015 | Sardi et al. |
| 2017/0239232 A1* | 8/2017 | Hinsby ............... A61K 9/0009 |
| 2019/0111041 A1 | 4/2019 | Hinsby et al. |
| 2020/0188492 A1 | 6/2020 | Jensen et al. |
| 2022/0133707 A1 | 5/2022 | Hinsby et al. |

FOREIGN PATENT DOCUMENTS

| | | |
|---|---|---|
| EP | 2145896 A2 | 1/2010 |
| EP | 2318032 B1 | 4/2012 |
| EP | 2481400 B1 | 6/2014 |
| EP | 2484371 B1 | 12/2014 |
| EP | 2659904 B1 | 9/2015 |
| GB | 1540028 A | 2/1979 |
| GB | 1582029 A | 12/1980 |
| WO | WO 198908661 A1 | 9/1989 |
| WO | WO 1990004584 A1 | 5/1990 |
| WO | WO 1990008131 A1 | 7/1990 |
| WO | WO 1995030649 A1 | 11/1995 |
| WO | WO 1997013 504 A1 | 4/1997 |
| WO | WO 1997016439 A1 | 5/1997 |
| WO | WO 1998006400 A2 | 2/1998 |
| WO | WO 1998043948 A1 | 10/1998 |
| WO | WO 2000014054 A1 | 3/2000 |
| WO | WO 2000035914 A1 | 6/2000 |
| WO | WO 2000050403 A1 | 8/2000 |
| WO | WO 2001017554 A1 | 3/2001 |
| WO | WO 2001034184 A2 | 5/2001 |
| WO | WO 2001052877 A1 | 7/2001 |
| WO | WO 2001052890 A1 | 7/2001 |
| WO | WO 2001079174 A1 | 10/2001 |
| WO | WO 2002034777 A1 | 5/2002 |
| WO | WO 2002065989 A2 | 8/2002 |
| WO | WO 2003026653 A1 | 4/2003 |
| WO | WO 2003029288 A2 | 4/2003 |
| WO | WO 2003049692 A2 | 6/2003 |
| WO | WO 2003061684 A2 | 7/2003 |
| WO | WO 2003086452 A2 | 10/2003 |
| WO | WO 2004007539 A2 | 1/2004 |
| WO | WO 2005041965 A1 | 5/2005 |
| WO | WO 2005120558 A2 | 12/2005 |
| WO | WO 2007041285 A2 | 4/2007 |
| WO | WO 2007150064 A2 | 12/2007 |
| WO | WO 2008021210 A2 | 2/2008 |
| WO | WO 2008039514 A1 | 4/2008 |
| WO | WO 2008070010 A2 | 6/2008 |
| WO | WO 2008112525 A2 | 9/2008 |
| WO | WO 2008117026 A1 | 10/2008 |
| WO | WO 2009095452 A1 | 8/2009 |
| WO | WO 2009100037 A1 | 8/2009 |
| WO | WO 2009137721 A2 | 11/2009 |
| WO | WO 2009137796 A2 | 11/2009 |
| WO | WO 2009141627 A1 | 11/2009 |
| WO | WO 2009155936 A1 | 12/2009 |
| WO | WO 2010015816 A2 | 2/2010 |
| WO | WO 2010022461 A1 | 3/2010 |
| WO | WO 2010053655 A2 | 5/2010 |
| WO | WO 2010086418 A1 | 8/2010 |
| WO | WO 2010092112 A1 | 8/2010 |
| WO | WO 2010102988 A1 | 9/2010 |
| WO | WO 2010116141 A2 | 10/2010 |
| WO | WO 2010148253 A2 | 12/2010 |
| WO | WO 2011019763 A2 | 2/2011 |
| WO | WO 2011075686 A2 | 6/2011 |
| WO | WO 2012012656 A2 | 1/2012 |
| WO | WO 2012072082 A1 | 6/2012 |
| WO | WO 2012177997 A1 | 12/2012 |
| WO | WO 2013006076 A1 | 1/2013 |
| WO | WO 2013148333 A1 | 10/2013 |
| WO | WO 2014071282 A1 | 5/2014 |
| WO | WO 2016041561 A1 | 3/2016 |

OTHER PUBLICATIONS

Alberti, S. et al., Granulostasis: Protein Quality Control of RNP Granules, Front. Mol. Neurosci., 10:84, Mar. 27, 2017, 14 pages.

Arnst, C., Biogen ALS Failure Highlights Clinical Trial Frustrations, Jan. 10, 2013.

Atkinson, B.N. et al. (2017) Regioselective and enantiospecific synthesis of the HSP co-inducer arimoclomol from chiral glycidyl derivatives. Org Biomol Chem, 15:9794-9799.

Au, Q. et al., High-content image-based screening for small-molecule chaperone amplifiers in heat shock, Journal of Biomolecular Screening, 13(19): 953-959, 2008.

(56) References Cited

OTHER PUBLICATIONS

Balabanov, S. et al., Quantitative proteomics analysis of BMS-214662 effects on CD34 positive cells from chronic myeloid leukaemia patients, Proteomics, 13: 153-68, 2013.

Balogh et al.; The hyperfluidization of mammalian cell membranes acts as a signal to initiate the heat shock protein response. FEBS Journal 272 (2005) 6077-6086.

Balwani, M. et al., Gaucher disease: When molecular testing and clinical presentation disagree—the novel c.1226A.>G(p.N370S)—RecNcil allefe, J Inherit Metab Dis, 34:789-793, 2011.

Benn et al., Putting the heat on ALS, *Nature Medicine*, 10(4): 345-347, 2004.

Bergamin, N. et al., A human neuronal model of Niemann Pick C disease developed from stem cells isolated from patient's skin, Orphant Journal of Rare Diseases, 8(1): 34, 2013.

Bligh, E. et al., A Rapid Method of Total Lipid Extraction and Purification, Canadian Journal of Biochemistry and Physiology, 37(8): 911-917, 1959.

Blom, T. et al., FTY720 Stimulates 27-Hydroxycholesterol Production and Confers Atheroprotective Effects in Human Primary Macrophages, Circ. Res. 106: 720-729, 2010.

Botzler et al.; Synergistic effects of heat and ET-18-OCH3 on membrane expression of hsp70 and lysis of leukemic K562 cells. Experimental Hematology 27 (1999) 470-478.

Bowling, A. et al., Bioenergetic and Oxidative Stress in neurodegenerative Diseases, *Life Sciences*, 56(14): 1151-71, 1995.

Boyum, A., Separation of white blood cells, Nature, 204: 793-794, Nov. 21, 1964.

Bruening, W. et al., Up-regulation of protein chaperones preserves viability of cells expressing toxic Cu/Zn-superoxide dismutase mutants associated with amyotrophic lateral sclerosis, J Neurochem, 72:693-699, 1999.

Brunk et al.: Lysosomal involvement in apoptosis. Redox Rep. 2001; 6(2):91-7.

Brunk et al.: Photo-oxidative disruption of lysosomal membranes causes apoptosis of cultured human fibroblasts. Free Radical Biology & Medicine, vol. 23, No. 4, pp. 616-626, 1997.

Cheung et al., Selecting promising ALS therapies in clinical trials, *Neurology*, 67(10):1748-1751, 2006.

Chung et al.; HSP72 protects against obesity-induced insulin resistance. PNAS Feb. 5, 2008 vol. 105, No. 5, 1739-1744.

Clark, L.N. et al. (2007) "Mutations in the glucocerebrosidase gene are associated with early-onset Parkinson disease" Neurology, 69(12): 1270-1277.

Cohen, F. et al., Therapeutic approaches to protein-misfolding diseases, Nature, 426:905-909, 2003.

Communication Pursuant to Article 94(3) EPC for Application No. 09768858.4 dated Jul. 26, 2011.

Csardi et al., "Pharmacokinetic study on a new antiischaemic agent (BRLP-42)", *Acta Physicologica Hungarica*, 82(4):321-326, 1994 (Abstract).

Cudkowicz, M. et al., Arimoclomol at Dosages up to 300 Mg/day is Well Tolerated and Safe in Amyotrophic Lateral Sclerosis, Muscle & Nerve, pp. 837-844, Jul. 2008.

Custer, S. et al., Transgenic Mice Expressing Mutant Forms VCP/p97 Recapitulate the Full Spectrum of IBMPFD Including Degeneration in Muscle, Brain and Bone, Hum Mol Genet. 1 ;19(9):1741-55, 2010.

Database GenBank Accession No. NM_005345.5 (May 2, 2019) "*Homo sapiens* heat shock protein family A (Hsp70) member 1A (HSPA1A), mRNA" Bethesda (MD): National Library of Medicine (US), National Center for Biotechnology Information [online]. Retrieved from: https://www.ncbi.nlm.nih.gov/nuccore/NM_005345.5, 5 pages.

Database GenBank Accession No. NM_005346.6 (Dec. 1, 20205) "*Homo sapiens* heat shock protein family A (Hsp70) member Ib (HSPA1B), mRNA" Bethesda (MD): National Library of Medicine (US), National Center for Biotechnology Information [online]. Retrieved from: https://www.ncbi.nlm.nih.gov/nuccore/NM_005346.6, 5 pages.

Daugaard et al., "The heat shock protein 70 family: Highly homologous proteins with overlapping and distinct functions," Febs Letters, Elsevier, Amsterdam, vol. 581, No. 19, Jul. 31, 2007, pp. 3702-3710.

Du, W. et al., Cell Growth Inhibition by Farnseyltransferase Inhibitors is Mediated by Gain of Geranylgeranylated RhoB, Molecular and Cellular Biology, 19(3): 1831-40, Mar. 1999.

European Extended Search Report; dated Aug. 28, 2009, European Application 08157425.3.

Ferlinz et al.; Stimulation of lysosomal sphingomyelin degradation by sphingolipid activator proteins. Chemistry and Physics of Lipids 102 (1999) 35-43.

Fleshner & Johnson: Endogenous extra-cellular heat shock protein 72: Releasing signal(s) and function. Int. J. Hyperthermia, Aug. 2005; 21(5):457-471.

Fog, C. et al. (2018) The heat shock protein amplifier arimoclomol improves refolding, maturation and lysosomal activity of glucocerebrosidase, EBioMedicine, 38:142-153, https://doi.org/10.1016/j.ebiom.2018.11.037.

Freeman, B. et al., The human cytosolic molecular chaperones hsp90 (hsc70) and hdj-1 have distinct roles in recognition of a non-native protein and protein refolding, The European Molecular Biology Journal, 15: 2969-79, 1996.

Gan-Or. Z. et al., Differential effects of severe vs mild GBA mutations on Parkinson disease, Neurology, 84: 880-887, Mar. 3, 2015.

Gehrmann et al.; Differential Up-Regulation of Cytosolic and Membrane-Bound Heat Shock Protein 70 in Tumor Cells by Anti-Inflammatory Drugs. Clinical Cancer Research vol. 10, 3354-3364, May 15, 2004.

Gehrmann et al.; Effects of Antineoplastic Agents on Cytoplasmic and Membrane-Bound Heat Shock Protein 70 (Hsp70) Levels. Biol. Chem., vol. 383, pp. 1715-1725, Nov. 2002.

Gehrmann et al.; The therapeutic implications of clinically applied modifiers of heat shock protein 70 (Hsp70) expression by tumor cells. Cell Stress and Chaperones (2008) 13: 1-10.

Goni, F. et al., Sphingomyelinases: enzymology and membrane activity, Federation of European Biochemical Societies, 531: 38-46, 2002.

Gotzl, J. et al., Impaired Protein Degradation in FTLD and Related Disorders, Aging Res Rev. Dec. 32:122-139, 2016.

Haldimann, P. et al., The novel hydroxylamine derivative NG-094 suppresses poly glutamine protein toxicity in Caenorhabditis elegans. J Biol Chem, May 27, 2011;286(21): 18784-94. doi:10.1074/jbc.M111.234773. Epub Apr. 6, 2011 (Abstract, 2 pages).

Hallows, J. et al., p35/p25 Is Not Essential for Tau and Cytoskeletal Pathology or Neuronal Loss in Niemann-Pick Type C Disease, The Journal of Neuroscience, 26: 2738-2744, 2006.

Haltia et al. (2006) The neuronal ceroid-lipofuscinoses: from past to present. Biochim Biophys Acta, 1762:850-856.

Harada et al.: Heat shock proteins and the antitumor T cell response. Biotherapy 10: 229-235, 1998.

Hargitai, J. et al., Bimoclomol, a heat shock protein co-inducer, acts by the prolonged activation of heat shock factor-1. Biochem Biophys Res Commun., Aug. 1, 2003;307(3):689-695. doi:10.1016/s0006-291x(03)01254-3 (Abstract, 2 pages).

Higuchi, M. et al., Axonal Degeneration Induced by Targeted Expression of Mutant Human Tau in Oligodendrocytes of Transgenic Mice That Model Glial Tauopathies, J Neurosci., 25 (41): 9434-9443, Oct. 2005.

Horváth, I. et al., Cell biology: Stability in times of Stress, Nature, 463(7280): 436-438, 2010.

Horvath, I. et al., Membrane-associated stress proteins: More than simply chaperones, Biochimica et Biophy sica Acta, 1778: 1653-64, 2008.

Hu, W. et al., Proteomic identification of heat shock protein 70 as a candidate target for enhancing apoptosis induced by farnesyltransferase inhibitor, Proteomics, 3: 1904-11, 2003.

Ingemann, L. et al., Lysosomal storage diseases and the heat shock response: convergences and therapeutic opportunities, Journal of Lipid Research, 55: 2198-2210, May 16, 2014.

International Search Report, dated Feb. 28, 2005, PCT Publication WO 2005/041965.

(56) References Cited

OTHER PUBLICATIONS

Ito, D. et al., RNA Binding Proteins and the Pathological Cascade in ALS/FTD Neurodegeneration, Sci Transl Med., 9(415):eeah5436, 2017.
Jaatela, M. et al., Emerging Role of Heat Shock Proteins in Biology and Medicine, Annals of Medicine, 24: 249-258, 1992.
Jeong, H. et al., Brain Inflammation and Microglia: Facts and Misconceptions, Exp Neurobiol., 22(2): 59-67, Jun. 2013.
Kabakov, A. et al., Pharmacological attenuation of apoptosis in reoxygenated endothelial cells, Cellular and Molecular Life Sciences, 61: 3076-86, 2004.
Kalmar, B. et al. (Jul. 1, 2002) "Upregulation of Heat Shock Proteins Rescues Motoneurones from Axotomy-Induced Cell Death in Neonatal Rats" Exp Neurol, 176(1):87-97.
Kalmar, B. et al. (2003) The effect of treatment with BRX-220, a co-inducer of heat shock proteins, on sensory fibers of the rat following peripheral nerve injury, Experimental Neurology, 184: 636-647.
Kalmar, B. et al. (2008) Late stage treatment with arimoclomol delays disease progression and prevents protein aggregation in the SOD1$^{G93A}$ mouse model of ALS. Journal of Neurochemisy, 107, 339-350.
Kalmar, B. & L. Greensmith (2009). Activation of the heath shock response in a primary cellular model of motoneuron neurodegeneration—evidence for neuroprotective and neurotoxic effects. Cell Mol Biol Lett, vol. 14, pp. 319-335.
Kalmar, B. et al. (Jan. 2014) The role of heat shock proteins in Amyotrophic Lateral Sclerosis: The therapeutic potential of Arimoclomol. Pharmacol Ther;141(1):40-54 (Abstract, 2 pages).
Keeling, K.M et al., "Gentamicin-mediated suppression of Hurler syndrome stop mutations restores a low level of alphaL-iduronidase activity and reduces lysosomal glycosaminoglycan accumulation", Human Molecular Genetics, 2001, vol. 10, No. 3, pp. 291-299.
Kelly et al., Nemoprotection: Heat Shock Proteins, Current Medical Research and Opinion®, 18, Suppl. 2, s55-60, 2002.
Kieran et al. (Apr. 2004) Treatment with arimoclomol, a coinducer of heat shock proteins, delays disease progression in ALS mice. Nature Medicine vol. 10, No. 4, pp. 402-405.
Kirkegaard T. et al. (2010) "Hsp70 stabilizes lysosomes and reverts Niemann-Pick disease-associated lysosomal pathology", Nature, vol. 463, No. 7280, pp. 549-554.
Kirkegaard-Sorenson (Feb. 2008). Hsp70 binding to BMP—A novel mechanism for cellular protection. Dep. of Apoptosis, Danish Cancer Society. PhD Thesis. University of Copenhagen, Faculty of Health Sciences.
Kirkegaard-Sorenson et al.; Interaction between Hsp70 and bis(monoacylglycero)phosphate stabilizes lysosomes and promotes cell survival. APMIS, 116(5): 436-437, 2008.
Kobayashi et al.: A lipid associated with the antiphospholipid syndrome regulates endosome structure and function. Nature Letters, vol. 392 Mar. 12, 1998.
Kocsy, G. et al., Glutathione reductase activity and chilling tolerance are induced by a hydroxylamine derivative BRX-156 in maize and soybean. Plant Sci, Apr. 2001;160(5):943-950. doi:10.1016/s0168-9452(01)00333-8 (Abstract, 1 page).
Kolzer et al.: Interactions of acid sphingomyelinase and lipid bilayers in the presence of the tricyclic antidepressant desipramine. FEBS Letters 559 (2004) 96-98.
Kurthy et al., Effect of BRX-220 against peripheral neuropathy and insulin resistance in Diabetic rat models, Annals of the New York Academy of Sciences, 967:482-489, 2002.
Lee, E. et al., Gains or losses: molecular mechanisms of TDP43-mediated nemodegeneration, Nat Rev Neurosci, 13:38-50, 2012.
Lepist, E. et al., Contribution of the organic anion transporter OAT2 to the renal active tubular secretion of creatinine and mechanism for serum creatinine elevations caused by cobicistat, Kidney International, 86: 350-357, 2014.
Li, Q. et al., The cleavage pattern of TDP-43 determines its rate of clearance and cytotoxicity, Nature Communications 5;6183, Jan. 29, 2015.
Liscic, R., Molecular basis of ALS and FTD: implications for translational studies, Arhiv za Hihijenu Rada I Toksikologiju, 66: 285-290, Dec. 1, 2015.
Literati-Nagy, Z. et al., A novel insulin sensitizer drug candidate-BGP-15-can prevent metabolic side effects of atypical antipsychotics. Pathol Oncol Res, Oct. 2012; 18(4):1071-6. doi:10.1007/s12253-012-9546-4. Epub Jun. 30, 2012 (Abstract, 1 page).
Liu, J. et al., Elevation of the Hsps70 chaperone does not affect toxicity in mouse models of familial amyotrophic lateral sclerosis, J. Neurochem., 93(4): 875-82, May 2005 (Abstract).
Love, Arimoclomol delays progression in ALS mouse model, Lancet Neurology, 3(5): 264, 2004.
Lubbers, N. et al., Oral bimoclomol elevates heat shock protein 70 and reduces myocardial infarct size in rats, European Journal of Pharmacology, 435: 79-83, 2002.
Magrané et al., Heat Shock Protein 70 Participates in the Neuroprotective Response to Intracellularly Expressed β-Amyloid in Neurons, The Journal of Neuroscience, 24(7):1700-1706, Feb. 18, 2004.
Mahalka, A. et al., Human heat shock protein 70 (Hsp70) as a peripheral membrane protein, Biochimica et Biophysica Acta, 1838: 1344-1361, Jan. 28, 2014.
Malik, B. et al., Co-induction of the heat shock response ameliorates disease progression in a mouse model of human spinal and bulbar muscular atrophy: implications for therapy, Brain, 136:926-43, 2013.
Marber, M. et al., Overexpression of the Rat Inducible 70-kD Heat Stress Protein in a Transgenic Mouse Increases the Resistance of the Heart to ischemic Injury, J. Clin. Invest, 95: 1446-56, Apr. 1995.
Mazieres, J. et al., Perspectives on farnesyl transferase inhibitors in cancer therapy, Cancer Letters, 206: 159-67, 2004.
McNeill et al., Ambroxol improves lysosomal biochemistry in glucocerebrosidase mutation-linked Parkinson disease cells, Brain, 137: 1481-1495, Feb. 25, 2014.
Meikle, P.J. et al., "Effect of lysosomal storage on bis(monoacylglycero)phosphate", Biochem J, 2008, vol. 411, No. part 1, pp. 71-78.
Mestril, R. et al., Heat Shock Proteins and Protection Against Myocardial Ischemia, J. Mol. Cell. Cardiol, 27: 45-52, 1995.
Micsenyi, M.C. et al. (Jun. 26, 2013) "Lysosomal Membrane Permeability Stimulates Protein Aggregate Formation in Neurons of a Lysosomal Disease" J Neurosci, 33(26):10815-10827.
Monahan, Z. et al., Stress granules at the intersection of autophagy and ALS, Brain Res. 1649(Pt B): 189-200, Oct. 15, 2016.
Mu, T., et al., Chemical and biological approaches synergize to ameliorate protein-folding diseases, Cell, 134: 769-81, Sep. 5, 2008.
Ng & Henikoff: Predicting deleterious amino acid substitutions. Genome Res. 2001, 11: 863-874.
Nylandsted et al.: Heat shock protein 70 promotes cell survival by inhibiting lysosomal membrane permeabilization. J. Exp. Med. vol. 200, No. 4, Aug. 16, 2004 425-435.
Ohtsuka et al.; Inducers and co-inducers of molecular chaperones. Int. J. Hyperthermia, Dec. 2005; 21 (8): 703-711.
Parfitt, D. et al., The heat-shock response co-inducer arimoclomol protects against retinal degeneration in rhodopsin retinitis pigmentosa, Cell Death and Disease, 5: 1-10, 2014.
Patterson, M. et al., Miglustat for treatment of Niemann-Pick C disease: a randomized controlled study, Lancet Neurology, 6: 765-772, 2007.
Polakowski, J.S. et al. (Jan. 1, 2002) "Bimoclomol elevates heat shock protein 70 and cytoprotects rat neonatal cardiomyocytes" Eur J Pharmacol, 435(1):73-77.
Porcu, G. et al., A yeast-based genomic strategy highlights the cell protein networks altered by FTase inhibitor peptidomimetics, Molecular Cancer, 9: 197, 2010.
Prendergast, G. et al., Farnesyltransferase Inhibition Causes Morphological Reversion of ras-Transformed Cells by a Complex Mechanism that Involves Regulation of the Actin Cytoskeleton, Molecular and Cellular Biology, 14(6): 4193-4202, Jun. 1994.
Qureshi, M. et al., The natural history of ALS is changing: Improved survival, Amyotrophic Lateral Sclerosis, 10: 324-31, 2009.
Rademakers et al., The Role of Tau (MAPT) in Frontotemporal Dementia and Related Tauopathies. Human Mutation, 24:277-295, 2004.

(56) References Cited

OTHER PUBLICATIONS

Rakonczay Jr., Z. et al., Nontoxic heat shock protein coinducer BRX-220 protects against acute pancreatitis in rats, Free Radical Biology and Medicine, 32(12): 1283-1292, 2002.
Ratti, A. et al., Physiological Functions and Pathobiology of TDP-43 and FUS/TLS Proteins, J Neurochem;138 Suppl 1 :95-111, Aug. 2016.
Report GDHC019POA, Section 7.2 Clinical Trial Design, GlobalData Report Store, published Jun. 2014.
Rokutan, Clinician, 45(3): 310-313, English translation attached, 1998.
Sambrook et al., Molecular Cloning, A Laboratory Manual, Cold Spring Harbor, Laboratory Press (1998), 1.101-1.104.
Sardi, S. et al. (Jul. 19, 2011) CNS expression of glucocerebrosidase corrects alpha-synuclein pathology and memory in a mouse model of Gaucher-related synucleinopathy. PNAS, 108(29):121010-12106.
Sardi, S. et al., Augmenting CNS glucocerebrosidase activity as a therapeutic strategy for parkinsonism and other Gaucher-related synucleinopathies, PNAS, 110(9): 3537-3542, Feb. 26, 2013.
Schapira, A. et al., Glucocerebrosidase and Parkinson disease: Recent advances, Molecular and Cellular Neuroscience, 66:37-42, 2015.
Šebököva et al., Comparison of the Extrapancreatic Action of BRX-220 and Pioglitazone in the High-Fat Diet-Induced Insulin Resistance, *Ann. N.Y. Acad. Sci.*, 967: 424-430, 2002.
Senkevich, K.A. et al. (2016) "Glucocerebrosidase Activity in Patients Having Parkinson's Disease Associated with Mutations within GEA Gene" Medical Academic Journal, 16(4):65-66 (Russian, with English translation, 2 pages).
Simons, K. et al., Jamming the Endosomal System: Lipid Rafts and Lysosomal Storage Diseases, Trends in Cell Biology, 10: 459-62, 2000.
Sorensen et al., Soluble Expression Of Recombinant Proteins In The Cytoplasm Of *Escherichia coli, Microbial Cell Factories*, 4: 1-8, 2005.
Suhadolnik, R.J. et al. (Jun. 1968) "Nucleoside Antibiotics" J Biol Chem, 243(12):3532-3537.
Tanida, I. et al., LC3 and Autophagy, Methods Mol Biol, 445, 77-88, 2008.
Tavaria et al.: A hitchhiker's guide to the humanHsp70 family, Mini-review. Cell stress & Chaperones (1996) 1(1), 23-28.
Thomas et al., "Increased Levels of Sialic Acid Associated with a Silidase Deficiency in 1-Cell Disease (Mucolipidosis II) Fibroblasts" Biochemical and Biophysical Research Communications, 71(1):188-195 (1976).
Tidwell et al.: Administration of Hsp70 in vivo inhibits motor and sensory neuron degeneration. Cell Stress & Chaperones (2004) 9(1) 88-98.
Torok et al.; Heat shock protein coinducers with no effect on protein denaturation specifically modulate the membrane lipid phase. PNAS Mar. 18, 2003, vol. 100, No. 6, 3131-3136.
Toth et al., Effect of bimoclomol 1 (N-(2-hydroxy-3-(l-piperidinyl) propoxy)-3 pyridine-carboximidoyl-chloride) on iminodipropionitri Ic-induced central effects, Neurochemistry International, 33(6): 513-518, 1998.
Tresse, E., et al., VCP/p97 is essential for maturation of ubiquitin-containing autophagosomes and this function is impaired by mutations that cause IBMPFD, Autophagy, 6: 217-227, 2010.
Tytell & Hooper; Heat Shock proteins: new keys to the development of cytoprotective therapies. Expert Opin Ther Targets, Apr. 2001;5(2):267-87.
Tytell: Release of heat shock proteins (Hsps) and the effects of extracellular Hsps on neural cells and tissues. Int J Hypothermia, Aug. 2005; 21 (5): 445-455.
Vigh et al., Bimoclomol: A nontoxic, hydroxylamine derivative with stress protein-inducing activity and cytoprotective effects, Nature Medicine, 3(10): 1150-54, Oct. 1997.
Vigh et al.; Can the stress protein response be controlled by membrane-lipid therapy? Trends in Biochemical Sciences vol. 32 No. 8 (2007).
Visy et al., Enantioselective Plasma Protein Binding of Bimoclomal, Chirality, 14:638-642, 2002.
Voellmy et al., Isolation and functional analysis of a human 70,000-dalton heat shock protein gene segment, Proc. Natl. Acad. Sci. USA, 82: 4949-53, 1985.
Wang, S. et al., ABCA1 and nascent HDL biogenesis, Biofactors 40(6): 547-554, Nov. 2014.
Wei et al.: Inhibition of proliferation and induction of apoptosis by abrogation of heat-shock protein (HSP) 70 expression in tumor cells. Cancer Immunol. Immunother. (1995) 40:73-78.
Werth, N. et al. (Apr. 2001) "Degradation of membrane-bound ganglioside GM2 by beta-hexosaminidase A. Stimulation by GM2 activator protein and lysosomal lipids" J Biol Chem, 276(16):12685-12690. https://doi.org/10.1074/jbc.M007970200.
Winchester, B. et al., The molecular basis of lysosomal storage disease, Biochemical Society Transactions, 28: 150-54, 2000.
Witte, M. et al., Ultrasensitive in situ visualization of active glucocerebrosidase molecules, Nature Chemical Biology, 6(12): 907-913, Oct. 31, 2010.
Wu, et al., Structure and expression of the human gene encoding major heat shock protein HSP70, Mol. Cell. Biol., 5(2): 330-41, 1985.
Xing, B. et al., Hsp70 plays an important role in high-fat diet induced gestational hyperglycemia in mice, J Physiol Biochem, 71: 649-658, Aug. 29, 2015.
Yenari, M. et al., The nemoprotective potential of heat shock protein 70 (HSP70), Molecular Medicine Today, 5: 525-31, 1999.
Yoshiyama, Y. et al., Frontotemporal Dementia and Tauopathy, Curr Neurol Neurosci Rep.; 1(5):413-21, Sep. 2001.
Yu et al.: Retinal uptake of intravitreally injected Hsc/Hsp70 and its effects on susceptibility to light damage. Molecular Vision 2001; 7:48-56.
Zhou et al., "Chloro-oxime derivatives as novel small molecule chaperone amplifiers" Bioorganic & Medicinal Chemistry Letters, 19:3128-3135 (2009).
Zhu Yunxiang et al. "Dexmethasone-mediated up-regulation of the mannose receptor improves the delivery of recombinant glucocerebrosidase to Gaucher macrophages," The Journal of Pharmacology and Experimental Therapeutics, Feb. 2004, vol. 308, No. 2, pp. 705-711.

\* cited by examiner

PROCESSES FOR PREPARING ARIMOCLOMOL CITRATE AND INTERMEDIATES THEREOF

RELATED APPLICATIONS

This application is a continuation of International Application No. PCT/EP2021/082294, filed on Nov. 19, 2021, which claims priority to, and the benefit of, U.S. Provisional Application No. 63/115,749, filed on Nov. 19, 2020, U.S. Provisional Application No. 63/211,809, filed on Jun. 17, 2021, and European Application No. EP 20209467.8 filed on Nov. 24, 2020, the entire contents of each of which are hereby incorporated by reference.

TECHNICAL FIELD

The present disclosure relates to a process for preparing arimoclomol, arimoclomol citrate and key intermediates, such as ORZY-01, thereof. The disclosure further relates to a process for preparing high purity arimoclomol citrate and methods of using the same.

BACKGROUND

Arimoclomol citrate is an active pharmaceutical ingredient (API) for the treatment of lysosomal storage disorders, including Niemann-Pick Disease Type C.

SUMMARY OF THE DISCLOSURE

The present disclosure provides an optimized four-step process for preparing an ultra-pure composition comprising arimoclomol citrate, i.e. N-{[(2R)-2-hydroxy-3-piperidin-1-ylpropyl]oxy}pyridine-3-carboximidoyl chloride 1-oxide citrate. The optimized process comprises a plurality of optimized sub-steps, each contributing to an overall improved process, providing the ultra-pure composition comprising arimoclomol citrate. The ultra-pure composition comprising arimoclomol citrate meets the medicines agencies' high regulatory requirements. An overview of the four-steps process is outlined below:

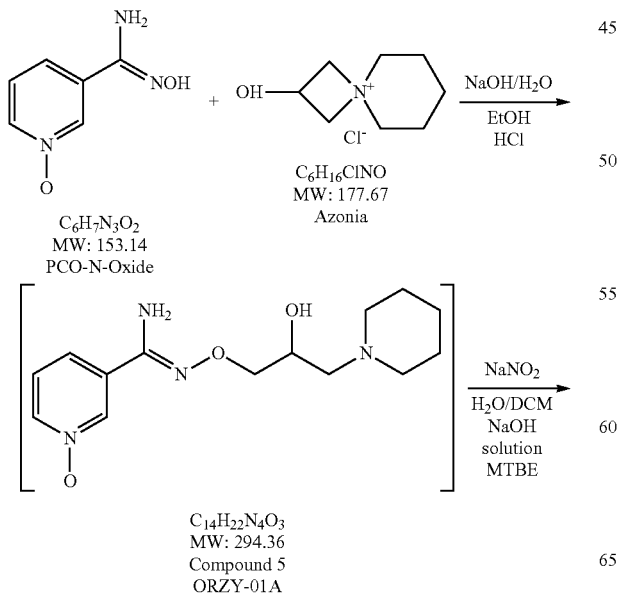

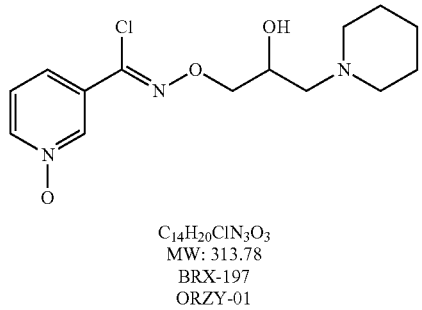

$C_{14}H_{20}ClN_3O_3$
MW: 313.78
BRX-197
ORZY-01

Step 1: Overview of process for preparing ORZY-01

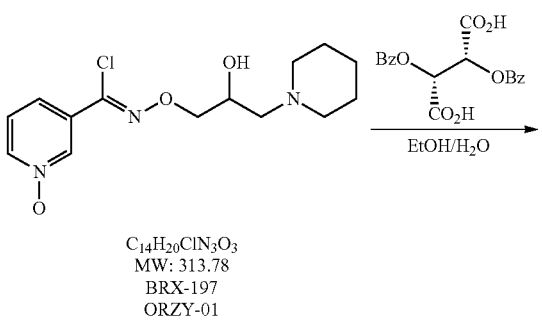

$C_{14}H_{20}ClN_3O_3$
MW: 313.78
BRX-197
ORZY-01

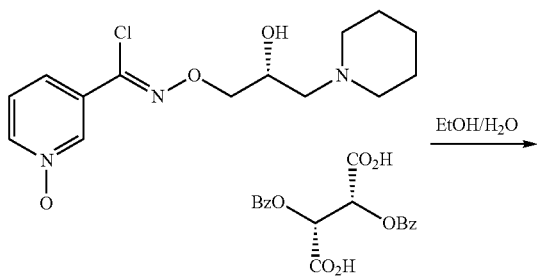

$C_{32}H_{34}ClN_3O_{11}$
MW: 627.08
Crude BRX-344
ORZY-02

$C_{32}H_{34}ClN_3O_{11}$
MW: 627.08
BRX-344
ORZY-03

Step 2: Overview of process for preparing ORZY-03

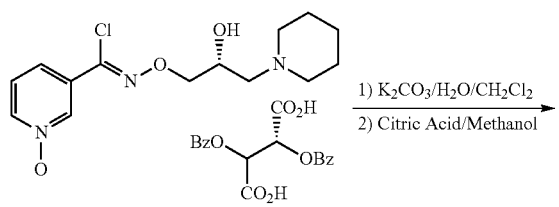

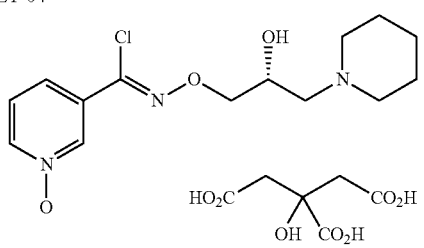

Step 3: Overview of process for preparing crude BRX-345 (ORZY-04)

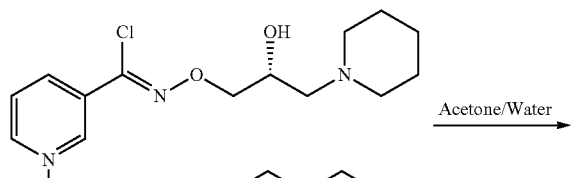

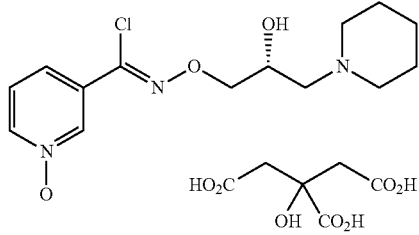

Step 4: Overview of process for preparing BRX-345 (ORZY-05)

The disclosed methods contribute to control of both the chiral purity (i.e., the enantiomeric excess) of N-{[(2R)-2-hydroxy-3-piperidin-1-ylpropyl]oxy}pyridine-3-carboximidoyl chloride 1-oxide citrate is above the threshold set by the regulatory authorities, and that the ultra-pure composition is essentially free of previously identified by-products, such as RRT 0.74, and N-nitrosopiperidine.

The chiral purity of the ultra-pure composition comprising arimoclomol citrate is resultant of the chiral resolution step, i.e. the method according to "Step 2" of the present disclosure. The present disclosure provides a correlation between the cooling rate of the crude reaction mixture in Step 2 and the chiral purity of ORZY-03 (See, Examples 4 and 5). The chiral purity of ORZY-03 obtained in Step 2 is retained toward the end-product, but may be further enhanced by re-crystallization.

The present disclosures identified a by-product RRT 0.74, as shown below, which is formed during the salt exchange in Step 3 in which "crude BRX-345" is prepared from ORZY-03.

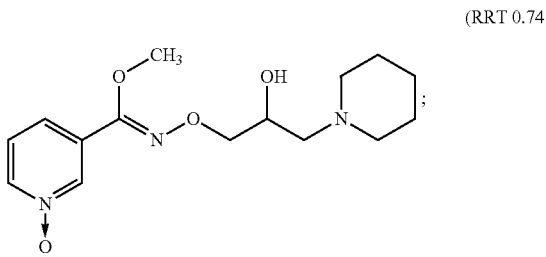 [SMILES: CO/C(=N\OCC(O)CN1CCCCC1)c1ccc[n+]([O-])c1]

methyl (Z)—N-(2-hydroxy-3-(piperidin-1-yl)propoxy)nicotinimidate 1-oxide)

The present disclosure provides an improved method incorporating an aqueous wash and addition of a catalytic amount of citric acid. In some embodiments, the additional wash and addition of a catalytic amount of citric acid results in removal of the RRT 0.74 by-product without a significant loss in yield of the desired product.

Further, the present disclosure provides an optimized process for making ORZY-01,

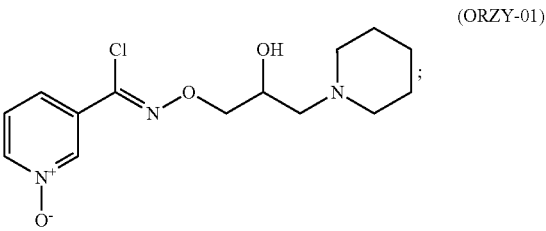 [SMILES: [O-][n+]1cccc(/C(Cl)=N/OCC(O)CN2CCCCC2)c1]

providing ORZY-01 in high (up to 80%) yield and in high purity, with reduced large scale process risks.

The previously reported two-step synthesis of ORZY-01 as shown below includes a 2 hour reflux in step 1A, followed by purification of intermediate compound (V) to increase the batch quality.

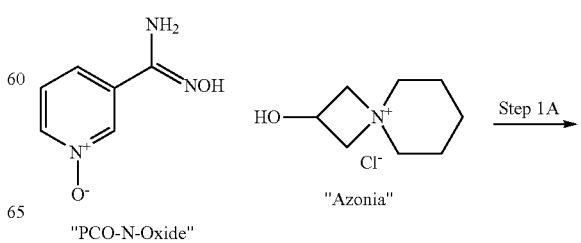

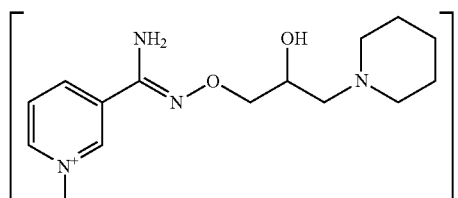

(V)

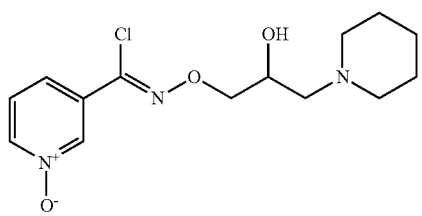

BRX-197

Further, the subsequent step from compound (V) to ORZY-01 carried out at from −5° C. to 0° C. as previously reported requires several charges of sodium nitrite to push the reaction to completion and results in a delayed exothermic reaction and gas evolution, raising safety concerns upon scale-up.

The process of the present disclosure, affords an improved reaction in step 1A, allowing direct subsequent transformation into ORZY-01 without isolation of compound (V). Further, step 1B of the present disclosure progresses to completion with a single charge of sodium nitrite in a safe and controllable operation without delayed gas evolution and process chemistry risks.

In a first aspect, a process for preparing ORZY-01 is provided, (ORZY-01)

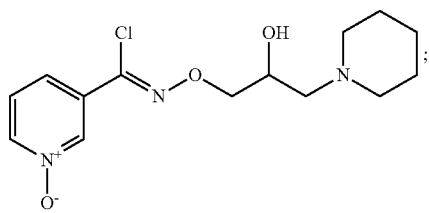

wherein the process comprises:

step 1A) mixing a compound of formula (I);

formula (I)

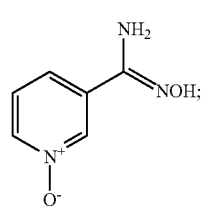

with a compound of formula (II);

formula (II)

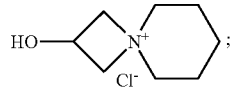

in a first solvent at a first temperature for more than 2 hours to provide an intermediate; followed by step 1B) wherein the intermediate is reacted with NaNO$_2$ at a second temperature in a second solvent to provide ORZY-01, thereby providing ORZY-01.

In a second aspect, a composition comprising ORZY-01 is provided, (ORZY-01)

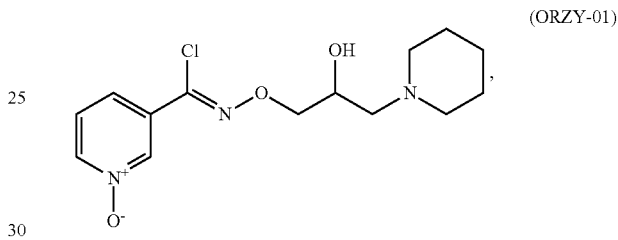

one or more impurities selected from the group consisting of:

(A)

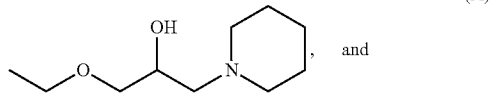, and (B)

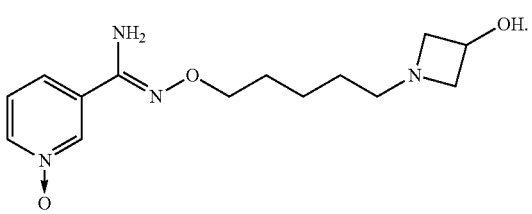

In a third aspect, a process for preparing arimoclomol citrate is provided,

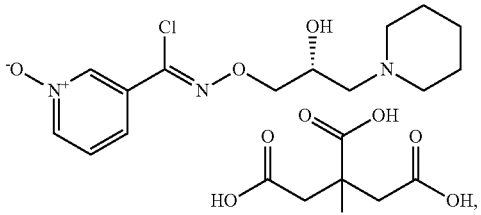

(arimoclomol citrate)

comprising the process as defined herein to provide ORZY-01,

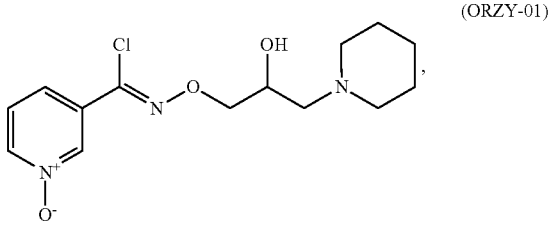 [SMILES: [O-][n+]1cccc(/C(Cl)=N/OCC(O)CN2CCCCC2)c1]

(ORZY-01)

followed by precipitating ORZY-01 with dibenzoyl L-tartaric acid to provide ORZY-03,

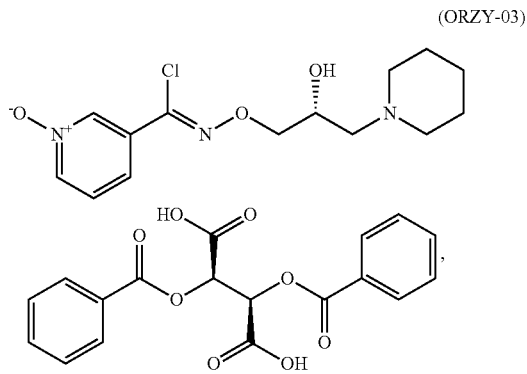

(ORZY-03)

reacting ORZY-03 with base and subsequently precipitating the resulting free base of ORZY-03 with citric acid to provide arimoclomol citrate.

In a fourth aspect, a process for preparing arimoclomol citrate is provided,

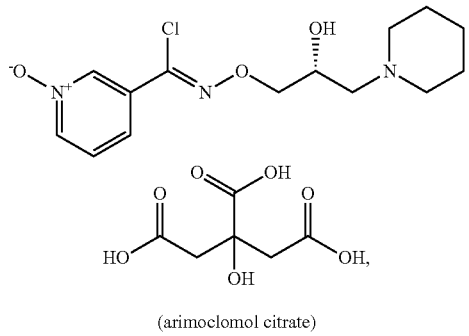

(arimoclomol citrate)

comprising the process as defined herein to provide ORZY-01.

In one aspect, the present disclosure relates to an oral formulation comprising N-{[(2R)-2-hydroxy-3-piperidin-1-ylpropyl]oxy}pyridine-3-carboximidoyl chloride 1-oxide, or a pharmaceutically acceptable salt thereof, and at least one pharmaceutically acceptable excipient.

In some embodiments, the pharmaceutically acceptable salt of N-{[(2R)-2-hydroxy-3-piperidin-1-ylpropyl]oxy}pyridine-3-carboximidoyl chloride 1-oxide is N-{[(2R)-2-hydroxy-3-piperidin-1-ylpropyl]oxy}pyridine-3-carboximidoyl chloride 1-oxide citrate.

In one aspect, the present disclosure provides a pharmaceutical composition comprising N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 98.0%.

In one aspect, the present disclosure provides a method of treating or preventing Niemann Pick disease, type C in a subject in need thereof, wherein the subject is administered a therapeutically effect amount of the oral formulation, pharmaceutical composition, or unit dosage of N-{[(2R)-2-hydroxy-3-piperidin-1-ylpropyl]oxy}pyridine-3-carboximidoyl chloride 1-oxide, or pharmaceutically acceptable salt thereof.

In one aspect, the present disclosure provides an oral formulation, pharmaceutical composition, or unit dosage of N-{[(2R)-2-hydroxy-3-piperidin-1-ylpropyl]oxy}pyridine-3-carboximidoyl chloride 1-oxide, or pharmaceutically acceptable salt thereof for use in treating or preventing Niemann Pick disease, type C in a subject in need thereof.

In one aspect, the present disclosure provides use of an oral formulation, pharmaceutical composition, or unit dosage of N-{[(2R)-2-hydroxy-3-piperidin-1-ylpropyl]oxy}pyridine-3-carboximidoyl chloride 1-oxide, or pharmaceutically acceptable salt thereof for use in the manufacture of a medicament for the treatment or prevention of Niemann Pick disease, type C in a subject in need thereof.

In one aspect, the present disclosure provides use of an oral formulation, pharmaceutical composition, or unit dosage of N-{[(2R)-2-hydroxy-3-piperidin-1-ylpropyl]oxy}pyridine-3-carboximidoyl chloride 1-oxide, or pharmaceutically acceptable salt thereof for the treatment or prevention of Niemann Pick disease, type C in a subject in need thereof.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the disclosure will be apparent from the following detailed description and claims.

DETAILED DESCRIPTION

Definitions

To facilitate the understanding of the following description, a number of definitions are presented in the following paragraphs.

As used herein, the term "polar protic solvent" refers to a polar solvent that is capable of exchanging protons with the reagents and that contains a polarizable proton. Examples of polar protic solvents are butanol, 2-propanol, propanol, ethanol, methanol, water and mixtures thereof.

As used herein, the term "pharmaceutically acceptable salt" refers to a salt used typically in the pharmaceutical field. Examples of a pharmaceutically acceptable salt include sodium salts, hydrochloride salts, magnesium salts, calcium salts, trifluoroacetic acid salts and potassium salts, but are not limited thereto. Further exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, olcate, tannate, pantothenate, bitartrate, ascorbate, succinate, malcate, gentisinate, fumarate, gluconate, glucuronate, saccharate, formate, benzoate, glutamate, methanesulfonate, ethanesulfonate, benzenesulfonate, p-toluenesulfonate, and pamoate.

The term "chlorinated hydrocarbon" refers to a hydrocarbon in which one or more of the hydrogen atoms have been replaced by chlorine. Examples of chlorinated hydrocarbons are without limitation intended to include dichloromethane, chloroform, carbontetrachloride, and dichloroethane. Dichloromethane is also known as DCM or $CH_2Cl_2$.

The term "ethanol" used herein should be understood to include ethanol having a purity of at least 95% by weight, denatured ethanol and hydrous ethanol containing water of 20 to 5% by weight. One example of the denatured ethanol is ethanol of 95% by weight mixed with isopropyl alcohol of 5% by weight and one example of the hydrous ethanol is ethanol of 83% by weight mixed with purified water of 17% by weight.

The term "PCO—N-oxide" as used herein refers to the compound N-Hydroxy-1-oxy-nicotinamidine. The structure of PCO—N-oxide is illustrated in formula (I) herein.

The term "Azonia" as used herein refers to the compound azonia-spiro[3,5]nonane chloride. the structure of azonia is illustrated in formula (II) herein.

The term "boiling point" as used herein refers to the boiling point of a liquid at 760 mm/Hg or a 2° C. deviation therefrom.

As used herein, the term "about" refers to a recited amount, value, or duration ±10% or less of said amount, value, or duration. In some embodiments, "about" refers to a recited amount, value, or duration ±10%, ±8%, ±6%, ±5%, ±4%, ±2%, 1%, or ±0.5%. In other embodiments, "about" refers to a recited amount, value, or duration ±10%, ±8%, ±6%, ±5%, 4%, or 2%. In other embodiments, "about" refers to a recited amount, value, or duration ±5%. In some embodiments, "about" refers to a listed amount, value, or duration ±2% or 1%. For example, in some embodiments, when the term "about" is used when reciting a temperature or temperature range, these terms refer to the recited temperature or temperature range ±5° C., ±2° C., or 1° C. In other embodiments, the term "about" refers to the recited temperature or temperature range ±2° C.

As used herein, "arimoclomol" refers to a compound of the following structure:

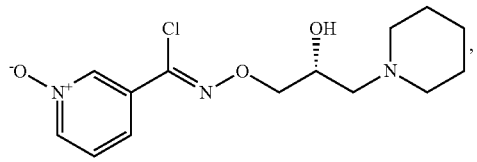

also referred to herein as N-{[(2R)-2-hydroxy-3-piperidin-1-ylpropyl]oxy}pyridine-3-carboximidoyl chloride 1-oxide.

As used herein, "arimoclomol S-enantiomer" refers to a compound of the following structure:

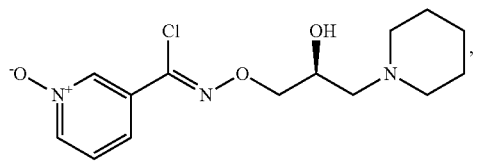

also referred to herein as N-{[(2S)-2-hydroxy-3-piperidin-1-ylpropyl]oxy}pyridine-3-carboximidoyl chloride 1-oxide.

As used herein, "arimoclomol citrate" refers to a compound of the following structure:

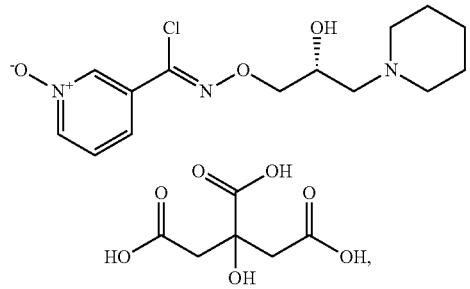

also referred to herein as "N-{[(2R)-2-hydroxy-3-piperidin-1-ylpropyl]oxy}pyridine-3-carboximidoyl chloride 1-oxide citrate", "ORZY-05", or "BRX-345".

As used herein, "RRT 0.74" refers to a compound of the following structure:

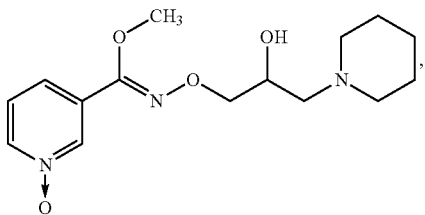 [SMILES: CO/C(=N\OCC(O)CN1CCCCC1)c1ccc[n+]([O-])c1]

also referred to herein as methyl (Z)—N-(2-hydroxy-3-(piperidin-1-yl)propoxy)nicotinimidate 1-oxide.

The term "container" used herein refers to all or part of a unit of manufacturing equipment in which a chemical reaction in the formation of a molecule, such as ORZY-01, ORZY-03, ORZY-04 or ORZY05 as described herein, takes place.

As used herein, "treating" or "treat" describes the management and care of a patient for the purpose of combating a disease, condition, or disorder and includes the administration of a compound of the present disclosure (e.g., N-{[(2R)-2-hydroxy-3-piperidin-1-ylpropyl]oxy}pyridine-3-carboximidoyl chloride 1-oxide citrate) to alleviate the symptoms or complications of a disease, condition or disorder, or to eliminate the disease, condition or disorder. The term "treat" can also include treatment of a cell in vitro or an animal model.

A compound of the present disclosure (e.g., N-{[(2R)-2-hydroxy-3-piperidin-1-ylpropyl]oxy}pyridine-3-carboximidoyl chloride 1-oxide citrate) can also be used to prevent a disease, condition or disorder, or used to identify suitable candidates for such purposes. As used herein, "preventing" or "prevent" describes reducing or eliminating the onset of the symptoms or complications of the disease, condition or disorder.

Processes and Conditions
Preparation of Seeds Crystals

Seed crystals of any of ORZY-01, ORZY-03, and ORZY-05 can be prepared by providing enantioenriched ORZY-01 at greater than about 95% chiral purity by preparative high-performance liquid chromatography (HPLC) or supercritical fluid chromatography (SFC) separation of the racemic mixture. Seeds crystals of the enantioenriched ORZY-01 obtained from HPLC or SFC can be grown from a suitable solvent. The enantioenriched ORZY-01 can then be precipitated with L-DBTA in a suitable solvent to provide seed crystals of ORZY-03. The enantioenriched ORZY-01 can further be precipitated with citric acid in a suitable solvent to provide seed crystals of ORZY-05.

In some embodiments, the process disclosed herein further comprises adding one or more seed crystals of ORZY-01 to the container. In some embodiments, the process disclosed herein further comprises adding one or more seed crystals of ORZY-03 to the container. In some embodiments, the process disclosed herein further comprises adding one or more seed crystals of ORZY-05 to the container.

In some embodiments, the seed crystals are added during preparation of the disclosed intermediates.

In some embodiments, the process disclosed herein further comprises as the first step, adding one or more seed crystals of ORZY-01 to the container. In some embodiments, the process disclosed herein further comprises as the first step, adding one or more seed crystals of ORZY-03 to the container. In some embodiments, the process disclosed herein further comprises as the first step, adding one or more seed crystals of ORZY-05 to the container.

Step 1 (ORZY-01)

As demonstrated by Example 1 of the present disclosure, optimization of the reaction conditions, reactant ratio, reaction time, and temperature allowed product ORZY-01 to be isolated in 79.6% yield without intermediate isolation. This yield is higher as compared to previous reports.

In some embodiments, a process for preparing ORZY-01 is provided,

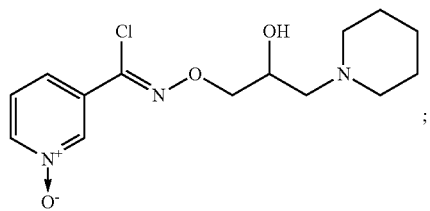
(ORZY-01)

wherein the process comprises
step 1A) mixing a compound of formula (I);

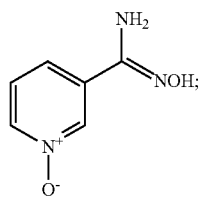
formula (I)

with a compound of formula (II);

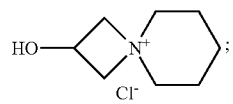
formula (II)

in a first solvent at a first temperature for more than 2 hours to provide an intermediate; followed by step 1B) wherein the intermediate is reacted with NaNO$_2$ at a second temperature in a second solvent to provide ORZY-01.

In some embodiments, the process for preparing ORZY-01 is performed in a container. Thus the steps described in the process may be conducted within a container. The skilled person may choose a suitable container depending on the batch size.

In some embodiments, a process for preparing ORZY-01 is provided,

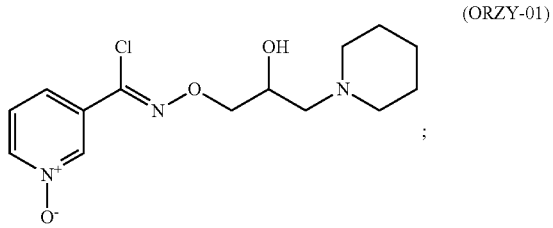 [SMILES: [O-][n+]1cccc(/C(Cl)=N/OCC(O)CN2CCCCC2)c1]
(ORZY-01)

wherein the process comprises
step 1A) mixing a compound of formula (I);

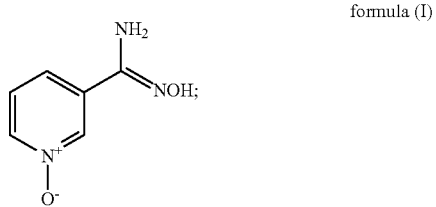
formula (I)

with a compound of formula (II) in a container;

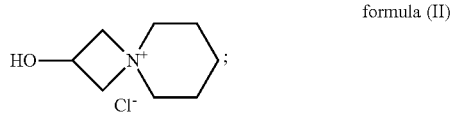
formula (II)

in a first solvent at a first temperature to provide an intermediate; followed by step 1B) wherein the intermediate is reacted with NaNO$_2$ at a second temperature in a second solvent to provide ORZY-01.

In some embodiments, the process is provided wherein the intermediate is isolated, optionally purified, prior to step 1B).

In some embodiments, the process is provided wherein the first solvent is a polar protic solvent or a mixture of polar protic solvents.

In some embodiments, the first solvent is selected from the group consisting of ethanol, water, methanol, 2-propanol, and any mixture thereof. In some embodiments, first solvent is a mixture of ethanol and water.

In some embodiments, the process is provided wherein step 1A is performed under basic conditions, such as by the addition of a hydroxide, such as NaOH or KOH. The NaOH is for example in aqueous solution NaOH (50% wt).

In some embodiments, the process is provided as defined herein, wherein, the second solvent is a chlorinated hydrocarbon or a mixture containing a chlorinated hydrocarbon. In some embodiments, the second solvent is a mixture of dichloromethane and water.

In some embodiments, the process is provided wherein the first solvent is different from the second solvent.

In some embodiments, the process is provided wherein the first temperature is at the boiling point of the solvent.

In some embodiments, the process is provided wherein the first temperature is higher than the second temperature.

In some embodiments, the first temperature is from about 70° C. to about 90° C., such as from about 72° C. to about 88° C., such as from about 74° C. to about 86° C., such as from about 76° C. to about 84° C., such as from about 78° C. to about 82° C., for example about 80° C. In some embodiments, the first temperature is from about 75° C. to about 85° C., such as about 80° C. In some embodiments, the first temperature is maintained for about 3.5 hours or more.

In some embodiments, the second temperature is from about 0° C. to about 15° C., such as from about 6° C. to about 14° C., such as from about 7° C. to about 13° C., such as from about 8° C. to about 12° C., such as from about 9° C. to about 11° C., for example about 10° C.

In some embodiments, the second temperature is about 0° C. or more, such as more than about 0° C. In one embodiment, the second temperature is about 15° C. or less.

In some embodiments, the second temperature is from about 0° C. to about 15° C., such as from about 0° C. to about 1° C., such as from about 1° C. to about 2° C., such as from about 2° C. to about 3° C., such as from about 3° C. to about 4° C., such as from about 5° C. to about 6° C., such as from about 6° C. to about 7° C., such as from about 7° C. to about 8° C., such as from about 8° C. to about 9° C., such as from about 9° C. to about 10° C., such as from about 10° C. to about 11° C., such as from about 11° C. to about 12° C., such as from about 12° C. to about 13° C., such as from about 13° C. to about 14° C., such as from about 14° C. to about 15° C.

In some embodiments, the second temperature is maintained for about 1 hour.

In some embodiments, the process as defined herein is provided, wherein the compound of formula (II),

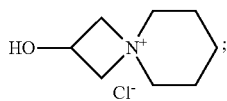

formula (II)

is mixed in a molar ratio of 1.3:1.0 with the compound of formula (I),

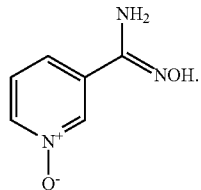

formula (I)

In some embodiments, the compound of formula (II) is mixed in a molar ratio of from 1.2:1.0 to 2.0:1.0 with the compound of formula (I), such as from 1.2:1.0 to 1.3:1.0, such as from 1.3:1.0 to 1.4:1.0, such as from 1.4:1.0 to 1.5:1.0, such as from 1.5:1.0 to 1.6:1.0, such as from 1.6:1.0 to 1.7:1.0, such as from 1.7:1.0 to 1.8:1.0, such as from 1.8:1.0 to 1.9:1.0, such as from 1.9:1.0 to 2.0:1.0.

In some embodiments, the intermediate is not isolated prior to the reaction with $NaNO_2$. In some embodiments, the intermediate not isolated prior to the reaction with $NaNO_2$ refers to compound (V) as disclosed herein and directly obtainable from step 1A. In some embodiments, the intermediate is of formula (V);

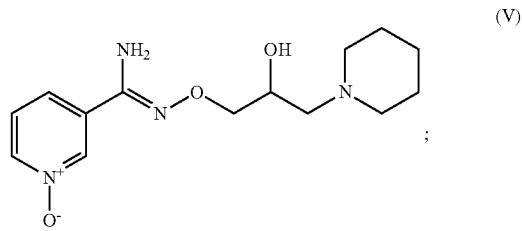 [SMILES: N/C(=N\OCC(O)CN1CCCCC1)c1ccc[n+]([O-])c1]

(V)

or a pharmaceutically acceptable salt thereof.

In some embodiments, the intermediate is reacted with from 1.2 to 1.6 equivalents $NaNO_2$, such as from 1.2 to 1.3 equivalents, such as from 1.3 to 1.4 equivalents, such as from 1.4 to 1.5 equivalents, such as from 1.5 to 1.6 equivalents.

In some embodiments, the intermediate is reacted with at least 1.2 equivalents $NaNO_2$.

In some embodiments, the first temperature provides for reflux of the first solvent, optionally wherein the first temperature provides for reflux of the first solvent for 2.5 hours or more, such as 3 hours or more, such as 4 hours or more, such as 5 hours or more, such as 6 hours or more. In this aspect, "the first temperature provides for reflux" means that the first temperature is such that the first solvent is at the boiling point or close enough to the boiling point to result in condensation vapours to provide a condensate and the return of the condensate to the system from which it originated.

In some embodiments, the first solvent is heated at from about 75° C. to about 85° C. for at least 3.5 hours.

In some embodiments, the first solvent is heated at from about 75° C. to about 85° C. for from 3.5 hours to 4.5 hours, such as from 3.5 hours to 4.0 hours, such as from 4.0 hours to 4.5 hours. In one embodiment, the first temperature is from 75° C. to 85° C. for from 3.5 hours to 4.5 hours, such as from 3.5 hours to 4.0 hours, such as from 4.0 hours to 4.5 hours In some embodiments, the first solvent is a mixture of ethanol, optionally denatured; and water, and the first solvent is maintained at 80° C. for more than 2 hours. In some embodiments, the first solvent is a mixture of ethanol, optionally denatured; and water, and the first solvent is maintained at about 80° C. for at least 3 hours.

Ethanol may be used both in denatured form and in non-denatured form. In Example 1 of the present disclosure, a denatured form is successfully used. A non-denatured form has also been found to work. The data for the non-denatured form is not shown herein.

In some embodiments, the first solvent is a mixture of ethanol, optionally denatured; and water, and the first solvent is maintained at about 80° C. for more than 2 hours; and wherein the second solvent is a mixture of dichloromethane and water. In one embodiment, the first solvent is a mixture of ethanol, optionally denatured; and water, and the first solvent is maintained at about 80° C. for at least 3 hours; and wherein the second solvent is a mixture of dichloromethane and water.

Drying of ORZY-01

In some embodiments, the wet product obtained from the process for preparing ORZY-01 is dried under vacuum. In some embodiments, the wet product is dried at less than 45° C. for at least 8 hours, such as overnight. In some embodiments, the wet product is dried at 40° C. for at least 8 hours, such as overnight.

Concentration of Solvents

In some embodiments, the concentration of the first solvent used in the process of the present disclosure is from 0.1M to 1.5M with respect to the "PCO—N-oxide". As an example, the first solvent can be a mixture of water (215 mL) with ethanol (1000 mL) for reacting 112 g, 653 mmol "PCO—N-Oxide" with 153 g (1.3 equivalents) "Azonia". This would provide a 0.5M concentration of PCO—N-Oxide with respect to the first solvent. The solvent concentrations can be scaled linearly to accommodate different batch sizes.

Composition of ORZY-01

In some embodiments, a composition is provided comprising ORZY-01, (ORZY-01)

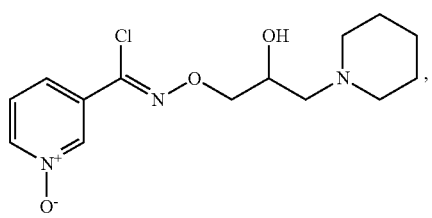

and
one or more impurities selected from the group consisting of:

(A)

, and (B)

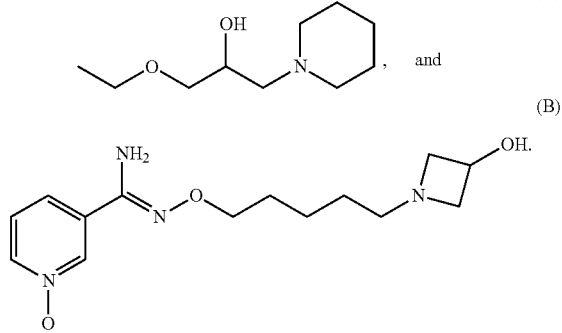

In some embodiments, the impurities are present below about 1% by weight in the composition provided comprising ORZY-01. In some embodiments, an additional recrystallization step may reduce the weight percentage of impurities in the composition provided comprising ORZY-01.

In some embodiments, (A) is present by weight in from 0.1% to 0.5% and/or (B) in from 0.1% to 0.5%.

In some embodiments, (A) is present by weight in from 0.1% to 0.5%, such as from 0.1% to 0.2%, such as from 0.2% to 0.3%, such as from 0.3% to 0.4%, such as 0.4% to 0.5%.

In some embodiments, (B) is present by weight in from 0.1% to 0.5%, such as from 0.1% to 0.2%, such as from 0.2% to 0.3%, such as from 0.3% to 0.4%, such as 0.4% to 0.5%.

Step 2 (ORZY-03)

As demonstrated by Example 4 of the present disclosure, by employing an amount of L-DBTA and a cooling rate of at least 15 K/h for the chiral resolution, a high chiral purity, as well as chemical purity, is obtained in the formation of ORZY-03. The chiral purity of ORZY-03 obtained in Step 2 is retained toward the end-product ORZY-05, and may be further enhanced by re-crystallization. The improved chiral resolution step, including the cooling rate of at least 15 K/h, enables the provision of an ultra-pure composition comprising arimoclomol citrate (ORZY-05). In some embodiments, the ultra-pure composition meets the regulatory requirements of the medicines agencies (e.g., FDA and EMA).

In some embodiments, a process for preparing ORZY-03 is provided, (ORZY-03)

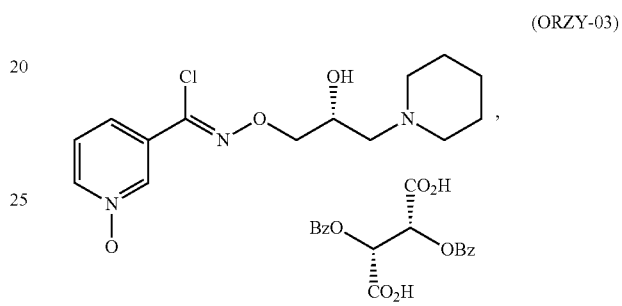

wherein the process comprises the consecutive steps of:
a) mixing ORZY-01, (ORZY-01)

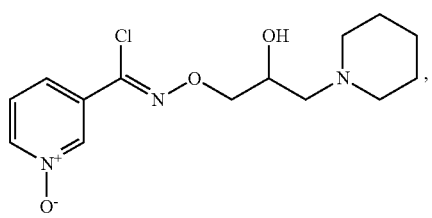

with dibenzoyl L-tartaric acid (L-DBTA) in a container in a first step 2 solvent and heating the first step 2 solvent to a first step 2 temperature, optionally agitating the first step 2 solvent;

b) cooling the first step 2 solvent to a second step 2 temperature at a cooling rate of 15 K/h or higher to provide a solid composition comprising ORZY-03; wherein the first step 2 temperature is higher than the second step 2 temperature; and c) separating the first step 2 solvent and the solid composition comprising ORZY-03, optionally wherein the separation is by filtration; thereby providing ORZY-03.

In some embodiments, the process further comprises step:
d) washing the solid composition comprising ORZY-03 one or more times with a first predefined volume of the first step 2 solvent.

In some embodiments, the process further comprises step:
e) drying the solid composition comprising ORZY-03 at reduced pressure.

In some embodiments, the process further comprises step a1) prior to step b), wherein the first step 2 solvent is cooled to a third step 2 temperature; wherein the third step 2 temperature is higher than the second step 2 temperature.

Step 2: Cooling Rates

The cooling rate in step 2 provides the enantioenriched salt, ORZY-03. In some embodiments, employing a cooling rate of 15 K/h or higher, increases chiral purity of ORZY-03.

In some embodiments, the cooling rate is selected from the group consisting of: 15 K/h; 16 K/h; 17 K/h; 18 K/h; 19 K/h; 20 K/h; 21 K/h; 22 K/h; 23 K/h; 24 K/h; 25 K/h; 26 K/h; 27 K/h; 28 K/h; 29 K/h; 30 K/h; 31 K/h; 32 K/h; 33 K/h; 34 K/h; 35 K/h; 36 K/h; 37 K/h; 38 K/h; 39 K/h; 40 K/h; 41 K/h; 42 K/h; 43 K/h; 44 K/h; 45 K/h; 46 K/h; 47 K/h; 48 K/h; 49 K/h; and 50 K/h.

In some embodiments, the cooling rate is from 15 K/h to 50 K/h, such as from 15 K/h to 16 K/h; such as from 16 K/h to 17 K/h; such as from 17 K/h to 18 K/h; such as from 18 K/h to 19 K/h; such as from 19 K/h to 20 K/h; such as from 20 K/h to 21 K/h; such as from 21 K/h to 22 K/h; such as from 22 K/h to 23 K/h; such as from 23 K/h to 24 K/h; such as from 24 K/h to 25 K/h; such as from 25 K/h to 26 K/h; such as from 26 K/h to 27 K/h; such as from 27 K/h to 28 K/h; such as from 28 K/h to 29 K/h; such as from 29 K/h to 30 K/h; such as from 30 K/h to 31 K/h; such as from 31 K/h to 32 K/h; such as from 32 K/h to 33 K/h; such as from 33 K/h to 34 K/h; such as from 34 K/h to 35 K/h; such as from 35 K/h to 36 K/h; such as from 36 K/h to 37 K/h; such as from 37 K/h to 38 K/h; such as from 38 K/h to 39 K/h; such as from 39 K/h to 40 K/h; such as from 40 K/h to 41 K/h; such as from 41 K/h to 42 K/h; such as from 42 K/h to 43 K/h; such as from 43 K/h to 44 K/h; such as from 44 K/h to 45 K/h; such as from 45 K/h to 46 K/h; such as from 46 K/h to 47 K/h; such as from 47 K/h to 48 K/h; such as from 48 K/h to 49 K/h; or such as from 49 K/h to 50 K/h.

In some embodiments, the cooling rate is from 15 K/h to 50 K/h. In some embodiments, the cooling rate is from 15 K/h to 40 K/h. In some embodiments, the cooling rate is from 15 K/h to 30 K/h. In some embodiments, the cooling rate is from 17 K/h to 30 K/h.

Step 2: Solvents

In some embodiments, the first step 2 solvent is a polar protic solvent or a mixture of polar protic solvents.

In some embodiments, the first step 2 solvent is selected from the group consisting of ethanol, water, methanol, 2-propanol, and any mixture thereof.

In some embodiments, the first step 2 solvent is a mixture of ethanol and water.

In some embodiments, the first step 2 solvent is from 20.5 to 23.5 kg water per 55 kg ORZY-01; and from 200 to 240 kg EtOH per 55 kg ORZY-01.

In some embodiments, the first step 2 solvent is 22 kg water per 55 kg ORZY-01; and 220 kg EtOH per 55 kg ORZY-01.

Step 2: Temperatures

In some embodiments, the first step 2 temperature is from about 60° C. to about 75° C., such as from about 61° C. to about 74° C., such as from about 62° C. to about 73° C., such as from about 63° C. to about 72° C., such as from about 64° C. to about 71° C., such as from about 65° C. to about 70° C., for example about 65° C.

In some embodiments, the second step 2 temperature is from about 10° C. to about 30° C., such as from about 11° C. to about 29° C., such as from about 12° C. to about 28° C., such as from about 13° C. to about 27° C., such as from about 14° C. to about 26° C., such as from about 15° C. to about 25° C., for example about 20° C.

In some embodiments, the third step 2 temperature is from about 45° C. to about 65° C., such as from about 46° C. to about 64° C., such as from about 47° C. to about 63° C., such as from about 48° C. to about 62° C., such as from about 49° C. to about 61° C., such as from about 50° C. to about 60° C., such as from about 51° C. to about 59° C., such as from about 52° C. to about 58° C., such as from about 53° C. to about 57° C., such as from about 54° C. to about 56° C., such as about 55° C.

Method Aspects of Step 2

In some embodiments, the third step 2 temperature is maintained for at least 30 minutes, such as at least 60 minutes.

In some embodiments, one or more seed crystals of ORZY-03 is added to the container prior to step b. In some embodiments, the one or more seed crystals of ORZY-03 has a chiral purity of at least 95%.

In some embodiments, the mass of the one or more seed crystals of ORZY-03 is from 0.2 to 0.8 kg per 55 kg ORZY-03, for example 0.55 kg per 55 kg ORZY-03.

In some embodiments, from 0.7 to 1.1 equivalents of L-DBTA is employed in step 2, for example 0.88 equivalents of L-DBTA based on 1 equivalent of ORZY-01. In some embodiments, from 0.7 to 1.1 equivalents of L-DBTA is employed, such as from 0.7 to 0.8, such as from 0.8 to 0.9, such as from 0.9 to 1.0, such as from 1.0 to 1.1 equivalents of L-DBTA based on 1 equivalent of ORZY-01.

In some embodiments, the first predefined volume of the first step 2 solvent is from 35 to 55 kg per 55 kg ORZY-03. In some embodiments, the first predefined volume of the first step 2 solvent is from 41 to 45 kg per 55 kg ORZY-03.

Step 3 (ORZY-04)

As demonstrated by Example 6 of the present disclosure, an optimized Step 3 including addition of a catalytic amount of citric acid before the solvent exchange from DCM to MeOH suppresses the formation of "methoxylated ORZY-04" (referred to herein as impurity RRT 0.74 herein). Example 6 further demonstrates that washing the combined DCM phases with water, further reduces the levels of impurities, such as RRT 0.74. The improved step 3 enables the provision of an ultra-pure composition comprising arimoclomol citrate (ORZY-05). In some embodiments, the ultra-pure composition meets the regulatory requirements of the medicines agencies (e.g., US or EMA).

In some embodiments, a process for preparing ORZY-05 is provided,

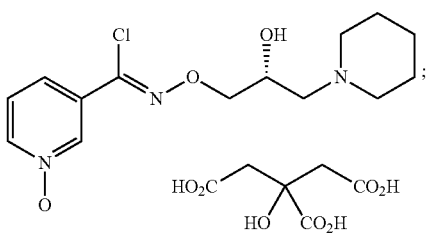

(ORZY-05)

wherein the process comprises the steps of:

a) adding a catalytic amount of citric acid to a solution of ORZY-03 in a container in a first step 3 solvent;

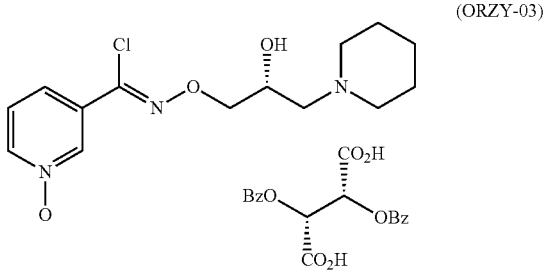

(ORZY-03)

b) exchanging the solvent of the mixture of step a) from the first step 3 solvent to a second step 3 solvent; wherein the first step 3 solvent is different from the second step 3 solvent;
c) adding about a stoichiometric amount of citric acid to the mixture obtained in step b) to form a suspension;
d) filtering the suspension provided in step c) to obtain ORZY-04, which is a crude of ORZY-05; and
e) purifying the ORZY-04 of step d) to obtain ORZY-05.

In some embodiments, the process of step 3 further comprises the steps of:
f) mixing the compound ORZY-03 with an aqueous solution of a first step 3 base; and
g) extracting the mixture obtained in step a) with the first step 3 solvent to afford a solution of ORZY-03 in the first step 3 solvent;
before adding the catalytic amount of citric acid according to step a) to the solution of ORZY-03 in the first step 3 solvent.

In some embodiments, the process further comprises washing the first step 3 solvent one or more times with water, wherein one or more by-products from the first step 3 solvent are removed.

In some embodiments, the process comprises the steps of:
a) mixing the compound ORZY-03 with an aqueous solution of the first step 3 base;

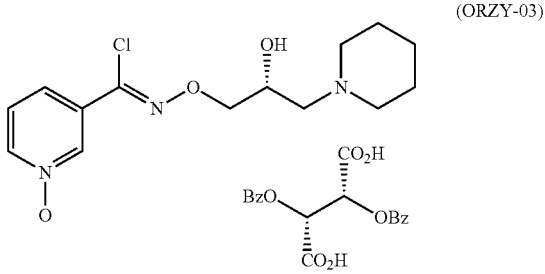

(ORZY-03)

b) extracting the mixture obtained in step a) with the first step 3 solvent;
c) adding a catalytic amount of citric acid to the organic phase(s) of step b);
d) exchanging the solvent of the mixture of step c) from the first step 3 solvent to the second step 3 solvent;
e) adding about a stoichiometric amount of citric acid to the mixture obtained in step d) to form a suspension; and
f) filtering the suspension provided in step e) to obtain crude ORZY-05 (ORZY-04).

Step 3: Solvents

In some embodiments, the first step 3 solvent referred to in step 3 is a chlorinated hydrocarbon or a mixture containing a chlorinated hydrocarbon.

In some embodiments, the first step 3 solvent is dichloromethane or dichloroethane, preferably dichloromethane.

In some embodiments, the second step 3 solvent is a polar protic solvent or a mixture of polar protic solvents.

In some embodiments, the second step 3 solvent is selected from the group consisting of methanol, water, ethanol, 2-propanol, and any mixture thereof. In some embodiments, the second step 3 solvent is methanol.

Step 3: Bases

In some embodiments, the first step 3 base referred to in step 3 is a carbonate. In some embodiments, the first step 3 base is a carbonate selected from the group consisting of: $K_2CO_3$ and $Cs_2CO_3$. In some embodiments, the first step 3 base is $K_2CO_3$. In some embodiments, the aqueous solution of $K_2CO_3$ comprises 16.8% $K_2CO_3$.

Method aspects of step 3

In some embodiments, the mixture of ORZY-03 and $K_2CO_3$ is extracted three times with $CH_2Cl_2$.

In some embodiments, exchanging the solvent of from $CH_2Cl_2$ to $CH_3OH$ comprises the steps of:
a. partly distilling the $CH_2Cl_2$ solution;
b. adding $CH_3OH$ to the distilled solution provided in step a);
c. partly distilling the solution provided in step b); and
d. adding $CH_3OH$ to the solution provided in step c).

In some embodiments, the amount distilled of in steps a) and c) at least corresponds to the amount of $CH_2Cl_2$ that ORZY-03 was dissolved in prior to the solvent exchange step. In some embodiments, the steps described above are consecutive steps.

In some embodiments, the process further comprises the step of passing the solution obtained after exchanging the solvent from $CH_2Cl_2$ to $CH_3OH$ through activated charcoal filter.

In some embodiments, step 3 further comprises the step of drying ORZY-04. In some embodiments, the drying step includes drying the ORZY-04 at 45° C. in vacuum for at least 12 h.

In some embodiments, the process comprises the consecutive steps of:
a) mixing the compound ORZY-03 with an 16.8% aqueous solution of $K_2CO_3$;

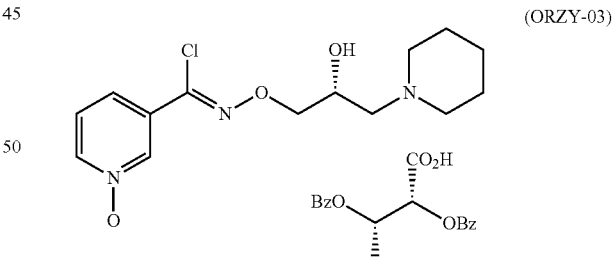

(ORZY-03)

b) extracting the mixture obtained in step a) with $CH_2Cl_2$ one or more times, such as three times; followed by one or more aqueous washes of the combined organic phases;
c) adding a catalytic amount of citric acid to the organic phase(s) of step b);
d) exchanging the solvent of the mixture of step c) from $CH_2Cl_2$ to $CH_3OH$ by
  i. partly distilling the $CH_2Cl_2$ solution of step c);
  ii. adding $CH_3OH$ to the distilled solution provided in step i);

iii. partly distilling the solution provided in step ii); and
iv. adding CH₃OH to the solution provided in step iii)

e) passing the solution obtained in step d) through an activated charcoal filter;

f) adding about a stoichiometric amount of citric acid to the mixture obtained in step e) to form a suspension;

g) filtering the suspension provided in step e) to obtain ORZY-04;

h) drying ORZY-04 obtained in step g) at 45° C. in vacuum for at least 12 h, and i) purifying the ORZY-04 of step h) to obtain ORZY-05.

Step 4 (ORZY-05)

As demonstrated in Example 7 of the present disclosure, recrystallization under the a selected set of conditions results in high chiral and chemical purity of ORZY-05, arimoclomol citrate.

In some embodiments, the step of purifying the ORZY-04 to obtain ORZY-05 as described herein comprises recrystallization of ORZY-04. In some embodiments, the solvent used in the recrystallization is acetone.

In some embodiments, the recrystallization comprises the steps of:

a. mixing ORZY-04 with H₂O and heating the mixture to 70±5° C. until a clear solution is observed;

b. cooling the solution formed in step a) to 30±5° C.;

c. adding acetone to the solution of step b);

d. cooling the mixture of step c) to 0±5° C.;

e. isolating ORZY-05 from the mixture of step d) by separation solids and solvents; and optionally drying the ORZY-05 obtained in step f) at 45° C. in vacuum for at least 12 h.

In some embodiments, the recrystallization comprises the steps of:

a. mixing ORZY-04 with H₂O and heating the mixture to 70±5° C. until a clear solution is observed;

b. cooling the solution formed in step a) to 30±5° C.;

c. adding acetone to the solution of step b);

d. cooling the mixture of step c) to 0±5° C.;

e. agitating the mixture of step d) for 12 h at 0±10° C. to generate a suspension;

f. isolating ORZY-05 from the suspension of step e) by filtering said suspension; and drying the ORZY-05 obtained in step f) at 45° C. in vacuum for at least 12 h.

In some embodiments, the cooling from 30° C.±5° C. to 0° C.±5° C. is done in 5.5 hours or less, such as 5 hours or less, such as 4.5 hours or less, such as 4 hours or less, such as 3.5 hours or less, such as 3 hours or less, such as 2.5 hours or less, such as 2 hours or less.

Preparation of Arimoclomol Citrate (ORZY-05)

The optimized four-steps process for preparing an ultra-pure composition comprising arimoclomol citrate, i.e. N-{[(2R)-2-hydroxy-3-piperidin-1-ylpropyl]oxy}pyridine-3-carboximidoyl chloride 1-oxide citrate is disclosed herein. The optimized process includes a plurality of optimized sub-steps, each contributing to an overall improved process, enabling the provision of the ultra-pure composition comprising arimoclomol citrate.

In some embodiments, a process for preparing arimoclomol citrate (ORZY-05) is provided,

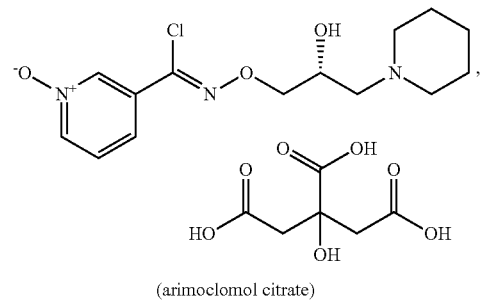

(arimoclomol citrate)

comprising one or more of the processes described herein to provide ORZY-01; ORZY-03; or ORZY-04; thereby providing ORZY-05.

In some embodiments, a process for preparing arimoclomol citrate is provided,

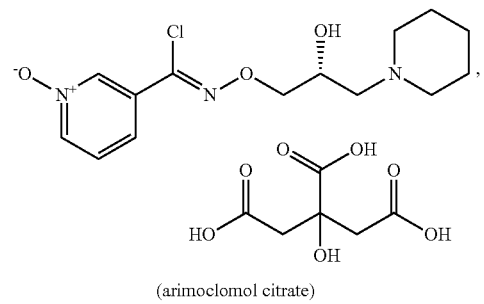

(arimoclomol citrate)

comprising the process as defined herein to provide ORZY-01, thereby providing arimoclomol citrate.

In some embodiments, a process for preparing arimoclomol citrate is provided,

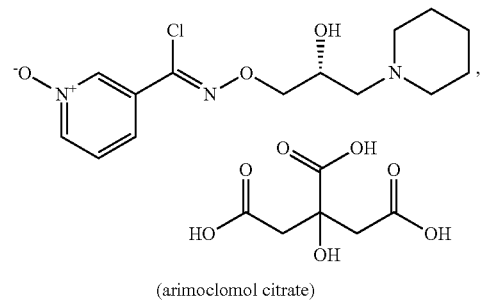

(arimoclomol citrate)

comprising the steps of:
a) the process as defined herein to provide ORZY-01,

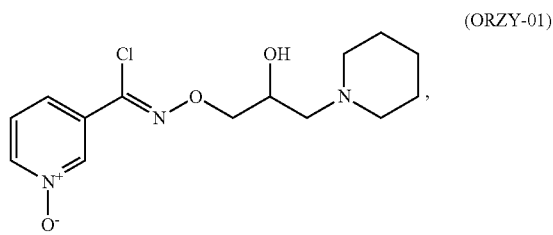 [SMILES: [O-][n+]1cccc(/C(Cl)=N/OCC(O)CN2CCCCC2)c1]

(ORZY-01)

b) precipitating ORZY-01 with dibenzoyl L-tartaric acid to provide ORZY-03,

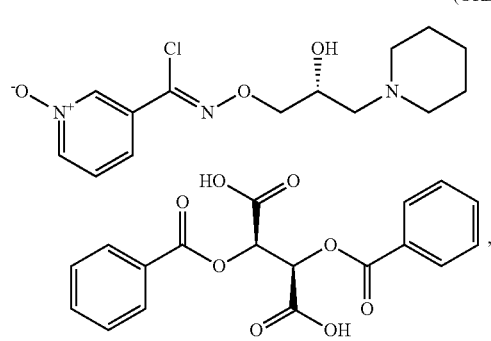

(ORZY-03)

c) reacting ORZY-03 with a base and subsequently precipitating the resulting free base of ORZY-03 with citric acid to provide arimoclomol citrate.

In some embodiments, a process for preparing arimoclomol citrate is provided,

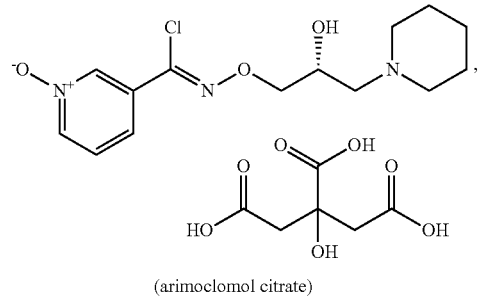

(arimoclomol citrate)

comprising the consecutive steps of:
a. providing ORZY-01,

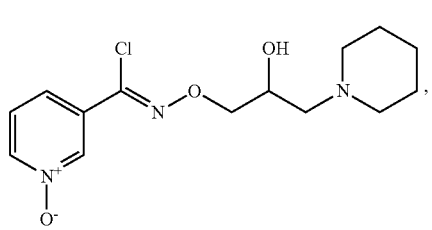

(ORZY-01)

b. the process as defined herein to provide ORZY-03,

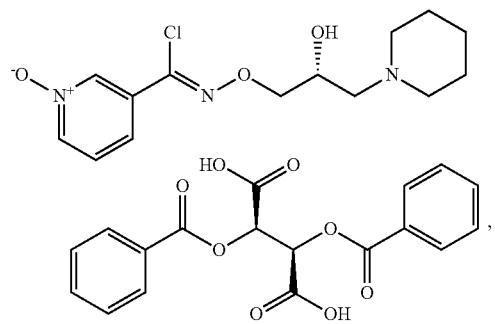

(ORZY-03)

c. reacting ORZY-03 with a base and subsequently precipitating the resulting free base of ORZY-03 with citric acid to provide arimoclomol citrate,
thereby providing arimoclomol citrate.

In some embodiments, a process for preparing arimoclomol citrate is provided,

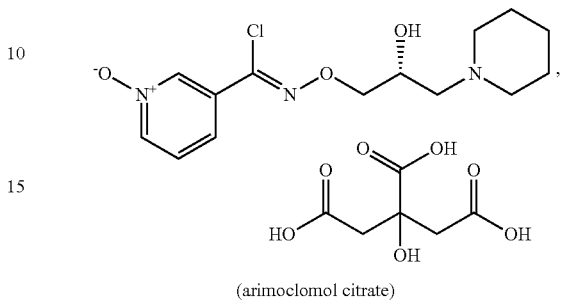

(arimoclomol citrate)

comprising the consecutive steps of:
a. providing ORZY-01,

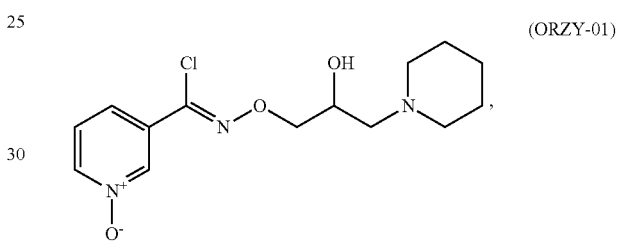

(ORZY-01)

b. precipitating ORZY-01 with dibenzoyl L-tartaric acid to provide ORZY-03,

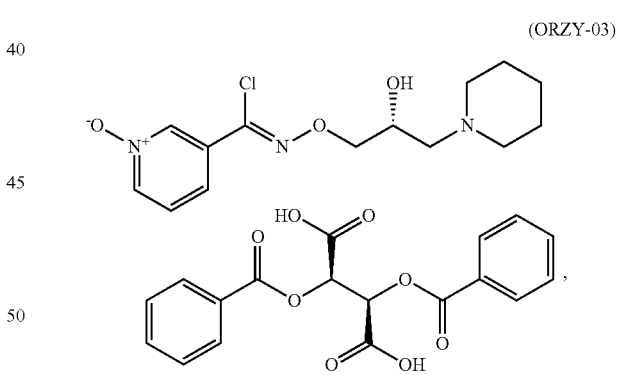

(ORZY-03)

c. the process as defined herein to provide ORZY-05;
thereby providing arimoclomol citrate.

Pharmaceutical Composition

In some embodiments, the present disclosure provides a pharmaceutical composition comprising N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 98.0% as determined by HPLC.

In some embodiments, the present disclosure provides a composition comprising N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 98.0% as determined by HPLC.

In some embodiments, the present disclosure provides a pharmaceutical composition comprising N-{[(2R)-2-hydroxy-3-piperidin-1-ylpropyl]oxy}pyridine-3-carboximidoyl chloride 1-oxide citrate having a purity greater than 98.0% as determined by HPLC.

In some embodiments, the present disclosure provides a pharmaceutical composition comprising N-{[(2R)-2-hydroxy-3-piperidin-1-ylpropyl]oxy}pyridine-3-carboximidoyl chloride 1-oxide citrate having a purity greater than or equal to 99.0% as determined by HPLC.

In some embodiments, the present disclosure provides a pharmaceutical composition wherein the enantiomeric excess (ee) of N-{[(2R)-2-hydroxy-3-piperidin-1-ylpropyl]oxy}pyridine-3-carboximidoyl chloride 1-oxide citrate is at least about 94%.

In some embodiments, the present disclosure provides a pharmaceutical composition, wherein the ee of N-{[(2R)-2-hydroxy-3-piperidin-1-ylpropyl]oxy}pyridine-3-carboximidoyl chloride 1-oxide citrate is at least about 95%.

In some embodiments, the present disclosure provides a pharmaceutical composition, wherein the ee of N-{[(2R)-2-hydroxy-3-piperidin-1-ylpropyl]oxy}pyridine-3-carboximidoyl chloride 1-oxide citrate is at least about 96%.

In some embodiments, the present disclosure provides a pharmaceutical composition, wherein the ee of N-{[(2R)-2-hydroxy-3-piperidin-1-ylpropyl]oxy}pyridine-3-carboximidoyl chloride 1-oxide citrate is at least about 97%.

In some embodiments, the present disclosure provides a pharmaceutical composition, wherein the ee of N-{[(2R)-2-hydroxy-3-piperidin-1-ylpropyl]oxy}pyridine-3-carboximidoyl chloride 1-oxide citrate is at least about 98%.

In some embodiments, the present disclosure provides a pharmaceutical composition, wherein the composition comprises:
a) at least about 94% ee of N-{[(2R)-2-hydroxy-3-piperidin-1-ylpropyl]oxy}pyridine-3-carboximidoyl chloride 1-oxide citrate, such as at least about 95% ee, such as at least about 96% ee, such as at least about 97% ee, or such as at least about 98% ee; and
b) 0.1% or less methyl (Z)—N-(2-hydroxy-3-(piperidin-1-yl)propoxy)nicotinimidate 1-oxide, or a pharmaceutically acceptable salt thereof.

In some embodiments, the present disclosure provides a pharmaceutical composition, wherein the composition comprises:
a) at least about 94% ee of N-{[(2R)-2-hydroxy-3-piperidin-1-ylpropyl]oxy}pyridine-3-carboximidoyl chloride 1-oxide citrate, such as at least about 95% ee, such as at least about 96% ee, such as at least about 97% ee, or such as at least about 98% ee;
b) 0.1% or less methyl (Z)—N-(2-hydroxy-3-(piperidin-1-yl)propoxy)nicotinimidate 1-oxide, or a pharmaceutically acceptable salt thereof, and
c) less than 2 ppm N-nitrosopiperidine.

In some embodiments, the present disclosure provides a pharmaceutical composition, wherein the purity of the composition is greater than or equal to 99.0% N-{[(2R)-2-hydroxy-3-piperidin-1-ylpropyl]oxy}pyridine-3-carboximidoyl chloride 1-oxide citrate as determined by HPLC.

In some embodiments, the present disclosure provides a pharmaceutical composition, comprising N-{[(2R)-2-hydroxy-3-piperidin-1-ylpropyl]oxy}pyridine-3-carboximidoyl chloride 1-oxide citrate particles having a D10 particle size determined using Malvern Mastersizer 3000 of from about 2.0 μm to about 20.0 μm.

In some embodiments, the present disclosure provides a pharmaceutical composition, comprising N-{[(2R)-2-hydroxy-3-piperidin-1-ylpropyl]oxy}pyridine-3-carboximidoyl chloride 1-oxide citrate particles having a D50 particle size determined using Malvern Mastersizer 3000 of from about 5.0 μm to about 60.0 μm.

In some embodiments, the present disclosure provides a pharmaceutical composition, comprising N-{[(2R)-2-hydroxy-3-piperidin-1-ylpropyl]oxy}pyridine-3-carboximidoyl chloride 1-oxide citrate particles having a D90 particle size determined using Malvern Mastersizer 3000 of from about 30.0 μm to about 130.0 μm.

In some embodiments, the present disclosure provides a pharmaceutical composition, wherein the composition comprises:
a) at least 98.0% N-{[(2R)-2-hydroxy-3-piperidin-1-ylpropyl]oxy}pyridine-3-carboximidoyl chloride 1-oxide citrate; and
b) 1.9% or less N-{[(2S)-2-hydroxy-3-piperidin-1-ylpropyl]oxy}pyridine-3-carboximidoyl chloride 1-oxide, or pharmaceutically acceptable salt thereof, and
c) 0.1% or less methyl (Z)—N-(2-hydroxy-3-(piperidin-1-yl)propoxy)nicotinimidate 1-oxide, or a pharmaceutically acceptable salt thereof.

In some embodiments, the present disclosure provides a pharmaceutical composition, wherein the composition comprises:
a) at least 98.0% N-{[(2R)-2-hydroxy-3-piperidin-1-ylpropyl]oxy}pyridine-3-carboximidoyl chloride 1-oxide citrate; and
b) 1.9% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof, and
d) less than 2 ppm N-nitrosopiperidine.

In some embodiments, a pharmaceutical composition is provided comprising ORZY-05 obtainable by a process disclosed herein for preparing ORZY-05.

In some embodiments, the present disclosure provides a composition, wherein the purity of the composition is greater than or equal to 99.0% N-{[(2R)-2-hydroxy-3-piperidin-1-ylpropyl]oxy}pyridine-3-carboximidoyl chloride 1-oxide citrate as determined by HPLC.

In some embodiments, the present disclosure provides a composition, comprising N-{[(2R)-2-hydroxy-3-piperidin-1-ylpropyl]oxy}pyridine-3-carboximidoyl chloride 1-oxide citrate particles having a D10 particle size determined using Malvern Mastersizer 3000 of from about 2.0 μm to about 20.0 μm.

In some embodiments, the present disclosure provides a composition, comprising N-{[(2R)-2-hydroxy-3-piperidin-1-ylpropyl]oxy}pyridine-3-carboximidoyl chloride 1-oxide citrate particles having a D50 particle size determined using Malvern Mastersizer 3000 of from about 5.0 μm to about 60.0 μm.

In some embodiments, the present disclosure provides a composition, comprising N-{[(2R)-2-hydroxy-3-piperidin-1-ylpropyl]oxy}pyridine-3-carboximidoyl chloride 1-oxide citrate particles having a D90 particle size determined using Malvern Mastersizer 3000 of from about 30.0 μm to about 130.0 μm.

In some embodiments, the present disclosure provides a composition, wherein the composition comprises:
a) at least 98.0% N-{[(2R)-2-hydroxy-3-piperidin-1-ylpropyl]oxy}pyridine-3-carboximidoyl chloride 1-oxide citrate; and b) 1.9% or less N-{[(2S)-2-hydroxy-3-piperidin-1-ylpropyl]oxy}pyridine-3-carboximidoyl chloride 1-oxide, or pharmaceutically acceptable salt thereof, and
c) 0.1% or less methyl (Z)—N-(2-hydroxy-3-(piperidin-1-yl)propoxy)nicotinimidate 1-oxide, or a pharmaceutically acceptable salt thereof.

In some embodiments, the present disclosure provides a composition, wherein the composition comprises:
a) at least 98.0% N-{[(2R)-2-hydroxy-3-piperidin-1-ylpropyl]oxy}pyridine-3-carboximidoyl chloride 1-oxide citrate; and
b) 1.9% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof, and
d) less than 2 ppm N-nitrosopiperidine.

In some embodiments, a composition comprising ORZY-05 is provided obtainable by a process disclosed herein for preparing ORZY-05.

In some embodiments, the pharmaceutical composition or composition has a certain purity with respect to N-{[(2R)-2-hydroxy-3-piperidin-1-ylpropyl]oxy}pyridine-3-carboximidoyl chloride 1-oxide citrate, which is determined using HPLC.

In some embodiments, the pharmaceutical composition has a purity of about 98.0%.
In some embodiments, the pharmaceutical composition has a purity of about 98.25%.
In some embodiments, the pharmaceutical composition has a purity of about 98.5%.
In some embodiments, the pharmaceutical composition has a purity of about 98.75%.
In some embodiments, the pharmaceutical composition has a purity of about 99.0%.
In some embodiments, the pharmaceutical composition has a purity of about 99.25%.
In some embodiments, the pharmaceutical composition has a purity of about 99.5%.
In some embodiments, the pharmaceutical composition has a purity of about 99.6%.
In some embodiments, the pharmaceutical composition has a purity of about 99.7%.
In some embodiments, the pharmaceutical composition has a purity of about 99.8%.
In some embodiments, the pharmaceutical composition has a purity of about 99.9%.
In some embodiments, the pharmaceutical composition has a purity greater than about 99.7%.
In some embodiments, the pharmaceutical composition comprises less than 2% of an impurity.
In some embodiments, the pharmaceutical composition comprises less than 1.9% of an impurity.
In some embodiments, the pharmaceutical composition comprises less than 1.8% of an impurity.
In some embodiments, the pharmaceutical composition comprises less than 1.7% of an impurity.
In some embodiments, the pharmaceutical composition comprises less than 1.6% of an impurity.
In some embodiments, the pharmaceutical composition comprises less than 1.5% of an impurity.
In some embodiments, the pharmaceutical composition comprises less than 1.4% of an impurity.
In some embodiments, the pharmaceutical composition comprises less than 1.3% of an impurity.
In some embodiments, the pharmaceutical composition comprises less than 1.2% of an impurity.
In some embodiments, the pharmaceutical composition comprises less than 1.1% of an impurity.
In some embodiments, the pharmaceutical composition comprises less than 1.0% of an impurity.
In some embodiments, the pharmaceutical composition comprises less than 0.9% of an impurity.
In some embodiments, the pharmaceutical composition comprises less than 0.8% of an impurity.
In some embodiments, the pharmaceutical composition comprises less than 0.7% of an impurity.
In some embodiments, the pharmaceutical composition comprises less than 0.6% of an impurity.
In some embodiments, the pharmaceutical composition comprises less than 0.5% of an impurity.
In some embodiments, the pharmaceutical composition comprises less than 0.4% of an impurity.
In some embodiments, the pharmaceutical composition comprises less than 0.3% of an impurity.
In some embodiments, the pharmaceutical composition comprises less than 0.2% of an impurity.
In some embodiments, the pharmaceutical composition comprises less than 0.1% of an impurity.
In some embodiments, the impurity is a chiral impurity.
In some embodiments, the impurity is a chemical impurity.
In some embodiments, the impurity is N-{[(2S)-2-hydroxy-3-piperidin-1-ylpropyl]oxy}pyridine-3-carboximidoyl chloride 1-oxide or pharmaceutically acceptable salt thereof.
In some embodiments, the impurity is methyl (Z)—N-(2-hydroxy-3-(piperidin-1-yl)propoxy)nicotinimidate 1-oxide or pharmaceutically acceptable salt thereof.
In some embodiments, the impurity is N-nitrosopiperidine.
In some embodiments, the impurity is a combination of N-{[(2S)-2-hydroxy-3-piperidin-1-ylpropyl]oxy}pyridine-3-carboximidoyl chloride 1-oxide or pharmaceutically acceptable salt thereof, methyl (Z)—N-(2-hydroxy-3-(piperidin-1-yl)propoxy)nicotinimidate 1-oxide or pharmaceutically acceptable salt thereof, and N-nitrosopiperidine.
In some embodiments, the impurity is a combination of N-{[(2S)-2-hydroxy-3-piperidin-1-ylpropyl]oxy}pyridine-3-carboximidoyl chloride 1-oxide or pharmaceutically acceptable salt thereof and methyl (Z)—N-(2-hydroxy-3-(piperidin-1-yl)propoxy)nicotinimidate 1-oxide or pharmaceutically acceptable salt thereof.
In some embodiments, the impurity is a combination of N-{[(2S)-2-hydroxy-3-piperidin-1-ylpropyl]oxy}pyridine-3-carboximidoyl chloride 1-oxide or pharmaceutically acceptable salt thereof and N-nitrosopiperidine.
In some embodiments, the impurity is a combination of methyl (Z)—N-(2-hydroxy-3-(piperidin-1-yl)propoxy)nicotinimidate 1-oxide or pharmaceutically acceptable salt thereof and N-nitrosopiperidine.
In some embodiments, N-{[(2R)-2-hydroxy-3-piperidin-1-ylpropyl]oxy}pyridine-3-carboximidoyl chloride 1-oxide, or a pharmaceutically acceptable salt thereof, has a chiral purity.
In some embodiments, N-{[(2R)-2-hydroxy-3-piperidin-1-ylpropyl]oxy}pyridine-3-carboximidoyl chloride 1-oxide citrate has a chiral purity.
In some embodiments, chiral purity refers to a minimum of 98% of N-{[(2R)-2-hydroxy-3-piperidin-1-ylpropyl]oxy}pyridine-3-carboximidoyl chloride 1-oxide, or a pharmaceutically acceptable salt thereof.

In some embodiments, chiral purity refers to a maximum of 2% N-{[(2S)-2-hydroxy-3-piperidin-1-ylpropyl]oxy}pyridine-3-carboximidoyl chloride 1-oxide, or a pharmaceutically acceptable salt thereof.

In some embodiments, chiral purity refers to a minimum of 98% of N-{[(2R)-2-hydroxy-3-piperidin-1-ylpropyl]oxy}pyridine-3-carboximidoyl chloride 1-oxide, or a pharmaceutically acceptable salt thereof, and maximum of 2% N-{[(2S)-2-hydroxy-3-piperidin-1-ylpropyl]oxy}pyridine-3-carboximidoyl chloride 1-oxide, or a pharmaceutically acceptable salt thereof.

In some embodiments, chiral purity refers to a minimum of 99% of N-{[(2R)-2-hydroxy-3-piperidin-1-ylpropyl]oxy}pyridine-3-carboximidoyl chloride 1-oxide, or a pharmaceutically acceptable salt thereof.

In some embodiments, chiral purity refers to a maximum of 1% N-{[(2S)-2-hydroxy-3-piperidin-1-ylpropyl]oxy}pyridine-3-carboximidoyl chloride 1-oxide, or a pharmaceutically acceptable salt thereof.

In some embodiments, chiral purity refers to a minimum of 99% of N-{[(2R)-2-hydroxy-3-piperidin-1-ylpropyl]oxy}pyridine-3-carboximidoyl chloride 1-oxide, or a pharmaceutically acceptable salt thereof, and maximum of 1% N-{[(2S)-2-hydroxy-3-piperidin-1-ylpropyl]oxy}pyridine-3-carboximidoyl chloride 1-oxide, or a pharmaceutically acceptable salt thereof.

In some embodiments, chiral purity refers to a composition of N-{[(2R)-2-hydroxy-3-piperidin-1-ylpropyl]oxy}pyridine-3-carboximidoyl chloride 1-oxide or a pharmaceutically acceptable salt thereof, wherein N-{[(2S)-2-hydroxy-3-piperidin-1-ylpropyl]oxy}pyridine-3-carboximidoyl chloride 1-oxide, or a pharmaceutically acceptable salt thereof, is not detectable.

In some embodiments, chiral purity refers to a composition of N-{[(2R)-2-hydroxy-3-piperidin-1-ylpropyl]oxy}pyridine-3-carboximidoyl chloride 1-oxide or a pharmaceutically acceptable salt thereof, wherein N-{[(2S)-2-hydroxy-3-piperidin-1-ylpropyl]oxy}pyridine-3-carboximidoyl chloride 1-oxide, or a pharmaceutically acceptable salt thereof, is not detectable and no other impurities are detected.

In some embodiments, chiral purity refers to a minimum of 98% of N-{[(2R)-2-hydroxy-3-piperidin-1-ylpropyl]oxy}pyridine-3-carboximidoyl chloride 1-oxide citrate.

In some embodiments, chiral purity refers to a maximum of 2% N-{[(2S)-2-hydroxy-3-piperidin-1-ylpropyl]oxy}pyridine-3-carboximidoyl chloride 1-oxide citrate.

In some embodiments, chiral purity refers to a minimum of 98% of N-{[(2R)-2-hydroxy-3-piperidin-1-ylpropyl]oxy}pyridine-3-carboximidoyl chloride 1-oxide citrate and maximum of 2% N-{[(2S)-2-hydroxy-3-piperidin-1-ylpropyl]oxy}pyridine-3-carboximidoyl chloride 1-oxide citrate.

In some embodiments, chiral purity refers to a minimum of 99% of N-{[(2R)-2-hydroxy-3-piperidin-1-ylpropyl]oxy}pyridine-3-carboximidoyl chloride 1-oxide citrate.

In some embodiments, chiral purity refers to a maximum of 1% N-{[(2S)-2-hydroxy-3-piperidin-1-ylpropyl]oxy}pyridine-3-carboximidoyl chloride 1-oxide citrate.

In some embodiments, chiral purity refers to a minimum of 99% of N-{[(2R)-2-hydroxy-3-piperidin-1-ylpropyl]oxy}pyridine-3-carboximidoyl chloride 1-oxide citrate and maximum of 1% N-{[(2S)-2-hydroxy-3-piperidin-1-ylpropyl]oxy}pyridine-3-carboximidoyl chloride 1-oxide citrate.

In some embodiments, chiral purity refers to a composition of N-{[(2R)-2-hydroxy-3-piperidin-1-ylpropyl]oxy}pyridine-3-carboximidoyl chloride 1-oxide citrate, wherein N-{[(2S)-2-hydroxy-3-piperidin-1-ylpropyl]oxy}pyridine-3-carboximidoyl chloride 1-oxide citrate is not detectable.

In some embodiments, chiral purity refers to a composition of N-{[(2R)-2-hydroxy-3-piperidin-1-ylpropyl]oxy}pyridine-3-carboximidoyl chloride 1-oxide citrate, wherein N-{[(2S)-2-hydroxy-3-piperidin-1-ylpropyl]oxy}pyridine-3-carboximidoyl chloride 1-oxide citrate is not detectable and no other impurities are detected.

In some embodiments, the enantiomeric excess of N-{[(2R)-2-hydroxy-3-piperidin-1-ylpropyl]oxy}pyridine-3-carboximidoyl chloride 1-oxide, or a pharmaceutically acceptable salt thereof, is from about 94% to about 99% ee.

In some embodiments, the enantiomeric excess of N-{[(2R)-2-hydroxy-3-piperidin-1-ylpropyl]oxy}pyridine-3-carboximidoyl chloride 1-oxide citrate is from about 94% to about 99% ee.

In some embodiments, the enantiomeric excess of N-{[(2R)-2-hydroxy-3-piperidin-1-ylpropyl]oxy}pyridine-3-carboximidoyl chloride 1-oxide, or a pharmaceutically acceptable salt thereof, is about 94%, about 94.5%, about 95%, about 95.5%, about 96%, about 96.5%, about 97%, about 97.5%, about 98%, about 98.1%, about 98.2%, about 98.3%, about 98.4%, about 98.5%, about 98.6%, about 98.7%, about 98.8%, about 98.9%, about 99%, about 99.1%, about 99.2%, about 99.3%, about 99.4%, about 99.5%, about 99.6%, about 99.7%, about 99.8%, or about 99.9% ee.

In some embodiments, the enantiomeric excess of N-{[(2R)-2-hydroxy-3-piperidin-1-ylpropyl]oxy}pyridine-3-carboximidoyl chloride 1-oxide citrate is about 94%, about 94.5%, about 95%, about 95.5%, about 96%, about 96.5%, about 97%, about 97.5%, about 98%, about 98.1%, about 98.2%, about 98.3%, about 98.4%, about 98.5%, about 98.6%, about 98.7%, about 98.8%, about 98.9%, about 99%, about 99.1%, about 99.2%, about 99.3%, about 99.4%, about 99.5%, about 99.6%, about 99.7%, about 99.8%, or about 99.9% ee.

In some embodiments, the enantiomeric excess of N-{[(2R)-2-hydroxy-3-piperidin-1-ylpropyl]oxy}pyridine-3-carboximidoyl chloride 1-oxide, or a pharmaceutically acceptable salt thereof, is about 96% ee.

In some embodiments, the enantiomeric excess of N-{[(2R)-2-hydroxy-3-piperidin-1-ylpropyl]oxy}pyridine-3-carboximidoyl chloride 1-oxide citrate is about 96% ee.

In some embodiments, the enantiomeric excess of N-{[(2R)-2-hydroxy-3-piperidin-1-ylpropyl]oxy}pyridine-3-carboximidoyl chloride 1-oxide citrate is at least about 94% ee.

In some embodiments, the enantiomeric excess of N-{[(2R)-2-hydroxy-3-piperidin-1-ylpropyl]oxy}pyridine-3-carboximidoyl chloride 1-oxide citrate is at least about 95% ee.

In some embodiments, the enantiomeric excess of N-{[(2R)-2-hydroxy-3-piperidin-1-ylpropyl]oxy}pyridine-3-carboximidoyl chloride 1-oxide citrate is at least about 96% ee.

In some embodiments, the enantiomeric excess of N-{[(2R)-2-hydroxy-3-piperidin-1-ylpropyl]oxy}pyridine-3-carboximidoyl chloride 1-oxide citrate is at least about 97% ee.

In some embodiments, the enantiomeric excess of N-{[(2R)-2-hydroxy-3-piperidin-1-ylpropyl]oxy}pyridine-3-carboximidoyl chloride 1-oxide citrate is at least about 98% ee.

In some embodiments, the enantiomeric excess of N-{[(2R)-2-hydroxy-3-piperidin-1-ylpropyl]oxy}pyridine-3-carboximidoyl chloride 1-oxide citrate is at least about 99% ee.

In some embodiments, N-{[(2R)-2-hydroxy-3-piperidin-1-ylpropyl]oxy}pyridine-3-carboximidoyl chloride 1-oxide, or a pharmaceutically acceptable salt thereof has a chemical purity.

In some embodiments, N-{[(2R)-2-hydroxy-3-piperidin-1-ylpropyl]oxy}pyridine-3-carboximidoyl chloride 1-oxide citrate has a chemical purity.

In some embodiments, chemical purity refers to a minimum of 98% of N-{[(2R)-2-hydroxy-3-piperidin-1-ylpropyl]oxy}pyridine-3-carboximidoyl chloride 1-oxide, or a pharmaceutically acceptable salt thereof.

In some embodiments, chemical purity refers to a minimum of 98% of N-{[(2R)-2-hydroxy-3-piperidin-1-ylpropyl]oxy}pyridine-3-carboximidoyl chloride 1-oxide citrate.

In some embodiments, chemical purity refers to a maximum of 2% methyl (Z)—N-(2-hydroxy-3-(piperidin-1-yl)propoxy)nicotinimidate 1-oxide, or a pharmaceutically acceptable salt thereof, or N-nitrosopiperidine.

In some embodiments, chemical purity refers to a minimum of 98% of N-{[(2R)-2-hydroxy-3-piperidin-1-ylpropyl]oxy}pyridine-3-carboximidoyl chloride 1-oxide, or a pharmaceutically acceptable salt thereof, and maximum of 2% methyl (Z)—N-(2-hydroxy-3-(piperidin-1-yl)propoxy)nicotinimidate 1-oxide, or a pharmaceutically acceptable salt thereof, or N-nitrosopiperidine.

In some embodiments, chemical purity refers to a minimum of 98% of N-{[(2R)-2-hydroxy-3-piperidin-1-ylpropyl]oxy}pyridine-3-carboximidoyl chloride 1-oxide citrate and maximum of 2% methyl (Z)—N-(2-hydroxy-3-(piperidin-1-yl)propoxy)nicotinimidate 1-oxide, or a pharmaceutically acceptable salt thereof, or N-nitrosopiperidine.

In some embodiments, chemical purity refers to a minimum of 99% of N-{[(2R)-2-hydroxy-3-piperidin-1-ylpropyl]oxy}pyridine-3-carboximidoyl chloride 1-oxide, or a pharmaceutically acceptable salt thereof.

In some embodiments, chemical purity refers to a minimum of 99% of N-{[(2R)-2-hydroxy-3-piperidin-1-ylpropyl]oxy}pyridine-3-carboximidoyl chloride 1-oxide citrate.

In some embodiments, chiral purity refers to a maximum of 1% methyl (Z)—N-(2-hydroxy-3-(piperidin-1-yl)propoxy)nicotinimidate 1-oxide, or a pharmaceutically acceptable salt thereof, or N-nitrosopiperidine.

In some embodiments, chemical purity refers to a minimum of 99% of N-{[(2R)-2-hydroxy-3-piperidin-1-ylpropyl]oxy}pyridine-3-carboximidoyl chloride 1-oxide, or a pharmaceutically acceptable salt thereof, and maximum of 1% methyl (Z)—N-(2-hydroxy-3-(piperidin-1-yl)propoxy)nicotinimidate 1-oxide, or a pharmaceutically acceptable salt thereof, or N-nitrosopiperidine.

In some embodiments, chemical purity refers to a minimum of 99% of N-{[(2R)-2-hydroxy-3-piperidin-1-ylpropyl]oxy}pyridine-3-carboximidoyl chloride 1-oxide citrate, and maximum of 1% methyl (Z)—N-(2-hydroxy-3-(piperidin-1-yl)propoxy)nicotinimidate 1-oxide, or a pharmaceutically acceptable salt thereof, or N-nitrosopiperidine.

In some embodiments, chemical purity refers to a composition of N-{[(2R)-2-hydroxy-3-piperidin-1-ylpropyl]oxy}pyridine-3-carboximidoyl chloride 1-oxide or a pharmaceutically acceptable salt thereof, wherein methyl (Z)—N-(2-hydroxy-3-(piperidin-1-yl)propoxy)nicotinimidate 1-oxide, or a pharmaceutically acceptable salt thereof, is not detectable.

In some embodiments, chemical purity refers to a composition of N-{[(2R)-2-hydroxy-3-piperidin-1-ylpropyl]oxy}pyridine-3-carboximidoyl chloride 1-oxide or a pharmaceutically acceptable salt thereof, wherein methyl (Z)—N-(2-hydroxy-3-(piperidin-1-yl)propoxy)nicotinimidate 1-oxide, or a pharmaceutically acceptable salt thereof, is not detectable and no other impurities are detected.

In some embodiments, chemical purity refers to a composition of N-{[(2R)-2-hydroxy-3-piperidin-1-ylpropyl]oxy}pyridine-3-carboximidoyl chloride 1-oxide or a pharmaceutically acceptable salt thereof, wherein N-nitrosopiperidine, is not detectable.

In some embodiments, chemical purity refers to a composition of N-{[(2R)-2-hydroxy-3-piperidin-1-ylpropyl]oxy}pyridine-3-carboximidoyl chloride 1-oxide or a pharmaceutically acceptable salt thereof, wherein N-nitrosopiperidine, is not detectable and no other impurities are detected.

In some embodiments, chemical purity refers to a composition of N-{[(2R)-2-hydroxy-3-piperidin-1-ylpropyl]oxy}pyridine-3-carboximidoyl chloride 1-oxide citrate, wherein methyl (Z)—N-(2-hydroxy-3-(piperidin-1-yl)propoxy)nicotinimidate 1-oxide, or a pharmaceutically acceptable salt thereof, and N-nitrosopiperidine are not detectable.

In some embodiments, chemical purity refers to a composition of N-{[(2R)-2-hydroxy-3-piperidin-1-ylpropyl]oxy}pyridine-3-carboximidoyl chloride 1-oxide citrate, wherein methyl (Z)—N-(2-hydroxy-3-(piperidin-1-yl)propoxy)nicotinimidate 1-oxide, or a pharmaceutically acceptable salt thereof, and N-nitrosopiperidine are not detectable and no other impurities are detected.

In some embodiments, chemical purity refers to a composition of N-{[(2R)-2-hydroxy-3-piperidin-1-ylpropyl]oxy}pyridine-3-carboximidoyl chloride 1-oxide citrate, wherein methyl (Z)—N-(2-hydroxy-3-(piperidin-1-yl)propoxy)nicotinimidate 1-oxide, or a pharmaceutically acceptable salt thereof, is not detectable.

In some embodiments, chemical purity refers to a composition of N-{[(2R)-2-hydroxy-3-piperidin-1-ylpropyl]oxy}pyridine-3-carboximidoyl chloride 1-oxide citrate, wherein methyl (Z)—N-(2-hydroxy-3-(piperidin-1-yl)propoxy)nicotinimidate 1-oxide, or a pharmaceutically acceptable salt thereof, is not detectable and no other impurities are detected.

In some embodiments, chemical purity refers to a composition of N-{[(2R)-2-hydroxy-3-piperidin-1-ylpropyl]oxy}pyridine-3-carboximidoyl chloride 1-oxide citrate, wherein N-nitrosopiperidine, is not detectable.

In some embodiments, chemical purity refers to a composition of N-{[(2R)-2-hydroxy-3-piperidin-1-ylpropyl]oxy}pyridine-3-carboximidoyl chloride 1-oxide citrate, wherein N-nitrosopiperidine, is not detectable and no other impurities are detected.

In some embodiments, impurities are detected by HPLC.

In some embodiments, the present disclosure provides a pharmaceutical composition comprising:

a) N-{[(2R)-2-hydroxy-3-piperidin-1-ylpropyl]oxy}pyridine-3-carboximidoyl chloride 1-oxide, or pharmaceutically acceptable salt thereof, having an enantiomeric excess of about 96% ee;

b) less than about 0.1% methyl (Z)—N-(2-hydroxy-3-(piperidin-1-yl)propoxy)nicotinimidate 1-oxide, or a pharmaceutically acceptable salt thereof;

c) less than about 2 ppm N-nitrosopiperidine.

In some embodiments, the present disclosure provides a pharmaceutical composition comprising:
a) N-{[(2R)-2-hydroxy-3-piperidin-1-ylpropyl]oxy}pyridine-3-carboximidoyl chloride 1-oxide citrate, having an enantiomeric excess of about 96% ee;
b) less than about 0.1% methyl (Z)—N-(2-hydroxy-3-(piperidin-1-yl)propoxy)nicotinimidate 1-oxide, or a pharmaceutically acceptable salt thereof;
c) less than about 2 ppm N-nitrosopiperidine.

In some embodiments, the present disclosure provides a pharmaceutical composition comprising:
a) about 98% N-{[(2R)-2-hydroxy-3-piperidin-1-ylpropyl]oxy}pyridine-3-carboximidoyl chloride 1-oxide, or pharmaceutically acceptable salt thereof;
b) about 2% N-{[(2S)-2-hydroxy-3-piperidin-1-ylpropyl]oxy}pyridine-3-carboximidoyl chloride 1-oxide, or pharmaceutically acceptable salt thereof;
c) less than about 0.1% methyl (Z)—N-(2-hydroxy-3-(piperidin-1-yl)propoxy)nicotinimidate 1-oxide, or a pharmaceutically acceptable salt thereof;
d) less than about 2 ppm N-nitrosopiperidine.

In some embodiments, the present disclosure provides a pharmaceutical composition comprising:
a) about 98% N-{[(2R)-2-hydroxy-3-piperidin-1-ylpropyl]oxy}pyridine-3-carboximidoyl chloride 1-oxide citrate;
b) about 2% N-{[(2S)-2-hydroxy-3-piperidin-1-ylpropyl]oxy}pyridine-3-carboximidoyl chloride 1-oxide, or pharmaceutically acceptable salt thereof;
c) less than about 0.1% methyl (Z)—N-(2-hydroxy-3-(piperidin-1-yl)propoxy)nicotinimidate 1-oxide, or a pharmaceutically acceptable salt thereof;
d) less than about 2 ppm N-nitrosopiperidine.

In some embodiments, the (Z)—N-(2-hydroxy-3-(piperidin-1-yl)propoxy)nicotinimidate 1-oxide, or a pharmaceutically acceptable salt thereof is not detectable.

In some embodiments, the N-nitrosopiperidine is not detectable.

In some embodiments, the present disclosure provides a pharmaceutical composition comprising:
a) at least 98.0% N-{[(2R)-2-hydroxy-3-piperidin-1-ylpropyl]oxy}pyridine-3-carboximidoyl chloride 1-oxide citrate; and
b) N-{[(2S)-2-hydroxy-3-piperidin-1-ylpropyl]oxy}pyridine-3-carboximidoyl chloride 1-oxide, or pharmaceutically acceptable salt thereof.

In some embodiments, the present disclosure provides a pharmaceutical composition comprising:
a) at least 98.2% N-{[(2R)-2-hydroxy-3-piperidin-1-ylpropyl]oxy}pyridine-3-carboximidoyl chloride 1-oxide citrate; and
b) N-{[(2S)-2-hydroxy-3-piperidin-1-ylpropyl]oxy}pyridine-3-carboximidoyl chloride 1-oxide, or pharmaceutically acceptable salt thereof.

In some embodiments, the present disclosure provides a pharmaceutical composition comprising:
a) at least 98.4% N-{[(2R)-2-hydroxy-3-piperidin-1-ylpropyl]oxy}pyridine-3-carboximidoyl chloride 1-oxide citrate; and
b) N-{[(2S)-2-hydroxy-3-piperidin-1-ylpropyl]oxy}pyridine-3-carboximidoyl chloride 1-oxide, or pharmaceutically acceptable salt thereof.

In some embodiments, the present disclosure provides a pharmaceutical composition comprising:
a) at least 98.6% N-{[(2R)-2-hydroxy-3-piperidin-1-ylpropyl]oxy}pyridine-3-carboximidoyl chloride 1-oxide citrate; and
b) N-{[(2S)-2-hydroxy-3-piperidin-1-ylpropyl]oxy}pyridine-3-carboximidoyl chloride 1-oxide, or pharmaceutically acceptable salt thereof.

In some embodiments, the present disclosure provides a pharmaceutical composition comprising:
a) at least 98.8% N-{[(2R)-2-hydroxy-3-piperidin-1-ylpropyl]oxy}pyridine-3-carboximidoyl chloride 1-oxide citrate; and
b) N-{[(2S)-2-hydroxy-3-piperidin-1-ylpropyl]oxy}pyridine-3-carboximidoyl chloride 1-oxide, or pharmaceutically acceptable salt thereof.

In some embodiments, the present disclosure provides a pharmaceutical composition comprising:
a) at least 99.0% N-{[(2R)-2-hydroxy-3-piperidin-1-ylpropyl]oxy}pyridine-3-carboximidoyl chloride 1-oxide citrate; and
b) N-{[(2S)-2-hydroxy-3-piperidin-1-ylpropyl]oxy}pyridine-3-carboximidoyl chloride 1-oxide, or pharmaceutically acceptable salt thereof.

In some embodiments, the present disclosure provides a pharmaceutical composition comprising:
a) at least 99.2% N-{[(2R)-2-hydroxy-3-piperidin-1-ylpropyl]oxy}pyridine-3-carboximidoyl chloride 1-oxide citrate; and
b) N-{[(2S)-2-hydroxy-3-piperidin-1-ylpropyl]oxy}pyridine-3-carboximidoyl chloride 1-oxide, or pharmaceutically acceptable salt thereof.

In some embodiments, the present disclosure provides a pharmaceutical composition comprising:
a) at least 99.4% N-{[(2R)-2-hydroxy-3-piperidin-1-ylpropyl]oxy}pyridine-3-carboximidoyl chloride 1-oxide citrate; and
b) N-{[(2S)-2-hydroxy-3-piperidin-1-ylpropyl]oxy}pyridine-3-carboximidoyl chloride 1-oxide, or pharmaceutically acceptable salt thereof.

In some embodiments, the present disclosure provides a pharmaceutical composition comprising:
a) at least 99.6% N-{[(2R)-2-hydroxy-3-piperidin-1-ylpropyl]oxy}pyridine-3-carboximidoyl chloride 1-oxide citrate; and
b) N-{[(2S)-2-hydroxy-3-piperidin-1-ylpropyl]oxy}pyridine-3-carboximidoyl chloride 1-oxide, or pharmaceutically acceptable salt thereof.

In some embodiments, the present disclosure provides a pharmaceutical composition comprising:
a) from 97.0 to 99.8% N-{[(2R)-2-hydroxy-3-piperidin-1-ylpropyl]oxy}pyridine-3-carboximidoyl chloride 1-oxide citrate, such as from 97.2 to 97.4%, such as from 97.4 to 97.6%, such as from 97.6 to 97.8%, such as from 97.8 to 98.0%, such as from 98.0 to 98.2%, such as from 98.2 to 98.4%, such as from 98.4 to 98.6%, such as from 98.6 to 98.8%, such as from 98.8 to 99.0%, such as from 99.0 to 99.2%, such as from 99.2 to 99.4%, such as from 99.4 to 99.6%, or such as from 99.6 to 99.8%; and
b) N-{[(2S)-2-hydroxy-3-piperidin-1-ylpropyl]oxy}pyridine-3-carboximidoyl chloride 1-oxide, or pharmaceutically acceptable salt thereof.

In some embodiments, the present disclosure provides a pharmaceutical composition comprising:
a) at least 98.0% N-{[(2R)-2-hydroxy-3-piperidin-1-ylpropyl]oxy}pyridine-3-carboximidoyl chloride 1-oxide citrate;
b) 1.9% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 98.1% N-{[(2R)-2-hydroxy-3-piperidin-1-yl-propyl]oxy}pyridine-3-carboximidoyl chloride 1-oxide citrate;
b) 1.8% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 98.2% N-{[(2R)-2-hydroxy-3-piperidin-1-yl-propyl]oxy}pyridine-3-carboximidoyl chloride 1-oxide citrate;
b) 1.7% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 98.3% N-{[(2R)-2-hydroxy-3-piperidin-1-yl-propyl]oxy}pyridine-3-carboximidoyl chloride 1-oxide citrate;
b) 1.6% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 98.4% N-{[(2R)-2-hydroxy-3-piperidin-1-yl-propyl]oxy}pyridine-3-carboximidoyl chloride 1-oxide citrate;
b) 1.5% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 98.5% N-{[(2R)-2-hydroxy-3-piperidin-1-yl-propyl]oxy}pyridine-3-carboximidoyl chloride 1-oxide citrate;
b) 1.4% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 98.6% N-{[(2R)-2-hydroxy-3-piperidin-1-yl-propyl]oxy}pyridine-3-carboximidoyl chloride 1-oxide citrate;
b) 1.3% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 98.7% N-{[(2R)-2-hydroxy-3-piperidin-1-yl-propyl]oxy}pyridine-3-carboximidoyl chloride 1-oxide citrate;
b) 1.2% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 98.8% N-{[(2R)-2-hydroxy-3-piperidin-1-yl-propyl]oxy}pyridine-3-carboximidoyl chloride 1-oxide citrate;
b) 1.1% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 98.9% N-{[(2R)-2-hydroxy-3-piperidin-1-yl-propyl]oxy}pyridine-3-carboximidoyl chloride 1-oxide citrate;
b) 1.0% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 99.0% N-{[(2R)-2-hydroxy-3-piperidin-1-yl-propyl]oxy}pyridine-3-carboximidoyl chloride 1-oxide citrate;
b) 0.9% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 99.1% N-{[(2R)-2-hydroxy-3-piperidin-1-yl-propyl]oxy}pyridine-3-carboximidoyl chloride 1-oxide citrate;
b) 0.8% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 99.2% N-{[(2R)-2-hydroxy-3-piperidin-1-ylpropyl]oxy}pyridine-3-carboximidoyl chloride 1-oxide citrate;
b) 0.7% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 99.3% N-{[(2R)-2-hydroxy-3-piperidin-1-ylpropyl]oxy}pyridine-3-carboximidoyl chloride 1-oxide citrate;
b) 0.6% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 99.4% N-{[(2R)-2-hydroxy-3-piperidin-1-ylpropyl]oxy}pyridine-3-carboximidoyl chloride 1-oxide citrate;
b) 0.5% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 99.5% N-{[(2R)-2-hydroxy-3-piperidin-1-ylpropyl]oxy}pyridine-3-carboximidoyl chloride 1-oxide citrate;
b) 0.4% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 99.6% N-{[(2R)-2-hydroxy-3-piperidin-1-ylpropyl]oxy}pyridine-3-carboximidoyl chloride 1-oxide citrate;
b) 0.3% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 99.7% N-{[(2R)-2-hydroxy-3-piperidin-1-ylpropyl]oxy}pyridine-3-carboximidoyl chloride 1-oxide citrate;
b) 0.2% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

In some embodiments, the present disclosure provides a pharmaceutical composition comprising:
a) at least 99.8% N-{[(2R)-2-hydroxy-3-piperidin-1-ylpropyl]oxy}pyridine-3-carboximidoyl chloride 1-oxide citrate;
b) 0.1% or less N-{[(2S)-2-hydroxy-3-piperidin-1-ylpropyl]oxy}pyridine-3-carboximidoyl chloride 1-oxide, or pharmaceutically acceptable salt thereof;
c) 0.1% or less methyl (Z)—N-(2-hydroxy-3-(piperidin-1-yl)propoxy)nicotinimidate 1-oxide, or a pharmaceutically acceptable salt thereof;
d) less than 2 ppm N-nitrosopiperidine.

Formulation

In some embodiments, the present disclosure provides an oral formulation comprising N-{[(2R)-2-hydroxy-3-piperidin-1-ylpropyl]oxy}pyridine-3-carboximidoyl chloride 1-oxide, or a pharmaceutically acceptable salt thereof, and at least one pharmaceutically acceptable excipient.

In some embodiments, the present disclosure provides an oral formulation comprising N-{[(2R)-2-hydroxy-3-piperidin-1-ylpropyl]oxy}pyridine-3-carboximidoyl chloride 1-oxide citrate, and at least one pharmaceutically acceptable excipient.

In some embodiments, the oral formulation comprises a capsule.

In some embodiments, the oral formulation comprises a filler.

In some embodiments, the oral formulation comprises a lubricant.

In some embodiments, the present disclosure provides a pharmaceutical composition comprising N-{[(2R)-2-hydroxy-3-piperidin-1-ylpropyl]oxy}pyridine-3-carboximidoyl chloride 1-oxide, or a pharmaceutically acceptable salt thereof, and at least one pharmaceutically acceptable excipient.

In some embodiments, the present disclosure provides a pharmaceutical composition comprising N-{[(2R)-2-hydroxy-3-piperidin-1-ylpropyl]oxy}pyridine-3-carboximidoyl chloride 1-oxide citrate and at least one pharmaceutically acceptable excipient.

In some embodiments, the pharmaceutical composition comprises a capsule.

In some embodiments, the pharmaceutical composition comprises a filler.

In some embodiments, the pharmaceutical composition comprises a lubricant.

In some embodiments, the capsule comprises a capsule shell.

In some embodiments, the capsule comprises hydroxypropyl methylcellulose (HPMC), titanium dioxide, and optionally one or more colorant.

In some embodiments, the capsule shell comprises hydroxypropyl methylcellulose (HPMC), titanium dioxide, and optionally one or more colorant.

In some embodiments, the filler is microcrystalline cellulose (MCC).

In some embodiments, the lubricant is magnesium stearate.

In some embodiments, the N-{[(2R)-2-hydroxy-3-piperidin-1-ylpropyl]oxy}pyridine-3-carboximidoyl chloride 1-oxide, or pharmaceutically acceptable salt thereof is present at a dosage from about 20 mg to about 500 mg.

In some embodiments, the N-{[(2R)-2-hydroxy-3-piperidin-1-ylpropyl]oxy}pyridine-3-carboximidoyl chloride 1-oxide is present at a dosage from about 20 mg to about 500 mg.

In some embodiments, the N-{[(2R)-2-hydroxy-3-piperidin-1-ylpropyl]oxy}pyridine-3-carboximidoyl chloride 1-oxide citrate is present at a dosage from about 20 mg to about 500 mg.

In some embodiments, the N-{[(2R)-2-hydroxy-3-piperidin-1-ylpropyl]oxy}pyridine-3-carboximidoyl chloride 1-oxide, or pharmaceutically acceptable salt thereof is present at a dosage from about 50 mg to about 500 mg.

In some embodiments, the N-{[(2R)-2-hydroxy-3-piperidin-1-ylpropyl]oxy}pyridine-3-carboximidoyl chloride 1-oxide is present at a dosage from about 50 mg to about 500 mg.

In some embodiments, the N-{[(2R)-2-hydroxy-3-piperidin-1-ylpropyl]oxy}pyridine-3-carboximidoyl chloride 1-oxide citrate is present at a dosage from about 50 mg to about 500 mg.

In some embodiments, the N-{[(2R)-2-hydroxy-3-piperidin-1-ylpropyl]oxy}pyridine-3-carboximidoyl chloride 1-oxide, or pharmaceutically acceptable salt thereof, is present at a dosage of about 31 mg, about 47 mg, about 62 mg, about 93 mg, or about 124 mg.

In some embodiments, the N-{[(2R)-2-hydroxy-3-piperidin-1-ylpropyl]oxy}pyridine-3-carboximidoyl chloride 1-oxide is present at a dosage of about 31 mg, about 47 mg, about 62 mg, about 93 mg, or about 124 mg.

In some embodiments, the N-{[(2R)-2-hydroxy-3-piperidin-1-ylpropyl]oxy}pyridine-3-carboximidoyl chloride 1-oxide, or pharmaceutically acceptable salt thereof, is present at a dosage of about 47 mg, about 62 mg, about 93 mg, or about 124 mg.

In some embodiments, the N-{[(2R)-2-hydroxy-3-piperidin-1-ylpropyl]oxy}pyridine-3-carboximidoyl chloride 1-oxide is present at a dosage of about 47 mg, about 62 mg, about 93 mg, or about 124 mg.

In some embodiments, the N-{[(2R)-2-hydroxy-3-piperidin-1-ylpropyl]oxy}pyridine-3-carboximidoyl chloride 1-oxide citrate is present at a dosage of about 50 mg, about 75 mg, about 100 mg, about 150 mg, about 200 mg, or about 400 mg.

In some embodiments, the N-{[(2R)-2-hydroxy-3-piperidin-1-ylpropyl]oxy}pyridine-3-carboximidoyl chloride 1-oxide citrate is present at a dosage of about 75 mg, about 100 mg, about 150 mg, about 200 mg, or about 400 mg.

In some embodiments, the N-{[(2R)-2-hydroxy-3-piperidin-1-ylpropyl]oxy}pyridine-3-carboximidoyl chloride 1-oxide citrate is present at a dosage of about 50 mg, about 75 mg, about 100 mg, about 150 mg, or about 200 mg.

In some embodiments, the N-{[(2R)-2-hydroxy-3-piperidin-1-ylpropyl]oxy}pyridine-3-carboximidoyl chloride 1-oxide citrate is present at a dosage of about 75 mg, about 100 mg, about 150 mg, or about 200 mg.

In some embodiments, the oral formulation comprises from about 20% to about 60% w/w of N-{[(2R)-2-hydroxy-3-piperidin-1-ylpropyl]oxy}pyridine-3-carboximidoyl chloride 1-oxide, or a pharmaceutically acceptable salt thereof.

In some embodiments, the oral formulation comprises about 20%, about 25%, about 30%, about 35%, about 40%, about 45%, about 50%, about 55%, or about 60% w/w of N-{[(2R)-2-hydroxy-3-piperidin-1-ylpropyl]oxy}pyridine-3-carboximidoyl chloride 1-oxide, or a pharmaceutically acceptable salt thereof.

In some embodiments, the oral formulation comprises from about 20% to about 60% w/w of N-{[(2R)-2-hydroxy-3-piperidin-1-ylpropyl]oxy}pyridine-3-carboximidoyl chloride 1-oxide citrate.

In some embodiments, the oral formulation comprises about 20%, about 25%, about 30%, about 35%, about 40%, about 45%, about 50%, about 55%, or about 60% w/w of N-{[(2R)-2-hydroxy-3-piperidin-1-ylpropyl]oxy}pyridine-3-carboximidoyl chloride 1-oxide citrate.

In some embodiments, the oral formulation comprises about 26.3% or about 52.6% w/w of N-{[(2R)-2-hydroxy-3-piperidin-1-ylpropyl]oxy}pyridine-3-carboximidoyl chloride 1-oxide citrate.

In some embodiments, the oral formulation comprises from about 40% to about 80% w/w of microcrystalline cellulose.

In some embodiments, the oral formulation comprises about 40%, about 45%, about 50%, about 55%, about 60%, about 65%, about 70%, about 75%, or about 80% w/w of microcrystalline cellulose.

In some embodiments, the oral formulation comprises about 73.2% or about 46.9% w/w of microcrystalline cellulose.

In some embodiments, the oral formulation comprises from about 0.0% to about 1.0% magnesium stearate.

In some embodiments, the oral formulation comprises about 0.0%, about 0.01%, about 0.02%, about 0.03%, about 0.04%, about 0.05%, about 0.06%, about 0.07%, about 0.08%, about 0.09%, or about 1.0% magnesium stearate.

In some embodiments, the oral formulation comprises about 0.5% magnesium stearate.

In some embodiments, the pharmaceutical composition comprises from about 20% to about 60% w/w of N-{[(2R)-2-hydroxy-3-piperidin-1-ylpropyl]oxy}pyridine-3-carboximidoyl chloride 1-oxide, or a pharmaceutically acceptable salt thereof.

In some embodiments, the pharmaceutical composition comprises about 20%, about 25%, about 30%, about 35%, about 40%, about 45%, about 50%, about 55%, or about 60% w/w of N-{[(2R)-2-hydroxy-3-piperidin-1-ylpropyl]oxy}pyridine-3-carboximidoyl chloride 1-oxide, or a pharmaceutically acceptable salt thereof.

In some embodiments, the pharmaceutical composition comprises from about 20% to about 60% w/w of N-{[(2R)-2-hydroxy-3-piperidin-1-ylpropyl]oxy}pyridine-3-carboximidoyl chloride 1-oxide citrate.

In some embodiments, the pharmaceutical composition comprises about 20%, about 25%, about 30%, about 35%, about 40%, about 45%, about 50%, about 55%, or about 60% w/w of N-{[(2R)-2-hydroxy-3-piperidin-1-ylpropyl]oxy}pyridine-3-carboximidoyl chloride 1-oxide citrate.

In some embodiments, the pharmaceutical composition comprises about 26.3% or about 52.6% w/w of N-{[(2R)-2-hydroxy-3-piperidin-1-ylpropyl]oxy}pyridine-3-carboximidoyl chloride 1-oxide citrate.

In some embodiments, the pharmaceutical composition comprises from about 40% to about 80% w/w of microcrystalline cellulose.

In some embodiments, the pharmaceutical composition comprises about 40%, about 45%, about 50%, about 55%, about 60%, about 65%, about 70%, about 75%, or about 80% w/w of microcrystalline cellulose.

In some embodiments, the pharmaceutical composition comprises about 73.2% or about 46.9% w/w of microcrystalline cellulose.

In some embodiments, the pharmaceutical composition comprises from about 0.0% to about 1.0% w/w of magnesium stearate.

In some embodiments, the pharmaceutical composition comprises about 0.0%, about 0.01%, about 0.02%, about 0.03%, about 0.04%, about 0.05%, about 0.06%, about 0.07%, about 0.08%, about 0.09%, or about 1.0% magnesium stearate.

In some embodiments, the pharmaceutical composition comprises about 0.5% w/w of magnesium stearate.

In some embodiments, the present disclosure provides an unit dosage form of the pharmaceutical composition comprising N-{[(2R)-2-hydroxy-3-piperidin-1-ylpropyl]oxy}pyridine-3-carboximidoyl chloride 1-oxide, or a pharmaceutically acceptable salt thereof and a pharmaceutically acceptable carrier or excipient.

In some embodiments, the present disclosure provides an unit dosage form of the pharmaceutical composition comprising N-{[(2R)-2-hydroxy-3-piperidin-1-ylpropyl]oxy}pyridine-3-carboximidoyl chloride 1-oxide citrate and a pharmaceutically acceptable carrier or excipient.

In some embodiments, the present disclosure provides an oral formulation comprising a unit dosage of the present disclosure and a pharmaceutically acceptable carrier or excipient.

In some embodiments, the unit dosage form comprises N-{[(2R)-2-hydroxy-3-piperidin-1-ylpropyl]oxy}pyridine-3-carboximidoyl chloride 1-oxide, or a pharmaceutically acceptable salt thereof at a dosage from about 50 mg to about 500 mg.

In some embodiments, the unit dosage form comprises N-{[(2R)-2-hydroxy-3-piperidin-1-ylpropyl]oxy}pyridine-3-carboximidoyl chloride 1-oxide at a dosage from about 50 mg to about 500 mg.

In some embodiments, the unit dosage form comprises N-{[(2R)-2-hydroxy-3-piperidin-1-ylpropyl]oxy}pyridine-3-carboximidoyl chloride 1-oxide citrate at a dosage from about 20 mg to about 500 mg.

In some embodiments, the oral formulation comprises the unit dosage form comprising N-{[(2R)-2-hydroxy-3-piperidin-1-ylpropyl]oxy}pyridine-3-carboximidoyl chloride 1-oxide, or a pharmaceutically acceptable salt thereof at a dosage from about 20 mg to about 500 mg.

In some embodiments, the oral formulation comprises the unit dosage form comprising N-{[(2R)-2-hydroxy-3-piperidin-1-ylpropyl]oxy}pyridine-3-carboximidoyl chloride 1-oxide at a dosage from about 20 mg to about 500 mg.

In some embodiments, the oral formulation comprises the unit dosage form comprising N-{[(2R)-2-hydroxy-3-piperidin-1-ylpropyl]oxy}pyridine-3-carboximidoyl chloride 1-oxide citrate at a dosage from about 20 mg to about 500 mg.

In some embodiments, the unit dosage form comprises N-{[(2R)-2-hydroxy-3-piperidin-1-ylpropyl]oxy}pyridine-3-carboximidoyl chloride 1-oxide citrate at a dosage from about 50 mg to about 500 mg.

In some embodiments, the oral formulation comprises the unit dosage form comprising N-{[(2R)-2-hydroxy-3-piperidin-1-ylpropyl]oxy}pyridine-3-carboximidoyl chloride 1-oxide, or a pharmaceutically acceptable salt thereof at a dosage from about 50 mg to about 500 mg.

In some embodiments, the oral formulation comprises the unit dosage form comprising N-{[(2R)-2-hydroxy-3-piperidin-1-ylpropyl]oxy}pyridine-3-carboximidoyl chloride 1-oxide at a dosage from about 50 mg to about 500 mg.

In some embodiments, the oral formulation comprises the unit dosage form comprising N-{[(2R)-2-hydroxy-3-piperidin-1-ylpropyl]oxy}pyridine-3-carboximidoyl chloride 1-oxide citrate at a dosage from about 50 mg to about 500 mg.

In some embodiments, the oral formulation comprises the unit dosage form comprising N-{[(2R)-2-hydroxy-3-piperidin-1-ylpropyl]oxy}pyridine-3-carboximidoyl chloride 1-oxide, or a pharmaceutically acceptable salt thereof at a dosage of about 31 mg, about 47 mg, about 62 mg, about 93 mg, or about 124 mg.

In some embodiments, the oral formulation comprises the unit dosage form comprising N-{[(2R)-2-hydroxy-3-piperidin-1-ylpropyl]oxy}pyridine-3-carboximidoyl chloride 1-oxide at a dosage of about 31 mg, about 47 mg, about 62 mg, about 93 mg, or about 124 mg.

In some embodiments, the oral formulation comprises the unit dosage form comprising N-{[(2R)-2-hydroxy-3-piperidin-1-ylpropyl]oxy}pyridine-3-carboximidoyl chloride 1-oxide, or a pharmaceutically acceptable salt thereof at a dosage of about 47 mg, about 62 mg, about 93 mg, or about 124 mg.

In some embodiments, the oral formulation comprises the unit dosage form comprising N-{[(2R)-2-hydroxy-3-piperidin-1-ylpropyl]oxy}pyridine-3-carboximidoyl chloride 1-oxide at a dosage of about 47 mg, about 62 mg, about 93 mg, or about 124 mg.

In some embodiments, the oral formulation comprises the unit dosage form comprising N-{[(2R)-2-hydroxy-3-piperidin-1-ylpropyl]oxy}pyridine-3-carboximidoyl chloride 1-oxide citrate at a dosage of about 50 mg, about 75 mg, about 100 mg, about 150 mg, about 200 mg, or about 400 mg.

In some embodiments, the oral formulation comprises the unit dosage form comprising N-{[(2R)-2-hydroxy-3-piperidin-1-ylpropyl]oxy}pyridine-3-carboximidoyl chloride 1-oxide citrate at a dosage of about 50 mg, about 75 mg, about 100 mg, about 150 mg, or about 200 mg.

In some embodiments, the oral formulation comprises the unit dosage form comprising N-{[(2R)-2-hydroxy-3-piperidin-1-ylpropyl]oxy}pyridine-3-carboximidoyl chloride 1-oxide citrate at a dosage of about 75 mg, about 100 mg, about 150 mg, about 200 mg, or about 400 mg.

In some embodiments, the oral formulation comprises the unit dosage form comprising N-{[(2R)-2-hydroxy-3-piperidin-1-ylpropyl]oxy}pyridine-3-carboximidoyl chloride 1-oxide citrate at a dosage of about 75 mg, about 100 mg, about 150 mg, or about 200 mg.

In some embodiments, the present disclosure provides a kit comprising a unit dosage form and instructions for administration.

In some embodiments, the kit further comprises prescribing information and/or multiple unit doses.

In some embodiments of the oral formulation, the capsule is blue, green, yellow, orange, or red.

In some embodiments of the pharmaceutical composition, the capsule is blue, green, yellow, orange, or red.

In some embodiments of the unit dosage, the capsule is blue, green, yellow, orange, or red.

In some embodiments of the oral formulation, the capsule has a white body.

In some embodiments of the pharmaceutical composition, the capsule has a white body.

In some embodiments of the unit dosage, the capsule has a white body.

In some embodiments of the oral formulation, the capsule is a size "0".

In some embodiments of the pharmaceutical composition, the capsule is a size "0".

In some embodiments of the unit dosage, the capsule is a size "0".

In some embodiments, the capsules comprise an N-{[(2R)-2-hydroxy-3-piperidin-1-ylpropyl]oxy}pyridine-3-carboximidoyl chloride 1-oxide citrate dosage of about 31 mg, about 50 mg, about 75 mg, about 100, about 150 mg, or about 200 mg.

In some embodiments, the capsules comprise an N-{[(2R)-2-hydroxy-3-piperidin-1-ylpropyl]oxy}pyridine-3-carboximidoyl chloride 1-oxide citrate dosage of about 50 mg, about 75 mg, about 100, about 150 mg, or about 200 mg.

In some embodiments, the capsules comprise an N-{[(2R)-2-hydroxy-3-piperidin-1-ylpropyl]oxy}pyridine-3-carboximidoyl chloride 1-oxide citrate dosage of about 50 mg, about 75 mg, or about 100.

In some embodiments, the capsule is filled with a low powder blend of N-{[(2R)-2-hydroxy-3-piperidin-1-ylpropyl]oxy}pyridine-3-carboximidoyl chloride 1-oxide citrate.

In some embodiments, the low powder blend comprises an 100 mg powder blend, wherein N-{[(2R)-2-hydroxy-3-piperidin-1-ylpropyl]oxy}pyridine-3-carboximidoyl chloride 1-oxide citrate is present in about 26.2% w/w.

In some embodiments, the capsules comprising an N-{[(2R)-2-hydroxy-3-piperidin-1-ylpropyl]oxy}pyridine-3-carboximidoyl chloride 1-oxide citrate dosage of about 50 mg, about 75 mg, or about 100, are filled with the low powder blend.

In some embodiments, the capsules comprise an N-{[(2R)-2-hydroxy-3-piperidin-1-ylpropyl]oxy}pyridine-3-carboximidoyl chloride 1-oxide citrate dosage of about 150 mg or about 200 mg.

In some embodiments, the capsule is filled with a high powder blend of N-{[(2R)-2-hydroxy-3-piperidin-1-ylpropyl]oxy}pyridine-3-carboximidoyl chloride 1-oxide citrate.

In some embodiments, the high powder blend comprises an 200 mg powder blend, wherein N-{[(2R)-2-hydroxy-3-piperidin-1-ylpropyl]oxy}pyridine-3-carboximidoyl chloride 1-oxide citrate is present in about 52.6% w/w.

In some embodiments, the capsules comprising an N-{[(2R)-2-hydroxy-3-piperidin-1-ylpropyl]oxy}pyridine-3-carboximidoyl chloride 1-oxide citrate dosage of about 150 mg or about 200 mg are filled with the high powder blend.

In some embodiments, the oral formulation comprises ultra-pure N-{[(2R)-2-hydroxy-3-piperidin-1-ylpropyl]oxy}pyridine-3-carboximidoyl chloride 1-oxide citrate.

In some embodiments, the pharmaceutical composition comprises ultra-pure N-{[(2R)-2-hydroxy-3-piperidin-1-ylpropyl]oxy}pyridine-3-carboximidoyl chloride 1-oxide citrate.

In some embodiments, the unit dosage comprises ultra-pure N-{[(2R)-2-hydroxy-3-piperidin-1-ylpropyl]oxy}pyridine-3-carboximidoyl chloride 1-oxide citrate.

In some embodiments, the purity is determined by HPLC.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 98.0%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 98.0%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 98.0%.

In some embodiments, the oral formulation comprises N-{[(2R)-2-hydroxy-3-piperidin-1-ylpropyl]oxy}pyridine-3-carboximidoyl chloride 1-oxide citrate having a purity greater than or equal to 98.0%.

In some embodiments, the pharmaceutical composition comprises N-{[(2R)-2-hydroxy-3-piperidin-1-ylpropyl]oxy}pyridine-3-carboximidoyl chloride 1-oxide citrate having a purity greater than or equal to 98.0%.

In some embodiments, the unit dosage comprises N-{[(2R)-2-hydroxy-3-piperidin-1-ylpropyl]oxy}pyridine-3-carboximidoyl chloride 1-oxide citrate having a purity greater than or equal to 98.0%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 98.5%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 98.5%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 98.5%.

In some embodiments, the oral formulation comprises N-{[(2R)-2-hydroxy-3-piperidin-1-ylpropyl]oxy}pyridine-3-carboximidoyl chloride 1-oxide citrate having a purity greater than or equal to 98.5%.

In some embodiments, the pharmaceutical composition comprises N-{[(2R)-2-hydroxy-3-piperidin-1-ylpropyl]oxy}pyridine-3-carboximidoyl chloride 1-oxide citrate having a purity greater than or equal to 98.5%.

In some embodiments, the unit dosage comprises N-{[(2R)-2-hydroxy-3-piperidin-1-ylpropyl]oxy}pyridine-3-carboximidoyl chloride 1-oxide citrate having a purity greater than or equal to 98.5%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.0%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.0%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.0%.

In some embodiments, the oral formulation comprises N-{[(2R)-2-hydroxy-3-piperidin-1-ylpropyl]oxy}pyridine-3-carboximidoyl chloride 1-oxide citrate having a purity greater than or equal to 99.0%.

In some embodiments, the pharmaceutical composition comprises N-{[(2R)-2-hydroxy-3-piperidin-1-ylpropyl]oxy}pyridine-3-carboximidoyl chloride 1-oxide citrate having a purity greater than or equal to 99.0%.

In some embodiments, the unit dosage comprises N-{[(2R)-2-hydroxy-3-piperidin-1-ylpropyl]oxy}pyridine-3- carboximidoyl chloride 1-oxide citrate having a purity greater than or equal to 99.0%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.25%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.25%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.25%.

In some embodiments, the oral formulation comprises N-{[(2R)-2-hydroxy-3-piperidin-1-ylpropyl]oxy}pyridine-3-carboximidoyl chloride 1-oxide citrate having a purity greater than or equal to 99.25%.

In some embodiments, the pharmaceutical composition comprises N-{[(2R)-2-hydroxy-3-piperidin-1-ylpropyl]oxy}pyridine-3-carboximidoyl chloride 1-oxide citrate having a purity greater than or equal to 99.25%.

In some embodiments, the unit dosage comprises N-{[(2R)-2-hydroxy-3-piperidin-1-ylpropyl]oxy}pyridine-3-carboximidoyl chloride 1-oxide citrate having a purity greater than or equal to 99.25%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.5%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.5%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.5%.

In some embodiments, the oral formulation comprises N-{[(2R)-2-hydroxy-3-piperidin-1-ylpropyl]oxy}pyridine-3-carboximidoyl chloride 1-oxide citrate having a purity greater than or equal to 99.5%.

In some embodiments, the pharmaceutical composition comprises N-{[(2R)-2-hydroxy-3-piperidin-1-ylpropyl]oxy}pyridine-3-carboximidoyl chloride 1-oxide citrate having a purity greater than or equal to 99.5%.

In some embodiments, the unit dosage comprises N-{[(2R)-2-hydroxy-3-piperidin-1-ylpropyl]oxy}pyridine-3-carboximidoyl chloride 1-oxide citrate having a purity greater than or equal to 99.5%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.6%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.6%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.6%.

In some embodiments, the oral formulation comprises N-{[(2R)-2-hydroxy-3-piperidin-1-ylpropyl]oxy}pyridine-3-carboximidoyl chloride 1-oxide citrate having a purity greater than or equal to 99.6%.

In some embodiments, the pharmaceutical composition comprises N-{[(2R)-2-hydroxy-3-piperidin-1-ylpropyl]oxy}pyridine-3-carboximidoyl chloride 1-oxide citrate having a purity greater than or equal to 99.6%.

In some embodiments, the unit dosage comprises N-{[(2R)-2-hydroxy-3-piperidin-1-ylpropyl]oxy}pyridine-3-carboximidoyl chloride 1-oxide citrate having a purity greater than or equal to 99.6%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.7%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.7%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.7%.

In some embodiments, the oral formulation comprises N-{[(2R)-2-hydroxy-3-piperidin-1-ylpropyl]oxy}pyridine-3-carboximidoyl chloride 1-oxide citrate having a purity greater than or equal to 99.7%.

In some embodiments, the pharmaceutical composition comprises N-{[(2R)-2-hydroxy-3-piperidin-1-ylpropyl]oxy}pyridine-3-carboximidoyl chloride 1-oxide citrate having a purity greater than or equal to 99.7%.

In some embodiments, the unit dosage comprises N-{[(2R)-2-hydroxy-3-piperidin-1-ylpropyl]oxy}pyridine-3-carboximidoyl chloride 1-oxide citrate having a purity greater than or equal to 99.7%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.8%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.8%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 99.8%.

In some embodiments, the oral formulation comprises N-{[(2R)-2-hydroxy-3-piperidin-1-ylpropyl]oxy}pyridine-3-carboximidoyl chloride 1-oxide citrate having a purity greater than or equal to 99.8%.

In some embodiments, the pharmaceutical composition comprises N-{[(2R)-2-hydroxy-3-piperidin-1-ylpropyl]oxy}pyridine-3-carboximidoyl chloride 1-oxide citrate having a purity greater than or equal to 99.8%.

In some embodiments, the unit dosage comprises N-{[(2R)-2-hydroxy-3-piperidin-1-ylpropyl]oxy}pyridine-3-carboximidoyl chloride 1-oxide citrate having a purity greater than or equal to 99.8%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a chiral purity.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a chiral purity.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a chiral purity.

In some embodiments, the oral formulation comprises N-{[(2R)-2-hydroxy-3-piperidin-1-ylpropyl]oxy}pyridine-3-carboximidoyl chloride 1-oxide citrate having a chiral purity.

In some embodiments, the pharmaceutical composition comprises N-{[(2R)-2-hydroxy-3-piperidin-1-ylpropyl]oxy}pyridine-3-carboximidoyl chloride 1-oxide citrate having a chiral purity.

In some embodiments, the unit dosage comprises N-{[(2R)-2-hydroxy-3-piperidin-1-ylpropyl]oxy}pyridine-3-carboximidoyl chloride 1-oxide citrate having a chiral purity.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a chiral purity greater than or equal to 98.0%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a chiral purity greater than or equal to 98.0%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a chiral purity greater than or equal to 98.0%.

In some embodiments, the oral formulation comprises N-{[(2R)-2-hydroxy-3-piperidin-1-ylpropyl]oxy}pyridine-3-carboximidoyl chloride 1-oxide citrate having a chiral purity greater than or equal to 98.0%.

In some embodiments, the pharmaceutical composition comprises N-{[(2R)-2-hydroxy-3-piperidin-1-ylpropyl]oxy}pyridine-3-carboximidoyl chloride 1-oxide citrate having a chiral purity greater than or equal to 98.0%.

In some embodiments, the unit dosage comprises N-{[(2R)-2-hydroxy-3-piperidin-1-ylpropyl]oxy}pyridine-3-carboximidoyl chloride 1-oxide citrate having a chiral purity greater than or equal to 98.0%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a chiral purity greater than or equal to 98.5%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a chiral purity greater than or equal to 98.5%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a chiral purity greater than or equal to 98.5%.

In some embodiments, the oral formulation comprises N-{[(2R)-2-hydroxy-3-piperidin-1-ylpropyl]oxy}pyridine-3-carboximidoyl chloride 1-oxide citrate having a chiral purity greater than or equal to 98.5%.

In some embodiments, the pharmaceutical composition comprises N-{[(2R)-2-hydroxy-3-piperidin-1-ylpropyl]oxy}pyridine-3-carboximidoyl chloride 1-oxide citrate having a chiral purity greater than or equal to 98.5%.

In some embodiments, the unit dosage comprises N-{[(2R)-2-hydroxy-3-piperidin-1-ylpropyl]oxy}pyridine-3-carboximidoyl chloride 1-oxide citrate having a chiral purity greater than or equal to 98.5%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a chiral purity greater than or equal to 99.0%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a chiral purity greater than or equal to 99.0%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a chiral purity greater than or equal to 99.0%.

In some embodiments, the oral formulation comprises N-{[(2R)-2-hydroxy-3-piperidin-1-ylpropyl]oxy}pyridine-3-carboximidoyl chloride 1-oxide citrate having a chiral purity greater than or equal to 99.0%.

In some embodiments, the pharmaceutical composition comprises N-{[(2R)-2-hydroxy-3-piperidin-1-ylpropyl]oxy}pyridine-3-carboximidoyl chloride 1-oxide citrate having a chiral purity greater than or equal to 99.0%.

In some embodiments, the unit dosage comprises N-{[(2R)-2-hydroxy-3-piperidin-1-ylpropyl]oxy}pyridine-3-carboximidoyl chloride 1-oxide citrate having a chiral purity greater than or equal to 99.0%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a chemical purity.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a chemical purity.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a chemical purity.

In some embodiments, the oral formulation comprises N-{[(2R)-2-hydroxy-3-piperidin-1-ylpropyl]oxy}pyridine-3-carboximidoyl chloride 1-oxide citrate having a chemical purity.

In some embodiments, the pharmaceutical composition comprises N-{[(2R)-2-hydroxy-3-piperidin-1-ylpropyl]oxy}pyridine-3-carboximidoyl chloride 1-oxide citrate having a chemical purity.

In some embodiments, the unit dosage comprises N-{[(2R)-2-hydroxy-3-piperidin-1-ylpropyl]oxy}pyridine-3-carboximidoyl chloride 1-oxide citrate having a chemical purity.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 98.0%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 98.0%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 98.0%.

In some embodiments, the oral formulation comprises N-{[(2R)-2-hydroxy-3-piperidin-1-ylpropyl]oxy}pyridine-3-carboximidoyl chloride 1-oxide citrate having a chemical purity greater than or equal to 98.0%.

In some embodiments, the pharmaceutical composition comprises N-{[(2R)-2-hydroxy-3-piperidin-1-ylpropyl]oxy}pyridine-3-carboximidoyl chloride 1-oxide citrate having a chemical purity greater than or equal to 98.0%.

In some embodiments, the unit dosage comprises N-{[(2R)-2-hydroxy-3-piperidin-1-ylpropyl]oxy}pyridine-3-carboximidoyl chloride 1-oxide citrate having a chemical purity greater than or equal to 98.0%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 98.5%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 98.5%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 98.5%.

In some embodiments, the oral formulation comprises N-{[(2R)-2-hydroxy-3-piperidin-1-ylpropyl]oxy}pyridine-3-carboximidoyl chloride 1-oxide citrate having a chemical purity greater than or equal to 98.5%.

In some embodiments, the pharmaceutical composition comprises N-{[(2R)-2-hydroxy-3-piperidin-1-ylpropyl]oxy}pyridine-3-carboximidoyl chloride 1-oxide citrate having a chemical purity greater than or equal to 98.5%.

In some embodiments, the unit dosage comprises N-{[(2R)-2-hydroxy-3-piperidin-1-ylpropyl]oxy}pyridine-3-carboximidoyl chloride 1-oxide citrate having a chemical purity greater than or equal to 98.5%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.0%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.0%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.0%.

In some embodiments, the oral formulation comprises N-{[(2R)-2-hydroxy-3-piperidin-1-ylpropyl]oxy}pyridine-3-carboximidoyl chloride 1-oxide citrate having a chemical purity greater than or equal to 99.0%.

In some embodiments, the pharmaceutical composition comprises N-{[(2R)-2-hydroxy-3-piperidin-1-ylpropyl]oxy}pyridine-3-carboximidoyl chloride 1-oxide citrate having a chemical purity greater than or equal to 99.0%.

In some embodiments, the unit dosage comprises N-{[(2R)-2-hydroxy-3-piperidin-1-ylpropyl]oxy}pyridine-3-carboximidoyl chloride 1-oxide citrate having a chemical purity greater than or equal to 99.0%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.25%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.25%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.25%.

In some embodiments, the oral formulation comprises N-{[(2R)-2-hydroxy-3-piperidin-1-ylpropyl]oxy}pyridine-3-carboximidoyl chloride 1-oxide citrate having a chemical purity greater than or equal to 99.25%.

In some embodiments, the pharmaceutical composition comprises N-{[(2R)-2-hydroxy-3-piperidin-1-ylpropyl]oxy}pyridine-3-carboximidoyl chloride 1-oxide citrate having a chemical purity greater than or equal to 99.25%.

In some embodiments, the unit dosage comprises N-{[(2R)-2-hydroxy-3-piperidin-1-ylpropyl]oxy}pyridine-3-carboximidoyl chloride 1-oxide citrate having a chemical purity greater than or equal to 99.25%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.5%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.5%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.5%.

In some embodiments, the oral formulation comprises N-{[(2R)-2-hydroxy-3-piperidin-1-ylpropyl]oxy}pyridine-3-carboximidoyl chloride 1-oxide citrate having a chemical purity greater than or equal to 99.5%.

In some embodiments, the pharmaceutical composition comprises N-{[(2R)-2-hydroxy-3-piperidin-1-ylpropyl]oxy}pyridine-3-carboximidoyl chloride 1-oxide citrate having a chemical purity greater than or equal to 99.5%.

In some embodiments, the unit dosage comprises N-{[(2R)-2-hydroxy-3-piperidin-1-ylpropyl]oxy}pyridine-3- carboximidoyl chloride 1-oxide citrate having a chemical purity greater than or equal to 99.5%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.6%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.6%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.6%.

In some embodiments, the oral formulation comprises N-{[(2R)-2-hydroxy-3-piperidin-1-ylpropyl]oxy}pyridine-3-carboximidoyl chloride 1-oxide citrate having a chemical purity greater than or equal to 99.6%.

In some embodiments, the pharmaceutical composition comprises N-{[(2R)-2-hydroxy-3-piperidin-1-ylpropyl]oxy}pyridine-3-carboximidoyl chloride 1-oxide citrate having a chemical purity greater than or equal to 99.6%.

In some embodiments, the unit dosage comprises N-{[(2R)-2-hydroxy-3-piperidin-1-ylpropyl]oxy}pyridine-3-carboximidoyl chloride 1-oxide citrate having a chemical purity greater than or equal to 99.6%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.7%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.7%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.7%.

In some embodiments, the oral formulation comprises N-{[(2R)-2-hydroxy-3-piperidin-1-ylpropyl]oxy}pyridine-3-carboximidoyl chloride 1-oxide citrate having a chemical purity greater than or equal to 99.7%.

In some embodiments, the pharmaceutical composition comprises N-{[(2R)-2-hydroxy-3-piperidin-1-ylpropyl]oxy}pyridine-3-carboximidoyl chloride 1-oxide citrate having a chemical purity greater than or equal to 99.7%.

In some embodiments, the unit dosage comprises N-{[(2R)-2-hydroxy-3-piperidin-1-ylpropyl]oxy}pyridine-3-carboximidoyl chloride 1-oxide citrate having a chemical purity greater than or equal to 99.7%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.8%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.8%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.8%.

In some embodiments, the oral formulation comprises N-{[(2R)-2-hydroxy-3-piperidin-1-ylpropyl]oxy}pyridine-3-carboximidoyl chloride 1-oxide citrate having a chemical purity greater than or equal to 99.8%.

In some embodiments, the pharmaceutical composition comprises N-{[(2R)-2-hydroxy-3-piperidin-1-ylpropyl]oxy}pyridine-3-carboximidoyl chloride 1-oxide citrate having a chemical purity greater than or equal to 99.8%.

In some embodiments, the unit dosage comprises N-{[(2R)-2-hydroxy-3-piperidin-1-ylpropyl]oxy}pyridine-3-carboximidoyl chloride 1-oxide citrate having a chemical purity greater than or equal to 99.8%.

In some embodiments, the oral formulation comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.9%.

In some embodiments, the pharmaceutical composition comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.9%.

In some embodiments, the unit dosage comprises N-{[(2R)-2-hydroxy-3-piperidin-1-ylpropyl]oxy}pyridine-3-carboximidoyl chloride 1-oxide, or pharmaceutically acceptable salt thereof, having a chemical purity greater than or equal to 99.9%.

In some embodiments, the oral formulation comprises N-{[(2R)-2-hydroxy-3-piperidin-1-ylpropyl]oxy}pyridine-3-carboximidoyl chloride 1-oxide citrate having a chemical purity greater than or equal to 99.9%.

In some embodiments, the pharmaceutical composition comprises N-{[(2R)-2-hydroxy-3-piperidin-1-ylpropyl]oxy}pyridine-3-carboximidoyl chloride 1-oxide citrate having a chemical purity greater than or equal to 99.9%.

In some embodiments, the unit dosage comprises N-{[(2R)-2-hydroxy-3-piperidin-1-ylpropyl]oxy}pyridine-3-carboximidoyl chloride 1-oxide citrate having a chemical purity greater than or equal to 99.9%.

In some embodiments, the oral formulation comprises less than 2 ppm impurity.

In some embodiments, the pharmaceutical composition comprises less than 2 ppm impurity.

In some embodiments, the unit dosage comprises less than 2 ppm impurity.

In some embodiments, the oral formulation comprises less than 1 ppm impurity.

In some embodiments, the pharmaceutical composition comprises less than 1 ppm impurity.

In some embodiments, the unit dosage comprises less than 1 ppm impurity.

In some embodiments, the oral formulation comprises no detectable impurity.

In some embodiments, the pharmaceutical composition comprises no detectable impurity.

In some embodiments, the unit dosage comprises no detectable impurity.

In some embodiments, the impurity is N-{[(2S)-2-hydroxy-3-piperidin-1-ylpropyl]oxy}pyridine-3-carboximidoyl chloride 1-oxide or pharmaceutically acceptable salt thereof.

In some embodiments, the impurity is methyl (Z)—N-(2-hydroxy-3-(piperidin-1-yl)propoxy)nicotinimidate 1-oxide or pharmaceutically acceptable salt thereof.

In some embodiments, the oral formulation comprises less than about 0.1% (Z)—N-(2-hydroxy-3-(piperidin-1-yl)propoxy)nicotinimidate 1-oxide or pharmaceutically acceptable salt thereof.

In some embodiments, the pharmaceutical composition comprises less than about 0.1% (Z)—N-(2-hydroxy-3-(piperidin-1-yl)propoxy)nicotinimidate 1-oxide or pharmaceutically acceptable salt thereof.

In some embodiments, the unit dosage comprises less than about 0.1% (Z)—N-(2-hydroxy-3-(piperidin-1-yl)propoxy)nicotinimidate 1-oxide or pharmaceutically acceptable salt thereof.

In some embodiments, the oral formulation comprises less than about 0.05% (Z)—N-(2-hydroxy-3-(piperidin-1-yl)propoxy)nicotinimidate 1-oxide or pharmaceutically acceptable salt thereof.

In some embodiments, the pharmaceutical composition comprises less than about 0.05% (Z)—N-(2-hydroxy-3-(piperidin-1-yl)propoxy)nicotinimidate 1-oxide or pharmaceutically acceptable salt thereof.

In some embodiments, the unit dosage comprises less than about 0.05% (Z)—N-(2-hydroxy-3-(piperidin-1-yl)propoxy)nicotinimidate 1-oxide or pharmaceutically acceptable salt thereof.

In some embodiments, the oral formulation comprises no detectable (Z)—N-(2-hydroxy-3-(piperidin-1-yl)propoxy)nicotinimidate 1-oxide or pharmaceutically acceptable salt thereof.

In some embodiments, the pharmaceutical composition comprises no (Z)—N-(2-hydroxy-3-(piperidin-1-yl)propoxy)nicotinimidate 1-oxide or pharmaceutically acceptable salt thereof.

In some embodiments, the unit dosage comprises no detectable (Z)—N-(2-hydroxy-3-(piperidin-1-yl)propoxy)nicotinimidate 1-oxide or pharmaceutically acceptable salt thereof.

In some embodiments, the impurity is N-nitrosopiperidine.

In some embodiments, the oral formulation comprises less than about 2 ppm N-nitrosopiperidine.

In some embodiments, the pharmaceutical composition comprises less than about 2 ppm N-nitrosopiperidine.

In some embodiments, the unit dosage comprises less than about 2 ppm N-nitrosopiperidine.

In some embodiments, the oral formulation comprises less than about 1.6 ppm N-nitrosopiperidine.

In some embodiments, the pharmaceutical composition comprises less than about 1.6 ppm N-nitrosopiperidine.

In some embodiments, the unit dosage comprises less than about 1.6 ppm N-nitrosopiperidine.

In some embodiments, the oral formulation comprises less than about 1 ppm N-nitrosopiperidine.

In some embodiments, the pharmaceutical composition comprises less than about 1 ppm N-nitrosopiperidine.

In some embodiments, the unit dosage comprises less than about 1 ppm N-nitrosopiperidine.

In some embodiments, the oral formulation comprises less than about 0.8 ppm N-nitrosopiperidine.

In some embodiments, the pharmaceutical composition comprises less than about 0.8 ppm N-nitrosopiperidine.

In some embodiments, the unit dosage comprises less than about 0.8 ppm N-nitrosopiperidine.

In some embodiments, the oral formulation comprises no detectable N-nitrosopiperidine.

In some embodiments, the pharmaceutical composition comprises no N-nitrosopiperidine.

In some embodiments, the unit dosage comprises no detectable N-nitrosopiperidine.

In some embodiments, the impurity is a combination of N-{[(2S)-2-hydroxy-3-piperidin-1-ylpropyl]oxy}pyridine-3-carboximidoyl chloride 1-oxide or pharmaceutically acceptable salt thereof, methyl (Z)—N-(2-hydroxy-3-(piperidin-1-yl)propoxy)nicotinimidate 1-oxide or pharmaceutically acceptable salt thereof, or N-nitrosopiperidine, and combinations thereof.

In some embodiments, the impurity is a combination of N-{[(2S)-2-hydroxy-3-piperidin-1-ylpropyl]oxy}pyridine-3-carboximidoyl chloride 1-oxide or pharmaceutically acceptable salt thereof and methyl (Z)—N-(2-hydroxy-3-(piperidin-1-yl)propoxy)nicotinimidate 1-oxide or pharmaceutically acceptable salt thereof.

In some embodiments, the impurity is a combination of N-{[(2S)-2-hydroxy-3-piperidin-1-ylpropyl]oxy}pyridine-3-carboximidoyl chloride 1-oxide or pharmaceutically acceptable salt thereof and N-nitrosopiperidine.

In some embodiments, the impurity is a combination of methyl (Z)—N-(2-hydroxy-3-(piperidin-1-yl)propoxy)nicotinimidate 1-oxide or pharmaceutically acceptable salt thereof and N-nitrosopiperidine.

In some embodiments, the pharmaceutically acceptable salt is N-{[(2R)-2-hydroxy-3-piperidin-1-ylpropyl]oxy}pyridine-3-carboximidoyl chloride 1-oxide citrate.

Medical Use

In some embodiments, the present disclosure provides a method of treating or preventing Niemann Pick disease, type C in a subject in need thereof, wherein the subject is administered a therapeutically effect amount of the oral formulation comprising N-{[(2R)-2-hydroxy-3-piperidin-1-ylpropyl]oxy}pyridine-3-carboximidoyl chloride 1-oxide, or a pharmaceutically acceptable salt thereof, and at least one pharmaceutically acceptable excipient.

In some embodiments, the present disclosure provides a method of treating or preventing Niemann Pick disease, type C in a subject in need thereof, wherein the subject is administered a therapeutically effect amount of the pharmaceutical composition comprising N-{[(2R)-2-hydroxy-3-piperidin-1-ylpropyl]oxy}pyridine-3-carboximidoyl chloride 1-oxide, or a pharmaceutically acceptable salt thereof, and at least one pharmaceutically acceptable excipient.

In some embodiments, the present disclosure provides a method of treating or preventing Niemann Pick disease, type C in a subject in need thereof, wherein the subject is administered a therapeutically effect amount of the unit dosage comprising N-{[(2R)-2-hydroxy-3-piperidin-1-ylpropyl]oxy}pyridine-3-carboximidoyl chloride 1-oxide, or a pharmaceutically acceptable salt thereof, and at least one pharmaceutically acceptable excipient.

In some embodiments, the present disclosure provides a method of treating or preventing Niemann Pick disease, type C in a subject in need thereof, wherein the subject is administered a therapeutically effect amount of the oral formulation comprising N-{[(2R)-2-hydroxy-3-piperidin-1-ylpropyl]oxy}pyridine-3-carboximidoyl chloride 1-oxide citrate, and at least one pharmaceutically acceptable excipient.

In some embodiments, the present disclosure provides a method of treating or preventing Niemann Pick disease, type C in a subject in need thereof, wherein the subject is administered a therapeutically effect amount of the pharmaceutical composition comprising N-{[(2R)-2-hydroxy-3-piperidin-1-ylpropyl]oxy}pyridine-3-carboximidoyl chloride 1-oxide citrate, and at least one pharmaceutically acceptable excipient.

In some embodiments, the present disclosure provides a method of treating or preventing Niemann Pick disease, type C in a subject in need thereof, wherein the subject is administered a therapeutically effect amount of the unit dosage comprising N-{[(2R)-2-hydroxy-3-piperidin-1-ylpropyl]oxy}pyridine-3-carboximidoyl chloride 1-oxide citrate, and at least one pharmaceutically acceptable excipient.

In some embodiments, the present disclosure provides an oral formulation of N-{[(2R)-2-hydroxy-3-piperidin-1-ylpropyl]oxy}pyridine-3-carboximidoyl chloride 1-oxide, or a pharmaceutically acceptable salt thereof, and at least one pharmaceutically acceptable excipient for use in treating or preventing Niemann Pick disease, type C in a subject in need thereof.

In some embodiments, the present disclosure provides a pharmaceutical composition of N-{[(2R)-2-hydroxy-3-piperidin-1-ylpropyl]oxy}pyridine-3-carboximidoyl chloride 1-oxide, or a pharmaceutically acceptable salt thereof, and at least one pharmaceutically acceptable excipient for use in treating or preventing Niemann Pick disease, type C in a subject in need thereof.

In some embodiments, the present disclosure provides an unit dosage of N-{[(2R)-2-hydroxy-3-piperidin-1-ylpropyl]oxy}pyridine-3-carboximidoyl chloride 1-oxide, or a pharmaceutically acceptable salt thereof, and at least one pharmaceutically acceptable excipient for use in treating or preventing Niemann Pick disease, type C in a subject in need thereof.

In some embodiments, the present disclosure provides an oral formulation of N-{[(2R)-2-hydroxy-3-piperidin-1-ylpropyl]oxy}pyridine-3-carboximidoyl chloride 1-oxide citrate and at least one pharmaceutically acceptable excipient for use in treating or preventing Niemann Pick disease, type C in a subject in need thereof.

In some embodiments, the present disclosure provides a pharmaceutical composition of N-{[(2R)-2-hydroxy-3-piperidin-1-ylpropyl]oxy}pyridine-3-carboximidoyl chloride 1-oxide citrate and at least one pharmaceutically acceptable excipient for use in treating or preventing Niemann Pick disease, type C in a subject in need thereof.

In some embodiments, the present disclosure provides an unit dosage of N-{[(2R)-2-hydroxy-3-piperidin-1-ylpropyl]oxy}pyridine-3-carboximidoyl chloride 1-oxide citrate and at least one pharmaceutically acceptable excipient for use in treating or preventing Niemann Pick disease, type C in a subject in need thereof.

In some embodiments, the present disclosure provides use of an oral formulation of N-{[(2R)-2-hydroxy-3-piperidin-1-ylpropyl]oxy}pyridine-3-carboximidoyl chloride 1-oxide, or a pharmaceutically acceptable salt thereof, and at least one pharmaceutically acceptable excipient for use in the manufacture of a medicament for the treatment or prevention of Niemann Pick disease, type C in a subject in need thereof.

In some embodiments, the present disclosure provides use of a pharmaceutical composition of N-{[(2R)-2-hydroxy-3-piperidin-1-ylpropyl]oxy}pyridine-3-carboximidoyl chloride 1-oxide, or a pharmaceutically acceptable salt thereof, and at least one pharmaceutically acceptable excipient for use in the manufacture of a medicament for the treatment or prevention of Niemann Pick disease, type C in a subject in need thereof.

In some embodiments, the present disclosure provides use of an unit dosage of N-{[(2R)-2-hydroxy-3-piperidin-1-ylpropyl]oxy}pyridine-3-carboximidoyl chloride 1-oxide, or a pharmaceutically acceptable salt thereof, and at least one pharmaceutically acceptable excipient for use in the manufacture of a medicament for the treatment or prevention of Niemann Pick disease, type C in a subject in need thereof.

In some embodiments, the present disclosure provides use of an oral formulation of N-{[(2R)-2-hydroxy-3-piperidin-1-ylpropyl]oxy}pyridine-3-carboximidoyl chloride 1-oxide citrate and at least one pharmaceutically acceptable excipient for use in the manufacture of a medicament for the treatment or prevention of Niemann Pick disease, type C in a subject in need thereof.

In some embodiments, the present disclosure provides use of a pharmaceutical composition of N-{[(2R)-2-hydroxy-3-piperidin-1-ylpropyl]oxy}pyridine-3-carboximidoyl chloride 1-oxide citrate and at least one pharmaceutically acceptable excipient for use in the manufacture of a medicament for the treatment or prevention of Niemann Pick disease, type C in a subject in need thereof.

In some embodiments, the present disclosure provides use of an unit dosage of N-{[(2R)-2-hydroxy-3-piperidin-1-ylpropyl]oxy}pyridine-3-carboximidoyl chloride 1-oxide citrate and at least one pharmaceutically acceptable excipient for use in the manufacture of a medicament for the treatment or prevention of Niemann Pick disease, type C in a subject in need thereof.

In some embodiments, the present disclosure provides use of an oral formulation of N-{[(2R)-2-hydroxy-3-piperidin-1-ylpropyl]oxy}pyridine-3-carboximidoyl chloride 1-oxide, or a pharmaceutically acceptable salt thereof, and at least one pharmaceutically acceptable excipient for the treatment or prevention of Niemann Pick disease, type C in a subject in need thereof.

In some embodiments, the present disclosure provides use of a pharmaceutical composition of N-{[(2R)-2-hydroxy-3-piperidin-1-ylpropyl]oxy}pyridine-3-carboximidoyl chloride 1-oxide, or a pharmaceutically acceptable salt thereof, and at least one pharmaceutically acceptable excipient for the treatment or prevention of Niemann Pick disease, type C in a subject in need thereof.

In some embodiments, the present disclosure provides use of an unit dosage of N-{[(2R)-2-hydroxy-3-piperidin-1-ylpropyl]oxy}pyridine-3-carboximidoyl chloride 1-oxide, or a pharmaceutically acceptable salt thereof, and at least one pharmaceutically acceptable excipient for the treatment or prevention of Niemann Pick disease, type C in a subject in need thereof.

In some embodiments, the present disclosure provides use of an oral formulation of N-{[(2R)-2-hydroxy-3-piperidin-1-ylpropyl]oxy}pyridine-3-carboximidoyl chloride 1-oxide citrate and at least one pharmaceutically acceptable excipient for the treatment or prevention of Niemann Pick disease, type C in a subject in need thereof.

In some embodiments, the present disclosure provides use of a pharmaceutical composition of N-{[(2R)-2-hydroxy-3-piperidin-1-ylpropyl]oxy}pyridine-3-carboximidoyl chloride 1-oxide citrate and at least one pharmaceutically acceptable excipient for the treatment or prevention of Niemann Pick disease, type C in a subject in need thereof.

In some embodiments, the present disclosure provides use of an unit dosage of N-{[(2R)-2-hydroxy-3-piperidin-1-ylpropyl]oxy}pyridine-3-carboximidoyl chloride 1-oxide citrate and at least one pharmaceutically acceptable excipient for the treatment or prevention of Niemann Pick disease, type C in a subject in need thereof.

In some embodiments, the oral formulation is administered one, two, three, or four times daily.

In some embodiments, pharmaceutical composition is administered one, two, three, or four times daily.

In some embodiments, unit dosage is administered one, two, three, or four times daily.

In some embodiments, the oral formulation is administered three times daily.

In some embodiments, pharmaceutical composition is administered three times daily.

In some embodiments, unit dosage is administered three times daily.

In some embodiments, the oral formulation is administered three times daily for six consecutive days.

In some embodiments, pharmaceutical composition is administered three times daily for six consecutive days.

In some embodiments, unit dosage is administered three times daily for six consecutive days.

In some embodiments, the oral formulation is administered under fasting conditions.

In some embodiments, pharmaceutical composition is administered under fasting conditions.

In some embodiments, unit dosage is administered under fasting conditions.

In some embodiments, the oral formulation is administered as a single morning dose.

In some embodiments, the pharmaceutical composition is administered as a single morning dose.

In some embodiments, the unit dosage is administered as a single morning dose.

In some embodiments, the oral formulation is administered to a subject weighing about 70 kg.

In some embodiments, pharmaceutical composition is administered to a subject weighing about 70 kg.

In some embodiments, unit dosage is administered to a subject weighing about 70 kg.

In some embodiments, the subject is a human.

In some embodiments, the human is an adult. In some embodiments, the human is a pediatric patient (e.g., two years of age or older).

In some embodiments, the oral formulation is administered as described in Table A.

In some embodiments, the pharmaceutical composition is administered as described in Table A.

In some embodiments, the unit dosage is administered as described in Table A.

In some embodiments, the oral formulation is administered as described in Table B.

In some embodiments, the pharmaceutical composition is administered as described in Table B.

In some embodiments, the unit dosage is administered as described in Table B.

TABLE A

| Subject Weight | Dosage (free base) | Dosage (citrate) | Administration Schedule |
|---|---|---|---|
| 8 kg to 15 kg | 31 mg | 50 mg | t.i.d |
| 15 kg to 22 kg | 47 mg | 75 mg | t.i.d |
| 22 kg to 38 kg | 62 mg | 100 mg | t.i.d |
| 38 kg to 55 kg | 93 mg | 150 mg | t.i.d |
| >55 kg | 124 mg | 200 mg | t.i.d |

TABLE B

| Subject Weight | Dosage | Dosage (citrate) | Administration Schedule |
|---|---|---|---|
| 8 kg to 15 kg | 47 mg | 75 mg | t.i.d |
| 15 kg to 30 kg | 62 mg | 100 mg | t.i.d |
| 30 kg to 55 kg | 93 mg | 150 mg | t.i.d |
| >55 kg | 124 mg | 200 mg | t.i.d |

In some embodiments, the oral formulation is administered to a pediatric subject having a body weight of about 8 kg to about 15 kg.

In some embodiments, the pharmaceutical composition is administered to a pediatric subject having a body weight of about 8 kg to about 15 kg.

In some embodiments, the unit dosage is administered to a pediatric subject having a body weight of about 8 kg to about 15 kg.

In some embodiments, the oral formulation is administered to a pediatric subject having a body weight of about 15 kg to about 22 kg.

In some embodiments, the pharmaceutical composition is administered to a pediatric subject having a body weight of about 15 kg to about 22 kg.

In some embodiments, the unit dosage is administered to a pediatric subject having a body weight of about 15 kg to about 22 kg.

In some embodiments, the oral formulation is administered at a dosage of about 31 mg.

In some embodiments, the pharmaceutical composition is administered at a dosage of about 31 mg.

In some embodiments, the unit dosage is administered at a dosage of about 31 mg.

In some embodiments, the oral formulation is administered at a dosage of about 50 mg.

In some embodiments, the pharmaceutical composition is administered at a dosage of about 50 mg.

In some embodiments, the unit dosage is administered at a dosage of about 50 mg.

In some embodiments, the oral formulation is administered at a dosage of about 47 mg.

In some embodiments, the pharmaceutical composition is administered at a dosage of about 47 mg.

In some embodiments, the unit dosage is administered at a dosage of about 47 mg.

In some embodiments, the oral formulation is administered at a dosage of about 75 mg.

In some embodiments, the pharmaceutical composition is administered at a dosage of about 75 mg.

In some embodiments, the unit dosage is administered at a dosage of about 75 mg.

In some embodiments, the oral formulation is administered to a subject having a body weight of about 15 kg to about 30 kg.

In some embodiments, the pharmaceutical composition is administered to a subject having a body weight of about 15 kg to about 30 kg.

In some embodiments, the unit dosage is administered to a subject having a body weight of about 15 kg to about 30 kg.

In some embodiments, the oral formulation is administered to a subject having a body weight of about 22 kg to about 38 kg.

In some embodiments, the pharmaceutical composition is administered to a subject having a body weight of about 22 kg to about 38 kg.

In some embodiments, the unit dosage is administered to a subject having a body weight of about 22 kg to about 38 kg.

In some embodiments, the oral formulation is administered at a dosage of about 62 mg.

In some embodiments, the pharmaceutical composition is administered at a dosage of about 62 mg.

In some embodiments, the unit dosage is administered at a dosage of about 62 mg.

In some embodiments, the oral formulation is administered at a dosage of about 100 mg.

In some embodiments, the pharmaceutical composition is administered at a dosage of about 100 mg.

In some embodiments, the unit dosage is administered at a dosage of about 100 mg.

In some embodiments, the oral formulation is administered to a subject having a body weight of about 30 kg to about 55 kg.

In some embodiments, the pharmaceutical composition is administered to a subject having a body weight of about 30 kg to about 55 kg.

In some embodiments, the unit dosage is administered to a subject having a body weight of about 30 kg to about 55 kg.

In some embodiments, the oral formulation is administered to a subject having a body weight of about 38 kg to about 55 kg.

In some embodiments, the pharmaceutical composition is administered to a subject having a body weight of about 38 kg to about 55 kg.

In some embodiments, the unit dosage is administered to a subject having a body weight of about 38 kg to about 55 kg.

In some embodiments, the oral formulation is administered at a dosage of about 93 mg.

In some embodiments, the pharmaceutical composition is administered at a dosage of about 93 mg.

In some embodiments, the unit dosage is administered at a dosage of about 93 mg.

In some embodiments, the oral formulation is administered at a dosage of about 150 mg.

In some embodiments, the pharmaceutical composition is administered at a dosage of about 150 mg.

In some embodiments, the unit dosage is administered at a dosage of about 150 mg.

In some embodiments, the oral formulation is administered to a subject having a body weight of greater than about 55 kg.

In some embodiments, the pharmaceutical composition is administered to a subject having a body weight of greater than about 55 kg.

In some embodiments, the unit dosage is administered to a subject having a body weight of greater than about 55 kg.

In some embodiments, the oral formulation is administered at a dosage of about 124 mg.

In some embodiments, the pharmaceutical composition is administered at a dosage of about 124 mg.

In some embodiments, the unit dosage is administered at a dosage of about 124 mg.

In some embodiments, the oral formulation is administered at a dosage of about 200 mg.

In some embodiments, the pharmaceutical composition is administered at a dosage of about 200 mg.

In some embodiments, the unit dosage is administered at a dosage of about 200 mg.

In some embodiments, not less than about 85% of the N-{[(2R)-2-hydroxy-3-piperidin-1-ylpropyl]oxy}pyridine-3-carboximidoyl chloride 1-oxide, or pharmaceutically acceptable salt thereof is dissolved into solution in about 15 minutes.

In some embodiments, not less than 85% of the N-{[(2R)-2-hydroxy-3-piperidin-1-ylpropyl]oxy}pyridine-3-carboximidoyl chloride 1-oxide, or pharmaceutically acceptable salt thereof is dissolved into solution in about 15 minutes at a pH of about 1.2, about 4.5 or about 6.8.

In some embodiments, not less than about 85% of the N-{[(2R)-2-hydroxy-3-piperidin-1-ylpropyl]oxy}pyridine-3-carboximidoyl chloride 1-oxide citrate is dissolved into solution in about 15 minutes.

In some embodiments, not less than 85% of the N-{[(2R)-2-hydroxy-3-piperidin-1-ylpropyl]oxy}pyridine-3-carboximidoyl chloride 1-oxide citrate is dissolved into solution in about 15 minutes at a pH of about 1.2, about 4.5 or about 6.8.

In some embodiments, not less than about 80% of the N-{[(2R)-2-hydroxy-3-piperidin-1-ylpropyl]oxy}pyridine-3-carboximidoyl chloride 1-oxide, or pharmaceutically acceptable salt thereof is dissolved into solution in about 30 minutes.

In some embodiments, not less than 80% of the N-{[(2R)-2-hydroxy-3-piperidin-1-ylpropyl]oxy}pyridine-3-carboximidoyl chloride 1-oxide, or pharmaceutically acceptable salt thereof is dissolved into solution in about 30 minutes at a pH of about 1.2, about 4.5 or about 6.8.

In some embodiments, not less than about 80% of the N-{[(2R)-2-hydroxy-3-piperidin-1-ylpropyl]oxy}pyridine-3-carboximidoyl chloride 1-oxide citrate is dissolved into solution in about 30 minutes.

In some embodiments, not less than 80/a of the N-{[(2R)-2-hydroxy-3-piperidin-1-ylpropyl]oxy}pyridine-3-carboximidoyl chloride 1-oxide citrate is dissolved into solution in about 30 minutes at a pH of about 1.2, about 4.5 or about 6.8.

In some embodiments, the capsule ingredients are mixed with a liquid for oral administration as a liquid.

In some embodiments, the liquid is less than or equal to 20 mL. In some embodiments, the liquid is less than or equal to 15 mL.

In some embodiments, the liquid is water. In some embodiments, the liquid is apple juice.

In some embodiments, the capsule ingredients are mixed with soft food for oral administration.

In some embodiments, the present disclosure provides an oral formulation comprising:
  about 50 mg N-{[(2R)-2-hydroxy-3-piperidin-1-ylpropyl]oxy}pyridine-3-carboximidoyl chloride 1-oxide citrate;
  about 139.05 mg microcrystalline cellulose; and
  about 0.95 mg magnesium stearate.

In some embodiments, the present disclosure provides a pharmaceutical composition comprising:
  about 50 mg N-{[(2R)-2-hydroxy-3-piperidin-1-ylpropyl]oxy}pyridine-3-carboximidoyl chloride 1-oxide citrate;
  about 139.05 mg microcrystalline cellulose; and
  about 0.95 mg magnesium stearate.

In some embodiments, the present disclosure provides a method of treating or preventing Niemann Pick disease, type C in a subject in need thereof, wherein the subject is administered a therapeutically effect amount of the oral formulation comprising:
  about 50 mg N-{[(2R)-2-hydroxy-3-piperidin-1-ylpropyl]oxy}pyridine-3-carboximidoyl chloride 1-oxide citrate;
  about 139.05 mg microcrystalline cellulose; and
  about 0.95 mg magnesium stearate,
wherein the subject has a body weight of about 8 kg to about 15 kg.

In some embodiments, the present disclosure provides a method of treating or preventing Niemann Pick disease, type C in a subject in need thereof, wherein the subject is administered a therapeutically effect amount of the pharmaceutical composition comprising:
    about 50 mg N-{[(2R)-2-hydroxy-3-piperidin-1-ylpropyl]oxy}pyridine-3-carboximidoyl chloride 1-oxide citrate;
    about 139.05 mg microcrystalline cellulose; and
    about 0.95 mg magnesium stearate,
wherein the subject is a pediatric subject having a body weight of about 8 kg to about 15 kg.

In some embodiments, the present disclosure provides an oral formulation comprising:
    about 50 mg N-{[(2R)-2-hydroxy-3-piperidin-1-ylpropyl]oxy}pyridine-3-carboximidoyl chloride 1-oxide citrate;
    about 139.05 mg microcrystalline cellulose; and
    about 0.95 mg magnesium stearate,
for use in treating or preventing Niemann Pick disease, type C in a subject in need thereof, wherein the subject is a pediatric subject having a body weight of about 8 kg to about 15 kg.

In some embodiments, the present disclosure provides a pharmaceutical composition comprising:
    about 50 mg N-{[(2R)-2-hydroxy-3-piperidin-1-ylpropyl]oxy}pyridine-3-carboximidoyl chloride 1-oxide citrate;
    about 139.05 mg microcrystalline cellulose; and
    about 0.95 mg magnesium stearate,
for use in treating or preventing Niemann Pick disease, type C in a subject in need thereof, wherein the subject is a pediatric subject having a body weight of about 8 kg to about 15 kg.

In some embodiments, the present disclosure provides use of an oral formulation comprising:
    about 50 mg N-{[(2R)-2-hydroxy-3-piperidin-1-ylpropyl]oxy}pyridine-3-carboximidoyl chloride 1-oxide citrate;
    about 139.05 mg microcrystalline cellulose; and
    about 0.95 mg magnesium stearate,
for use in the manufacture of a medicament for the treatment or prevention of Niemann Pick disease, type C in a subject in need thereof, wherein the subject is a pediatric subject having a body weight of about 8 kg to about 15 kg.

In some embodiments, the present disclosure provides use of a pharmaceutical composition comprising:
    about 50 mg N-{[(2R)-2-hydroxy-3-piperidin-1-ylpropyl]oxy}pyridine-3-carboximidoyl chloride 1-oxide citrate;
    about 139.05 mg microcrystalline cellulose; and
    about 0.95 mg magnesium stearate,
for use in the manufacture of a medicament for the treatment or prevention of Niemann Pick disease, type C in a subject in need thereof, wherein the subject is a pediatric subject having a body weight of about 8 kg to about 15 kg.

In some embodiments, the present disclosure provides use of an oral formulation comprising:
    about 50 mg N-{[(2R)-2-hydroxy-3-piperidin-1-ylpropyl]oxy}pyridine-3-carboximidoyl chloride 1-oxide citrate;
    about 139.05 mg microcrystalline cellulose; and
    about 0.95 mg magnesium stearate,
for the treatment or prevention of Niemann Pick disease, type C in a subject in need thereof, wherein the subject is a pediatric subject having a body weight of about 8 kg to about 15 kg.

In some embodiments, the present disclosure provides use of a pharmaceutical composition comprising:
    about 50 mg N-{[(2R)-2-hydroxy-3-piperidin-1-ylpropyl]oxy}pyridine-3-carboximidoyl chloride 1-oxide citrate;
    about 139.05 mg microcrystalline cellulose; and
    about 0.95 mg magnesium stearate,
for the treatment or prevention of Niemann Pick disease, type C in a subject in need thereof, wherein the subject is a pediatric subject having a body weight of about 8 kg to about 15 kg.

In some embodiments, the present disclosure provides an oral formulation comprising:
    about 75 mg N-{[(2R)-2-hydroxy-3-piperidin-1-ylpropyl]oxy}pyridine-3-carboximidoyl chloride 1-oxide citrate;
    about 208.57 mg microcrystalline cellulose; and
    about 1.43 mg magnesium stearate.

In some embodiments, the present disclosure provides a pharmaceutical composition comprising:
    about 75 mg N-{[(2R)-2-hydroxy-3-piperidin-1-ylpropyl]oxy}pyridine-3-carboximidoyl chloride 1-oxide citrate;
    about 208.57 mg microcrystalline cellulose; and
    about 1.43 mg magnesium stearate.

In some embodiments, the present disclosure provides a method of treating or preventing Niemann Pick disease, type C in a subject in need thereof, wherein the subject is administered a therapeutically effect amount of the oral formulation comprising:
    about 75 mg N-{[(2R)-2-hydroxy-3-piperidin-1-ylpropyl]oxy}pyridine-3-carboximidoyl chloride 1-oxide citrate;
    about 208.57 mg microcrystalline cellulose; and
    about 1.43 mg magnesium stearate,
wherein the subject is a pediatric subject having a body weight of about 8 kg to about 15 kg.

In some embodiments, the present disclosure provides a method of treating or preventing Niemann Pick disease, type C in a subject in need thereof, wherein the subject is administered a therapeutically effect amount of the pharmaceutical composition comprising:
    about 75 mg N-{[(2R)-2-hydroxy-3-piperidin-1-ylpropyl]oxy}pyridine-3-carboximidoyl chloride 1-oxide citrate;
    about 208.57 mg microcrystalline cellulose; and
    about 1.43 mg magnesium stearate,
wherein the subject is a pediatric subject having a body weight of about 8 kg to about 15 kg.

In some embodiments, the present disclosure provides an oral formulation comprising:
    about 75 mg N-{[(2R)-2-hydroxy-3-piperidin-1-ylpropyl]oxy}pyridine-3-carboximidoyl chloride 1-oxide citrate;
    about 208.57 mg microcrystalline cellulose; and
    about 1.43 mg magnesium stearate,
for use in treating or preventing Niemann Pick disease, type C in a subject in need thereof, wherein the subject is a pediatric subject having a body weight of about 8 kg to about 15 kg.

In some embodiments, the present disclosure provides a pharmaceutical composition comprising:
    about 75 mg N-{[(2R)-2-hydroxy-3-piperidin-1-ylpropyl]oxy}pyridine-3-carboximidoyl chloride 1-oxide citrate;
    about 208.57 mg microcrystalline cellulose; and
    about 1.43 mg magnesium stearate,
for use in treating or preventing Niemann Pick disease, type C in a subject in need thereof, wherein the subject is a pediatric subject having a body weight of about 8 kg to about 15 kg.

In some embodiments, the present disclosure provides use of an oral formulation comprising:
    about 75 mg N-{[(2R)-2-hydroxy-3-piperidin-1-ylpropyl]oxy}pyridine-3-carboximidoyl chloride 1-oxide citrate;
    about 208.57 mg microcrystalline cellulose; and
    about 1.43 mg magnesium stearate,
for use in the manufacture of a medicament for the treatment or prevention of Niemann Pick disease, type C in a subject in need thereof, wherein the subject is a pediatric subject having a body weight of about 8 kg to about 15 kg.

In some embodiments, the present disclosure provides use of a pharmaceutical composition comprising:
about 75 mg N-{[(2R)-2-hydroxy-3-piperidin-1-ylpropyl]oxy}pyridine-3-carboximidoyl chloride 1-oxide citrate;
about 208.57 mg microcrystalline cellulose; and
about 1.43 mg magnesium stearate,
for use in the manufacture of a medicament for the treatment or prevention of Niemann Pick disease, type C in a subject in need thereof, wherein the subject is a pediatric subject having a body weight of about 8 kg to about 15 kg.

In some embodiments, the present disclosure provides use of an oral formulation comprising:
about 75 mg N-{[(2R)-2-hydroxy-3-piperidin-1-ylpropyl]oxy}pyridine-3-carboximidoyl chloride 1-oxide citrate;
about 208.57 mg microcrystalline cellulose; and
about 1.43 mg magnesium stearate,
for the treatment or prevention of Niemann Pick disease, type C in a subject in need thereof, wherein the subject is a pediatric subject having a body weight of about 8 kg to about 15 kg.

In some embodiments, the present disclosure provides use of a pharmaceutical composition comprising:
about 75 mg N-{[(2R)-2-hydroxy-3-piperidin-1-ylpropyl]oxy}pyridine-3-carboximidoyl chloride 1-oxide citrate;
about 208.57 mg microcrystalline cellulose; and
about 1.43 mg magnesium stearate,
for the treatment or prevention of Niemann Pick disease, type C in a subject in need thereof, wherein the subject is a pediatric subject having a body weight of about 8 kg to about 15 kg.

In some embodiments, the present disclosure provides a method of treating or preventing Niemann Pick disease, type C in a subject in need thereof, wherein the subject is administered a therapeutically effect amount of the oral formulation comprising:
about 75 mg N-{[(2R)-2-hydroxy-3-piperidin-1-ylpropyl]oxy}pyridine-3-carboximidoyl chloride 1-oxide citrate;
about 208.57 mg microcrystalline cellulose; and
about 1.43 mg magnesium stearate,
wherein the subject is a pediatric subject having a body weight of about 15 kg to about 22 kg.

In some embodiments, the present disclosure provides a method of treating or preventing Niemann Pick disease, type C in a subject in need thereof, wherein the subject is administered a therapeutically effect amount of the pharmaceutical composition comprising:
about 75 mg N-{[(2R)-2-hydroxy-3-piperidin-1-ylpropyl]oxy}pyridine-3-carboximidoyl chloride 1-oxide citrate;
about 208.57 mg microcrystalline cellulose; and
about 1.43 mg magnesium stearate,
wherein the subject is a pediatric subject having a body weight of about 15 kg to about 22 kg.

In some embodiments, the present disclosure provides an oral formulation comprising:
about 75 mg N-{[(2R)-2-hydroxy-3-piperidin-1-ylpropyl]oxy}pyridine-3-carboximidoyl chloride 1-oxide citrate;
about 208.57 mg microcrystalline cellulose; and
about 1.43 mg magnesium stearate,
for use in treating or preventing Niemann Pick disease, type C in a subject in need thereof, wherein the subject is a pediatric subject having a body weight of about 15 kg to about 22 kg.

In some embodiments, the present disclosure provides a pharmaceutical composition comprising:
about 75 mg N-{[(2R)-2-hydroxy-3-piperidin-1-ylpropyl]oxy}pyridine-3-carboximidoyl chloride 1-oxide citrate;
about 208.57 mg microcrystalline cellulose; and
about 1.43 mg magnesium stearate,
for use in treating or preventing Niemann Pick disease, type C in a subject in need thereof, wherein the subject is a pediatric subject having a body weight of about 15 kg to about 22 kg.

In some embodiments, the present disclosure provides use of an oral formulation comprising:
about 75 mg N-{[(2R)-2-hydroxy-3-piperidin-1-ylpropyl]oxy}pyridine-3-carboximidoyl chloride 1-oxide citrate;
about 208.57 mg microcrystalline cellulose; and
about 1.43 mg magnesium stearate,
for use in the manufacture of a medicament for the treatment or prevention of Niemann Pick disease, type C in a subject in need thereof, wherein the subject is a pediatric subject having a body weight of about 15 kg to about 22 kg.

In some embodiments, the present disclosure provides use of a pharmaceutical composition comprising:
about 75 mg N-{[(2R)-2-hydroxy-3-piperidin-1-ylpropyl]oxy}pyridine-3-carboximidoyl chloride 1-oxide citrate;
about 208.57 mg microcrystalline cellulose; and
about 1.43 mg magnesium stearate,
for use in the manufacture of a medicament for the treatment or prevention of Niemann Pick disease, type C in a subject in need thereof, wherein the subject is a pediatric subject having a body weight of about 15 kg to about 22 kg.

In some embodiments, the present disclosure provides use of an oral formulation comprising:
about 75 mg N-{[(2R)-2-hydroxy-3-piperidin-1-ylpropyl]oxy}pyridine-3-carboximidoyl chloride 1-oxide citrate;
about 208.57 mg microcrystalline cellulose; and
about 1.43 mg magnesium stearate,
for the treatment or prevention of Niemann Pick disease, type C in a subject in need thereof, wherein the subject is a pediatric subject having a body weight of about 15 kg to about 22 kg.

In some embodiments, the present disclosure provides use of a pharmaceutical composition comprising:
about 75 mg N-{[(2R)-2-hydroxy-3-piperidin-1-ylpropyl]oxy}pyridine-3-carboximidoyl chloride 1-oxide citrate;
about 208.57 mg microcrystalline cellulose; and
about 1.43 mg magnesium stearate,
for the treatment or prevention of Niemann Pick disease, type C in a subject in need thereof, wherein the subject is a pediatric subject having a body weight of about 15 kg to about 22 kg.

In some embodiments, the present disclosure provides an oral formulation comprising:
about 100 mg N-{[(2R)-2-hydroxy-3-piperidin-1-ylpropyl]oxy}pyridine-3-carboximidoyl chloride 1-oxide citrate;
about 278.1 mg microcrystalline cellulose; and
about 1.90 mg magnesium stearate.

In some embodiments, the present disclosure provides a pharmaceutical composition comprising:
about 100 mg N-{[(2R)-2-hydroxy-3-piperidin-1-ylpropyl]oxy}pyridine-3-carboximidoyl chloride 1-oxide citrate;
about 278.1 mg microcrystalline cellulose; and
about 1.90 mg magnesium stearate.

In some embodiments, the present disclosure provides a method of treating or preventing Niemann Pick disease, type C in a subject in need thereof, wherein the subject is administered a therapeutically effect amount of the oral formulation comprising:
about 100 mg N-{[(2R)-2-hydroxy-3-piperidin-1-ylpropyl]oxy}pyridine-3-carboximidoyl chloride 1-oxide citrate;

about 278.1 mg microcrystalline cellulose; and
about 1.90 mg magnesium stearate,
wherein the subject has a body weight of greater than about 15 kg to about 30 kg.

In some embodiments, the present disclosure provides a method of treating or preventing Niemann Pick disease, type C in a subject in need thereof, wherein the subject is administered a therapeutically effect amount of the pharmaceutical composition comprising:
about 100 mg N-{[(2R)-2-hydroxy-3-piperidin-1-ylpropyl]oxy}pyridine-3-carboximidoyl chloride 1-oxide citrate;
about 278.1 mg microcrystalline cellulose; and
about 1.90 mg magnesium stearate,
wherein the subject has a body weight of greater than about 15 kg to about 30 kg.

In some embodiments, the present disclosure provides an oral formulation comprising:
about 100 mg N-{[(2R)-2-hydroxy-3-piperidin-1-ylpropyl]oxy}pyridine-3-carboximidoyl chloride 1-oxide citrate;
about 278.1 mg microcrystalline cellulose; and
about 1.90 mg magnesium stearate,
for use in treating or preventing Niemann Pick disease, type C in a subject in need thereof, wherein the subject has a body weight of greater than about 15 kg to about 30 kg.

In some embodiments, the present disclosure provides a pharmaceutical composition comprising:
about 100 mg N-{[(2R)-2-hydroxy-3-piperidin-1-ylpropyl]oxy}pyridine-3-carboximidoyl chloride 1-oxide citrate;
about 278.1 mg microcrystalline cellulose; and
about 1.90 mg magnesium stearate,
for use in treating or preventing Niemann Pick disease, type C in a subject in need thereof, wherein the subject has a body weight of greater than about 15 kg to about 30 kg.

In some embodiments, the present disclosure provides use of an oral formulation comprising:
about 100 mg N-{[(2R)-2-hydroxy-3-piperidin-1-ylpropyl]oxy}pyridine-3-carboximidoyl chloride 1-oxide citrate;
about 278.1 mg microcrystalline cellulose; and
about 1.90 mg magnesium stearate,
for use in the manufacture of a medicament for the treatment or prevention of Niemann Pick disease, type C in a subject in need thereof, wherein the subject has a body weight of greater than about 15 kg to about 30 kg.

In some embodiments, the present disclosure provides use of a pharmaceutical composition comprising:
about 100 mg N-{[(2R)-2-hydroxy-3-piperidin-1-ylpropyl]oxy}pyridine-3-carboximidoyl chloride 1-oxide citrate;
about 278.1 mg microcrystalline cellulose; and
about 1.90 mg magnesium stearate,
for use in the manufacture of a medicament for the treatment or prevention of Niemann Pick disease, type C in a subject in need thereof, wherein the subject has a body weight of greater than about 15 kg to about 30 kg.

In some embodiments, the present disclosure provides use of an oral formulation comprising:
about 100 mg N-{[(2R)-2-hydroxy-3-piperidin-1-ylpropyl]oxy}pyridine-3-carboximidoyl chloride 1-oxide citrate;
about 278.1 mg microcrystalline cellulose; and
about 1.90 mg magnesium stearate,
for the treatment or prevention of Niemann Pick disease, type C in a subject in need thereof, wherein the subject has a body weight of greater than about 15 kg to about 30 kg.

In some embodiments, the present disclosure provides use of a pharmaceutical composition comprising:
about 100 mg N-{[(2R)-2-hydroxy-3-piperidin-1-ylpropyl]oxy}pyridine-3-carboximidoyl chloride 1-oxide citrate;
about 278.1 mg microcrystalline cellulose; and
about 1.90 mg magnesium stearate,
for the treatment or prevention of Niemann Pick disease, type C in a subject in need thereof, wherein the subject has a body weight of greater than about 15 kg to about 30 kg.

In some embodiments, the present disclosure provides a method of treating or preventing Niemann Pick disease, type C in a subject in need thereof, wherein the subject is administered a therapeutically effect amount of the oral formulation comprising:
about 100 mg N-{[(2R)-2-hydroxy-3-piperidin-1-ylpropyl]oxy}pyridine-3-carboximidoyl chloride 1-oxide citrate;
about 278.1 mg microcrystalline cellulose; and
about 1.90 mg magnesium stearate,
wherein the subject has a body weight of greater than about 22 kg to about 38 kg.

In some embodiments, the present disclosure provides a method of treating or preventing Niemann Pick disease, type C in a subject in need thereof, wherein the subject is administered a therapeutically effect amount of the pharmaceutical composition comprising:
about 100 mg N-{[(2R)-2-hydroxy-3-piperidin-1-ylpropyl]oxy}pyridine-3-carboximidoyl chloride 1-oxide citrate;
about 278.1 mg microcrystalline cellulose; and
about 1.90 mg magnesium stearate,
wherein the subject has a body weight of greater than about 22 kg to about 38 kg.

In some embodiments, the present disclosure provides an oral formulation comprising:
about 100 mg N-{[(2R)-2-hydroxy-3-piperidin-1-ylpropyl]oxy}pyridine-3-carboximidoyl chloride 1-oxide citrate;
about 278.1 mg microcrystalline cellulose; and
about 1.90 mg magnesium stearate,
for use in treating or preventing Niemann Pick disease, type C in a subject in need thereof, wherein the subject has a body weight of greater than about 22 kg to about 38 kg.

In some embodiments, the present disclosure provides a pharmaceutical composition comprising:
about 100 mg N-{[(2R)-2-hydroxy-3-piperidin-1-ylpropyl]oxy}pyridine-3-carboximidoyl chloride 1-oxide citrate;
about 278.1 mg microcrystalline cellulose; and
about 1.90 mg magnesium stearate,
for use in treating or preventing Niemann Pick disease, type C in a subject in need thereof, wherein the subject has a body weight of greater than about 22 kg to about 38 kg.

In some embodiments, the present disclosure provides use of an oral formulation comprising:
about 100 mg N-{[(2R)-2-hydroxy-3-piperidin-1-ylpropyl]oxy}pyridine-3-carboximidoyl chloride 1-oxide citrate;
about 278.1 mg microcrystalline cellulose; and
about 1.90 mg magnesium stearate,
for use in the manufacture of a medicament for the treatment or prevention of Niemann Pick disease, type C in a subject in need thereof, wherein the subject has a body weight of greater than about 22 kg to about 38 kg.

In some embodiments, the present disclosure provides use of a pharmaceutical composition comprising:
about 100 mg N-{[(2R)-2-hydroxy-3-piperidin-1-ylpropyl]oxy}pyridine-3-carboximidoyl chloride 1-oxide citrate;
about 278.1 mg microcrystalline cellulose; and
about 1.90 mg magnesium stearate,
for use in the manufacture of a medicament for the treatment or prevention of Niemann Pick disease, type C in a subject in need thereof, wherein the subject has a body weight of greater than about 22 kg to about 38 kg.

In some embodiments, the present disclosure provides use of an oral formulation comprising:
- about 100 mg N-{[(2R)-2-hydroxy-3-piperidin-1-ylpropyl]oxy}pyridine-3-carboximidoyl chloride 1-oxide citrate;
- about 278.1 mg microcrystalline cellulose; and
- about 1.90 mg magnesium stearate, for the treatment or prevention of Niemann Pick disease, type C in a subject in need thereof, wherein the subject has a body weight of greater than about 22 kg to about 38 kg.

In some embodiments, the present disclosure provides use of a pharmaceutical composition comprising:
- about 100 mg N-{[(2R)-2-hydroxy-3-piperidin-1-ylpropyl]oxy}pyridine-3-carboximidoyl chloride 1-oxide citrate;
- about 278.1 mg microcrystalline cellulose; and
- about 1.90 mg magnesium stearate, for the treatment or prevention of Niemann Pick disease, type C in a subject in need thereof, wherein the subject has a body weight of greater than about 22 kg to about 38 kg.

In some embodiments, the present disclosure provides an oral formulation comprising:
- about 150 mg N-{[(2R)-2-hydroxy-3-piperidin-1-ylpropyl]oxy}pyridine-3-carboximidoyl chloride 1-oxide citrate;
- about 133.57 mg microcrystalline cellulose; and
- about 1.43 mg magnesium stearate.

In some embodiments, the present disclosure provides a pharmaceutical composition comprising:
- about 150 mg N-{[(2R)-2-hydroxy-3-piperidin-1-ylpropyl]oxy}pyridine-3-carboximidoyl chloride 1-oxide citrate;
- about 133.57 mg microcrystalline cellulose; and
- about 1.43 mg magnesium stearate.

In some embodiments, the present disclosure provides a method of treating or preventing Niemann Pick disease, type C in a subject in need thereof, wherein the subject is administered a therapeutically effect amount of the oral formulation comprising:
- about 150 mg N-{[(2R)-2-hydroxy-3-piperidin-1-ylpropyl]oxy}pyridine-3-carboximidoyl chloride 1-oxide citrate;
- about 133.57 mg microcrystalline cellulose; and
- about 1.43 mg magnesium stearate, wherein the subject has a body weight of greater than about 30 kg to about 55 kg.

In some embodiments, the present disclosure provides a method of treating or preventing Niemann Pick disease, type C in a subject in need thereof, wherein the subject is administered a therapeutically effect amount of the pharmaceutical composition comprising:
- about 150 mg N-{[(2R)-2-hydroxy-3-piperidin-1-ylpropyl]oxy}pyridine-3-carboximidoyl chloride 1-oxide citrate;
- about 133.57 mg microcrystalline cellulose; and
- about 1.43 mg magnesium stearate, wherein the subject has a body weight of greater than about 30 kg to about 55 kg.

In some embodiments, the present disclosure provides an oral formulation comprising:
- about 150 mg N-{[(2R)-2-hydroxy-3-piperidin-1-ylpropyl]oxy}pyridine-3-carboximidoyl chloride 1-oxide citrate;
- about 133.57 mg microcrystalline cellulose; and
- about 1.43 mg magnesium stearate, for use in treating or preventing Niemann Pick disease, type C in a subject in need thereof, wherein the subject has a body weight of greater than about 30 kg to about 55 kg.

In some embodiments, the present disclosure provides a pharmaceutical composition comprising:
- about 150 mg N-{[(2R)-2-hydroxy-3-piperidin-1-ylpropyl]oxy}pyridine-3-carboximidoyl chloride 1-oxide citrate;
- about 133.57 mg microcrystalline cellulose; and
- about 1.43 mg magnesium stearate, for use in treating or preventing Niemann Pick disease, type C in a subject in need thereof, wherein the subject has a body weight of greater than about 30 kg to about 55 kg.

In some embodiments, the present disclosure provides use of an oral formulation comprising:
- about 150 mg N-{[(2R)-2-hydroxy-3-piperidin-1-ylpropyl]oxy}pyridine-3-carboximidoyl chloride 1-oxide citrate;
- about 133.57 mg microcrystalline cellulose; and
- about 1.43 mg magnesium stearate, for use in the manufacture of a medicament for the treatment or prevention of Niemann Pick disease, type C in a subject in need thereof, wherein the subject has a body weight of greater than about 30 kg to about 55 kg.

In some embodiments, the present disclosure provides use of a pharmaceutical composition comprising:
- about 150 mg N-{[(2R)-2-hydroxy-3-piperidin-1-ylpropyl]oxy}pyridine-3-carboximidoyl chloride 1-oxide citrate;
- about 133.57 mg microcrystalline cellulose; and
- about 1.43 mg magnesium stearate, for use in the manufacture of a medicament for the treatment or prevention of Niemann Pick disease, type C in a subject in need thereof, wherein the subject has a body weight of greater than about 30 kg to about 55 kg.

In some embodiments, the present disclosure provides use of an oral formulation comprising:
- about 150 mg N-{[(2R)-2-hydroxy-3-piperidin-1-ylpropyl]oxy}pyridine-3-carboximidoyl chloride 1-oxide citrate;
- about 133.57 mg microcrystalline cellulose; and
- about 1.43 mg magnesium stearate, for the treatment or prevention of Niemann Pick disease, type C in a subject in need thereof, wherein the subject has a body weight of greater than about 30 kg to about 55 kg.

In some embodiments, the present disclosure provides use of a pharmaceutical composition comprising:
- about 150 mg N-{[(2R)-2-hydroxy-3-piperidin-1-ylpropyl]oxy}pyridine-3-carboximidoyl chloride 1-oxide citrate;
- about 133.57 mg microcrystalline cellulose; and
- about 1.43 mg magnesium stearate, for the treatment or prevention of Niemann Pick disease, type C in a subject in need thereof, wherein the subject has a body weight of greater than about 30 kg to about 55 kg.

In some embodiments, the present disclosure provides a method of treating or preventing Niemann Pick disease, type C in a subject in need thereof, wherein the subject is administered a therapeutically effect amount of the oral formulation comprising:
- about 150 mg N-{[(2R)-2-hydroxy-3-piperidin-1-ylpropyl]oxy}pyridine-3-carboximidoyl chloride 1-oxide citrate;
- about 133.57 mg microcrystalline cellulose; and
- about 1.43 mg magnesium stearate, wherein the subject has a body weight of greater than about 38 kg to about 55 kg.

In some embodiments, the present disclosure provides a method of treating or preventing Niemann Pick disease, type C in a subject in need thereof, wherein the subject is administered a therapeutically effect amount of the pharmaceutical composition comprising:
- about 150 mg N-{[(2R)-2-hydroxy-3-piperidin-1-ylpropyl]oxy}pyridine-3-carboximidoyl chloride 1-oxide citrate;
- about 133.57 mg microcrystalline cellulose; and
- about 1.43 mg magnesium stearate, wherein the subject has a body weight of greater than about 38 kg to about 55 kg.

In some embodiments, the present disclosure provides an oral formulation comprising:
- about 150 mg N-{[(2R)-2-hydroxy-3-piperidin-1-ylpropyl]oxy}pyridine-3-carboximidoyl chloride 1-oxide citrate;

about 133.57 mg microcrystalline cellulose; and
about 1.43 mg magnesium stearate,
for use in treating or preventing Niemann Pick disease, type C in a subject in need thereof, wherein the subject has a body weight of greater than about 38 kg to about 55 kg.

In some embodiments, the present disclosure provides a pharmaceutical composition comprising:
about 150 mg N-{[(2R)-2-hydroxy-3-piperidin-1-ylpropyl]oxy}pyridine-3-carboximidoyl chloride 1-oxide citrate;
about 133.57 mg microcrystalline cellulose; and
about 1.43 mg magnesium stearate,
for use in treating or preventing Niemann Pick disease, type C in a subject in need thereof, wherein the subject has a body weight of greater than about 38 kg to about 55 kg.

In some embodiments, the present disclosure provides use of an oral formulation comprising:
about 150 mg N-{[(2R)-2-hydroxy-3-piperidin-1-ylpropyl]oxy}pyridine-3-carboximidoyl chloride 1-oxide citrate;
about 133.57 mg microcrystalline cellulose; and
about 1.43 mg magnesium stearate,
for use in the manufacture of a medicament for the treatment or prevention of Niemann Pick disease, type C in a subject in need thereof, wherein the subject has a body weight of greater than about 38 kg to about 55 kg.

In some embodiments, the present disclosure provides use of a pharmaceutical composition comprising:
about 150 mg N-{[(2R)-2-hydroxy-3-piperidin-1-ylpropyl]oxy}pyridine-3-carboximidoyl chloride 1-oxide citrate;
about 133.57 mg microcrystalline cellulose; and
about 1.43 mg magnesium stearate,
for use in the manufacture of a medicament for the treatment or prevention of Niemann Pick disease, type C in a subject in need thereof, wherein the subject has a body weight of greater than about 38 kg to about 55 kg.

In some embodiments, the present disclosure provides use of an oral formulation comprising:
about 150 mg N-{[(2R)-2-hydroxy-3-piperidin-1-ylpropyl]oxy}pyridine-3-carboximidoyl chloride 1-oxide citrate;
about 133.57 mg microcrystalline cellulose; and
about 1.43 mg magnesium stearate,
for the treatment or prevention of Niemann Pick disease, type C in a subject in need thereof, wherein the subject has a body weight of greater than about 38 kg to about 55 kg.

In some embodiments, the present disclosure provides use of a pharmaceutical composition comprising:
about 150 mg N-{[(2R)-2-hydroxy-3-piperidin-1-ylpropyl]oxy}pyridine-3-carboximidoyl chloride 1-oxide citrate;
about 133.57 mg microcrystalline cellulose; and
about 1.43 mg magnesium stearate,
for the treatment or prevention of Niemann Pick disease, type C in a subject in need thereof, wherein the subject has a body weight of greater than about 38 kg to about 55 kg.

In some embodiments, the present disclosure provides an oral formulation comprising:
about 200 mg N-{[(2R)-2-hydroxy-3-piperidin-1-ylpropyl]oxy}pyridine-3-carboximidoyl chloride 1-oxide citrate;
about 178.1 mg microcrystalline cellulose; and
about 1.9 mg magnesium stearate.

In some embodiments, the present disclosure provides a pharmaceutical composition comprising:
about 200 mg N-{[(2R)-2-hydroxy-3-piperidin-1-ylpropyl]oxy}pyridine-3-carboximidoyl chloride 1-oxide citrate;
about 178.1 mg microcrystalline cellulose; and
about 1.9 mg magnesium stearate.

In some embodiments, the present disclosure provides a method of treating or preventing Niemann Pick disease, type C in a subject in need thereof, wherein the subject is administered a therapeutically effect amount of the oral formulation comprising:
about 200 mg N-{[(2R)-2-hydroxy-3-piperidin-1-ylpropyl]oxy}pyridine-3-carboximidoyl chloride 1-oxide citrate;
about 178.1 mg microcrystalline cellulose; and
about 1.9 mg magnesium stearate,
wherein the subject has a body weight of greater than about 55 kg.

In some embodiments, the present disclosure provides a method of treating or preventing Niemann Pick disease, type C in a subject in need thereof, wherein the subject is administered a therapeutically effect amount of the pharmaceutical composition comprising:
about 200 mg N-{[(2R)-2-hydroxy-3-piperidin-1-ylpropyl]oxy}pyridine-3-carboximidoyl chloride 1-oxide citrate;
about 178.1 mg microcrystalline cellulose; and
about 1.9 mg magnesium stearate,
wherein the subject has a body weight of greater than about 55 kg.

In some embodiments, the present disclosure provides an oral formulation comprising:
about 200 mg N-{[(2R)-2-hydroxy-3-piperidin-1-ylpropyl]oxy}pyridine-3-carboximidoyl chloride 1-oxide citrate;
about 178.1 mg microcrystalline cellulose; and
about 1.9 mg magnesium stearate,
for use in treating or preventing Niemann Pick disease, type C in a subject in need thereof, wherein the subject has a body weight of greater than about 55 kg.

In some embodiments, the present disclosure provides a pharmaceutical composition comprising:
about 200 mg N-{[(2R)-2-hydroxy-3-piperidin-1-ylpropyl]oxy}pyridine-3-carboximidoyl chloride 1-oxide citrate;
about 178.1 mg microcrystalline cellulose; and
about 1.9 mg magnesium stearate,
for use in treating or preventing Niemann Pick disease, type C in a subject in need thereof, wherein the subject has a body weight of greater than about 55 kg.

In some embodiments, the present disclosure provides use of an oral formulation comprising:
about 200 mg N-{[(2R)-2-hydroxy-3-piperidin-1-ylpropyl]oxy}pyridine-3-carboximidoyl chloride 1-oxide citrate;
about 178.1 mg microcrystalline cellulose; and
about 1.9 mg magnesium stearate,
for use in the manufacture of a medicament for the treatment or prevention of Niemann Pick disease, type C in a subject in need thereof, wherein the subject has a body weight of greater than about 55 kg.

In some embodiments, the present disclosure provides use of a pharmaceutical composition comprising:
about 200 mg N-{[(2R)-2-hydroxy-3-piperidin-1-ylpropyl]oxy}pyridine-3-carboximidoyl chloride 1-oxide citrate;
about 178.1 mg microcrystalline cellulose; and
about 1.9 mg magnesium stearate,
for use in the manufacture of a medicament for the treatment or prevention of Niemann Pick disease, type C in a subject in need thereof, wherein the subject has a body weight of greater than about 55 kg.

In some embodiments, the present disclosure provides use of an oral formulation comprising:
about 200 mg N-{[(2R)-2-hydroxy-3-piperidin-1-ylpropyl]oxy}pyridine-3-carboximidoyl chloride 1-oxide citrate;
about 178.1 mg microcrystalline cellulose; and
about 1.9 mg magnesium stearate,
for the treatment or prevention of Niemann Pick disease, type C in a subject in need thereof, wherein the subject has a body weight of greater than about 55 kg.

In some embodiments, the present disclosure provides use of a pharmaceutical composition comprising:

about 200 mg N-{[(2R)-2-hydroxy-3-piperidin-1-ylpropyl]oxy}pyridine-3-carboximidoyl chloride 1-oxide citrate;
about 178.1 mg microcrystalline cellulose; and
about 1.9 mg magnesium stearate, for the treatment or prevention of Niemann Pick disease, type C in a subject in need thereof, wherein the subject has a body weight of greater than about 55 kg.

In some embodiments, the oral formulation comprises a capsule.

In some embodiments, the pharmaceutical composition comprises a capsule.

In some embodiments, the geometric mean $C_{max}$ is measure as compared to a 70 kg male.

In some embodiments, the geometric mean $C_{max}$ of the oral formulation is within about 80.00% to about 125.00% of a $C_{max}$ of 1749 (CV 49%) ng/mL, after administration of a single dose.

In some embodiments, the geometric mean $C_{max}$ of the pharmaceutical composition is within about 80.00% to about 125.00% of a $C_{max}$ of 1749 (CV 49%) ng/mL, after administration of a single dose.

In some embodiments, the geometric mean $C_{max}$ of the unit dosage is within about 80.00% to about 125.00% of a $C_{max}$ of 1749 (CV 49%) ng/mL, after administration of a single dose.

In some embodiments, the $AUC_{0-8\ hrs}$ of the oral formulation is within about 80.00% to about 125.00% of a $AUC_{0-8\ hrs}$ of 5317 (CV 17%) h ng/mL, after administration of a single dose.

In some embodiments, the $AUC_{0-8\ hrs}$ of the pharmaceutical composition is within about 80.00% to about 125.00% of a $AUC_{0-8\ hrs}$ of 5317 (CV 17%) h ng/mL, after administration of a single dose.

In some embodiments, the $AUC_{0-8\ hrs}$ of the unit dosage is within about 80.00% to about 125.00% of a $AUC_{0-8\ hrs}$ of 5317 (CV 17%) h ng/mL, after administration of a single dose.

In some embodiments, the $AUC_{0-infinity}$ of the oral formulation is within about 80.00% to about 125.00% of a $AUC_{0-infinity}$ of 6331 (CV 17%) h ng/mL, after administration of a single dose.

In some embodiments, the $AUC_{0-infinity}$ of the pharmaceutical composition is within about 80.00% to about 125.00% of a $AUC_{0-infinity}$ of 6331 (CV 17%) h ng/mL, after administration of a single dose.

In some embodiments, the $AUC_{0-infinity}$ of the oral dosage is within about 80.00% to about 125.00% of a $AUC_{0-infinity}$ of 6331 (CV 17%) h ng/mL, after administration of a single dose.

In some embodiments, the geometric mean $C_{max,steady\ state}$ of the oral formulation at steady state is within about 80.00% to about 125.00% of a $C_{max,steady\ state}$ of 2090 (CV 23%) ng/mL, after administration.

In some embodiments, the geometric mean $C_{max,steady\ state}$ of the pharmaceutical composition at steady state is within about 80.00% to about 125.00% of a $C_{max,steady\ state}$ of 2090 (CV 23%) ng/mL, after administration.

In some embodiments, the geometric mean $C_{max,steady\ state}$ of the unit dosage at steady state is within about 80.00% to about 125.00% of a $C_{max,steady\ state}$ of 2090 (CV 23%) ng/mL, after administration.

In some embodiments, the $AUC_{0-8\ hrs,\ steady\ state}$ of the oral formulation is within about 80.00% to about 125.00% of a $AUC_{0-8\ hrs,\ steady\ state}$ of 7207 (CV 19%) h ng/mL, after administration.

In some embodiments, the $AUC_{0-8\ hrs,\ steady\ state}$ of the pharmaceutical composition is within about 80.00% to about 125.00% of a $AUC_{0-8\ hrs,\ steady\ state}$ of 7207 (CV 19%) h ng/mL, after administration.

In some embodiments, the $AUC_{0-8\ hrs,\ steady\ state}$ of the unit dosage is within about 80.00% to about 125.00% of a $AUC_{0-8\ hrs,\ steady\ state}$ of 7207 (CV 19%) h ng/mL, after administration.

In some embodiments, the N-{[(2R)-2-hydroxy-3-piperidin-1-ylpropyl]oxy}pyridine-3-carboximidoyl chloride 1-oxide, or pharmaceutically acceptable salt thereof, is measured in plasma.

In some embodiments, the geometric mean $C_{max,steady\ state}$ of the oral formulation at steady state is within about 80.00% to about 125.00% of a $C_{max,steady\ state}$ of 533 ng/mL (368-770 ng/mL $5^{th}$ and $95^{th}$ percentiles), after administration of said oral formulation in a human weighing from about 8 kg to about 15 kg.

In some embodiments, the geometric mean $C_{max,steady\ state}$ of the pharmaceutical composition at steady state is within about 80.00% to about 125.00% of a $C_{max,steady\ state}$ of 533 ng/mL (368-770 ng/mL $5^{th}$ and $95^{th}$ percentiles), after administration of said pharmaceutical composition in a human weighing from about 8 kg to about 15 kg.

In some embodiments, the geometric mean $C_{max,steady\ state}$ of the unit dosage at steady state is within about 80.00% to about 125.00% of a $C_{max,steady\ state}$ of 533 ng/mL (368-770 ng/mL $5^{th}$ and $95^{th}$ percentiles), after administration of said unit dosage in a human weighing from about 8 kg to about 15 kg.

In some embodiments, the $AUC_{0-8\ hrs,\ steady\ state}$ of the oral formulation is within about 80.00% to about 125.00% of a $AUC_{0-8\ hrs,\ steady\ state}$ of 2916 h ng/mL (1924-4436 h ng/mL $5^{th}$ and $95^{th}$ percentiles), after administration of said oral formulation in a human weighing from about 8 kg to about 15 kg.

In some embodiments, the $AUC_{0-8\ hrs,\ steady\ state}$ of the pharmaceutical composition is within about 80.00% to about 125.00% of a $AUC_{0-8\ hrs,\ steady\ state}$ of 2916 h ng/mL (1924-4436 h ng/mL $5^{th}$ and $95^{th}$ percentiles), after administration of said pharmaceutical composition in a human weighing from about 8 kg to about 15 kg.

In some embodiments, the $AUC_{0-8\ hrs,\ steady\ state}$ of the unit dosage is within about 80.00% to about 125.00% of a $AUC_{0-8\ hrs,\ steady\ state}$ of 2916 h ng/mL (1924-4436 h ng/mL $5^{th}$ and $95^{th}$ percentiles), after administration of said unit dosage in a human weighing from about 8 kg to about 15 kg.

In some embodiments, the geometric mean $C_{max,steady\ state}$ of the oral formulation at steady state is within about 80.00% to about 125.00% of a $C_{max,steady\ state}$ of 593 ng/mL (395-878 ng/mL $5^{th}$ and $95^{th}$ percentiles), after administration of said oral formulation in a human weighing from greater than about 15 kg to about 30 kg.

In some embodiments, the geometric mean $C_{max,steady\ state}$ of the pharmaceutical composition at steady state is within about 80.00% to about 125.00% of a $C_{max,steady\ state}$ of 593 ng/mL (395-878 ng/mL $5^{th}$ and $95^{th}$ percentiles), after administration of said pharmaceutical composition in a human weighing from greater than about 15 kg to about 30 kg.

In some embodiments, the geometric mean $C_{max,steady\ state}$ of the unit dosage at steady state is within about 80.00% to about 125.00% of a $C_{max,steady\ state}$ of 593 ng/mL (395-878 ng/mL $5^{th}$ and $95^{th}$ percentiles), after administration of said unit dosage in a human weighing from greater than about 15 kg to about 30 kg.

In some embodiments, the $AUC_{0\text{-}8\ hrs,\ steady\ state}$ of the oral formulation is within about 80.00% to about 125.00% of a $AUC_{0\text{-}8\ hrs,\ steady\ state}$ of 3043 h ng/mL (1938-4763 h ng/mL $5^{th}$ and $95^{th}$ percentiles), after administration of said oral formulation in a human weighing from greater than about 15 kg to about 30 kg.

In some embodiments, the $AUC_{0\text{-}8\ hrs,\ steady\ state}$ of the pharmaceutical composition is within about 80.00% to about 125.00% of a $AUC_{0\text{-}8\ hrs,\ steady\ state}$ of 3043 h ng/mL (1938-4763 h ng/mL $5^{th}$ and $95^{th}$ percentiles), after administration of said pharmaceutical composition in a human weighing from greater than about 15 kg to about 30 kg.

In some embodiments, the $AUC_{0\text{-}8\ hrs,\ steady\ state}$ of the unit dosage is within about 80.00% to about 125.00% of a $AUC_{0\text{-}8\ hrs,\ steady\ state}$ of 3043 h ng/mL (1938-4763 h ng/mL $5^{th}$ and $95^{th}$ percentiles), after administration of said unit dosage in a human weighing from greater than about 15 kg to about 30 kg.

In some embodiments, the geometric mean $C_{max,steady\ state}$ of the oral formulation at steady state is within about 80.00% to about 125.00% of a $C_{max,steady\ state}$ of 679 ng/mL (450-1024 ng/mL $5^{th}$ and $95^{th}$ percentiles), after administration of said oral formulation in a human weighing from greater than about 30 to about 55 kg.

In some embodiments, the geometric mean $C_{max,steady\ state}$ of the pharmaceutical composition at steady state is within about 80.00% to about 125.00% of a $C_{max,steady\ state}$ of 679 ng/mL (450-1024 ng/mL $5^{tH}$ and $95^{th}$ percentiles), after administration of said pharmaceutical composition in a human weighing from greater than about 30 to about 55 kg.

In some embodiments, the geometric mean $C_{max,steady\ state}$ of the unit dosage at steady state is within about 80.00% to about 125.00% of a $C_{max,steady\ state}$ of 679 ng/mL (450-1024 ng/mL $5^{th}$ and $95^{th}$ percentiles), after administration of said unit dosage in a human weighing from greater than about 30 to about 55 kg.

In some embodiments, the $AUC_{0\text{-}8\ hrs,\ steady\ state}$ of the oral formulation is within about 80.00% to about 125.00% of a $AUC_{0\text{-}8\ hrs,\ steady\ state}$ of 3149 h ng/mL (2010-4855 h ng/mL $5^{th}$ and $95^{th}$ percentiles), after administration of said oral formulation in a human weighing from greater than about 30 kg to about 55 kg.

In some embodiments, the $AUC_{0\text{-}8\ hrs,\ steady\ state}$ of the pharmaceutical composition is within about 80.00% to about 125.00% of a $AUC_{0\text{-}8\ hrs,\ steady\ state}$ of 3149 h ng/mL (2010-4855 h ng/mL $5^{th}$ and $95^{th}$ percentiles), after administration of said pharmaceutical composition in a human weighing from greater than about 30 kg to about 55 kg.

In some embodiments, the $AUC_{0\text{-}8\ hrs,\ steady\ state}$ of the unit dosage is within about 80.00% to about 125.00% of a $AUC_{0\text{-}8\ hrs,\ steady\ state}$ of 3149 h ng/mL (2010-4855 h ng/mL $5^{th}$ and $95^{th}$ percentiles), after administration of said unit dosage in a human weighing from greater than about 30 kg to about 55 kg.

In some embodiments, the geometric mean $C_{max,steady\ state}$ of the oral formulation at steady state is within about 80.00% to about 125.00% of a $C_{max,steady\ state}$ of 743 ng/mL (479-743 ng/mL $5^{th}$ and $95^{th}$ percentiles), after administration of said oral formulation in a human weighing greater than about 55 kg.

In some embodiments, the geometric mean $C_{max,steady\ state}$ of the pharmaceutical composition at steady state is within about 80.00% to about 125.00% of a $C_{max,steady\ state}$ of 743 ng/mL (479-743 ng/mL 5 and $95^{th}$ percentiles), after administration of said pharmaceutical composition in a human weighing greater than about 55 kg.

In some embodiments, the geometric mean $C_{max,steady\ state}$ of the unit dosage at steady state is within about 80.00% to about 125.00% of a $C_{max,steady\ state}$ of 743 ng/mL (479-743 ng/mL $5^{th}$ and $95^{th}$ percentiles), after administration of said unit dosage in a human weighing greater than about 55 kg.

In some embodiments, the $AUC_{0\text{-}8\ hrs,\ steady\ state}$ of the oral formulation is within about 80.00% to about 125.00% of a $AUC_{0\text{-}8\ hrs,\ steady\ state}$ of 3182 h ng/mL (2057-4921 h ng/mL $5^{th}$ and $95^{th}$ percentiles), after administration of said oral formulation in a human weighing greater than about 55 kg.

In some embodiments, the $AUC_{0\text{-}8\ hrs,\ steady\ state}$ of the pharmaceutical composition is within about 80.00% to about 125.00% of a $AUC_{0\text{-}8\ hrs,\ steady\ state}$ of 3182 h ng/mL (2057-4921 h ng/mL $5^{th}$ and $95^{th}$ percentiles), after administration of said pharmaceutical composition in a human weighing greater than about 55 kg.

In some embodiments, the $AUC_{0\text{-}8\ hrs,\ steady\ state}$ of the unit dosage is within about 80.00% to about 125.00% of a $AUC_{0\text{-}8\ hrs,\ steady\ state}$ of 3182 h ng/mL (2057-4921 h ng/mL $5^{th}$ and $95^{th}$ percentiles), after administration of said unit dosage in a human weighing greater than about 55 kg.

In some embodiments, the geometric mean $C_{max,steady\ state}$ of the oral formulation at steady state is within about 80.00% to about 125.00% of a $C_{max,steady\ state}$ of 352 ng/mL (240-514 ng/mL $5^{th}$ and $95^{th}$ percentiles), after administration of said oral formulation in a human weighing from about 8 kg to about 15 kg.

In some embodiments, the geometric mean $C_{max,steady\ state}$ of the pharmaceutical composition at steady state is within about 80.00% to about 125.00% of a $C_{max,steady\ state}$ of 352 ng/mL (240-514 ng/mL $5^{th}$ and $95^{th}$ percentiles), after administration of said pharmaceutical composition in a human weighing from about 8 kg to about 15 kg.

In some embodiments, the geometric mean $C_{max,steady\ state}$ of the unit dosage at steady state is within about 80.00% to about 125.00% of a $C_{max,steady\ state}$ of 352 ng/mL (240-514 ng/mL $5^{th}$ and $95^{th}$ percentiles), after administration of said unit dosage in a human weighing from about 8 kg to about 15 kg.

In some embodiments, the $AUC_{0\text{-}8\ hrs,\ steady\ state}$ of the oral formulation is within about 80.00% to about 125.00% of a $AUC_{0\text{-}8\ hrs,\ steady\ state}$ of 1918 h ng/mL (1255-2908 h ng/mL $5^{th}$ and $95^{th}$ percentiles), after administration of said oral formulation in a human weighing from about 8 kg to about 15 kg.

In some embodiments, the $AUC_{0\text{-}8\ hrs,\ steady\ state}$ of the pharmaceutical composition is within about 80.00% to about 125.00% of a $AUC_{0\text{-}8\ hrs,\ steady\ state}$ of 1918 h ng/mL (1255-2908 h ng/mL 5' and 95' percentiles), after administration of said pharmaceutical composition in a human weighing from about 8 kg to about 15 kg.

In some embodiments, the $AUC_{0\text{-}8\ hrs,\ steady\ state}$ of the unit dosage is within about 80.00% to about 125.00% of a $AUC_{0\text{-}8\ hrs,\ steady\ state}$ of 1918 h ng/mL (1255-2908 h ng/mL $5^{th}$ and $95^{th}$ percentiles), after administration of said unit dosage in a human weighing from about 8 kg to about 15 kg.

In some embodiments, the geometric mean $C_{max,steady\ state}$ of the oral formulation at steady state is within about 80.00% to about 125.00% of a $C_{0\text{-}8\ hrs,\ steady\ state}$ of 473 ng/mL (323-688 ng/mL $5^{th}$ and $95^{th}$ percentiles), after administration of said oral formulation in a human weighing from greater than about 15 kg to about 22 kg.

In some embodiments, the geometric mean $C_{0\text{-}8\ hrs,\ steady\ state}$ of the pharmaceutical composition at steady state is within about 80.00% to about 125.00% of a $C_{0\text{-}8\ hrs,\ steady\ state}$ of 473 ng/mL (323-688 ng/mL $5^{th}$ and $95^{th}$ percentiles), after administration of said pharmaceutical composition in a human weighing from greater than about 15 kg to about 22 kg.

In some embodiments, the geometric mean $C_{0-8\ hrs,\ steady\ state}$ of the unit dosage at steady state is within about 80.00% to about 125.00% of a $C_{0-8\ hrs,\ steady\ state}$ of 473 ng/mL (323-688 ng/mL $5^{th}$ and $95^{th}$ percentiles), after administration of said unit dosage in a human weighing from greater than about 15 kg to about 22 kg.

In some embodiments, the $AUC_{0-8\ hrs,\ steady\ state}$ of the oral formulation is within about 80.00% to about 125.00% of a $AUC_{0-8\ hrs,\ steady\ state}$ of 2479 h ng/mL (1640-3771 h ng/mL $5^{th}$ and $95^{th}$ percentiles), after administration of said oral formulation in a human weighing from greater than about 15 kg to about 22 kg.

In some embodiments, the $AUC_{0-8\ hrs,\ steady\ state}$ of the pharmaceutical composition is within about 80.00% to about 125.00% of a $AUC_{0-8\ hrs,\ steady\ state}$ of 2479 h ng/mL (1640-3771 h ng/mL $5^{th}$ and $95^{th}$ percentiles), after administration of said pharmaceutical composition in a human weighing from greater than about 15 kg to about 22 kg.

In some embodiments, the $AUC_{0-8\ hrs,\ steady\ state}$ of the unit dosage is within about 80.00% to about 125.00% of a $AUC_{0-8\ hrs,\ steady\ state}$ of 2479 h ng/mL (1640-3771 h ng/mL $5^{th}$ and $95^{th}$ percentiles), after administration of said unit dosage in a human weighing from greater than about 15 kg to about 22 kg.

In some embodiments, the geometric mean $C_{max,steady\ state}$ of the oral formulation at steady state is within about 80.00% to about 125.00% of a $C_{max,steady\ state}$ of 522 ng/mL (349-770 ng/mL $5^{th}$ and $95^{th}$ percentiles), after administration of said oral formulation in a human weighing from greater than about 22 kg to about 38 kg.

In some embodiments, the geometric mean $C_{max,steady\ state}$ of the pharmaceutical composition at steady state is within about 80.00% to about 125.00% of a $C_{max,steady\ state}$ of 522 ng/mL (349-770 ng/mL $5^{th}$ and $95^{th}$ percentiles), after administration of said pharmaceutical composition in a human weighing from greater than about 22 kg to about 38 kg.

In some embodiments, the geometric mean $C_{max,steady\ state}$ of the unit dosage at steady state is within about 80.00% to about 125.00% of a $C_{max,steady\ state}$ of 522 ng/mL (349-770 ng/mL $5^{th}$ and $95^{th}$ percentiles), after administration of said unit dosage in a human weighing from greater than about 22 kg to about 38 kg.

In some embodiments, the $AUC_{0-8\ hrs,\ steady\ state}$ of the oral formulation is within about 80.00% to about 125.00% of a $AUC_{0-8\ hrs,\ steady\ state}$ of 2557 h ng/mL (1663-3942 h ng/mL $5^{th}$ and $95^{th}$ percentiles), after administration of said oral formulation in a human weighing from greater than about 22 kg to about 38 kg.

In some embodiments, the $AUC_{0-8\ hrs,\ steady\ state}$ of the pharmaceutical composition is within about 80.00% to about 125.00% of a $AUC_{0-8\ hrs,\ steady\ state}$ of 2557 h ng/mL (1663-3942 h ng/mL $5^{th}$ and $95^{th}$ percentiles), after administration of said pharmaceutical composition in a human weighing from greater than about 22 kg to about 38 kg.

In some embodiments, the $AUC_{0-8\ hrs,\ steady\ state}$ of the unit dosage is within about 80.00% to about 125.00% of a $AUC_{0-8\ hrs,\ steady\ state}$ of 2557 h ng/mL (1663-3942 h ng/mL $5^{th}$ and $95^{th}$ percentiles), after administration of said unit dosage in a human weighing from greater than about 22 kg to about 38 kg.

In some embodiments, the geometric mean $C_{max,steady\ state}$ of the oral formulation at steady state is within about 80.00% to about 125.00% of a $C_{max,steady\ state}$ of 651 ng/mL (435-974 ng/mL $5^{th}$ and $95^{th}$ percentiles), after administration of said oral formulation in a human weighing from greater than about 38 kg to about 55 kg.

In some embodiments, the geometric mean $C_{max,steady\ state}$ of the pharmaceutical composition at steady state is within about 80.00% to about 125.00% of a $C_{max,steady\ state}$ of 651 ng/mL (435-974 ng/mL $5^{th}$ and $95^{th}$ percentiles), after administration of said pharmaceutical composition in a human weighing from greater than about 38 kg to about 55 kg.

In some embodiments, the geometric mean $C_{max,steady\ state}$ of the unit dosage at steady state is within about 80.00% to about 125.00% of a $C_{max,steady\ state}$ of 651 ng/mL (435-974 ng/mL $5^{th}$ and $95^{th}$ percentiles), after administration of said unit dosage in a human weighing from greater than about 38 kg to about 55 kg.

In some embodiments, the $AUC_{0-8\ hrs,\ steady\ state}$ of the oral formulation is within about 80.00% to about 125.00% of a $AUC_{0-8\ hrs,\ steady\ state}$ of 2954 h ng/mL (1958-4465 h ng/mL $5^{th}$ and $95^{th}$ percentiles), after administration of said oral formulation in a human weighing from greater than about 38 kg to about 55 kg.

In some embodiments, the $AUC_{0-8\ hrs,\ steady\ state}$ of the pharmaceutical composition is within about 80.00% to about 125.00% of a $AUC_{0-8\ hrs,\ steady\ state}$ of 2954 h ng/mL (1958-4465 h ng/mL $5^{th}$ and $95^{th}$ percentiles), after administration of said pharmaceutical composition in a human weighing from greater than about 38 kg to about 55 kg.

In some embodiments, the $AUC_{0-8\ hrs,\ steady\ state}$ of the unit dosage is within about 80.00% to about 125.00% of a $AUC_{0-8\ hrs,\ steady\ state}$ of 2954 h ng/mL (1958-4465 h ng/mL $5^{th}$ and $95^{th}$ percentiles), after administration of said unit dosage in a human weighing from greater than about 38 kg to about 55 kg.

In some embodiments, the geometric mean $C_{max,steady\ state}$ of the oral formulation at steady state is within about 80.00% to about 125.00% of a $C_{max,steady\ state}$ of 739 ng/mL (483-1130 ng/mL $5^{th}$ and $95^{th}$ percentiles), after administration of said oral formulation in a human weighing greater than about 55 kg.

In some embodiments, the geometric mean $C_{max,steady\ state}$ of the pharmaceutical composition at steady state is within about 80.00% to about 125.00% of a $C_{max,steady\ state}$ of 739 ng/mL (483-1130 ng/mL $5^{th}$ and $95^{th}$ percentiles), after administration of said pharmaceutical composition in a human weighing greater than about 55 kg.

In some embodiments, the geometric mean $C_{max,steady\ state}$ of the unit dosage at steady state is within about 80.00% to about 125.00% of a $C_{max,steady\ state}$ of 739 ng/mL (483-1130 ng/mL $5^{th}$ and $95^{th}$ percentiles), after administration of said unit dosage in a human weighing greater than about 55 kg.

In some embodiments, the $AUC_{0-8\ hrs,\ steady\ state}$ of the oral formulation is within about 80.00% to about 125.00% of a $AUC_{0-8\ hrs,\ steady\ state}$ of 3191 h ng/mL (2054-4948 h ng/mL $5^{th}$ and $95^{th}$ percentiles), after administration of said oral formulation in a human weighing greater than about 55 kg.

In some embodiments, the $AUC_{0-8\ hrs,\ steady\ state}$ saw of the pharmaceutical composition is within about 80.00% to about 125.00% of a $AUC_{0-8\ hrs,\ steady\ state}$ of 3191 h ng/mL (2054-4948 h ng/mL $5^{th}$ and $95^{th}$ percentiles), after administration of said pharmaceutical composition in a human weighing greater than about 55 kg.

In some embodiments, the $AUC_{0-8\ hrs,\ steady\ state}$ of the unit dosage is within about 80.00% to about 125.00% of a $AUC_{0-8\ hrs,\ steady\ state}$ of 3191 h ng/mL (2054-4948 h ng/mL $5^{th}$ and $95^{th}$ percentiles), after administration of said unit dosage in a human weighing greater than about 55 kg.

In some embodiments, the N-{[(2R)-2-hydroxy-3-piperidin-1-ylpropyl]oxy}pyridine-3-carboximidoyl chloride 1-oxide citrate exposure increases dose-proportionally following a single oral dosage from about 31 mg to about 496 mg, wherein the estimates of the proportionality coefficient (90% CI) for $C_{max}$ is 1,149 (1,07-1,20) and for $AUC_{0\text{-}inf}$ is 1,027 (0,98-1,08).

In some embodiments, the overall median $t_{max}$ following administration is 0.25 to 3.0 hours.

In some embodiments, the median $t_{max}$ following administration is about 0.5 hours.

In some embodiments, the N-{[(2R)-2-hydroxy-3-piperidin-1-ylpropyl]oxy}pyridine-3-carboximidoyl chloride 1-oxide, or pharmaceutically acceptable salt thereof, is metabolized after ingestion.

In some embodiments, the N-{[(2R)-2-hydroxy-3-piperidin-1-ylpropyl]oxy}pyridine-3-carboximidoyl chloride 1-oxide, or pharmaceutically acceptable salt thereof, metabolite is a cysteine conjugate.

In some embodiments, the N-{[(2R)-2-hydroxy-3-piperidin-1-ylpropyl]oxy}pyridine-3-carboximidoyl chloride 1-oxide, or pharmaceutically acceptable salt thereof, metabolite is the O-glucuronide.

In some embodiments, the oral formulation has a shelf-life of at least 24 months from about 20° C. to about 25° C.

In some embodiments, the pharmaceutical composition has a shelf-life of at least 24 months from about 20° C. to about 25° C.

In some embodiments, the unit dosage has a shelf-life of at least 24 months from about 20° C. to about 25° C.

In some embodiments, the oral formulation comprises ultra-pure N-{[(2R)-2-hydroxy-3-piperidin-1-ylpropyl]oxy}pyridine-3-carboximidoyl chloride 1-oxide, or pharmaceutically acceptable salt thereof.

In some embodiments, the pharmaceutical composition comprises ultra-pure N-{[(2R)-2-hydroxy-3-piperidin-1-ylpropyl]oxy}pyridine-3-carboximidoyl chloride 1-oxide, or pharmaceutically acceptable salt thereof.

In some embodiments, the unit dosage comprises ultra-pure N-{[(2R)-2-hydroxy-3-piperidin-1-ylpropyl]oxy}pyridine-3-carboximidoyl chloride 1-oxide, or pharmaceutically acceptable salt thereof.

Particle Size Distribution

In some embodiments, the N-{[(2R)-2-hydroxy-3-piperidin-1-ylpropyl]oxy}pyridine-3-carboximidoyl chloride 1-oxide citrate forms particles having a preferred particle size distribution. In some embodiments, the pharmaceutical composition is provided comprising N-{[(2R)-2-hydroxy-3-piperidin-1-ylpropyl]oxy}pyridine-3-carboximidoyl chloride 1-oxide citrate particles that have the preferred particle size distribution listed herein. The particle size distribution (PSD) can be determined using static automated imaging (Morphology 4) as in Example 8 (Table 3A) presented herein. In some embodiments, the PSD is determined using Malvern Mastersizer, for example Malvern Mastersizer 3000. The methods employed in the present disclosure for determining PSD are described in detail in Example 11.

In some embodiments, the N-{[(2R)-2-hydroxy-3-piperidin-1-ylpropyl]oxy}pyridine-3-carboximidoyl chloride 1-oxide citrate forms particles having a Number CE Diameter D10 of from about 0.5 µm to about 3.5 µm; such as the N-{[(2R)-2-hydroxy-3-piperidin-1-ylpropyl]oxy}pyridine-3-carboximidoyl chloride 1-oxide citrate particles have a Number CE Diameter D10 of from about 0.5 µm to about 3.5 µm.

In some embodiments, the N-{[(2R)-2-hydroxy-3-piperidin-1-ylpropyl]oxy}pyridine-3-carboximidoyl chloride 1-oxide citrate forms particles having a D10 particle size with a Number CE Diameter D10 of about 0.5 µm, about 0.6 µm, about 0.7 µm, about 0.8 µm, about 0.9 µm, about 1.0 µm, about 1.1 µm, about 1.2 µm, about 1.3 µm, about 1.4 µm, about 1.5 µm, about 1.6 µm, about 1.7 µm, about 1.8 µm, about 1.9 µm, about 2.0 µm, about 2.1 µm, about 2.2 µm, about 2.3 µm, about 2.4 µm, about 2.5 µm, about 2.6 µm, about 2.7 µm, about 2.8 µm, about 2.9 µm, about 3.0 µm, about 3.1 µm, about 3.2 µm, about 3.3 µm, about 3.4 µm, or about 3.5 µm.

In some embodiments, the N-{[(2R)-2-hydroxy-3-piperidin-1-ylpropyl]oxy}pyridine-3-carboximidoyl chloride 1-oxide citrate forms particles having a D10 particle size with a Number CE Diameter D10 of about 0.5 µm, about 0.6 µm, about 0.7 µm, about 0.8 µm, about 0.9 µm, about 1.0 µm, about 1.1 µm, about 1.2 µm, about 1.3 µm, about 1.4 µm, about 1.5 µm, about 1.6 µm, about 1.7 µm, about 1.8 µm, about 1.9 µm, about 2.0 µm, about 2.1 µm, about 2.2 µm, about 2.3 µm, about 2.4 µm, about 2.5 µm, about 2.6 µm, about 2.7 µm, about 2.8 µm, about 2.9 µm, about 3.0 µm, about 3.1 µm, about 3.2 µm, about 3.3 µm, about 3.4 µm, or about 3.5 µm.

In some embodiments, the N-{[(2R)-2-hydroxy-3-piperidin-1-ylpropyl]oxy}pyridine-3-carboximidoyl chloride 1-oxide citrate forms particles having a D10 particle size with a Number CE Diameter D10 of from about 0.5 µm to about 3.5 µm, such as from about 0.5 µm to about 1.0 µm, such as from about 1.0 µm to about 1.5 µm, such as from about 1.5 µm to about 2.0 µm, such as from about 2.0 µm to about 2.5 µm, such as from about 2.5 µm to about 3.0 µm, such as from about 3.0 µm to about 3.5 µm.

In some embodiments, the N-{[(2R)-2-hydroxy-3-piperidin-1-ylpropyl]oxy}pyridine-3-carboximidoyl chloride 1-oxide citrate forms particles having a D10 particle size with a Number CE Diameter D10 of about 0.6 µm, about 0.7 µm, about 0.8 µm, about 0.9 µm, about 1.0 µm, about 1.1 µm, about 2.4 µm, or about 2.5 µm.

In some embodiments, the N-{[(2R)-2-hydroxy-3-piperidin-1-ylpropyl]oxy}pyridine-3-carboximidoyl chloride 1-oxide citrate forms particles having a Volume CE Diameter D10 of from about 2.0 µm to about 17.0 µm.

In some embodiments, the N-{[(2R)-2-hydroxy-3-piperidin-1-ylpropyl]oxy}pyridine-3-carboximidoyl chloride 1-oxide citrate forms particles having a D10 particle size with a Volume CE Diameter D10 of about 2.0 µm, about 2.5 µm, about 3.0 µm, about 3.5 µm, about 4.0 µm, about 4.5 µm, about 5.0 µm, about 5.5 µm, about 6.0 µm, about 6.5 µm, about 7.0 µm, about 7.5 µm, about 8.0 µm, about 8.5 µm, about 9.0 µm, about 9.5 µm, about 10.0 µm, about 10.5 µm, about 11.0 µm, about 11.5 µm, about 12.0 µm, about 12.5 µm, about 13.0 µm, about 13.5 µm, about 14.0 µm, about 14.5 µm, about 15.0 µm, about 15.5 µm, about 16.0 µm, about 16.5 µm, or about 17.0 µm.

In some embodiments, the N-{[(2R)-2-hydroxy-3-piperidin-1-ylpropyl]oxy}pyridine-3-carboximidoyl chloride 1-oxide citrate forms particles having a D10 particle size with a Volume CE Diameter D10 of from about 2.0 µm to about 17.0 µm, such as from about 2.0 µm to about 3.0 µm, such as from about 3.0 µm to about 4.0 µm, such as from about 4.0 µm to about 5.0 µm, such as from about 5.0 µm to about 6.0 µm, such as from about 6.0 µm to about 7.0 µm, such as from about 7.0 µm to about 8.0 µm, such as from about 8.0 µm to about 9.0 µm, such as from about 9.0 µm to about 10.0 µm, such as from about 10.0 µm to about 11.0 µm, such as from about 11.0 µm to about 12.0 µm, such as from about 12.0 µm to about 13.0 µm, such as from about 13.0 µm to about 14.0 µm, such as from about 14.0 µm to about 15.0

µm, such as from about 15.0 µm to about 16.0 µm, such as from about 16.0 µm to about 17.0 µm.

In some embodiments, the N-{[(2R)-2-hydroxy-3-piperidin-1-ylpropyl]oxy}pyridine-3-carboximidoyl chloride 1-oxide citrate forms particles having a D10 particle size with a Volume CE Diameter D10 of about 4.6 µm, about 6.2 µm, about 9.4 µm, about 10.7 µm about 10.9 µm, about 11.2 µm, about 12.4 µm, about 12.6 µm, or about 13.1 µm.

In some embodiments, the N-{[(2R)-2-hydroxy-3-piperidin-1-ylpropyl]oxy}pyridine-3-carboximidoyl chloride 1-oxide citrate forms particles having a Number Length D10 of from about 0.5 µm to about 5.0 µm.

In some embodiments, the N-{[(2R)-2-hydroxy-3-piperidin-1-ylpropyl]oxy}pyridine-3-carboximidoyl chloride 1-oxide citrate forms particles having a D10 particle size with a Number Length D10 of about 0.5 µm, about 0.6 µm, about 0.7 µm, about 0.8 µm, about 0.9 µm, about 1.0 µm, about 1.1 µm, about 1.2 µm, about 1.3 µm, about 1.4 µm, about 1.5 µm, about 1.6 µm, about 1.7 µm, about 1.8 µm, about 1.9 µm, about 2.0 µm, about 2.1 µm, about 2.2 µm, about 2.3 µm, about 2.4 µm, or about 2.5 µm, about 2.6 µm, about 2.7 µm, about 2.8 µm, about 2.9 µm, about 3.0 µm, about 3.1 µm, about 3.2 µm, about 3.3 µm, about 3.4 µm, about 3.5 µm, about 3.6 µm, about 3.7 µm, about 3.8 µm, about 3.9 µm, about 4.0 µm, about 4.1 µm, about 4.2 µm, about 4.3 µm, about 4.4 µm, or about 4.5 µm, about 4.6 µm, about 4.7 µm, about 4.8 µm, about 4.9 µm, or about 5.0 µm.

In some embodiments, the N-{[(2R)-2-hydroxy-3-piperidin-1-ylpropyl]oxy}pyridine-3-carboximidoyl chloride 1-oxide citrate forms particles having a D10 particle size with a Number Length D10 of from about 0.5 µm to about 5.0 µm, such as from about 0.5 µm, to about 1.0 µm, such as from about 1.0 µm to about 1.5 µm, such as from about 1.5 µm to about 2.0 µm, such as from about 2.0 µm to about 2.5 µm, such as from about 2.5 µm to about 3.0 µm, such as from about 3.0 µm to about 3.5 µm, such as from about 3.5 µm to about 4.0 µm, such as from about 4.0 µm to about 4.5 µm, such as from about 4.5 µm to about 5.0 µm.

In some embodiments, the N-{[(2R)-2-hydroxy-3-piperidin-1-ylpropyl]oxy}pyridine-3-carboximidoyl chloride 1-oxide citrate forms particles having a D10 particle size with a Number Length D10 of about 1.1 µm, about 1.4 µm, about 1.5 µm, about 1.7 µm, about 1.8 µm, about 2.8 µm, about 2.9 µm about 3.5 µm, or about 4.2 µm.

In some embodiments, the N-{[(2R)-2-hydroxy-3-piperidin-1-ylpropyl]oxy}pyridine-3-carboximidoyl chloride 1-oxide citrate particles have a D10 particle size determined using Malvern Mastersizer 3000 of from about 2.0 µm to about 20.0 µm.

In some embodiments, the N-{[(2R)-2-hydroxy-3-piperidin-1-ylpropyl]oxy}pyridine-3-carboximidoyl chloride 1-oxide citrate particles have a D10 particle size determined using Malvern Mastersizer 3000 of about 2.0 µm, about 2.5 µm, about 3.0 µm, about 3.5 µm, about 4.0 µm, about 4.5 µm, about 5.0 µm, about 5.5 µm, about 6.0 µm, about 6.5 µm, about 7.0 µm, about 7.5 µm, about 8.0 µm, about 8.5 µm, about 9.0 µm, about 9.5 µm, about 10.0 µm, about 10.5 µm, about 11.0 µm, about 11.5 µm, about 12.0 µm, about 12.5 µm, about 13.0 µm, about 13.5 µm, about 14.0 µm, about 14.5 µm, about 15.0 µm, about 15.5 µm, about 16.0 µm, about 16.5 µm, about 17.0 µm, about 17.5 µm, about 18.0 µm, about 18.5 µm, about 19.0 µm, about 19.5 µm, about 20.0 µm.

In some embodiments, the N-{[(2R)-2-hydroxy-3-piperidin-1-ylpropyl]oxy}pyridine-3-carboximidoyl chloride 1-oxide citrate particles have a D10 particle size determined using Malvern Mastersizer 3000 of from about 2.0 µm to about 20.0 µm, such as from about 2.0 µm to about 2.5 µm, such as from about 2.5 µm to about 3.0 µm, such as from about 3.0 µm to about 3.5 µm, such as from about 3.5 µm to about 4.0 µm, such as from about 4.0 µm to about 4.5 µm, such as from about 4.5 µm to about 5.0 µm, such as from about 5.0 µm to about 5.5 µm, such as from about 5.5 µm to about 6.0 µm, such as from about 6.0 µm to about 6.5 µm, such as from about 6.5 µm to about 7.0 µm, such as from about 7.0 µm to about 7.5 µm, such as from about 7.5 µm to about 8.0 µm, such as from about 8.0 µm to about 8.5 µm, such as from about 8.5 µm to about 9.0 µm, such as from about 9.0 µm to about 9.5 µm, such as from about 9.5 µm to about 10.0 µm, such as from about 10.0 µm to about 10.5 µm, such as from about 10.5 µm to about 11.0 µm, such as from about 11.0 µm to about 11.5 µm, such as from about 11.5 µm to about 12.0 µm, such as from about 12.0 µm to about 12.5 µm, such as from about 12.5 µm to about 13.0 µm, such as from about 13.0 µm to about 13.5 µm, such as from about 13.5 µm to about 14.0 µm, such as from about 14.0 µm to about 14.5 µm, such as from about 14.5 µm to about 15.0 µm, such as from about 15.0 µm to about 15.5 µm, such as from about 15.5 µm to about 16.0 µm, such as from about 16.0 µm to about 16.5 µm, such as from about 16.5 µm to about 17.0 µm, such as from about 17.0 µm to about 17.5 µm, such as from about 17.5 µm to about 18.0 µm, such as from about 18.0 µm to about 18.5 µm, such as from about 18.5 µm to about 19.0 µm, such as from about 19.0 µm to about 19.5 µm, such as from about 19.5 µm to about 20.0 µm.

In some embodiments, the N-{[(2R)-2-hydroxy-3-piperidin-1-ylpropyl]oxy}pyridine-3-carboximidoyl chloride 1-oxide citrate forms particles having a Number CE Diameter D50 of from about 1.0 µm to about 10.0 µm, such as the N-{[(2R)-2-hydroxy-3-piperidin-1-ylpropyl]oxy}pyridine-3-carboximidoyl chloride 1-oxide citrate particles have a Number CE Diameter D50 of from about 1.0 µm to about 10.0 µm.

In some embodiments, the N-{[(2R)-2-hydroxy-3-piperidin-1-ylpropyl]oxy}pyridine-3-carboximidoyl chloride 1-oxide citrate forms particles having a D50 particle size with a Number CE Diameter D50 of about 1.0 µm, about 1.1 µm, about 1.2 µm, about 1.3 µm, about 1.4 µm, about 1.5 µm, about 1.6 µm, about 1.7 µm, about 1.8 µm, about 1.9 µm, about 2.0 µm, about 2.1 µm, about 2.2 µm, about 2.3 µm, about 2.4 µm, about 2.5 µm, about 2.6 µm, about 2.7 µm, about 2.8 µm, about 2.9 µm, about 3.0 µm, about 3.1 µm, about 3.2 µm, about 3.3 µm, about 3.4 µm, about 3.5 µm, about 3.6 µm, about 3.7 µm, about 3.8 µm, about 3.9 µm, about 4.0 µm, about 4.1 µm, about 4.2 µm, about 4.3 µm, about 4.4 µm, about 4.5 µm, about 4.6 µm, about 4.7 µm, about 4.8 µm, about 4.9 µm, about 5.0 µm, about 5.1 µm, about 5.2 µm, about 5.3 µm, about 5.4 µm, about 5.5 µm, about 5.6 µm, about 5.7 µm, about 5.8 µm, about 5.9 µm, about 6.0 µm, about 6.1 µm, about 6.2 µm, about 6.3 µm, about 6.4 µm, about 6.5 µm, about 6.6 µm, about 6.7 µm, about 6.8 µm, about 6.9 µm, about 7.0 µm, about 7.1 µm, about 7.2 µm, about 7.3 µm, about 7.4 µm, about 7.5 µm, about 7.6 µm, about 7.7 µm, about 7.8 µm, about 7.9 µm, about 8.0 µm, about 8.1 µm, about 8.2 µm, about 8.3 µm, about 8.4 µm, about 8.5 µm, about 8.6 µm, about 8.7 µm, about 8.8 µm, about 8.9 µm, about 9.0 µm, about 9.1 µm, about 9.2 µm, about 9.3 µm, about 9.4 µm, about 9.5 µm, about 9.6 µm, about 9.7 µm, about 9.8 µm, about 9.9 µm, or about 10.0 µm.

In some embodiments, the N-{[(2R)-2-hydroxy-3-piperidin-1-ylpropyl]oxy}pyridine-3-carboximidoyl chloride 1-oxide citrate forms particles having a D50 particle size with a Number CE Diameter D50 of from about 1.0 µm to about 10.0 µm, such as from about 1.0 µm to about 2.0 µm, such as from about 2.0 µm to about 3.0 µm, such as from about 3.0 µm to about 4.0 µm, such as from about 4.0 µm to about 5.0 µm, such as from about 5.0 µm to about 6.0 µm, such as from about 6.0 µm to about 7.0 µm, such as from about 7.0 µm to about 8.0 µm, such as from about 8.0 µm to about 9.0 µm, such as from about 9.0 µm to about 10.0 µm.

In some embodiments, the N-{[(2R)-2-hydroxy-3-piperidin-1-ylpropyl]oxy}pyridine-3-carboximidoyl chloride 1-oxide citrate forms particles having a D50 particle size with a Number CE Diameter D50 of about 1.6 µm, about 2.0 µm, about 2.2 µm, about 2.5 µm, about 2.9 µm, about 3.3 µm, about 5.6 µm, or about 5.3 µm.

In some embodiments, the N-{[(2R)-2-hydroxy-3-piperidin-1-ylpropyl]oxy}pyridine-3-carboximidoyl chloride 1-oxide citrate forms particles having a Volume CE Diameter D50 of from about 10.0 µm to about 39.0 µm.

In some embodiments, the N-{[(2R)-2-hydroxy-3-piperidin-1-ylpropyl]oxy}pyridine-3-carboximidoyl chloride 1-oxide citrate forms particles having a D50 particle size with a Volume CE Diameter D50 of about 10.0 µm, about 11.0 µm, about 12.0 µm, about 13.0 µm, about 14.0 µm, about 15.0 µm, about 16.0 µm, about 17.0 µm, about 18.0 µm, about 19.0 µm, about 20 µm, about 21.0 µm, about 22.0 µm, about 23.0 µm, about 24.0 µm, about 25.0 µm, about 26.0 µm, about 27.0 µm, about 28.0 µm, about 29.0 µm, about 30.0 µm, about 31.0, about 32.0 µm, about 33.0 µm, about 34.0 µm, about 35.0 µm, about 36.0 µm, about 37.0 µm, about 38.0 µm, or about 39.0 µm.

In some embodiments, the N-{[(2R)-2-hydroxy-3-piperidin-1-ylpropyl]oxy}pyridine-3-carboximidoyl chloride 1-oxide citrate forms particles having a D50 particle size with a Volume CE Diameter D50 of from about 10.0 µm to about 39.0 µm, such as from about 10.0 µm to about 12.0 µm, such as from about 12.0 µm to about 14.0 µm, such as from about 14.0 µm to about 16.0 µm, such as from about 16.0 µm to about 18.0 µm, such as from about 18.0 µm to about 20.0 µm, such as from about 20.0 µm to about 22.0 µm, such as from about 22.0 µm to about 24.0 µm, such as from about 24.0 µm to about 26.0 µm, such as from about 26.0 µm to about 28.0 µm, such as from about 28.0 µm to about 30.0 µm, such as from about 30.0 to about 32.0 µm, such as from about 32.0 µm to about 34.0 µm, such as from about 34.0 µm to about 36.0 µm, such as from about 36.0 µm to about 38.0 µm, such as from about 38.0 µm to about 39.0 µm.

In some embodiments, the N-{[(2R)-2-hydroxy-3-piperidin-1-ylpropyl]oxy}pyridine-3-carboximidoyl chloride 1-oxide citrate forms particles having a D50 particle size with a Volume CE Diameter D50 of about 11.1 µm, about 14.0 µm, about 20.6 µm, about 22.7 µm, about 24.7 µm, about 25.0 µm, about 26.0 µm, about 26.4 µm, about 32.1 µm, or about 38.9 µm.

In some embodiments, the N-{[(2R)-2-hydroxy-3-piperidin-1-ylpropyl]oxy}pyridine-3-carboximidoyl chloride 1-oxide citrate forms particles having a Number Length D50 of from about 3.0 µm to about 12.0 µm.

In some embodiments, the N-{[(2R)-2-hydroxy-3-piperidin-1-ylpropyl]oxy}pyridine-3-carboximidoyl chloride 1-oxide citrate forms particles having a D50 particle size with a Number Length D50 of about 3.0 µm, about 3.1 µm, about 3.2 µm, about 3.3 µm, about 3.4 µm, about 3.5 µm, about 3.6 µm, about 3.7 µm, about 3.8 µm, about 3.9 µm, about 4.0 µm, about 4.1 µm, about 4.2 µm, about 4.3 µm, about 4.4 µm, about 4.5 µm, about 4.6 µm, about 4.7 µm, about 4.8 µm, about 4.9 µm, about 5.0 µm, about 5.1 µm, about 5.2 µm, about 5.3 µm, about 5.4 µm, about 5.5 µm, about 5.6 µm, about 5.7 µm, about 5.8 µm, about 5.9 µm, about 6.0 µm, about 6.1 µm, about 6.2 µm, about 6.3 µm, about 6.4 µm, about 6.5 µm, about 6.6 µm, about 6.7 µm, about 6.8 µm, about 6.9 µm, about 7.0 µm about 7.1 µm, about 7.2 µm, about 7.3 µm, about 7.4 µm, about 7.5 µm, about 7.6 µm, about 7.7 µm, about 7.8 µm, about 7.9 µm, about 8.0 µm, about 8.1 µm, about 8.2 µm, about 8.3 µm, about 8.4 µm, about 8.5 µm, about 8.6 µm, about 8.7 µm, about 8.8 µm, about 8.9 µm, about 9.0 µm about 9.1 µm, about 9.2 µm, about 9.3 µm, about 9.4 µm, about 9.5 µm, about 9.6 µm, about 9.7 µm, about 9.8 µm, about 9.9 µm, about 10.0 µm, about 10.1 µm, about 10.2 µm, about 10.3 µm, about 10.4 µm, about 10.5 µm, about 10.6 µm, about 10.7 µm, about 10.8 µm, about 10.9 µm, about 11.0 µm, about 11.1 µm, about 11.2 µm, about 11.3 µm, about 11.4 µm, about 11.5 µm, about 11.6 µm, about 11.7 µm, about 11.8 µm, about 11.9 µm, or about 12.0 µm.

In some embodiments, the N-{[(2R)-2-hydroxy-3-piperidin-1-ylpropyl]oxy}pyridine-3-carboximidoyl chloride 1-oxide citrate forms particles having a D50 particle size with a Number Length D50 of from about 3.0 µm to about 12.0 µm, such as from about 3.0 µm to about 3.5 µm, such as from about 3.5 µm to about 4.0 µm, such as from about 4.0 µm to about 4.5 µm, such as from about 4.5 µm to about 5.0 µm, such as from about 5.0 µm to about 5.5 µm, such as from about 5.5 µm, to about 6.0 µm, such as from about 6.0 µm to about 6.5 µm, such as from about 6.5 µm to about 7.0 µm, such as from about 7.0 µm to about 7.5 µm, such as from about 7.5 µm to about 8.0 µm, such as from about 8.0 µm to about 8.5 µm, such as from about 8.5 µm to about 9.0 µm, such as from about 9.0 µm to about 9.5 µm, such as from about 9.5 µm to about 10.0 µm, such as from about 10.0 µm to about 10.5 µm, such as from about 10.5 µm to about 11.0 µm, such as from about 11.0 µm to about 11.5 µm, such as from about 11.5 µm to about 12.0 µm.

In some embodiments, the N-{[(2R)-2-hydroxy-3-piperidin-1-ylpropyl]oxy}pyridine-3-carboximidoyl chloride 1-oxide citrate forms particles having a D50 particle size with a Number Length D50 of about 3.2 µm, about 3.6 µm, about 4.0 µm, about 4.1 µm, about 4.7 µm, about 6.2 µm, about 7.0 µm, about 7.4 µm, or about 9.5 µm.

In some embodiments, the N-{[(2R)-2-hydroxy-3-piperidin-1-ylpropyl]oxy}pyridine-3-carboximidoyl chloride 1-oxide citrate forms particles having a Number CE Diameter D90 of from about 5.0 µm to about 22.0 µm.

In some embodiments, the N-{[(2R)-2-hydroxy-3-piperidin-1-ylpropyl]oxy}pyridine-3-carboximidoyl chloride 1-oxide citrate particles have a D50 particle size determined using Malvern Mastersizer 3000 of from about 5.0 µm to about 60.0 µm.

In some embodiments, the N-{[(2R)-2-hydroxy-3-piperidin-1-ylpropyl]oxy}pyridine-3-carboximidoyl chloride 1-oxide citrate particles have a D50 particle size determined using Malvern Mastersizer 3000 of about 5 µm, about 6 µm, about 7 µm, about 8 µm, about 9 µm, about 10 µm, about 11 µm, about 12 µm, about 13 µm, about 14 µm, about 15 µm, about 16 µm, about 17 µm, about 18 µm, about 19 µm, about 20 µm, about 21 µm, about 22 µm, about 23 µm, about 24 µm, about 25 µm, about 26 µm, about 27 µm, about 28 µm, about 29 µm, about 30 µm, about 31 µm, about 32 µm, about 33 µm, about 34 µm, about 35 µm, about 36 µm, about 37 µm, about 38 µm, about 39 µm, about 40 µm, about 41 µm, about 42 µm, about 43 µm, about 44 µm, about 45 µm, about 46 µm, about 47 µm, about 48 µm, about 49 µm, about 50

μm, about 51 μm, about 52 μm, about 53 μm, about 54 μm, about 55 μm, about 56 μm, about 57 μm, about 58 μm, about 59 μm, or about 60 μm.

In some embodiments, the N-{[(2R)-2-hydroxy-3-piperidin-1-ylpropyl]oxy}pyridine-3-carboximidoyl chloride 1-oxide citrate particles have a D50 particle size determined using Malvern Mastersizer 3000 of from about 5.0 μm to about 60.0 μm, such as from about 5.0 μm to about 6.0 μm, such as from about 6.0 μm to about 7.0 μm, such as from about 7.0 μm to about 8.0 μm, such as from about 8.0 μm to about 9.0 μm, such as from about 9.0 μm to about 10.0 μm, such as from about 10.0 μm to about 11.0 μm, such as from about 11.0 μm to about 12.0 μm, such as from about 12.0 μm to about 13.0 μm, such as from about 13.0 μm to about 14.0 μm, such as from about 14.0 μm to about 15.0 μm, such as from about 15.0 μm to about 16.0 μm, such as from about 16.0 μm to about 17.0 μm, such as from about 17.0 μm to about 18.0 μm, such as from about 19.0 μm to about 20.0 μm, such as from about 20.0 μm to about 21.0 μm, such as from about 21.0 μm to about 22.0 μm, such as from about 22.0 μm to about 23.0 μm, such as from about 23.0 μm to about 24.0 μm, such as from about 24.0 μm to about 25.0 μm, such as from about 25.0 μm to about 26.0 μm, such as from about 26.0 μm to about 27.0 μm, such as from about 27.0 μm to about 28.0 μm, such as from about 28.0 μm to about 29.0 μm, such as from about 29.0 μm to about 30.0 μm, such as from about 30.0 μm to about 31.0 μm, such as from about 31.0 μm to about 32.0 μm, such as from about 32.0 μm to about 33.0 μm, such as from about 33.0 μm to about 34.0 μm, such as from about 34.0 μm to about 35.0 μm, such as from about 35.0 μm to about 36.0 μm, such as from about 36.0 μm to about 37.0 μm, such as from about 37.0 μm to about 38.0 μm, such as from about 38.0 μm to about 39.0 μm, such as from about 39.0 μm to about 40.0 μm, such as from about 40.0 μm to about 41.0 μm, such as from about 41.0 μm to about 42.0 μm, such as from about 42.0 μm to about 43.0 μm, such as from about 43.0 μm to about 44.0 μm, such as from about 44.0 μm to about 45.0 μm, such as from about 45.0 μm to about 46.0 μm, such as from about 46.0 μm to about 47.0 μm, such as from about 47.0 μm to about 48.0 μm, such as from about 48.0 μm to about 49.0 μm, such as from about 49.0 μm to about 50.0 μm, such as from about 50.0 μm to about 51.0 μm, such as from about 51.0 μm to about 52.0 μm, such as from about 52.0 μm to about 53.0 μm, such as from about 53.0 μm to about 54.0 μm, such as from about 54.0 μm to about 55.0 μm, such as from about 55.0 μm to about 56.0 μm, such as from about 56.0 μm to about 57.0 μm, such as from about 57.0 μm to about 58.0 μm, such as from about 58.0 μm to about 59.0 μm, or such as from about 59.0 μm to about 60.0 μm.

In some embodiments, the N-{[(2R)-2-hydroxy-3-piperidin-1-ylpropyl]oxy}pyridine-3-carboximidoyl chloride 1-oxide citrate forms particles having a D90 particle size with a Number CE Diameter D90 of about 5.0 μm, about 5.5 μm, about 6.0 μm, about 6.5 μm, about 7.0 μm, about 7.5 μm, about 8.0 μm, about 8.5 μm, about 9.0 μm, about 9.5 μm, about 10.0 μm, about 10.5 μm, about 11.0 μm, about 11.5 μm, about 12.0 μm, about 12.5 μm, about 13.0 μm, about 13.5 μm, about 14.0 μm, about 14.5 μm, about 15.0 μm, about 15.5 μm, about 16.0 μm, about 16.5 μm, about 17.0 μm, about 17.5 μm, about 18.0 μm, about 18.5 μm, about 19.0 μm, about 19.5 μm, about 20.0 μm, about 20.5 μm, about 21.0 μm, about 21.5 μm, or about 22.0 μm.

In some embodiments, the N-{[(2R)-2-hydroxy-3-piperidin-1-ylpropyl]oxy}pyridine-3-carboximidoyl chloride 1-oxide citrate forms particles having a D90 particle size with a Number CE Diameter D90 of from about 5.0 μm to about 22.0 μm, such as from about 5.0 μm to about 6.0 μm, such as from about 6.0 μm, to about 7.0 μm, such as from about 7.0 μm to about 8.0 μm, such as from about 8.0 μm to about 9.0 μm, such as from about 9.0 μm to about 10.0 μm, such as from about 10.0 μm to about 11.0 μm, such as from about 11.0 μm to about 12.0 μm such as from about 12.0 μm to about 13.0 μm, such as from about 13.0 μm to about 14.0 μm, such as from about 14.0 μm to about 15.0 μm, such as from about 15.0 μm to about 16.0 μm, such as from about 16.0 μm to about 17.0 μm, such as from about 17.0 μm to about 18.0 μm, such as from about 18.0 μm to about 19.0 μm, such as from about 19.0 μm to about 20.0 μm, such as from about 20.0 μm to about 21.0 μm, such as from about 21.0 μm to about 22.0 μm.

In some embodiments, the N-{[(2R)-2-hydroxy-3-piperidin-1-ylpropyl]oxy}pyridine-3-carboximidoyl chloride 1-oxide citrate forms particles having a D90 particle size with a Number CE Diameter D90 of about 5.8 μm, about 7.4 μm, about 9.4 μm, about 10.1 μm, about 10.7 μm, about 13.3 μm, about 14.1 μm, about 15.0 μm, or about 17.8 μm.

In some embodiments, the N-{[(2R)-2-hydroxy-3-piperidin-1-ylpropyl]oxy}pyridine-3-carboximidoyl chloride 1-oxide citrate forms particles having a Volume CE Diameter D90 of from about 10.0 μm to about 55.0 μm, such as the N-{[(2R)-2-hydroxy-3-piperidin-1-ylpropyl]oxy}pyridine-3-carboximidoyl chloride 1-oxide citrate particles have a Number CE Diameter D90 of from about 10.0 μm to about 55.0 μm.

In some embodiments, the N-{[(2R)-2-hydroxy-3-piperidin-1-ylpropyl]oxy}pyridine-3-carboximidoyl chloride 1-oxide citrate forms particles having a Volume CE Diameter D90 of from about 25.0 μm to about 55.0 μm.

In some embodiments, the N-{[(2R)-2-hydroxy-3-piperidin-1-ylpropyl]oxy}pyridine-3-carboximidoyl chloride 1-oxide citrate forms particles having a D90 particle size with a Volume CE Diameter D90 of about 25.0 μm, about 26.0 μm, about 27.0 μm, about 28.0 μm, about 29.0 μm, about 30.0 μm, about 31.0 μm, about 32.0 μm, about 33.0 μm, about 34.0 μm, about 35.0 μm, about 36.0 μm, about 37.0 μm, about 38.0 μm, about 39.0 μm, about 40.0 μm, about 41.0 μm, about 42.0 μm, about 43.0 μm, about 44.0 μm, about 45.0 μm, about 46.0 μm, about 47.0 μm, about 48.0 μm, about 49.0 μm, about 50.0 μm, about 51.0 μm, about 52.0 μm, about 53.0 μm, about 54.0 μm, or about 55.0 μm.

In some embodiments, the N-{[(2R)-2-hydroxy-3-piperidin-1-ylpropyl]oxy}pyridine-3-carboximidoyl chloride 1-oxide citrate forms particles having a D90 particle size with a Volume CE Diameter D90 of from about 25.0 μm to about 55.0 μm, such as from about 25.0 μm to about 30.0 μm, such as from about 30.0 μm to about 35.0 μm, such as from about 35.0 μm to about 40.0 μm, such as from about 40.0 μm to about 45.0 μm, such as from about 45.0 μm to about 50.0 μm, such as from about 50.0 μm to about 55.0 μm.

In some embodiments, the N-{[(2R)-2-hydroxy-3-piperidin-1-ylpropyl]oxy}pyridine-3-carboximidoyl chloride 1-oxide citrate forms particles having a D90 particle size with a Volume CE Diameter D90 of about 26.7 μm, about 34.5 μm, about 35.0 μm, about 36.0 μm, about 37.6 μm, about 43.5 μm, about 44.4 μm, about 47.1 μm, or about 52.2 μm.

In some embodiments, the N-{[(2R)-2-hydroxy-3-piperidin-1-ylpropyl]oxy}pyridine-3-carboximidoyl chloride 1-oxide citrate forms particles having a Volume CE Diameter D[4,3] of from about 8.0 μm to about 40.0 μm.

In some embodiments, the N-{[(2R)-2-hydroxy-3-piperidin-1-ylpropyl]oxy}pyridine-3-carboximidoyl chloride 1-oxide citrate forms particles having a D90 particle size with a Volume CE Diameter D[4,3] of about 8.0 μm, about 9.0 μm, about 10.0 μm, about 11.0 μm, about 12.0 μm, about 13.0 μm, about 14.0 μm, about 15.0 μm, about 16.0 μm, about 17.0 μm, about 18.0 μm, about 19.0 μm, about 20.0 μm, about 21.0 μm, about 22.0 μm, about 23.0 μm, about 24.0 μm, about 25.0 μm, about 26.0 μm, about 27.0 μm, about 28.0 μm, about 29.0 μm, about 30.0 μm, about 31.0 μm, about 32.0 μm, about 33.0 μm, about 34.0 μm, about 35.0 μm, about 36.0 μm, about 37.0 μm, about 38.0 μm, about 39.0 μm, or about 40.0 μm.

In some embodiments, the N-{[(2R)-2-hydroxy-3-piperidin-1-ylpropyl]oxy}pyridine-3-carboximidoyl chloride 1-oxide citrate forms particles having a D90 particle size with a Volume CE Diameter D[4,3] of from about 8.0 μm to about 40.0 μm, such as from about 8.0 μm to about 12.0 μm, such as from about 12.0 μm to about 16.0 μm, such as from about 16.0 μm to about 20.0 μm, such as from about 20.0 μm to about 24.0 μm, such as from about 24.0 μm to about 28.0 μm, such as from about 28.0 μm to about 32.0 μm, such as from about 32.0 μm to about 36.0 μm, such as from about 36.0 μm to about 40.0 μm.

In some embodiments, the N-{[(2R)-2-hydroxy-3-piperidin-1-ylpropyl]oxy}pyridine-3-carboximidoyl chloride 1-oxide citrate forms particles having a D90 particle size with a Volume CE Diameter D[4,3] of about 13.7 μm, about 17.1 μm, about 22.1 μm, about 23.3 μm, about 25.4 μm, about 25.7 μm, about 27.1 μm, about 29.5 μm, about 38.8 μm, or about 39.4 μm.

In some embodiments, the N-{[(2R)-2-hydroxy-3-piperidin-1-ylpropyl]oxy}pyridine-3-carboximidoyl chloride 1-oxide citrate forms particles having a Volume CE Diameter D[3,2] of from about 5.0 μm to about 30.0 μm.

In some embodiments, the N-{[(2R)-2-hydroxy-3-piperidin-1-ylpropyl]oxy}pyridine-3-carboximidoyl chloride 1-oxide citrate forms particles having a D90 particle size with a Volume CE Diameter D[3,2] of about 5.0 μm, about 6.0 μm, about 7.0 μm, about 8.0 μm, about 9.0 μm, about 10.0 μm, about 11.0 μm, about 12.0 μm, about 13.0 μm, about 14.0 μm, about 15.0 μm, about 16.0 μm, about 17.0 μm, about 18.0 μm, about 19.0 μm, about 20.0 μm, about 21.0 μm, about 22.0 μm, about 23.0 μm, about 24.0 μm, about 25.0 μm, about 26.0 μm, about 27.0 μm, about 28.0 μm, about 29.0 μm, or about 30.0 μm.

In some embodiments, the N-{[(2R)-2-hydroxy-3-piperidin-1-ylpropyl]oxy}pyridine-3-carboximidoyl chloride 1-oxide citrate forms particles having a D90 particle size with a Volume CE Diameter D[3,2] of from about 5.0 μm to about 30.0 μm, such as from about 5.0 μm to about 10.0 μm, such as from about 10.0 μm to about 15.0 μm, such as from about 15.0 μm to about 20.0 μm, such as from about 20.0 μm to about 25.0 μm, such as from about 25.0 μm to about 30.0 μm.

In some embodiments, the N-{[(2R)-2-hydroxy-3-piperidin-1-ylpropyl]oxy}pyridine-3-carboximidoyl chloride 1-oxide citrate forms particles having a D90 particle size with a Volume CE Diameter D[3,2] of about 8.8 μm, about 11.4 μm, about 17.7 μm, about 17.5 μm, about 17.9 μm, about 19.5 μm, about 20.5 μm, about 21.8 μm, about 24.2 μm, or about 34.2 μm.

In some embodiments, the N-{[(2R)-2-hydroxy-3-piperidin-1-ylpropyl]oxy}pyridine-3-carboximidoyl chloride 1-oxide citrate forms particles having a D90 length of from about 10.0 μm to about 20.0 μm.

In some embodiments, the N-{[(2R)-2-hydroxy-3-piperidin-1-ylpropyl]oxy}pyridine-3-carboximidoyl chloride 1-oxide citrate forms particles having a Number CE Diameter Mean of from about 1.0 μm to about 12.0 μm.

In some embodiments, the N-{[(2R)-2-hydroxy-3-piperidin-1-ylpropyl]oxy}pyridine-3-carboximidoyl chloride 1-oxide citrate forms particles having a Number CE Diameter Mean of about 1.0 μm, about 1.5 μm, about 2.0 μm, about 2.5 μm, about 3.0 μm, about 3.5 μm, about 4.0 μm, about 4.5 μm, about 5.0 μm, about 5.5 μm, about 6.0 μm, about 6.5 μm, about 7.0 μm, about 7.5 μm, about 8.0 μm, about 8.5 μm, about 9.0 μm, about 9.5 μm, about 10.0 μm, about 10.5 μm, about 11.0 μm, about 11.5 μm, or about 12.0 μm.

In some embodiments, the N-{[(2R)-2-hydroxy-3-piperidin-1-ylpropyl]oxy}pyridine-3-carboximidoyl chloride 1-oxide citrate forms particles having a Number CE Diameter Mean of from about 1.0 μm to about 12.0 μm, such as from about 1.0 μm to about 2.0 μm, such as from about 2.0 μm to about 3.0 μm, such as from about 3.0 μm to about 4.0 μm, such as from about 4.0 μm to about 5.0 μm, such as from about 5.0 μm to about 6.0 μm, such as from about 6.0 μm to about 7.0 μm, such as from about 7.0 μm to about 8.0 μm, such as from about 8.0 μm to about 9.0 μm, such as from about 9.0 μm to about 10.0 μm, such as from about 10.0 μm to about 11.0 μm, such as from about 11.0 μm to about 12.0 μm.

In some embodiments, the N-{[(2R)-2-hydroxy-3-piperidin-1-ylpropyl]oxy}pyridine-3-carboximidoyl chloride 1-oxide citrate forms particles having a Number CE Diameter Mean of about 2.9 μm, about 3.4 μm, about 3.7 μm, about 4.2 μm, about 4.6 μm, about 5.3 μm, about 5.8 μm, about 6.7 μm, about 7.7 μm, or about 8.2 μm.

In some embodiments, the N-{[(2R)-2-hydroxy-3-piperidin-1-ylpropyl]oxy}pyridine-3-carboximidoyl chloride 1-oxide citrate forms particles having a D90 particle size with a Number Length D90 of about 10.0 μm, about 10.5 μm, about 11.0 μm, about 11.5 μm, about 12.0 μm, about 12.5 μm, about 13.0 μm, about 13.5 μm, about 14.0 μm, about 14.5 μm, about 15.0 μm, about 15.5 μm, about 16.0 μm, about 16.5 μm, about 17.0 μm, about 17.5 μm, about 18.0 μm, about 18.5 μm, about 19.0 μm, about 19.5 μm, or about 20.0 μm.

In some embodiments, the N-{[(2R)-2-hydroxy-3-piperidin-1-ylpropyl]oxy}pyridine-3-carboximidoyl chloride 1-oxide citrate forms particles having a D90 particle size with a Number Length D90 of from about 10.0 μm to about 20.0 μm, such as from about 10.0 μm to about 11.0 μm, such as from about 11.0 μm to about 12.0 μm, such as from about 12.0 μm to about 13.0 μm, such as from about 13.0 μm to about 14.0 μm, such as from about 14.0 μm to about 15.0 μm, such as from about 15.0 μm to about 16.0 μm, such as from about 16.0 μm to about 17.0 μm, such as from about 17.0 μm to about 18.0 μm, such as from about 18.0 μm to about 19.0 μm, such as from about 19.0 μm to about 20.0 μm.

In some embodiments, the N-{[(2R)-2-hydroxy-3-piperidin-1-ylpropyl]oxy}pyridine-3-carboximidoyl chloride 1-oxide citrate forms particles having a D90 particle size with a Number Length D90 of about 10.5 μm, about 13.9 μm, about 16.6 μm, about 16.8 μm, about 22.2 μm, about 24.8 μm, about 25.5 μm, or about 26.7 μm.

In some embodiments, the N-{[(2R)-2-hydroxy-3-piperidin-1-ylpropyl]oxy}pyridine-3-carboximidoyl chloride 1-oxide citrate forms particles having a D90 particle size with a Number Length D90 of from about 7.0 μm to about 35.0 μm.

In some embodiments, the N-{[(2R)-2-hydroxy-3-piperidin-1-ylpropyl]oxy}pyridine-3-carboximidoyl chloride 1-oxide citrate particles have a D90 particle size determined using Malvern Mastersizer 3000 of from about 30.0 μm to about 130.0 μm.

In some embodiments, the N-{[(2R)-2-hydroxy-3-piperidin-1-ylpropyl]oxy}pyridine-3-carboximidoyl chloride 1-oxide citrate particles have a D90 particle size determined using Malvern Mastersizer 3000 of about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, about 100 μm, about 105 μm, about 110 μm, about 115 μm, about 120 μm, about 125 μm, or about 130 μm.

In some embodiments, the N-{[(2R)-2-hydroxy-3-piperidin-1-ylpropyl]oxy}pyridine-3-carboximidoyl chloride 1-oxide citrate particles have a D90 particle size determined using Malvern Mastersizer 3000 of from about 30.0 μm to about 130.0 μm, such as from about 30.0 μm to about 35.0 μm, such as from about 35.0 μm to about 40.0 μm, such as from about 40.0 μm to about 45.0 μm, such as from about 45.0 μm to about 50.0 μm, such as from about 50.0 μm to about 55.0 μm, such as from about 55.0 μm to about 60.0 μm, such as from about 60.0 μm to about 65.0 μm, such as from about 65.0 μm to about 70.0 μm, such as from about 70.0 μm to about 75.0 μm, such as from about 75.0 μm to about 80.0 μm, such as from about 80.0 μm to about 85.0 μm, such as from about 85.0 μm to about 90.0 μm, such as from about 90.0 μm to about 95.0 μm, such as from about 95.0 μm to about 100.0 μm, such as from about 100.0 μm to about 105.0 μm, such as from about 105.0 μm to about 110.0 μm, such as from about 110.0 μm to about 115.0 μm, such as from about 115.0 μm to about 120.0 μm, such as from about 120.0 μm to about 125.0 μm, or such as from about 125.0 μm to about 130.0 μm.

Items

1. A process for preparing ORZY-01,

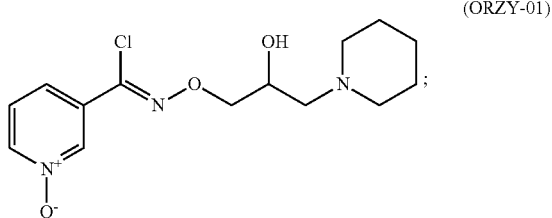 [SMILES: [O-][n+]1cccc(/C(Cl)=N/OCC(O)CN2CCCCC2)c1]
(ORZY-01)

wherein the process comprises
step 1A) mixing a compound of formula (I);

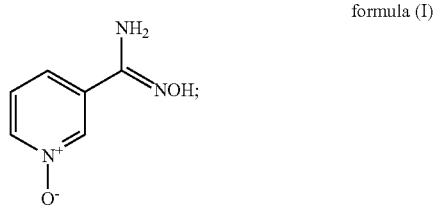
formula (I)

with a compound of formula (II) in a container;

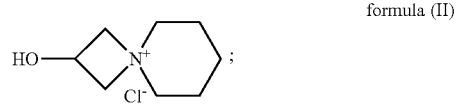
formula (II)

in a first solvent at a first temperature for more than 2 hours to provide an intermediate; followed by
step 1B) wherein the intermediate is reacted with NaNO$_2$ at a second temperature in a second solvent to provide ORZY-01,
thereby providing ORZY-01.

2. A process for preparing ORZY-01,

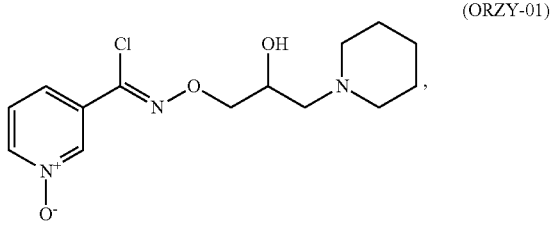 [SMILES: [O-][n+]1cccc(/C(Cl)=N/OCC(O)CN2CCCCC2)c1]
(ORZY-01)

wherein the process comprises
step 1A) mixing a compound of formula (I);

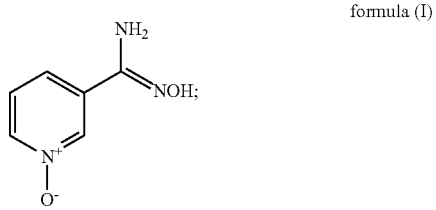
formula (I)

with a compound of formula (II) in a container;

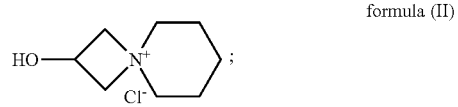
formula (II)

in a first solvent at a first temperature to provide an intermediate; followed by step 1B) wherein the intermediate is reacted with NaNO$_2$ at a second temperature in a
second solvent to provide ORZY-01,
thereby providing ORZY-01.

3. The process according to any one of the preceding items, wherein the intermediate is isolated, optionally purified, prior to step 1B).

4. The process according to any one of the preceding items, wherein the first solvent is a polar protic solvent or a mixture of polar protic solvents.

5. The process according to any one of the preceding items, wherein the first solvent is selected from the group consisting of ethanol, water, methanol, 2-propanol, and any mixture thereof.

6. The process according to any one of the preceding items, wherein the first solvent is a mixture of ethanol and water.

7. The process according to any one of the preceding items, wherein step 1A is performed under basic conditions, such as by the addition of a hydroxide, such as NaOH or KOH.

8. The process according to any one of the preceding items, wherein the second solvent is a chlorinated hydrocarbon or a mixture containing a chlorinated hydrocarbon.

9. The process according to any one of the preceding items, wherein the second solvent is a mixture of dichloromethane and water.

10. The process according to any one of the preceding items, wherein the first solvent is different from the second solvent.

11. The process according to any one of the preceding items, wherein the first temperature is at the boiling point of the solvent.

12. The process according to any one of the preceding items, wherein the first temperature is higher than the second temperature.

13. The process according to any one of the preceding items, wherein the first temperature is from 70° C. to 90° C., such as from 72° C. to 88° C., such as from 74° C. to 86° C., such as from 76° C. to 84° C., such as from 78° C. to 82° C., for example 80° C.

14. The process according to any one of the preceding items, wherein the second temperature is from 0° C. to 15° C., such as from 0° C. to 1° C., such as from 1° C. to 2° C., such as from 2° C. to 3° C., such as from 3° C. to 4° C., such as from 5° C. to 6° C., such as from 6° C. to 7° C., such as from 7° C. to 8° C., such as from 8° C. to 9° C., such as from 9° C. to 10° C., such as from 10° C. to 11° C., such as from 11° C. to 12° C., such as from 12° C. to 13° C., such as from 13° C. to 14° C., such as from 14° C. to 15° C.

15. The process according to any one of the preceding items, wherein the second temperature is maintained for 1 hour.

16. The process according to any one of the preceding items, wherein the compound of formula (II) is mixed in a molar ratio of 1.3:1.0 with the compound of formula (I).

17. The process according to any one of the preceding items, wherein the intermediate is not isolated prior to the reaction with $NaNO_2$.

18. The process according to any one of the preceding items, wherein the intermediate is reacted with at least 1.2 equivalents $NaNO_2$.

19. The process according to any one of the preceding items, wherein the intermediate is reacted with from 1.2 to 1.6 equivalents $NaNO_2$.

20. The process according to any one of the preceding items, wherein the first solvent is heated under reflux for at least 2.5 hours, such as 3 hours or more, such as 4 hours or more, such as 5 hours or more, such as 6 hours or more.

21. The process according to any one of the preceding items, wherein the first solvent is heated at from 75° C. to 85° C., such as 80° C. for at least 3.5 hours.

22. The process according to any one of the preceding items, wherein the first solvent is a mixture of ethanol, optionally denatured; and water, and the first solvent is maintained at 80° C. for at least 3 hours.

23. The process according to any one of the preceding items, wherein the first solvent is a mixture of ethanol, optionally denatured; and water, and the first solvent is maintained at 80° C. for at least 3 hours; and wherein the second solvent is a mixture of dichloromethane and water.

24. A process for preparing ORZY-03, (ORZY-03)

wherein the process comprises the consecutive steps of:
a) mixing ORZY-01, (ORZY-01)

with dibenzoyl L-tartaric acid (L-DBTA) in a container in a first step 2 solvent and heating the first step 2 solvent to a first step 2 temperature, optionally agitating the first step 2 solvent;
b) cooling the first step 2 solvent to a second step 2 temperature at a cooling rate of 15 K/h or higher to provide a solid composition comprising ORZY-03; wherein the first step 2 temperature is higher than the second step 2 temperature; and
c) separation the first step 2 solvent and the solid composition comprising ORZY-03, optionally the separation is by filtration;
thereby providing ORZY-03.

25. The process according to item 24, further comprising step:
d) washing the solid composition comprising ORZY-03 one or more times with a first predefined volume of the first step 2 solvent.

26. The process according to any one of items 24-25, further comprising step:
e) drying the solid composition comprising ORZY-03 at reduced pressure.

27. The process according to any one of items 24-26, further comprising step a1) prior to step b), wherein the first step 2 solvent is cooled to a third step 2 temperature; wherein the third step 2 temperature is higher than the second step 2 temperature.

28. The process according to any one of items 24-27, wherein the cooling rate is selected from the group consisting of: 15 K/h; 16 K/h; 17 K/h; 18 K/h; 19 K/h; 20 K/h; 21 K/h; 22 K/h; 23 K/h; 24 K/h; 25 K/h; 26 K/h; 27 K/h; 28 K/h; 29 K/h; 30 K/h; 31 K/h; 32 K/h; 33 K/h; 34 K/h; 35 K/h; 36 K/h; 37 K/h; 38 K/h; 39 K/h; 40 K/h; 41 K/h; 42 K/h; 43 K/h; 44 K/h; 45 K/h; 46 K/h; 47 K/h; 48 K/h; 49 K/h; and 50 K/h.

29. The process according to any one of items 24-28, wherein the cooling rate is from 15 K/h to 50 K/h, such as from 15 K/h to 16 K/h; such as from 16 K/h to 17 K/h; such as from 17 K/h to 18 K/h; such as from 18 K/h to 19 K/h; such as from 19 K/h to 20 K/h; such as from 20 K/h to 21

K/h; such as from 21 K/h to 22 K/h; such as from 22 K/h to 23 K/h; such as from 23 K/h to 24 K/h; such as from 24 K/h to 25 K/h; such as from 25 K/h to 26 K/h; such as from 26 K/h to 27 K/h; such as from 27 K/h to 28 K/h; such as from 28 K/h to 29 K/h; such as from 29 K/h to 30 K/h; such as from 30 K/h to 31 K/h; such as from 31 K/h to 32 K/h; such as from 32 K/h to 33 K/h; such as from 33 K/h to 34 K/h; such as from 34 K/h to 35 K/h; such as from 35 K/h to 36 K/h; such as from 36 K/h to 37 K/h; such as from 37 K/h to 38 K/h; such as from 38 K/h to 39 K/h; such as from 39 K/h to 40 K/h; such as from 40 K/h to 41 K/h; such as from 41 K/h to 42 K/h; such as from 42 K/h to 43 K/h; such as from 43 K/h to 44 K/h; such as from 44 K/h to 45 K/h; such as from 45 K/h to 46 K/h; such as from 46 K/h to 47 K/h; such as from 47 K/h to 48 K/h; such as from 48 K/h to 49 K/h; such as from 49 K/h to 50 K/h.

30. The process according to any one of items 24-29, wherein the cooling rate is from 15 K/h to 50 K/h.

31. The process according to any one of items 24-30, wherein the cooling rate is from 15 K/h to 40 K/h.

32. The process according to any one of items 24-31, wherein the cooling rate is from 15 K/h to 30 K/h.

33. The process according to any one of items 24-32, wherein the cooling rate is from 17 K/h to 30 K/h.

34. The process according to any one of items 24-33, wherein the first step 2 solvent is a polar protic solvent or a mixture of polar protic solvents.

35. The process according to any one of items 24-34, wherein the first step 2 solvent is selected from the group consisting of ethanol, water, methanol, 2-propanol, and any mixture thereof.

36. The process according to any one of items 24-35, wherein the first step 2 solvent is a mixture of ethanol and water.

37. The process according to any one of items 24-36, wherein the first step 2 solvent is from 20.5 to 23.5 kg water per 55 kg ORZY-01; and from 200 to 240 kg EtOH per 55 kg ORZY-01.

38. The process according to any one of items 24-37, wherein the first step 2 solvent is 22 kg water per 55 kg ORZY-01; and 220 kg EtOH per 55 kg ORZY-01.

39. The process according to any one of items 24-38, wherein the first step 2 temperature is from 60 to 75° C., such as from 61 to 74° C., such as from 62 to 73° C., such as from 63 to 72° C., such as from 64 to 71° C., such as from 65 to 70° C., for example 65° C.

40. The process according to any one of items 24-39, wherein the second step 2 temperature is from 10 to 30° C., such as from 11 to 29° C., such as from 12 to 28° C., such as from 13 to 27° C., such as from 14 to 26° C., such as from 15 to 25° C., for example 20° C.

41. The process according to any one of items 24-40, wherein the third step 2 temperature is from 45 to 65° C., such as from 46 to 64° C., such as from 47 to 63° C., such as from 48 to 62° C., such as from 49 to 61° C., such as from 50 to 60° C., such as from 51 to 59° C., such as from 52 to 58° C., such as from 53 to 57° C., such as from 54 to 56° C., such as 55° C.

42. The process according to any one of items 24-41, wherein the third step 2 temperature is maintained for at least 30 minutes, such as at least 60 minutes.

43. The process according to any one of items 24-42, wherein one or more seed crystals of ORZY-03 is added to the container prior to step b.

44. The process according to any one of items 24-43, wherein the one or more seed crystals of ORZY-03 has a chiral purity of at least 95%.

45. The process according to any one of items 24-44, wherein the mass of the one or more seed crystals of ORZY-03 is from 0.2 to 0.8 kg per 55 kg ORZY-03, for example 0.55 kg per 55 kg ORZY-03.

46. The process according to any one of items 24-45, wherein the first predefined volume of the first step 2 solvent is from 35 to 55 kg per 55 kg ORZY-03.

47. The process according to any one of items 24-46, wherein the first predefined volume of the first step 2 solvent is from 41 to 45 kg per 55 kg ORZY-03.

48. A process for preparing ORZY-05,

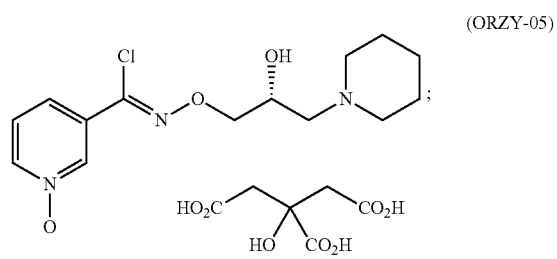

wherein the process comprises the steps of:
a) adding a catalytic amount of citric acid to a solution of ORZY-03 in a container in a first step 3 solvent;

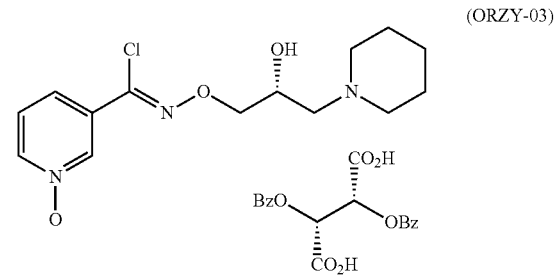

b) exchanging the solvent of the mixture of step a) from the first step 3 solvent to a second step 3 solvent; wherein the first step 3 solvent is different from the second step 3 solvent;
c) adding about a stoichiometric amount of citric acid to the mixture obtained in step b) to form a suspension;
d) filtering the suspension provided in step c) to obtain ORZY-04, which is a crude of ORZY-05; and
e) purifying the ORZY-04 of step d) to obtain ORZY-05.

49. The process according to item 48, wherein the process further comprises the steps of:
i) mixing the compound ORZY-03 with an aqueous solution of a first step 3 base; and
ii) extracting the mixture obtained in step a) with the first step 3 solvent to afford a solution of ORZY-03 in the first step 3 solvent; before adding the catalytic amount of citric acid according to step a) of item 48 to the solution of ORZY-03 in the first step 3 solvent.

50. The process according to any one of items 48 to 49, wherein the process further comprises washing the first step 3 solvent one or more times with water whereby one or more by-products from the first step 3 solvent are removed.

51. The process according to any one of items 48 to 50, wherein the process further comprises washing the first step 3 solvent one or more times with water subsequent to the addition of the first step 3 base, whereby one or more by-products from the first step 3 solvent are removed.

52. The process according to any one of items 48 to 51, wherein the process comprises the steps of:
    a) mixing the compound ORZY-03 with an aqueous solution of the first step 3 base;

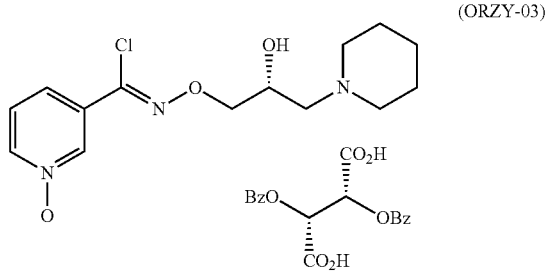
(ORZY-03)

b) extracting the mixture obtained in step a) with the first step 3 solvent;
   c) adding a catalytic amount of citric acid to the organic phase(s) of step b);
   d) exchanging the solvent of the mixture of step c) from the first step 3 solvent to the second step 3 solvent;
   e) adding about a stoichiometric amount of citric acid to the mixture obtained in step d) to form a suspension; and
   f) filtering the suspension provided in step e) to obtain crude ORZY-05 (ORZY-04).

53. The process according to any one of items 48 to 52, wherein the first step 3 solvent is a chlorinated hydrocarbon or a mixture containing a chlorinated hydrocarbon.
54. The process according to any one of items 48 to 53, wherein the first step 3 solvent is dichloromethane or dichloroethane, preferably dichloromethane.
55. The process according to any one of items 48 to 54, wherein the second step 3 solvent is a polar protic solvent or a mixture of polar protic solvents.
56. The process according to any one of items 48 to 55, wherein the second step 3 solvent is selected from the group consisting of methanol, water, ethanol, 2-propanol, and any mixture thereof.
57. The process according to any one of items 48 to 56, wherein the second step 3 solvent is methanol.
58. The process according to any one of items 48 to 57, wherein the first step 3 base is a carbonate.
59. The process according to any one of items 48 to 58, wherein the first step 3 base is a carbonate selected from the group consisting of: $K_2CO_3$ and $Cs_2CO_3$.
60. The process according to any one of items 48 to 59, wherein the first step 3 base is $K_2CO_3$.
61. The process according to any one of items 48 to 60, wherein the aqueous solution of $K_2CO_3$ comprises 16.8% $K_2CO_3$.
62. The process according to any one of items 48 to 61, wherein the mixture of ORZY-03 and $K_2CO_3$ is extracted three times with $CH_2Cl_2$
63. The process according to any one of items 48 to 62, wherein exchanging the solvent of from $CH_2Cl_2$ to $CH_3OH$ comprises the steps of:
    a. partly distilling the $CH_2Cl_2$ solution;
    b. adding $CH_3OH$ to the distilled solution provided in step a);
    c. partly distilling the solution provided in step b); and
    d. adding $CH_3OH$ to the solution provided in step c).

64. The process according to item 63, wherein the amount distilled of in steps a) and c) at least corresponds to the amount of $CH_2Cl_2$ that ORZY-03 was dissolved in prior to the solvent exchange step.
65. The process according to any one of items 63 to 64, wherein the process further comprise the step of passing the solution obtained after exchanging the solvent from $CH_2Cl_2$ to $CH_3OH$ through activated charcoal filter.
66. The process according to any one of items 48 to 65, further comprising the step of drying ORZY-04.
67. The process according to item 66, wherein the drying step includes drying the ORZY-04 at 45° C. in vacuum for at least 12 h.
68. The process according to item 48, wherein the process comprises the consecutive steps of:
    a) mixing the compound ORZY-03 with an 16.8% aqueous solution of $K_2CO_3$;

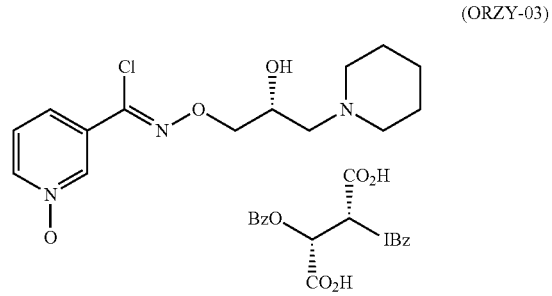
(ORZY-03)

b) extracting the mixture obtained in step a) with $CH_2Cl_2$ one or more times, such as three times; followed by one or more aqueous washes of the combined organic phases;
   c) adding a catalytic amount of citric acid to the organic phase(s) of step b);
   d) exchanging the solvent of the mixture of step c) from $CH_2Cl_2$ to $CH_3OH$ by
      i. partly distilling the $CH_2Cl_2$ solution of step c);
      ii. adding $CH_3OH$ to the distilled solution provided in step i);
      iii. partly distilling the solution provided in step ii); and
      iv. adding $CH_3OH$ to the solution provided in step iii)
   e) passing the solution obtained in step d) through an activated charcoal filter;
   f) adding about a stoichiometric amount of citric acid to the mixture obtained in step e) to form a suspension;
   g) filtering the suspension provided in step e) to obtain ORZY-04;
   h) drying ORZY-04 obtained in step g) at 45° C. in vacuum for at least 12 h, and
   i) purifying the ORZY-04 of step h) to obtain ORZY-05.

69. The process according to any one of items 48 to 68, wherein the step of purifying the ORZY-04 to obtain ORZY-05 comprises recrystallization of ORZY-04.
70. The process according to item 69, wherein the solvent used in the recrystallization is acetone.
71. The process according to any one of items 69 to 70, wherein the recrystallization comprises the steps of:
    a. mixing ORZY-04 with $H_2O$ and heating the mixture to 70±5° C. until a clear solution is observed;
    b. cooling the solution formed in step a) to 30±5° C.;
    c. adding acetone to the solution of step b);
    d. cooling the mixture of step c) to 0±5° C.;

e. agitating the mixture of step d) for 12 h at 0±10° C. to generate a suspension;
f. isolating ORZY-05 from the suspension of step e) by filtering said suspension; and drying the ORZY-05 obtained in step f) at 45° C. in vacuum for at least 12 h.

72. A composition comprising ORZY-01,

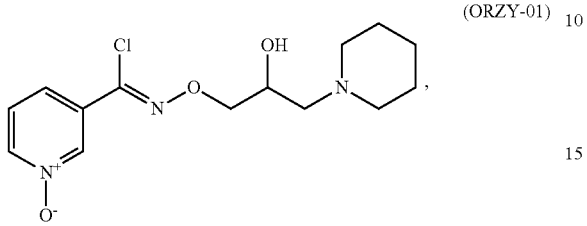
(ORZY-01)

and
one or more impurities selected from the group consisting of:

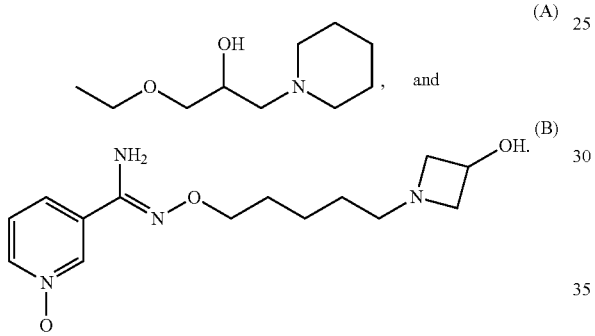

(A)

, and (B)

73. The composition according to item 72, wherein (A) is present by weight in from 0.1% to 0.5% and/or (B) in from 0.1% to 0.5%.
74. The composition according to any one of items 72 to 73, wherein (A) is present by weight in from 0.1% to 0.5%, such as from 0.1% to 0.2%, such as from 0.2% to 0.3%, such as from 0.3% to 0.4%, such as 0.4% to 0.5%.
75. The composition according to any one of items 72 to 74, wherein (B) is present by weight in from 0.1% to 0.5%, such as from 0.1% to 0.2%, such as from 0.2% to 0.3%, such as from 0.3% to 0.4%, such as 0.4% to 0.5%.
76. A process for preparing arimoclomol citrate (ORZY-05),

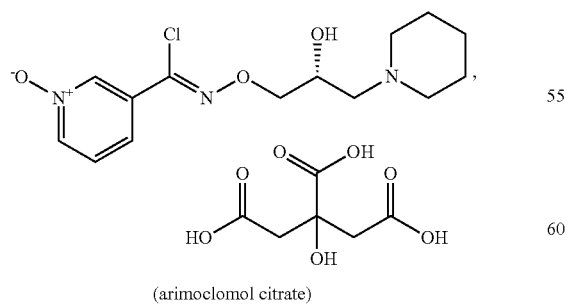
(arimoclomol citrate)

comprising one or more of the processes defined in any one of the preceding items to provide ORZY-01; ORZY-03; or ORZY-04.

77. A process for preparing arimoclomol citrate (ORZY-05),

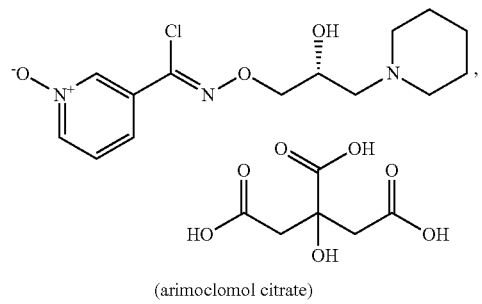
(arimoclomol citrate)

comprising the consecutive steps of:
a. the process as defined in any one of items 1 to 23 to provide ORZY-01,

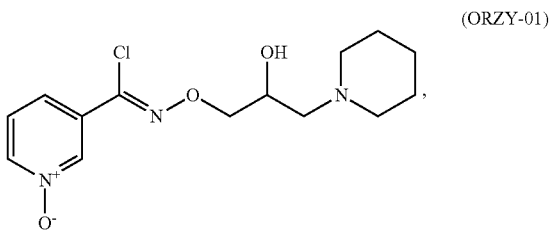 [SMILES: [O-][n+]1cccc(/C(Cl)=N/OCC(O)CN2CCCCC2)c1]
(ORZY-01)

b. precipitating ORZY-01 with dibenzoyl L-tartaric acid to provide ORZY-03,

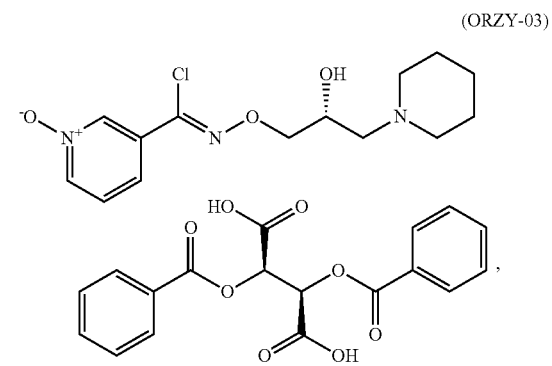
(ORZY-03)

c. reacting ORZY-03 with a base and subsequently precipitating the resulting free base of ORZY-03 with citric acid to provide arimoclomol citrate,
thereby providing arimoclomol citrate.

78. A process for preparing arimoclomol citrate,

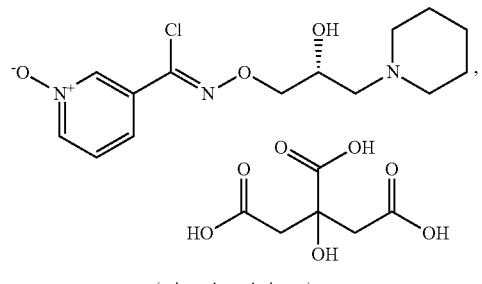
(arimoclomol citrate)

comprising the consecutive steps of:
a. providing ORZY-01,

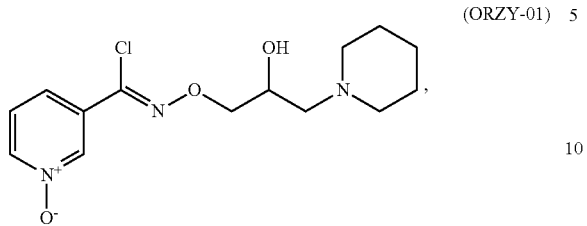
(ORZY-01)

b. the process as defined in any one of items 24 to 47 to provide ORZY-03,

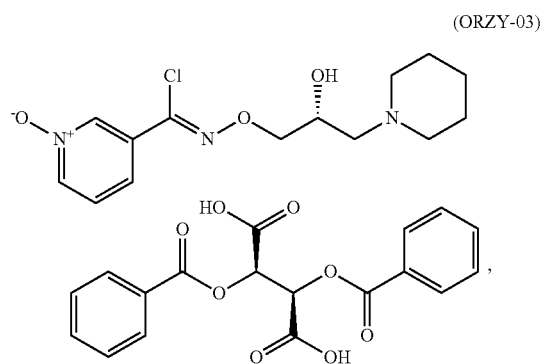
(ORZY-03)

c. reacting ORZY-03 with a base and subsequently precipitating the resulting free base of ORZY-03 with citric acid to provide arimoclomol citrate,
thereby providing arimoclomol citrate.

79. A process for preparing arimoclomol citrate,

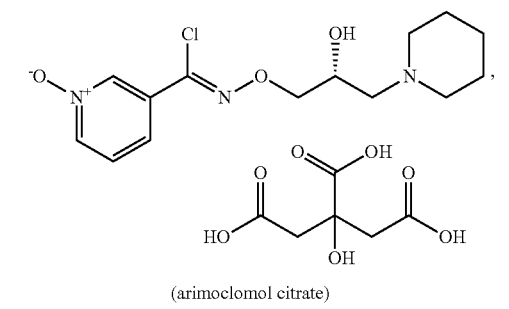

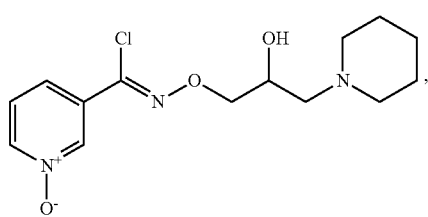
(arimoclomol citrate)

comprising the consecutive steps of:
a. providing ORZY-01, (ORZY-01)

b. precipitating ORZY-01 with dibenzoyl L-tartaric acid to provide ORZY-03,

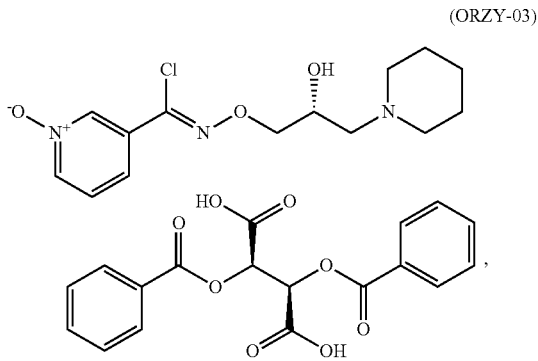
(ORZY-03)

and
c. the process as defined in any one of items 48 to 77 to provide ORZY-05; thereby providing arimoclomol citrate.

80. The process according to any one of the preceding items, further comprising adding one or more seed crystals of ORZY-01 to the container.

81. The process according to any one of the preceding items, further comprising adding one or more seed crystals of ORZY-03 to the container.

82. The process according to any one of the preceding items, further comprising adding one or more seed crystals of ORZY-05 to the container.

83. The process according to any one of the preceding items, as the first step, adding one or more seed crystals of ORZY-01 to the container.

84. The process according to any one of the preceding items, as the first step, adding one or more seed crystals of ORZY-03 to the container.

85. The process according to any one of the preceding items, as the first step, adding one or more seed crystals of ORZY-05 to the container.

86. An oral formulation comprising N-{[(2R)-2-hydroxy-3-piperidin-1-ylpropyl]oxy}pyridine-3-carboximidoyl chloride 1-oxide, or a pharmaceutically acceptable salt thereof, and at least one pharmaceutically acceptable excipient.

87. The oral formulation of item 86, wherein the pharmaceutically acceptable salt is N-{[(2R)-2-hydroxy-3-piperidin-1-ylpropyl]oxy}pyridine-3-carboximidoyl chloride 1-oxide citrate.

88. The oral formulation of item 86 or item 87, wherein the oral formulation comprises a capsule.

89. The oral formulation of any one of items 86-88, wherein the formulation comprises a filler.

90. The oral formulation of any one of items 86-89, wherein the formulation comprises a lubricant.

91. The oral formulation of any one of items 86-90, wherein the capsule comprises hydroxypropyl methylcellulose (HPMC), titanium dioxide, and optionally one or more colorant.

92. The oral formulation of any one of items 86-91, wherein the filler is microcrystalline cellulose (MCC).

93. The oral formulation of any one of items 86-92, wherein the lubricant is magnesium stearate.

94. The oral formulation of any one of items 86-93, wherein the N-{[(2R)-2-hydroxy-3-piperidin-1-ylpropyl]oxy}pyridine-3-carboximidoyl chloride 1-oxide, or pharmaceutically acceptable salt thereof is present at a dosage from about 50 mg to about 500 mg.

95. The oral formulation of any one of items 86-94, wherein the N-{[(2R)-2-hydroxy-3-piperidin-1-ylpropyl]oxy}pyridine-3-carboximidoyl chloride 1-oxide, or pharmaceutically acceptable salt thereof, is present at a dosage of about 47 mg, about 62 mg, about 93 mg, or about 124 mg.

96. The oral formulation of any one of items 86-94, wherein the N-{[(2R)-2-hydroxy-3-piperidin-1-ylpropyl]oxy}pyridine-3-carboximidoyl chloride 1-oxide citrate is present at a dosage of about 75 mg, about 100 mg, about 150 mg, about 200 mg, or about 400 mg.

97. The oral formulation of any one of items 86-96, wherein the oral formulation comprises from about 20% to about 60% w/w of N-{[(2R)-2-hydroxy-3-piperidin-1-ylpropyl]oxy}pyridine-3-carboximidoyl chloride 1-oxide, or a pharmaceutically acceptable salt thereof.

98. The oral formulation of any one of items 86-97, wherein the oral formulation comprises about 26.3% or about 52.6% w/w of N-{[(2R)-2-hydroxy-3-piperidin-1-ylpropyl]oxy}pyridine-3-carboximidoyl chloride 1-oxide, or a pharmaceutically acceptable salt thereof.

99. The oral formulation of any one of items 86-98, wherein the oral formulation comprises from about 40% to about 80% w/w of microcrystalline cellulose.

100. The oral formulation of any one of items 86-99, wherein the oral formulation comprises about 73.2% or about 46.9% w/w of microcrystalline cellulose.

101. The oral formulation of any one of items 86-100, wherein the oral formulation comprises from about 0.0% to about 1.0% magnesium stearate.

102. The oral formulation of any one of items 86-101, wherein the oral formulation comprises about 0.5% magnesium stearate.

103. A pharmaceutical composition comprising N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 98.0% as determined by HPLC.

104. The pharmaceutical composition of item 103, wherein the composition contains less than 2% of an impurity selected from N-{[(2S)-2-hydroxy-3-piperidin-1-ylpropyl]oxy}pyridine-3-carboximidoyl chloride 1-oxide or pharmaceutically acceptable salt thereof, methyl (Z)—N-(2-hydroxy-3-(piperidin-1-yl)propoxy)nicotinimidate 1-oxide or pharmaceutically acceptable salt thereof, or N-nitrosopiperidine, and combinations thereof.

105. A unit dosage form of the pharmaceutical composition according to item 103 or item 104 and a pharmaceutically acceptable carrier or excipient.

106. The unit dosage form of item 105, comprising N-{[(2R)-2-hydroxy-3-piperidin-1-ylpropyl]oxy}pyridine-3-carboximidoyl chloride 1-oxide, or a pharmaceutically acceptable salt thereof at a dosage from about 50 mg to about 500 mg.

107. The unit dosage form of item 105, or the oral formulation of item 49, comprising N-{[(2R)-2-hydroxy-3-piperidin-1-ylpropyl]oxy}pyridine-3-carboximidoyl chloride 1-oxide, or a pharmaceutically acceptable salt thereof at a dosage of about 47 mg, about 62 mg, about 93 mg, or about 124 mg.

108. A kit comprising a unit dosage form of any one of items 105-107 and instructions for administration.

109. The kit of item 108, wherein the kit further comprises prescribing information and/or multiple unit doses.

110. A method of treating or preventing Niemann Pick disease, type C in a subject in need thereof, wherein the subject is administered a therapeutically effect amount of the oral formulation, pharmaceutical composition, or unit dosage of any one of items 86-107.

111. An oral formulation, pharmaceutical composition, or unit dosage of any one of items 86-107 for use in treating or preventing Niemann Pick disease, type C in a subject in need thereof.

112. Use of an oral formulation, pharmaceutical composition, or unit dosage of any one of items 86-107 for use in the manufacture of a medicament for the treatment or prevention of Niemann Pick disease, type C in a subject in need thereof.

113. Use of an oral formulation, pharmaceutical composition, or unit dosage of any one of items 86-107 for the treatment or prevention of Niemann Pick disease, type C in a subject in need thereof.

114. The method, the oral formulation, pharmaceutical composition, or unit dosage for use, or use of the oral formulation, pharmaceutical composition, or unit dosage of any one of items 110-113, wherein the oral formulation, pharmaceutical composition, or unit dosage is administered three times daily.

115. The method, the oral formulation, pharmaceutical composition, or unit dosage for use, or use of the oral formulation, pharmaceutical composition, or unit dosage of any one of items 110-114, wherein the oral formulation, pharmaceutical composition, or unit dosage is administered to a pediatric subject having a body weight of about 8 kg to about 15 kg.

116. The method, the oral formulation, pharmaceutical composition, or unit dosage for use, or use of the oral formulation, pharmaceutical composition, or unit dosage of item 115, wherein the oral formulation, pharmaceutical composition, or unit dosage is administered at a dosage of 47 mg.

117. The method, the oral formulation, pharmaceutical composition, or unit dosage for use, or use of the oral formulation, pharmaceutical composition, or unit dosage of item 115, wherein the oral formulation, pharmaceutical composition, or unit dosage is administered at a dosage of 75 mg.

118. The method, the oral formulation, pharmaceutical composition, or unit dosage for use, or use of the oral formulation, pharmaceutical composition, or unit dosage of any one of items 110-114, wherein the oral formulation, pharmaceutical composition, or unit dosage is administered to a subject having a body weight of greater than about 15 kg to about 30 kg.

119. The method, the oral formulation, pharmaceutical composition, or unit dosage for use, or use of the oral formulation, pharmaceutical composition, or unit dosage of item 118, wherein the oral formulation, pharmaceutical composition, or unit dosage is administered at a dosage of 62 mg.

120. The method, the oral formulation, pharmaceutical composition, or unit dosage for use, or use of the oral formulation, pharmaceutical composition, or unit dosage of item 118, wherein the oral formulation, pharmaceutical composition, or unit dosage is administered at a dosage of 100 mg.

121. The method, the oral formulation, pharmaceutical composition, or unit dosage for use, or use of the oral formulation, pharmaceutical composition, or unit dosage of any one of items 110-114, wherein the oral formulation, pharmaceutical composition, or unit dosage is administered to a subject having a body weight of greater than about 30 kg to about 55 kg.

122. The method, the oral formulation, pharmaceutical composition, or unit dosage for use, or use of the oral formulation, pharmaceutical composition, or unit dosage of item 121, wherein the oral formulation, pharmaceutical composition, or unit dosage is administered at a dosage of 93 mg.
123. The method, the oral formulation, pharmaceutical composition, or unit dosage for use, or use of the oral formulation, pharmaceutical composition, or unit dosage of item 121, wherein the oral formulation, pharmaceutical composition, or unit dosage is administered at a dosage of 150 mg.
124. The method, the oral formulation, pharmaceutical composition, or unit dosage for use, or use of the oral formulation, pharmaceutical composition, or unit dosage of any one of items 110-114, wherein the oral formulation, pharmaceutical composition, or unit dosage is administered to a subject having a body weight of greater than about 55 kg.
125. The method, the oral formulation, pharmaceutical composition, or unit dosage for use, or use of the oral formulation, pharmaceutical composition, or unit dosage of item 124, wherein the oral formulation, pharmaceutical composition, or unit dosage is administered at a dosage of 124 mg.
126. The method, the oral formulation, pharmaceutical composition, or unit dosage for use, or use of the oral formulation, pharmaceutical composition, or unit dosage of item 124, wherein the oral formulation, pharmaceutical composition, or unit dosage is administered at a dosage of 200 mg.
127. The method, the oral formulation, pharmaceutical composition, or unit dosage for use, or use of the oral formulation, pharmaceutical composition, or unit dosage of any one of items 110-126, wherein not less than about 85% of the N-{[(2R)-2-hydroxy-3-piperidin-1-ylpropyl]oxy}pyridine-3-carboximidoyl chloride 1-oxide, or pharmaceutically acceptable salt thereof is dissolved into solution in about 15 minutes.
128. The method, the oral formulation, pharmaceutical composition, or unit dosage for use, or use of the oral formulation, pharmaceutical composition, or unit dosage of any one of items 110-127, wherein the capsule ingredients are mixed with a liquid for oral administration as a liquid.
129. The method, the oral formulation, pharmaceutical composition, or unit dosage for use, or use of the oral formulation, pharmaceutical composition, or unit dosage of any one of items 110-128, wherein the geometric mean $C_{max}$ of the composition is within about 80.00% to about 125.00% of a $C_{max}$ of 1749 (CV 49%) ng/mL, after administration of a single dose.
130. The method, the oral formulation, pharmaceutical composition, or unit dosage for use, or use of the oral formulation, pharmaceutical composition, or unit dosage of any one of items 110-128, wherein the $AUC_{0-8\ hrs}$ of the composition is within about 80.00% to about 125.00% of a $AUC_{0-8\ hrs}$ of 5317 (CV 17%) h ng/mL, after administration of a single dose.
131. The method, the oral formulation, pharmaceutical composition, or unit dosage for use, or use of the oral formulation, pharmaceutical composition, or unit dosage of any one of items 110-128, wherein the $AUC_{0-infinity}$ of the composition is within about 80.00% to about 125.00% of a $AUC_{0-infinity}$ of 6331 (CV 17%) h ng/mL, after administration of a single dose.
132. The method, the oral formulation, pharmaceutical composition, or unit dosage for use, or use of the oral formulation, pharmaceutical composition, or unit dosage of any one of items 110-128, wherein the geometric mean $C_{max,steady\ state}$ of the composition at steady state is within about 80.00% to about 125.00% of a $C_{max,steady\ state}$ of 2090 (CV 23%) ng/mL, after administration.
133. The method, the oral formulation, pharmaceutical composition, or unit dosage for use, or use of the oral formulation, pharmaceutical composition, or unit dosage of any one of items 110-128, wherein the $AUC_{0-8\ hrs,\ steady\ state}$ of the composition is within about 80.00% to about 125.00% of a $AUC_{0-8\ hrs,\ steady\ state}$ of 7207 (CV 19%) h ng/mL, after administration.
134. The method, the oral formulation, pharmaceutical composition, or unit dosage for use, or use of the oral formulation, pharmaceutical composition, or unit dosage of any one of items 129-133, wherein the N-[(2R, Z)-2-hydroxy-3-(1-piperidyl)propoxy]pyridine-3-carboximidoyl chloride, 1-oxide, or pharmaceutically acceptable salt thereof, is measured in plasma.
135. The method, the oral formulation, pharmaceutical composition, or unit dosage for use, or use of the oral formulation, pharmaceutical composition, or unit dosage of any one of items 110-114, wherein the geometric mean $C_{max,steady\ state}$ of the composition at steady state is within about 80.00% to about 125.00% of a $C_{max,steady\ state}$ of 533 ng/mL (368-770 ng/mL $5^{th}$ and $95^{th}$ percentiles), after administration of said composition in a human weighing from about 8 kg to about 15 kg.
136. The method, the oral formulation, pharmaceutical composition, or unit dosage for use, or use of the oral formulation, pharmaceutical composition, or unit dosage of any one of items 110-114, wherein the $AUC_{0-8\ hrs,\ steady\ state}$ of the composition is within about 80.00% to about 125.00% of a $AUC_{0-8\ hrs,\ steady\ state}$ of 2916 h ng/mL (1924-4436 h ng/mL $5^{th}$ and $95^{th}$ percentiles), after administration of said composition in a human weighing from about 8 kg to about 15 kg.
137. The method, the oral formulation, pharmaceutical composition, or unit dosage for use, or use of the oral formulation, pharmaceutical composition, or unit dosage of any one of items 110-114, wherein the geometric mean $C_{max,steady\ state}$ of the composition at steady state is within about 80.00% to about 125.00% of a $C_{max,steady\ state}$ of 593 ng/mL (395-878 ng/mL $5^{th}$ and $95^{th}$ percentiles), after administration of said composition in a human weighing from greater than about 15 kg to about 30 kg.
138. The method, the oral formulation, pharmaceutical composition, or unit dosage for use, or use of the oral formulation, pharmaceutical composition, or unit dosage of any one of items 110-114, wherein the $AUC_{0-8\ hrs,\ steady\ state}$ of the composition is within about 80.00% to about 125.00% of a $AUC_{0-8\ hrs,\ steady\ state}$ of 3043 h ng/mL (1938-4763 h ng/mL $5^{th}$ and $95^{th}$ percentiles), after administration of said composition in a human weighing from greater than about 15 kg to about 30 kg.
139. The method, the oral formulation, pharmaceutical composition, or unit dosage for use, or use of the oral formulation, pharmaceutical composition, or unit dosage of any one of items 110-114, wherein the geometric mean $C_{max,steady\ state}$ of the composition at steady state is within about 80.00% to about 125.00% of a $C_{max,steady\ state}$ of 679 ng/mL (450-1024 ng/mL $5^{th}$ and $95^{th}$ percentiles), after administration of said composition in a human weighing from greater than about 30 to about 55 kg.
140. The method, the oral formulation, pharmaceutical composition, or unit dosage for use, or use of the oral formulation, pharmaceutical composition, or unit dosage of any one of items 110-114, wherein the $AUC_{0-8\ hrs,\ steady\ state}$ of the composition is within about 80.00% to about 125.00% of a $AUC_{0-8\ hrs,\ steady\ state}$ of 3149 h ng/mL (2010-4855 h ng/mL $5^{th}$ and $95^{th}$ percentiles), after administration of said composition in a human weighing from great than about 30 kg to about 55 kg.
141. The method, the oral formulation, pharmaceutical composition, or unit dosage for use, or use of the oral formulation, pharmaceutical composition, or unit dosage of any one of items 110-114, wherein the geometric mean $C_{max,steady\ state}$ of the composition at steady state is within about 80.00% to about 125.00% of a $C_{max,steady\ state}$ of 743 ng/mL (479-743 ng/mL $5^{th}$ and $95^{th}$ percentiles), after administration of said composition in a human weighing greater than about 55 kg.

142. The method, the oral formulation, pharmaceutical composition, or unit dosage for use, or use of the oral formulation, pharmaceutical composition, or unit dosage of any one of items 110-114, wherein the $AUC_{0-8\ hrs,\ steady\ state}$ of the composition is within about 80.00% to about 125.00% of a $AUC_{0-8\ hrs,\ steady\ state}$ of 3182 h ng/mL (2057-4921 h ng/mL $5^{th}$ and $95^{th}$ percentiles), after administration of said composition in a human weighing greater than about 55 kg.

143. The method, the oral formulation, pharmaceutical composition, or unit dosage for use, or use of the oral formulation, pharmaceutical composition, or unit dosage of any one of items 110-114, wherein N-{[(2R)-2-hydroxy-3-piperidin-1-ylpropyl]oxy}pyridine-3-carboximidoyl chloride 1-oxide citrate exposure increases dose-proportionally following a single oral dosage from about 31 mg to about 496 mg, wherein the estimates of the proportionality coefficient (90% CI) for $C_{max}$ is 1,149 (1,07-1,20) and for $AUC_{0-inf}$ is 1,027 (0,98-1,08).

144. The method, the oral formulation, pharmaceutical composition, or unit dosage for use, or use of the oral formulation, pharmaceutical composition, or unit dosage of any one of items 110-114, wherein the overall median $t_{max}$ after administration is 0.25 to 3.0 hours.

145. The method, the oral formulation, pharmaceutical composition, or unit dosage for use, or use of the oral formulation, pharmaceutical composition, or unit dosage of any one of items 110-114, wherein the median $t_{max}$ after administration is about 0.5 hours.

146. The oral formulation, pharmaceutical composition, or unit dosage of any one of items 86-107, wherein the oral formulation, pharmaceutical composition, or unit dosage has a shelf-life of at least 24 months from about 20° C. to about 25° C.

147. The oral formulation, pharmaceutical composition, or unit dosage of any one of items 86-107, wherein the oral formulation, pharmaceutical composition, or unit dosage comprises N-{[(2R)-2-hydroxy-3-piperidin-1-ylpropyl]oxy}pyridine-3-carboximidoyl chloride 1-oxide, or pharmaceutically acceptable salt thereof, having a purity greater than or equal to 98.0% as determined by HPLC.

148. A pharmaceutical composition comprising:
   a) N-{[(2R)-2-hydroxy-3-piperidin-1-ylpropyl]oxy}pyridine-3-carboximidoyl chloride 1-oxide, or pharmaceutically acceptable salt thereof, having an enantiomeric excess of about 96% ee;
   b) less than about 0.1% methyl (Z)—N-(2-hydroxy-3-(piperidin-1-yl)propoxy)nicotinimidate 1-oxide, or a pharmaceutically acceptable salt thereof;
   c) less than about 2 ppm N-nitrosopiperidine.

149. A pharmaceutical composition comprising:
   a) N-{[(2R)-2-hydroxy-3-piperidin-1-ylpropyl]oxy}pyridine-3-carboximidoyl chloride 1-oxide citrate, having an enantiomeric excess of about 96% ee;
   b) less than about 0.1% methyl (Z)—N-(2-hydroxy-3-(piperidin-1-yl)propoxy)nicotinimidate 1-oxide, or a pharmaceutically acceptable salt thereof;
   c) less than about 2 ppm N-nitrosopiperidine.

150. A pharmaceutical composition comprising:
   a) about 98% N-{[(2R)-2-hydroxy-3-piperidin-1-ylpropyl]oxy}pyridine-3-carboximidoyl chloride 1-oxide, or pharmaceutically acceptable salt thereof,
   b) about 2% N-{[(2S)-2-hydroxy-3-piperidin-1-ylpropyl]oxy}pyridine-3-carboximidoyl chloride 1-oxide, or pharmaceutically acceptable salt thereof,
   c) up to about 0.1% methyl (Z)—N-(2-hydroxy-3-(piperidin-1-yl)propoxy)nicotinimidate 1-oxide, or a pharmaceutically acceptable salt thereof,
   d) up to about 2 ppm N-nitrosopiperidine.

151. A pharmaceutical composition comprising:
   a) about 98% N-{[(2R)-2-hydroxy-3-piperidin-1-ylpropyl]oxy}pyridine-3-carboximidoyl chloride 1-oxide citrate;
   b) about 2% N-{[(2S)-2-hydroxy-3-piperidin-1-ylpropyl]oxy}pyridine-3-carboximidoyl chloride 1-oxide, or pharmaceutically acceptable salt thereof,
   c) up to about 0.1% methyl (Z)—N-(2-hydroxy-3-(piperidin-1-yl)propoxy)nicotinimidate 1-oxide, or a pharmaceutically acceptable salt thereof,
   d) up to about 2 ppm N-nitrosopiperidine.

152. The pharmaceutical composition of any one of items 148-151, wherein the N-nitrosopiperidine is not detectable.

EXAMPLES

Example 1: Preparation of ORZY-01

ORZY-01 may be prepared according to the optimized step 1 method described herein below, and may also be prepared using the process as described in WO 01/79174.

Materials

Ethanol: SDA-3C was used. SDA (Specially Denatured Alcohol), 200 proof, SDA 3C, containing Isopropanol, N-Hydroxy-1-oxy-nicotinamidine "PCO—N-oxide", and 2-Hydroxy-4-azonia-spiro[3,5]nonane chloride "Azonia" are supplied by Chiral Quest.

Method

One or more seeding crystals of ORZY-01 can be added to the reaction container to completely remove the genotoxic compound, N-nitrosopiperidine in the product of Step 1, ORZY-01.

Sodium hydroxide (50% solution in water, 68.4 g, 855.0 mmol, 1.31 eq.) was mixed with water (215.8 mL), then cooled to 10-20° C. 2-Hydroxy-4-azonia-spiro[3,5]nonane chloride "Azonia" (153.0 g, 1.32 eq) was charged, the mixture was cooled to 5-10° C. and agitated for 40 minutes.

Ethanol (SDA-3C, 1000 mL) was charged, followed by N-Hydroxy-1-oxy-nicotinamidine "PCO—N-oxide" (112.0 g, 653.0 mmol, KF=11%). The mixture was heated to reflux (~80° C.) for 4 hours. A ~95% Conversion was achieved for the coupling reaction. At the completion of the reaction, the batch was cooled to ambient temperature (~25° C.) and left overnight. The mixture was cooled to ambient temperature (~25° C.). Water (100 mL) and conc. HCl (68.4 mL) was charged to adjust the pH between 5 and 7 units (additional 6 ml 6N HCl was used for pH adjustment). The internal temperature was maintained below 30° C. during the neutralization. The batch was distilled to ~5 vol. Conc. HCl (370 mL) was charged. The batch was cooled to 0-5° C. A solution of sodium nitrite (55.4 g, 803.0 mmol, 1.23 eq) in water (75 mL) was slowly charged maintaining the internal temperature between 5-15° C. Almost complete conversion was observed. The mixture was left at 5-15° C. overnight. DCM (600 mL) was charged, followed by 40% an aqueous sodium hydroxide solution (491.6 g) maintaining the internal temperature below 15° C. (pH >13.1). The DCM layer was separated, and the aqueous layer back extracted with DCM (500 mL). The organic phase was distilled to ~5 vol. MTBE (5 vol, 500 mL) was charged. The mixture was distilled to ~5 vol. MTBE (5 vol, 500 mL) was charged, the mixture was distilled to 5 vol again.

MTBE (5.5 vol, mL) was charged, the batch was cooled to 0-5° C. for 3 hours.

The slurry was filtered. The wet cake was washed with MTBE (1.5 vol, 150 mL), then dried under vacuum overnight. 163.2 g isolated product ORZY-01 was obtained with 79.6% yield (99.7% purity).

Results

The optimized process provided the isolated ORZY-01 in 79.6% yield (99.7% purity).

By optimization of the reaction conditions, the optimal reactant ratio, reaction time, and temperature were developed allowing product ORZY-01 to be isolated in 79.6% yield without intermediate isolation or unnecessary steps. This yield is significantly higher compared to previous reports.

When other factors were taken into consideration (e.g. minimize formation of impurities), the optimized conditions are: 1.32 eq of "Azonia" and 3.6 hours reaction time at 80'° C. If the eq. of "Azonia" increases to ~2 eq, the reaction will finish in 2 hours. However, too much "Azonia" leads to more impurity formation and thus leads to extra difficulties for the isolation of ORZY-01. If the eq. of "Azonia" decreases to lower than 1.1 eq., the reaction fails to reach a 95% conversion after 6 hours.

The step 1A coupling reaction should optimally be carried out at reflux temperature of water/denatured ethanol (SDA-3C) mixture at ~78-82° C. and for more than 2 hours. Based on the present studies, a lower temperature significantly slows the reaction.

Example 2: Step 1A Optimization

Example 3: Step 1B Optimization

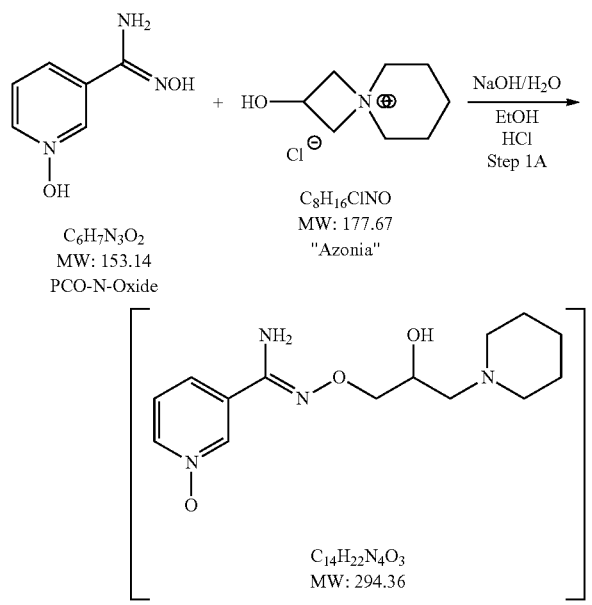

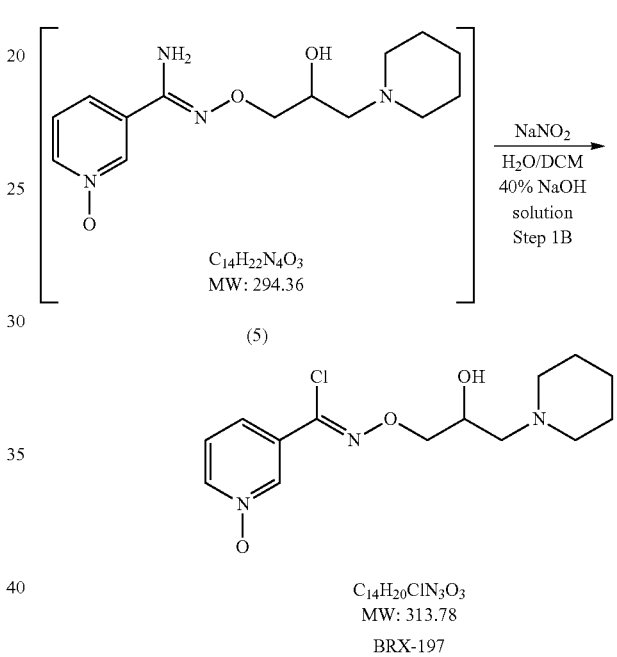

As summarized in table 1, a study was set up to understand the key reaction parameters impacting the overall results of the reaction. Three factors, eq. of "Azonia", reaction temperature and reaction time, were studied against five responses: PCO—N-Oxide (%), Product (%), impurity A (%), impurity C (%) and reaction conversion (%).

Step 1B optimization was carried out after the completion of step 1A optimization. After completion of Step 1A, the mixture was subdivided into several equal portions and these portions were utilized for step 1B optimization to ensure that step 1B experiments began at the same point, which would offer comparable results for the study.

TABLE 1

Reaction conditions and results. Entries 3, 6, 7, and 8 resulted in high conversion and yield.

| Entry | "Azonia" (eq.) | Temp. (° C.) | Reaction time (h) | PCO-N-Oxide (%) | Intermediate product (%) | Impurity A (%) | Impurity B (%) | Conversion (%) |
|---|---|---|---|---|---|---|---|---|
| 1 | 1.5 | 60 | 3.5 | 25.6 | 71.1 | 0.3 | 2 | 73.5 |
| 2 | 1.5 | 80 | 1 | 7.1 | 89.2 | 0.6 | 1.8 | 92.6 |
| 3 | 1.5 | 80 | 6 | 1.3 | 94.3 | 2.4 | 0.3 | 98.6 |
| 4 | 2 | 60 | 6 | 12.9 | 83.2 | 0.9 | 1.8 | 86.6 |
| 5 | 1.5 | 40 | 6 | 78.1 | 21 | 0 | 0.7 | 21.2 |
| 6 | 2 | 80 | 3.5 | 0.6 | 94.4 | 2.9 | 1.8 | 99.4 |
| 7 | 1.5 | 80 | 3 | 1.5 | 94.1 | 1.5 | 0.9 | 98.4 |
| 8 | 1.5 | 80 | 6 | 1.1 | 94.4 | 2.1 | 0.4 | 98.8 |
| 9 | 2 | 60 | 3 | 28.7 | 68 | 0.3 | 1.9 | 70.3 |
| 10 | 1 | 80 | 1.5 | 20.9 | 76 | 0.6 | 1.7 | 78.4 |

Two factors, eq. of Sodium nitrite and reaction temperature, were studied against two responses: reaction conversion (%) and product purity (%). For a minimum of 95% conversion and 80% batch purity (before isolation), at least 1.2 of sodium nitrite is needed at a temperature between 5° C. to 15° C. Additional sodium nitrite may be added if the reaction conversion is less than 95%. The reaction temperature range for step 1B has previously reported as −5° C. targeting 0° C. This temperature range for step 1B led to an incomplete reaction at the beginning and required several recharges of the sodium nitrite solution to push the reaction to completion.

In addition to incomplete reaction, a delayed exothermic reaction was observed at 0° C., which is a potential safety concern for a larger scale process. Therefore, the target reaction temperature was increased to 5-15° C. for step 1B successfully resulting in the reaction finishing with a single sodium nitrite charge. The in situ generated diazonium salt is quickly converted to ORZY-01 by HCl without any delayed exothermic reaction observed. The optimized reaction time of step 1B is approximately 1 hour.

The reaction temperature for step 1B was optimized to 10±5° C. A delayed exothermic reaction may be observed when the reaction temperature was lower than 5° C. A temperature higher than 15° C. will result in a very vigorous reaction and prompt safety concerns.

Example 4: Step 2—Chiral Resolution

Overview of reaction step

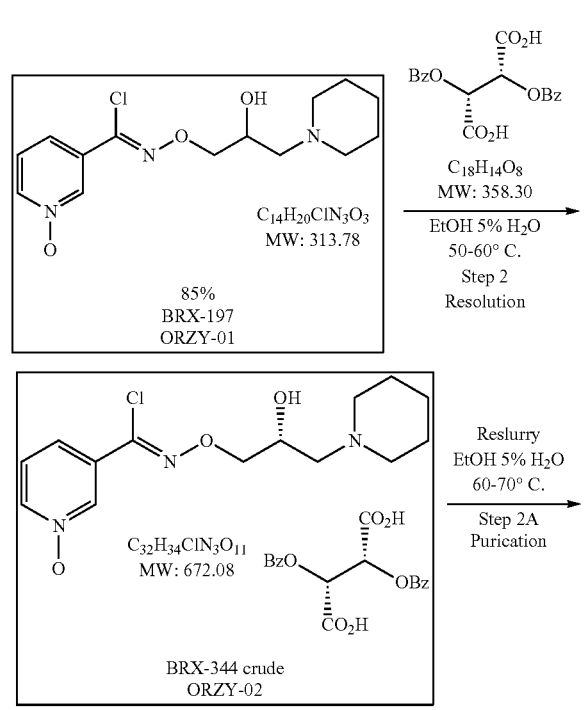

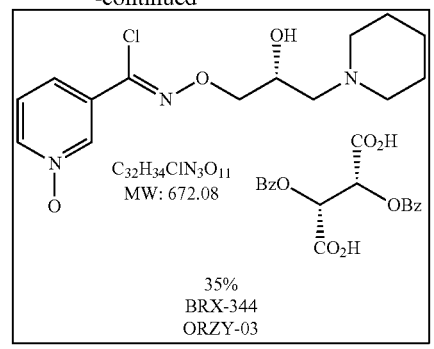

Materials
List that refers to supplier/laboratory code, lot number and specified quality.

| Raw Material | CAS # | MW [g/mol] | Assay [%] | Supplier/ Manufacturer | Lot # |
|---|---|---|---|---|---|
| ORZY-01 | 289893-25-0 | 313.78 | 100 | Patheon Greenville | O50551-18-009 |
| L-DBTA | 62708-56-9 | 376.33 | 95.21 | Apollo-Scientific | LY20180427 |
| Ethanol | 64-17-5 | 46.07 | 100 | Fisher | 1912096 |
| water | 7732-18-5 | 18.02 | 100 | PW-Net R + D labs | — |
| ORZY-03 seeds | 368860-20-2 | 672.08 | 100 | Patheon Greenville | LRR3SA1001 |

All processing is carried out under a nitrogen atmosphere.
Method
A container was charged with water (6 mL), EtOH (95.06 mL), L-DBTA (15.83 g, 0.88 eq.), and ORZY-01 (15.00 g, 1.00 eq.) at 20° C., and the container was subsequently rinsed with EtOH (19 mL). The mixture was subsequently heated to 65-70° C. and stirred for 0.5 h. Subsequently, the mixture was cooled to 55±5° C. and the mixture was stirred for 1 h at 55±5° C. ORZY-03 seeds (0.15 g) were added; and the mixture was cooled to 20±5° C. at a cooling rate of 30 K/h. The mixture was subsequently stirred for 12 h at 20±5° C. and the solid composition was subjected to trituration with EtOH (15.02 mL). The washed solid composition was re-charged in a container, and EtOH (72.24 mL) and water (3.60 mL) were added to the container. The mixture was heated to 55±5° C.; and stirred for 1 h at 55±5° C. Subsequently, the mixture was cooled to 20° C. and stirring was continued for 2 h at 20±5° C., and the solid composition was subjected to trituration with EtOH (15.02 mL). The triturated solid composition was subsequently dried at 45° C. to provide ORZY-03.
Results
ORZY-03 was provided in 29% yield based on ORZY-01 with 100% chemical purity and 98.1% chiral purity.

CONCLUSION

The present example demonstrates that by employing a carefully selected amount of L-DBTA and a cooling rate of at least 15 K/h for the chiral resolution, a surprisingly high chiral purity as well as chemical purity is obtained. The chiral purity of ORZY-03 obtained in Step 2 is retained toward the end-product ORZY-05, and may be further enhanced by re-crystallization. The improved chiral resolution step, including the cooling rate of at least 15 K/h, enables the provision of an ultra-pure composition comprising arimoclomol citrate (ORZY-05) meeting the regulatory requirements of the medicines agencies.

Example 5: Step 2—Correlation of Cooling Rate with Chiral Purity

Materials & Methods

The materials & methods were essentially as in Example 4. In the present example, the cooling rate of the first cooling step to 20±5° C. was varied and its influence on the chemical and chiral purity of ORZY-03 was determined.

Results

The results of the present example is shown in the following Table 2.

TABLE 2

Cooling rates and the resulting chemical and chiral purities of ORZY-03

| Entry | Cooling rate to 20 ± 5° C.; first cooling step | Chemical purity (ORZY-03) | Chiral purity (ORZY-03) |
|---|---|---|---|
| 1 | 8K/h | 100% | 94.0% |
| 2 | 15K/h | 100% | 96.3% |
| 3 | 17K/h | 100% | 96.7% |
| 4 | 20K/h | 100% | 97.2% |
| 5 | 30K/h | 100% | 98.1% |

A cooling rate of 15 K/h or higher, results in an increased chiral purity. A chiral purity of 98.1% means that 98.1% of the composition corresponds to enantiomerically pure ORZY-03.

The cooling rate is a critical process parameter in the chiral resolution of ORZY-01 to provide the enantioenriched salt, ORZY-03. Surprisingly, by employing a cooling rate of 15 K/h or higher, a significantly increased chiral purity of ORZY-03 is provided.

Example 6: Step 3—Salt Exchange

Overview of Reaction Step

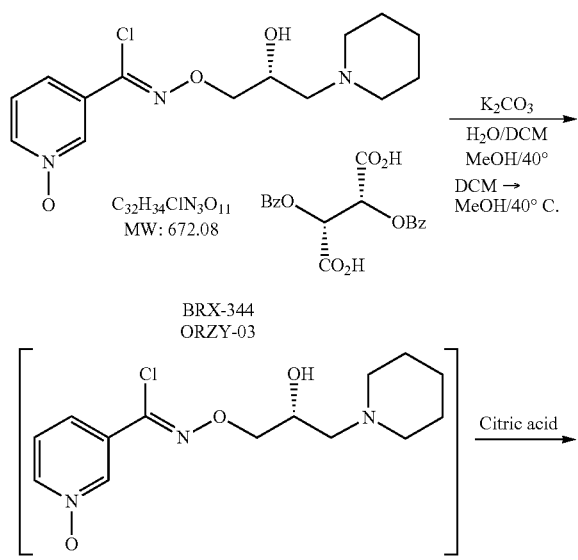

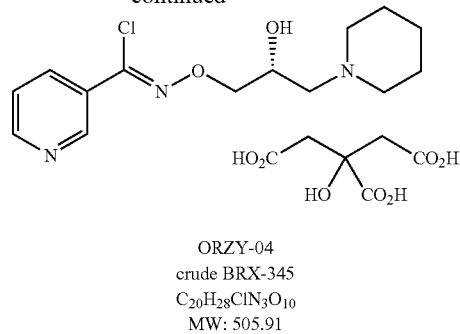

ORZY-04
crude BRX-345
$C_{20}H_{28}ClN_3O_{10}$
MW: 505.91

Materials

List that refers to supplier/laboratory code, lot number and specified quality.

| Raw Material | CAS # | MW [g/mol] | Assay [%] | Supplier/ Manufacturer | Lot # |
|---|---|---|---|---|---|
| ORZY-03 | — | 672.08 | — | Patheon Greenville | LRR3SA- 18-007 |
| potassium carbonate | 584-08-7 | 138.21 | — | Evonik | 44221951 |
| water | — | 18.02 | — | Netz Bau 70 | — |
| dichloromethane | 75-09-2 | 84.93 | — | Merck | K51814950 |
| methanol | 67-56-1 | 32.04 | — | Fisher | 1928066 |
| citric acid, anhydrous | 77-92-2 | 192.12 | — | Merck | BCCC1488 |

Method

A container was charged with $K_2CO_3$ (16.8% aq. sol., 140 mL, 2.4 eq.) and ORZY-03 (54.0 g, 30 mL) at 20° C., and the mixture was stirred for 5 min. DCM (130 mL) was charged to the container at 20° C., and the mixture was stirred for 5 min. After the phases had settled, the phases were split. DCM (120 mL) was added to the aq. phase, and the mixture was then stirred for 5 min. After having settled, the phases were split. DCM (130 mL) was added to the aq. phase, and the mixture was then stirred for 5 min. After having settled, the phases were split. $H_2O$ (480 mL) was added to the combined org. phases (370 mL), and the mixture was stirred for 5 min. After having settled, the phases were split and the aq. phase was discarded. The container was rinsed with DCM (32 mL).

The combined org. phases (400 mL) were charged into a container at 20° C., and citric acid (anhydrous, 0.37 g, 1 mL, 0.02 eq.) was added. The solution was distilled at 40° C. to a target volume of 200 mL. MeOH (150 mL) was added to the solution, and the solution was distilled at 40° C. to a target volume of 250 mL. MeOH (320 mL) was added and the solution was passed through activated charcoal filter (Carbofil CA) at 20° C., and the filter was rinsed with MeOH (10 mL). The color of the solution was subsequently determined to be >B6 using IPC-1.

A citric acid solution was prepared by charging citric acid (15.01 g, 130 mL) and MeOH (100 mL) in a separate container and stirring for 5 min. at 20° C. The citric acid solution was then charged to the container containing the reaction solution, and the mixture was cooled to 0° C. and stirred for at least 12 h at 0° C. ORZY-04 was then isolated by filtration of the obtained suspension, and washed with MeOH (40 mL). Finally, the solids were dried at 45° C. in vacuum.

Results

ORZY-04 was obtained as a solid in 89% yield based on ORZY-03 with 99.10% chiral purity.

This example describes conversion of ORZY-03 to ORZY-04 by removal of the dibenzoyl-L-tartaric acid via treatment with potassium carbonate ($K_2CO_3$), followed by treatment with citric acid to afford ORZY-04.

The present example demonstrates that addition of a catalytic amount of citric acid before the solvent exchange from DCM to MeOH suppresses the formation of "methoxylated ORZY-04" (also referred to as RRT 0.74). The example further demonstrates that washing the combined DCM phases with water, further reduces the levels of impurities, such as RRT 0.74.

Further, this example demonstrates that extraction of ORZY-03 after neutralization with aqueous $K_2CO_3$ solution efficiently removes the by-product called "Hydrolyzed ORZY-03".

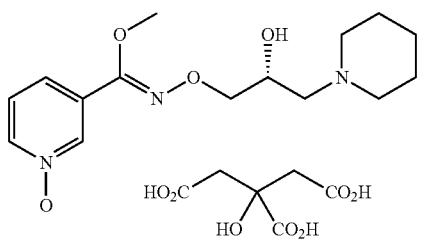

$C_{21}H_{31}N_3O_{11}$
MW: 501.49
Methoxylated ORZY-04 (RRT 0.74)

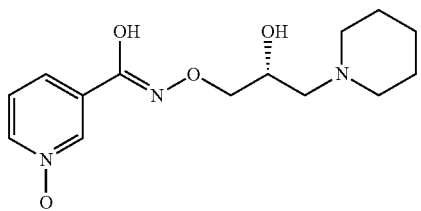

$C_{14}H_{21}N_3O_4$
MW: 295.34
Hydrolyzed ORZY-03

Thus, a high chiral purity and chemical purity is obtained.

Finally, this example demonstrates that ORZY-04 is stable after 168 h of drying at 45° C. in vacuum.

Example 7: Step 4—Purification

Overview of Reaction Step:

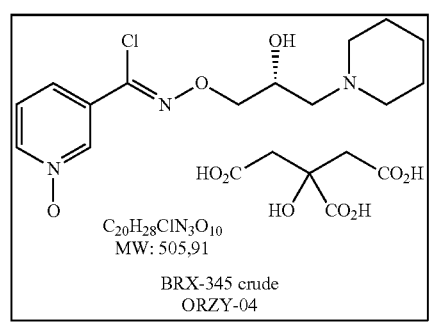

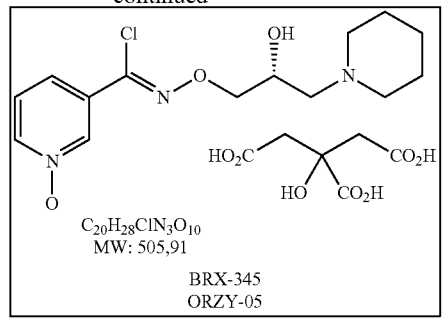

$C_{20}H_{28}ClN_3O_{10}$
MW: 505.91

BRX-345
ORZY-05

Materials

List that refers to supplier/laboratory code, lot number and specified quality.

| Raw Material | CAS # | MW [g/mol] | Assay [%] | Supplier/Manufacturer | Lot # |
|---|---|---|---|---|---|
| ORZY-04 | 368860-21-3 | 505.91 | — | Patheon Linz | R&D sample* |
| water | 7732-18-5 | 18.02 | — | Netz Bau 70 | — |
| acetone | 67-64-1 | 58.08 | — | Merck | K46104714 |

Method

ORZY-04 (30.0 g, 15 mL) and $H_2O$ (58 mL) were charged in a container and heated to 70±5° C. until a clear solution was observed. The solution was then cooled to 30±5° C. Acetone (291 mL) was added, and the mixture was cooled to 0±5° C. The mixture was agitated for 12 h at 0±10° C. The suspension was filtered and the isolated solid was washed with acetone (38 mL) at 20° C. Finally, the solids were dried at 45° C. in vacuum for at least 12 h.

Results

ORZY-05 was obtained as a solid in 90% yield based on ORZY-04 with 99.96% chiral purity.

The impurity "Hydrolized ORZY-04" may be formed during storage of ORZY-04 in water. However, after crystallization of the product as outlined in this example, the impurity remains in the mother liquor.

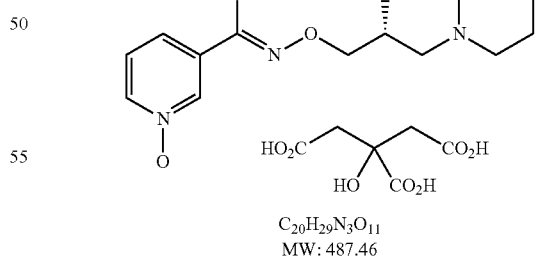

$C_{20}H_{29}N_3O_{11}$
MW: 487.46

By-Product "Hydrolized ORZY-04"

This example demonstrates that recrystallization under the given conditions results in high chiral and chemical purity.

Example 8: Step 4—Correlation of Cooling Time and Particle Size of ORZY-05

Materials & Methods

The materials and methods were essentially as in Example 7. In the present example, the cooling time of the cooling step of from 30° C. to 0° C. subsequent to addition of acetone was varied and its influence on the particle size of ORZY-05 was determined. The cooling time is a measure of how long it takes to reach 0° C. from 30° C. The particle size distribution (PSD) data shown in Table 3 were acquired using static automated imaging (Morphology 4).

Results

The results of the resent example is shown in the following Table 3A.

TABLE 3A

Relationship between cooling time and particle size distribution (PSD) of the batches from campaign "O502FP-17" and "O505FP-18". CE used herein refers to the Circle equivalent diameter of the ORZY-05 particles. The present example demonstrates a correlation between particle size, determined as PSD, and the cooling time of from 30° C. to 0° C. in the cooling step subsequent to addition of acetone. A shorter cooling time leads to smaller particle sizes. Based on the data of the present example, a cooling time below 5.5 hours results in smaller particles, determined by their mean diameters. The smaller sizes ease the preparation of dosage forms requiring a predefined amount of substance, and the smaller sizes increase the encapsulation yield when the dosage forms are capsules.

| Batch number | 17-001 | 17-002 | 17-003 | 17-004 | 18-001 | 18-002 | 18-003 | 18-004 | 1001 | 1002 | 1003 | 1004 |
|---|---|---|---|---|---|---|---|---|---|---|---|---|
| Batch cooling time | 42 min | 28 min | 43 min | 27 min | 2 hours | 2 hours | 14 hours | 5.5 hours | 73 min | 89 min | 78 min | 70 min |
| Number CE Diameter D10 (μm) | 0.60 | 0.70 | 1.00 | 0.80 | 0.80 | 0.90 | 4.40 | 3.70 | 2.41 | 2.45 | 0.89 | 1.05 |
| Number CE Diameter D50 (μm) | 1.60 | 2.20 | 2.00 | 2.00 | 2.50 | 2.20 | 21.80 | 12.00 | 5.28 | 5.61 | 3.34 | 2.86 |
| Number CE Diameter D90 (μm) | 9.40 | 7.40 | 5.80 | 23.50 | 10.70 | 10.10 | 38.20 | 29.20 | 17.81 | 15.01 | 14.14 | 13.33 |
| Number CE Diameter Mean (μm) | 3.70 | 3.40 | 2.90 | 6.70 | 4.60 | 4.20 | 22.10 | 14.90 | 8.16 | 7.71 | 5.79 | 5.31 |
| Number Length D10 (μm) | 1.70 | 1.10 | 1.40 | 1.50 | 1.80 | 1.50 | 8.00 | 5.30 | 2.90 | 3.46 | 4.20 | 2.82 |
| Number Length D50 (μm) | 4.70 | 3.20 | 3.20 | 4.00 | 4.10 | 3.60 | 29.90 | 15.40 | 7.03 | 7.37 | 9.50 | 6.18 |
| Number Length D90 (μm) | 22.00 | 13.90 | 10.50 | 40.70 | 16.80 | 16.60 | 56.10 | 40.00 | 26.69 | 22.17 | 25.49 | 24.80 |
| Volume CE Diameter D10 (μm) | 9.40 | 6.20 | 4.60 | 24.60 | 11.20 | 10.90 | 24.00 | 19.40 | 13.10 | 12.39 | 10.66 | 12.62 |
| Volume CE Diameter D50 (μm) | 24.70 | 14.00 | 11.10 | 38.90 | 26.40 | 22.70 | 37.60 | 39.80 | 25.95 | 32.12 | 20.58 | 25.00 |
| Volume CE Diameter D90 (μm) | 44.40 | 35.00 | 26.70 | 52.20 | 37.60 | 36.00 | 58.30 | 81.20 | 47.14 | 73.60 | 34.54 | 43.46 |
| Volume CE diameter D[4, 3] (μm) | 25.70 | 17.10 | 13.70 | 38.80 | 25.40 | 23.30 | 41.10 | 45.90 | 29.46 | 39.38 | 22.10 | 27.06 |

TABLE 3A-continued

Relationship between cooling time and particle size distribution (PSD) of the batches from campaign "O502FP-17" and "O505FP-18". CE used herein refers to the Circle equivalent diameter of the ORZY-05 particles. The present example demonstrates a correlation between particle size, determined as PSD, and the cooling time of from 30° C. to 0° C. in the cooling step subsequent to addition of acetone. A shorter cooling time leads to smaller particle sizes. Based on the data of the present example, a cooling time below 5.5 hours results in smaller particles, determined by their mean diameters. The smaller sizes ease the preparation of dosage forms requiring a predefined amount of substance, and the smaller sizes increase the encapsulation yield when the dosage forms are capsules.

| Batch number | 17-001 | 17-002 | 17-003 | 17-004 | 18-001 | 18-002 | 18-003 | 18-004 | 1001 | 1002 | 1003 | 1004 |
|---|---|---|---|---|---|---|---|---|---|---|---|---|
| Volume CE diameter D[3, 2] (μm) | 17.7 | 11.4 | 8.80 | 34.20 | 19.50 | 17.90 | 35.40 | 33.90 | 21.77 | 24.24 | 17.52 | 20.53 |

Further batches of ORZY-05 were prepared essentially as in Example 7 and the ORZY-05 particles were examined using Malvern Mastersizer 3000 as described in Example 11. The PSDs obtained are shown in Table 3B.

TABLE 3B

Overview of ORZY-05 batches and PSDs determined using Malvern Mastersizer 3000.

| Batch number | 1001 | 1002 | 1003 | 1004 | 2001 | 2002 | 2003 | 2004 | 2005 | 2006 |
|---|---|---|---|---|---|---|---|---|---|---|
| D10 (μm) | 7.00 | 14.00 | 6.00 | 8.00 | 17.2 | 4.33 | 4.65 | 10.2 | 11.2 | 11.6 |
| 50 (μm) | 21.00 | 53.00 | 17.00 | 22.00 | 47.2 | 12.5 | 13.5 | 34.8 | 35.6 | 35.6 |
| D90 (μm) | 63.00 | 118.00 | 47.00 | 68.00 | 112 | 37.9 | 40.7 | 87 | 82.6 | 77.7 |

Example 9. Capsule Formation

Arimoclomol citrate was formulated into size "0", bi-colored hard HPMC capsules for oral administration in the strengths of 50 mg, 75 mg, 100 mg 150 mg and 200 mg (corresponding to 31, 47, 62, 93 and 124 mg arimoclomol free base). The 50 mg, 75 mg and 100 mg strength capsules were manufactured using a 100 mg powder blend comprising 26.2% arimoclomol citrate with a homothetic fill (proportional decrease of the filling weight to the strength) of the capsules. Correspondingly, the 150 mg and 200 mg strength capsules were manufactured using a 200 mg powder blend comprising 52.6% arimoclomol citrate with a homothetic fill of the capsules. The capsules were packed in high density polyethylene (HDPE) bottles (185 mL), induction heat sealed with a foil liner at the neck opening and closed with a HDPE child resistant cap.

The manual wet granulation was replaced with dry granulation using roller compaction to avoid contact with moisture and omit the need for heat in the process.

The capsules can be swallowed whole or emptied for administration to patients with swallowing disabilities (e.g., emptying the Coni-Snap® sprinkle capsules).

The capsule contents can be dispersed into 10-30 mL of liquid (i.e. water or apple juice) as the patient or caregiver find most convenient, or it can be dispersed into one tablespoon of soft food (i.e. yogurt, apple puree, or pudding) before administration. The dispersed content can also be used for administration via gastric feeding tube. Stability of up to two hours in the dispersion has been demonstrated.

The qualitative composition as well as the function of each excipient is provided in Table 4.

TABLE 4

Composition of 50 mg, 75 mg, 100 mg, 150 mg, and 200 mg arimoclomol citrate capsules

| | | | mg/capsule | | | | |
|---|---|---|---|---|---|---|---|
| Ingredient | Standard | Function | 50 mg | 75 mg | 100 mg | 150 mg | 200 mg |
| Arimoclomol citrate | In-house | Active ingredient | 50.00$^a$ | 75.00$^a$ | 100.00$^a$ | 150.00$^a$ | 200.00$^a$ |
| Microcrystalline cellulose (MCC) | Ph. Eur., NF | Filler | 139.05 | 208.57 | 278.10 | 133.57 | 178.10 |
| Magnesium stearate | Ph. Eur., NF | Lubricant | 0.95 | 1.43 | 1.90 | 1.43 | 1.90 |
| Total | | | 190.00 | 285.00 | 380.00 | 285.00 | 380.00 |

TABLE 4-continued

Composition of 50 mg, 75 mg, 100 mg, 150 mg, and 200 mg arimoclomol citrate capsules

| | | | mg/capsule | | | | |
|---|---|---|---|---|---|---|---|
| Ingredient | Standard | Function | 50 mg | 75 mg | 100 mg | 150 mg | 200 mg |
| HPMC capsule Blue cap, white body | Ph. Eur., USP | Capsule shell[b] | 1 unit | NA | NA | NA | NA |
| HPMC capsule Green cap, white body | Ph. Eur., USP | Capsule shell[b] | NA | 1 unit | NA | NA | NA |
| HPMC capsule Yellow cap, white body | Ph. Eur., USP | Capsule shell[b] | NA | NA | 1 unit | NA | NA |
| HPMC capsule Orange cap, white body | Ph. Eur., USP | Capsule shell[b] | NA | NA | NA | 1 unit | NA |
| HPMC capsule Red cap, white body | Ph. Eur., USP | Capsule shell[b] | NA | NA | NA | NA | 1 unit |

HPMC: Hydroxypropyl methylcellulose;
MCC: Microcrystalline cellulose;
NA: Not applicable;
Ph. Eur.: European Pharmacopoeia;
USP: United States Pharmacopoeia;
NF: National Formulary
[a] 50 mg, 75 mg, 100 mg, 150 mg, or 200 mg of arimoclomol citrate equivalent to 31 mg, 47 mg, 62 mg, 93 mg, or 124 mg of arimoclomol, respectively
[b] HPMC Coni-Snap® sprinkle capsules (Size 0)

Dissolution

The method used for assessing the dissolution rate of the drug product was a Ph.Eur. paddle method (apparatus 2) using 1000 mL of 0.1M NaCl/HCl buffer (USP simulated gastric fluid without enzymes), the paddle rotation speed was 75 rpm, the samples were placed in standard Ph.Eur. wire sinkers with 10 mL samples taken at 5, 10, 15, 30 and 60 minutes, without replenishment, and filtered through 10 µm full flow cannula filters followed by final filtration through 0.45 µm nylon filters. Samples were analysed using a UV method with detection at 260 nm. External standards were used for quantification.

Evaluation of the dissolution profiles of the five different strengths showed little variation between the mean results for each strength.

The dissolution method for all strengths of arimoclomol citrate capsules was conducted according to USP <711> and Ph. Eur. 2.9.3 with apparatus 2. Percentage of drug substance dissolved was measured after 30 minutes, either with in line or off-line UV readings with detection at 260 nm.

Dissolution Conditions

| Parameter | Equipment |
|---|---|
| Apparatus | Paddle apparatus (USP and Ph. Eur. apparatus 2) |
| Paddle speed | 75 rpm ± 3 rpm |
| Dissolution media | Hydrochloric Acid Buffer Solution |
| Dissolution media volume | 1000 mL |
| Dissolution media temperature | 37° C. ± 0.5° C. |
| Sinkers | Wire (Stainless steel) |
| Sample volume | 10 mL (without replacement) or direct in-line measurement |
| Sample filter | 0.2 µm nylon membrane filter (or GF/D, GF/B or GF/F), reject the first 1 mL for manual analysis, and GF/D or GF/B filter for online analysis |
| Sampling point | 30 minutes |
| Sample analysis | UV at 260 nm |
| Cuvette | 5 mm for 31 and 47 mg capsules 2 mm for 62, 93 and 124 mg capsules |

GF: Glass fiber;
rpm: Rotations per minute;
UV: Ultraviolet

HPLC Validation

The HPLC analytical procedure for Identification, Content Uniformity and Assay was validated with testing of Specificity, Range, Linearity, Accuracy, Repeatability, Intermediate precision, Robustness, stability of solution and filter compatibility.

Stability Study

Stability studies of 50 mg, 75 mg, 100 mg, 150 mg, and 200 mg arimoclomol citrate capsules demonstrated good stability, 30%/75% RH.

Twenty-four months of long term storage of 100 mg and 200 mg strength capsules showed that there was no significant change to any of the key quality attributes (e.g., appearance, assay, impurities, moisture, and dissolution) over the time period at 25° C./60%/RH and 30° C./75% RH, as well as accelerated conditions of 40° C./75% RH. The stability was tested in open storage and accelerated conditions (40° C./75% RH and 40° C./95% RH), which showed no significant change to any of the key quality attributes.

Example 10. Pharmacokinetic Studies

The population PK covariate model (popPK model; RUNU030), was used to simulate exposure variables ($AUC_{0-8\ h,ss}$, $C_{max,ss}$) according to the dose regimens in Table 5 and Table 6. Steady state was ensured through calculation of the exposure variables following 7 days of dose administration at an 8-hour interval. For each body-weight band, 5000 sets of bodyweight and age were sampled from the NHANES III database using age range of ≥2 years to ≤18 years. 5000 virtual subject PK profiles (per weight band), were then generated using the updated popPK model with inter-individual variability included.

TABLE 5

| Dosage Regimen 1 | |
|---|---|
| Subject Body Weight | Recommended Dosage |
| 8 kg to 15 kg | 31 mg three times a day |
| >15 kg to 22 kg | 47 mg three times a day |
| >22 kg to 38 kg | 62 mg three times a day |

TABLE 5-continued

Dosage Regimen 1

| Subject Body Weight | Recommended Dosage |
|---|---|
| >38 kg to 55 kg | 93 mg three times a day |
| >55 kg | 124 mg three times a day |

TABLE 6

Dosing Regimen 2

| Subject Body Weight | Recommended Dosage |
|---|---|
| 8 kg to 15 kg | 47 mg three times a day |
| >15 kg to 30 kg | 62 mg three times a day |
| >30 kg to 60 kg | 93 mg three times a day |
| >60 kg | 124 mg three times a day |

The dosing regimens in Table 6 result in higher exposure in the lower weight bands compared to Table 5, whereas the exposure levels in the higher weight bands are generally comparable between the two dosing regimens, see Table 7 and Table 8.

TABLE 7

Simulated $AUC_{0-8,ss}$ and $C_{max,ss}$ from Table 5 Dosing Regimens

| | | Weight band (kg) [dose (mg)] | | | | |
|---|---|---|---|---|---|---|
| Statistics | | 8-15 [31] | >15-22 [47] | >22-38 [62] | >38-55 [93] | >55 [124] |
| | n | 5000 | 5000 | 5000 | 5000 | 5000 |
| $AUC_{0-8h,ss}$ (h · ng/mL) | mean | 1918 | 2479 | 2557 | 2954 | 3191 |
| | 5$^{th}$ percentile | 1255 | 1640 | 1663 | 1958 | 2054 |
| | 95$^{th}$ percentile | 2908 | 3771 | 3942 | 4465 | 4948 |
| $C_{max,ss}$ (ng/mL) | mean | 352 | 473 | 522 | 651 | 739 |
| | 5$^{th}$ percentile | 240 | 323 | 349 | 435 | 483 |
| | 95$^{th}$ percentile | 514 | 688 | 770 | 974 | 1130 |

TABLE 8

Simulated $AUC_{0-8,ss}$ and $C_{max,ss}$ from Table 6 Dosing Regimens

| | | Weight band (kg) [dose (mg)] | | | |
|---|---|---|---|---|---|
| Statistics | | 8-15 [47] | >15-30 [62] | >30-60 [93] | >60 [124] |
| | n | 5000 | 5000 | 5000 | 5000 |
| $AUC_{0-8,ss}$ (h · ng/mL) | mean | 2903 | 3066 | 3064 | 3107 |
| | 5$^{th}$ percentile | 1891 | 1961 | 1976 | 2010 |
| | 95$^{th}$ percentile | 4415 | 4749 | 4798 | 4748 |
| $C_{max,ss}$ (ng/mL) | mean | 533 | 595 | 666 | 727 |
| | 5$^{th}$ percentile | 362 | 400 | 440 | 477 |
| | 95$^{th}$ percentile | 779 | 881 | 993 | 1103 |

Absorption and Bioavailability

The PK parameters of arimoclomol after single dose and multiple dose administrations of arimoclomol were studied. After single- and multiple-dose oral administration of arimoclomol, the overall median $t_{max}$, was 0.25 to 3.00 hours.

Following oral administration of arimoclomol, absorption is both rapid and extensive. In the human trial, 77.5% of drug-related material was recovered in the urine and 12% in faeces. The drug substance has demonstrated stability in both gastric fluid and intestinal fluid. The stability permits that the permeability of arimoclomol is high based on urinary recovery in human mass balance trial.

Arimoclomol exhibits linear and dose-proportional pharmacokinetics after single oral doses of 31 mg to 496 mg. The absolute bioavailability of arimoclomol following oral administration was 85% in rats (77% in males and 90% in females) and 75% in dogs relative to arimoclomol i.v. administration (based on $AUC_{0-inf}$).

The estimates of the proportionality coefficient (90% CI) for $C_{max}$ and $AUC_{0-inf}$ were 1.14 (1.07-1.20) and 1.03 (0.98-1.08), respectively; all values fell within the range of 0.8 to 1.25, which indicates dose-proportionality. Thus, arimoclomol is considered dose proportional following single dose within the dose range 31 mg to 496 mg (free base).

Arimoclomol PK parameters ($C_{max}$ and $AUC_{0-8}$) increase in proportion to the dose after multiple-dose administration of 62-372 mg arimoclomol (free base) t.i.d. Arimoclomol PK parameters ($C_{max}$ and $AUC_{0-8}$) increase in proportion to the dose after single-dose administration of 31-496 mg arimoclomol (free base).

Example 11: Determination of Particle Size Distribution (PSD)

Malvern Mastersizer 3000: Particle size distribution of Arimoclomol citrate (ORZY-05) was determined by light scattering using a Malvern Mastersizer 3000 particle size analyzer (Malvern Instruments Ltd, Grovewood Road, Malvern, Worcestershire WR14 1XZ, United Kingdom) with a Hydro MV wet-dispersion unit attached. 2-Propanol with 1.8 g/L SPAN-85 additive was used as a dispersion medium ("dispersant") and added to the dispersion unit. Prior to sample addition, the background counts of the system were determined by circulating the dispersant through the measurement cell under measurement conditions (2500 rpm stirrer speed). Samples for analysis were prepared by adding a suitable amount of Arimoclomol citrate to a 10 mL vial and pre-dispersing it with dispersant under light agitation for a few seconds. The pre-dispersed sample was then pipetted into the Hydro MV dispersion unit filled with dispersant to meet a laser obscuration range of 10-15%. A single-use PE pipette was used for this and representative sampling from the 10 mL vial was ensured by continuous agitation. Ultrasonication was not applied on the added sample, as it was found to brake Arimoclomol citrate particles. Volume distributions were obtained and the D10, D50 and D90 were calculated from these distributions and reported. For each sample, a single sample preparation was analyzed using red light measurement only. Upon measurement completion, the sample cell was emptied and cleaned.

Morphologi 4: The Particle size distribution of Arimoclomol citrate (ORZY-05) was also measured using a Malvern Morphologi 4 equipment.

Wet measurement was used for the needle shaped particles. Different solvents were tested, and 2-propanol was found to give the best results with regards to non solubilization of the API. Measurements were made using a thin path wet cell (75*75 mm). Samples were prepared by adding 20 mL of dispersant to 10 mg of API, followed by 30 s of stirring and 2 min of sonication in order to break the agglomerates. A microscope magnifier of ×10 or ×20 was used, and segmentation sharp edge and/or thresholding was used to improve the focus microscope focus.

EQUIVALENTS

The details of one or more embodiments of the invention are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly indicates otherwise.

The invention claimed is:

1. A composition comprising:
   a) at least 98.0% N-{[(2R)-2-hydroxy-3-piperidin-1-ylpropyl]oxy}pyridine-3-carboximidoyl chloride 1-oxide citrate;
   b) about 1.0% to about 1.9% N-{[(2S)-2-hydroxy-3-piperidin-1-ylpropyl]oxy}pyridine-3-carboximidoyl chloride 1-oxide, or pharmaceutically acceptable salt thereof; and
   c) about 0.05% to about 0.1% methyl (Z)—N-(2-hydroxy-3-(piperidin-1-yl)propoxy)nicotinimidate 1-oxide, or a pharmaceutically acceptable salt thereof.

2. The composition of claim 1, wherein the composition is a pharmaceutical composition.

3. The pharmaceutical composition of claim 2, wherein the composition further comprises less than 2 ppm N-nitrosopiperidine.

4. The pharmaceutical composition of claim 3, wherein the composition comprises about 0.8 to about 2 ppm N-nitrosopiperidine.

5. An oral formulation comprising the composition of claim 1 and at least one pharmaceutically acceptable excipient.

6. The oral formulation of claim 5, wherein the N-{[(2R)-2-hydroxy-3-piperidin-1-ylpropyl]oxy}pyridine-3-carboximidoyl chloride 1-oxide citrate is present at a dosage from about 50 mg to about 500 mg.

7. The oral formulation of claim 5, wherein the oral formulation comprises from about 20% to about 60% w/w of N-{[(2R)-2-hydroxy-3-piperidin-1-ylpropyl]oxy}pyridine-3-carboximidoyl chloride 1-oxide citrate.

8. The oral formulation of claim 5, comprising N-{[(2R)-2-hydroxy-3-piperidin-1-ylpropyl]oxy}pyridine-3-carboximidoyl chloride 1-oxide citrate at a dosage of about 47 mg, about 62 mg, about 93 mg, or about 124 mg.

9. A unit dosage form of the composition of claim 1 and a pharmaceutically acceptable carrier or excipient.

10. The unit dosage form of claim 9, comprising N-{[(2R)-2-hydroxy-3-piperidin-1-ylpropyl]oxy}pyridine-3-carboximidoyl chloride 1-oxide citrate at a dosage from about 50 mg to about 500 mg.

11. The unit dosage form of claim 9, comprising N-{[(2R)-2-hydroxy-3-piperidin-1-ylpropyl]oxy}pyridine-3-carboximidoyl chloride 1-oxide citrate at a dosage of about 47 mg, about 62 mg, about 93 mg, or about 124 mg.

12. A method of treating Niemann Pick disease, type C in a subject in need thereof, wherein the subject is administered a pharmaceutical composition of claim 2.

13. A method of treating Niemann Pick disease, type C in a subject in need thereof, wherein the subject is administered an oral formulation of claim 5.

14. A method of treating Niemann Pick disease, type C in a subject in need thereof, wherein the subject is administered a unit dosage form of claim 9.

15. A composition comprising:
   a) at least 98.0% N-{[(2R)-2-hydroxy-3-piperidin-1-ylpropyl]oxy}pyridine-3-carboximidoyl chloride 1-oxide citrate;
   b) about 1.0% to about 1.9% N-{[(2S)-2-hydroxy-3-piperidin-1-ylpropyl]oxy}pyridine-3-carboximidoyl chloride 1-oxide, or pharmaceutically acceptable salt thereof; and
   c) about 0.8 to about 2 ppm N-nitrosopiperidine, or a pharmaceutically acceptable salt thereof.

16. The composition of claim 15, wherein the composition is a pharmaceutical composition.

17. The pharmaceutical composition of claim 16, wherein the composition further comprises less than about 0.1% methyl (Z)—N-(2-hydroxy-3-(piperidin-1-yl)propoxy)nicotinimidate 1-oxide, or a pharmaceutically acceptable salt thereof.

18. The pharmaceutical composition of claim 17, wherein the composition comprises about 0.05% to about 0.1% methyl (Z)—N-(2-hydroxy-3-(piperidin-1-yl)propoxy)nicotinimidate 1-oxide, or a pharmaceutically acceptable salt thereof.

19. An oral formulation comprising the composition of claim 15, and at least one pharmaceutically acceptable excipient.

20. The oral formulation of claim 19, wherein the N-{[(2R)-2-hydroxy-3-piperidin-1-ylpropyl]oxy}pyridine-3-carboximidoyl chloride 1-oxide citrate is present at a dosage from about 50 mg to about 500 mg.

21. The oral formulation of claim 19, wherein the oral formulation comprises from about 20% to about 60% w/w of N-{[(2R)-2-hydroxy-3-piperidin-1-ylpropyl]oxy}pyridine-3-carboximidoyl chloride 1-oxide citrate.

22. The oral formulation of claim 19, comprising N-{[(2R)-2-hydroxy-3-piperidin-1-ylpropyl]oxy}pyridine-3-carboximidoyl chloride 1-oxide citrate at a dosage of about 47 mg, about 62 mg, about 93 mg, or about 124 mg.

23. A unit dosage form of the composition of claim 15, and a pharmaceutically acceptable carrier or excipient.

24. The unit dosage form of claim 23, comprising N-{[(2R)-2-hydroxy-3-piperidin-1-ylpropyl]oxy}pyridine-3-carboximidoyl chloride 1-oxide citrate at a dosage from about 50 mg to about 500 mg.

25. The unit dosage form of claim 23, comprising N-{[(2R)-2-hydroxy-3-piperidin-1-ylpropyl]oxy}pyridine-3-carboximidoyl chloride 1-oxide citrate at a dosage of about 47 mg, about 62 mg, about 93 mg, or about 124 mg.

26. A method of treating Niemann Pick disease, type C in a subject in need thereof, wherein the subject is administered a pharmaceutical composition of claim 16.

27. A method of treating Niemann Pick disease, type C in a subject in need thereof, wherein the subject is administered an oral formulation of claim 19.

28. A method of treating Niemann Pick disease, type C in a subject in need thereof, wherein the subject is administered a unit dosage form of claim 23.

* * * * *